(12) United States Patent  
Kugimiya et al.

(10) Patent No.: US 8,143,285 B2  
(45) Date of Patent: Mar. 27, 2012

(54) INDOLECARBOXYLIC ACID DERIVATIVE HAVING PGD2 RECEPTOR ANTAGONISTIC ACTIVITY

(75) Inventors: Akira Kugimiya, Osaka (JP); Yuki Tachibana, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 579 days.

(21) Appl. No.: 11/991,551

(22) PCT Filed: Sep. 4, 2006

(86) PCT No.: PCT/JP2006/317419
§ 371 (c)(1),
(2), (4) Date: Mar. 6, 2008

(87) PCT Pub. No.: WO2007/029629
PCT Pub. Date: Mar. 15, 2007

(65) Prior Publication Data
US 2009/0105274 A1    Apr. 23, 2009

(30) Foreign Application Priority Data
Sep. 6, 2005    (JP) ................. 2005-257358

(51) Int. Cl.
*A61K 31/404* (2006.01)
*C07D 401/04* (2006.01)
*C07D 401/06* (2006.01)
*C07D 401/12* (2006.01)

(52) U.S. Cl. ..................... 514/323; 546/201
(58) Field of Classification Search .............. 546/201
See application file for complete search history.

(56) References Cited

U.S. PATENT DOCUMENTS

| 6,043,257 A | 3/2000 | Dominguez et al. |
| 2002/0013310 A1 | 1/2002 | Choi-Sledeski et al. |
| 2003/0092679 A1 | 5/2003 | Siev et al. |
| 2004/0102450 A1 | 5/2004 | Ewing et al. |
| 2004/0236102 A1 | 11/2004 | Brockunier et al. |
| 2005/0096376 A1 | 5/2005 | Sundermann et al. |
| 2006/0004013 A1 | 1/2006 | Kimura et al. |

FOREIGN PATENT DOCUMENTS

| EP | 0 704 757 | 4/1996 |
| EP | 0 810 214 | 12/1997 |
| EP | 1 308 439 | 5/2003 |
| EP | 1 424 325 | 6/2004 |
| EP | 1 424 335 | 6/2004 |
| EP | 1 477 489 | 11/2004 |
| EP | 1 505 061 | 2/2005 |
| EP | 1 600 440 | 11/2005 |
| EP | 1 757 591 | 2/2007 |
| EP | 1 847 535 | 10/2007 |
| FR | 2 679 561 | 1/1993 |
| GB | 2 407 318 | 4/2005 |
| WO | 97/32879 | 9/1997 |
| WO | 98/30548 | 7/1998 |
| WO | 99/47497 | 9/1999 |
| WO | 01/19829 | 3/2001 |
| WO | 01/39759 | 6/2001 |
| WO | 01/79169 | 10/2001 |
| WO | 02/080926 | 10/2002 |
| WO | 02/094830 | 11/2002 |
| WO | 03/051871 | 6/2003 |
| WO | 03/062200 | 7/2003 |
| WO | 03/066046 | 8/2003 |
| WO | 03/066047 | 8/2003 |

(Continued)

OTHER PUBLICATIONS

Vippagunta, et al. Advanced Drug Delivery Reviews 48 (2001) 3-26.*
Multiple sclerosis [online] retrieved from the internet on Feb. 23, 2011.   URL;   http://www.medicinenet.com/script/main/art.asp?articlekey=422.*
International Search Report issued Oct. 3, 2006 in the International (PCT) Application PCT/JP2006/317419 of which the present application is the U.S. National Stage.
Robert A. Coleman et al., "VIII. International Union of Pharmacology Classification of Prostanoid Receptors: Properties, Distribution, and Structure of the Receptors and Their Subtypes", Pharmacological Reviews, vol. 46, No. 2, pp. 205-229, 1994.

(Continued)

*Primary Examiner* — Shawquia Young
(74) *Attorney, Agent, or Firm* — Wenderoth, Lind & Ponack, L.L.P.

(57) ABSTRACT

The present invention provides an indolecarboxylic acid derivative having DP receptor antagonistic activity and a pharmaceutical composition comprising the said compound as an active ingredient, and further a therapeutic agent for treating allergic diseases.
A compound of the general formula (I):

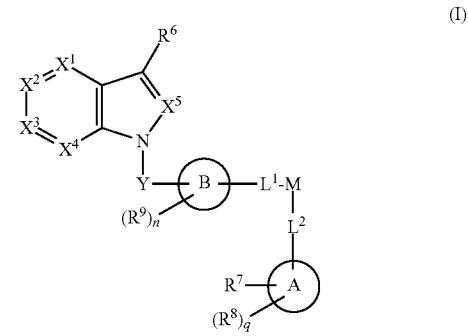

wherein the ring A is an aromatic carbocyclic ring etc.; the ring B is a nitrogen-containing non-aromatic heterocyclic ring etc.; the formula of $-X^1=X^2-X^3=X^4-$ is a formula of $-C(R^1)=C(R^2)-C(R^3)=C(R^4)-$ etc.; $X^5$ is $C(R^5)$ or N; $R^1$, $R^2$, $R^3$, $R^4$ and $R^5$ is independently a hydrogen atom, a halogen atom etc; $R^6$ is a formula of $-Z-R^{10}$ etc. wherein Z is alkylene etc., and $R^{10}$ is carboxy etc.; $R^7$ is optionally substituted alkyloxy etc.; $R^8$ is independently a halogen atom etc.; $R^9$ is independently optionally substituted alkyl etc.; Y is a single bond etc.; n is 0 etc.; q is 0 etc.;
a pharmaceutically acceptable salt or a solvate thereof.

20 Claims, No Drawings

FOREIGN PATENT DOCUMENTS

| WO | 03/097598 | 11/2003 |
|---|---|---|
| WO | 2004/024730 | 3/2004 |
| WO | 2004/033427 | 4/2004 |
| WO | 2004/039807 | 5/2004 |
| WO | 2004/103970 | 12/2004 |
| WO | 2004/111047 | 12/2004 |
| WO | 2005/023806 | 3/2005 |
| WO | 2005/040112 | 5/2005 |
| WO | 2005/056527 | 6/2005 |

OTHER PUBLICATIONS

Franciszek Saczewski et al., "Synthesis, structure ad antiaggregatory effects of some N-(4,5-dihydro-1H-imidazol-2-yl)indoles", IL Farmaco, vol. 55(1), pp. 56-64, 2000.

Celia Dominguez et al., "Design and Synthesis of Potent and Selective 5,6-Fused Heterocyclic Thrombin Inhibitors", Bioorganic & Medicinal Chemistry Letters, 9(7), pp. 925-930, 1999.

Dooseop Kim et al., "Design, Synthesis, and SAR of Heterocycle-Containing Antagonists of the Human CCR5 Receptor for the Treatment of HIV-1 Infection", Bioorganic & Medicinal Chemistry Letters, 11(24), pp. 3103-3106, 2001.

Christian Hotzel et al., "Design, synthesis, DNA-binding and cytotoxicity evaluation of new potential combilexines", European Journal of Medical Chemistry, 37(5), pp. 367-378, 2002.

Valerie Grumel et al., "Design and synthesis of a series of indole glycoprotein IIb/IIIa inhibitors", European Journal of Medical Chemistry, 37(1), pp. 45-62, 2002.

Douglas G. Batt et al., "Disubstituted Indazoles as Potent Antagonists of the Integrin $\alpha_v\beta_3$", Journal of Medicinal Chemistry, 43(1), pp. 41-58, 2000.

* cited by examiner

INDOLECARBOXYLIC ACID DERIVATIVE HAVING PGD2 RECEPTOR ANTAGONISTIC ACTIVITY

TECHNICAL FIELD

This invention relates to an indolecarboxylic acid derivative having DP receptor antagonistic activity and a medicinal use thereof.

BACKGROUND ART

Prostaglandin D2(PGD2) is a metabolic product of arachidonic acid through PGG2 and PGH2, and known to have various potent physiological activities. For example, in non-patent literature 1 it is described that PGD2 is involved in sleeping and secretion of hormones in central nervous system, and in inhibiting activity of platelet aggregation, contraction of bronchial smooth muscle, vasodilation and constriction of a blood vessel etc. in peripheral system. Moreover, PGD2 is considered to be involved in forming pathological condition of an allergic disease such as bronchial asthma since it is a major metabolic product of arachidonic acid produced from a mast cell, and has a potent bronchoconstricting effect, causing an increase of vascular permeability and migration of inflammatory cell such as eosinophils.

A DP receptor (also called DP1 receptor) or CRTH2 receptor (also called DP2 receptor) is known as a receptor of PGD2 but these are completely different receptors. In Patent literatures 1-10 indole derivatives having a DP receptor antagonistic activity is disclosed, and in Patent literatures 11-15 indole derivatives having a CRTH2 receptor-antagonistic activity is disclosed Also, indole derivatives having inhibitory activity against noradrenalin re-uptake are disclosed in Patent literature 16.
Patent literature 1: WO 2001/079169 Pamphlet
Patent literature 2: WO 2002/094830 Pamphlet
Patent literature 3: WO 2003/062200 Pamphlet
Patent literature 4: WO 2004/039807 Pamphlet
Patent literature 5: WO 2004/103970 Pamphlet
Patent literature 6: WO 2004/111047 Pamphlet
Patent literature 7: WO 2005/056527 Pamphlet
Patent literature 8: WO 2003/022813 Pamphlet
Patent literature 9: WO 2003/022814 Pamphlet
Patent literature 10: WO 2004/078719 Pamphlet
Patent literature 11: WO 2003/097598 Pamphlet
Patent literature 12: WO 2003/066046 Pamphlet
Patent literature 13: WO 2003/066047 Pamphlet
Patent literature 14: WO 2005/040112 Pamphlet
Patent literature 15: GB 2407318 Pamphlet
Patent literature 16: WO 2005/019208 Pamphlet
Non-patent literature 1: Pharmacol. Review, Vol. 46, page 205-229 (1994)
Non-patent literature 2: Pharmaco., Vol. 55(1), page 56-64 (2000)

DISCLOSURE OF INVENTION

Problem to be Solved

The present invention provides an indolecarboxylic acid derivative having DP receptor antagonistic activity and a pharmaceutical composition comprising the said compound as an active ingredient. The said pharmaceutical composition is useful as a therapeutic agent for treating allergic diseases.

Means for Solving Problem

The present inventors have found that the indolecarboxylic acid derivative shown below has a potent DP receptor antagonistic activity, and the pharmaceutical composition comprising the said compound as an active ingredient is useful as a therapeutic agent for treating allergic diseases.

The present invention relates to
1) a compound of the general formula (I):

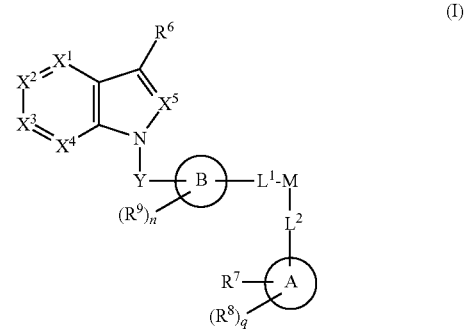

(I)

wherein the ring A is an aromatic carbocyclic ring or an aromatic heterocyclic ring;
the ring B is a nitrogen-containing non-aromatic heterocyclic ring or a nitrogen-containing aromatic heterocyclic ring;
$X^1$ is —N= or —C($R^1$)=;
$X^2$ is —N= or —C($R^2$)=;
$X^3$ is —N= or —C($R^3$)=;
$X^4$ is —N= or —C($R^4$)=;
$X^5$ is —N= or —C($R^5$)=;
$R^1$, $R^2$, $R^3$, $R^4$, $R^5$ and $R^6$ are independently a hydrogen atom, a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, an optionally substituted non-aromatic heterocyclic group or a group of the formula: -$L^3$-$R^{10}$, wherein $R^{10}$ is hydroxyalkyl, carboxy, alkyloxycarbonyl, optionally substituted carbamoyl or a carboxy equivalent, and $L^3$ is a single bond, optionally substituted alkylene optionally containing one or two heteroatom(s), optionally substituted alkenylene optionally containing one or two heteroatom(s), optionally substituted alkynylene optionally containing one or two heteroatom(s), an oxygen atom, a sulfur atom or —N ($R^{11}$)—, provided that at least one of $R^1$ to $R^6$ is a group of -$L^3$-$R^{10}$;

$R^7$ is a hydrogen atom, optionally substituted alkyloxy, optionally substituted alkenyloxy, optionally substituted alkynyloxy, optionally substituted cycloalkyloxy, optionally substituted cycloalkenyloxy, optionally substituted aryloxy, optionally substituted heteroaryloxy, optionally substituted alkylthio, optionally substituted alkenylthio, optionally substituted alkynylthio, optionally substituted cycloalkylthio, optionally substituted cycloalkenylthio, optionally substituted arylthio or optionally substituted heteroarylthio;

$R^8$ is independently a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^9$ is independently a halogen atom, optionally substituted alkyl, optionally substituted alkenyl, optionally substituted alkynyl, optionally substituted cycloalkyl, optionally substituted alkyloxy, oxo, optionally substituted aryl, optionally substituted heteroaryl or an optionally substituted non-aromatic heterocyclic group;

M is carbonyl or sulfonyl;

Y is a single bond, optionally substituted alkylene optionally containing one or two heteroatom(s), optionally substituted alkenylene optionally containing one or two heteroatom(s), optionally substituted alkynylene optionally containing one or two heteroatom(s), an oxygen atom, a sulfur atom or —N($R^{11}$)—;

$L^1$ and $L^2$ are independently a single bond, optionally substituted alkylene optionally containing one or two heteroatom(s), optionally substituted alkenylene optionally containing one or two heteroatom(s), optionally substituted alkynylene optionally containing one or two heteroatom(s), or —N($R^{11}$)—;

$R^{11}$ and $R^{12}$ are independently a hydrogen atoms, optionally substituted alkyl, optionally substituted alkenyl, optionally substituted alkynyl, optionally substituted cycloalkyl, acyl, optionally substituted alkyloxy, optionally substituted aryl, optionally substituted heteroaryl or an optionally substituted non-aromatic heterocyclic group;

n is 0, 1 or 2; and q is 0, 1, 2 or 3, provided that $R^7$ is not a hydrogen atom when the ring B is an imidazoline ring and all of Y, $L^1$ and $L^2$ are single bonds;

a pharmaceutically acceptable salt or solvate thereof, 2) a compound of 1) wherein the formula of -$X^1$=$X^2$-$X^3$=$X^4$- is —C($R^1$)=C($R^2$)—C($R^3$)=C($R^4$)—, —N=C($R^2$)—C($R^3$)=C($R^4$)—, —C($R^1$)=N—C($R^3$)=C($R^4$)—, —C($R^1$)=C($R^2$)—N=C($R^4$)— or —C($R^1$)=C($R^2$)—C($R^3$)=N—;

a pharmaceutically acceptable salt or solvate thereof, 3) a compound of 1) or 2) wherein $R^1$ is a group of the formula: -$L^3$-$R^{10}$;

a pharmaceutically acceptable salt or solvate thereof, 4) a compound of 1) or 2) wherein $R^2$ is a group of the formula: -$L^3$-$R^{11}$;

a pharmaceutically acceptable salt or solvate thereof, 5) a compound of 1) or 2) wherein $R^3$ is a group of the formula: -$L^3$-$R^{10}$;

a pharmaceutically acceptable salt or solvate thereof, 6) a compound of 1) or 2) wherein $R^4$ is a group of the formula: -$L^3$-$R^{10}$;

a pharmaceutically acceptable salt or solvate thereof, 7) a compound of 1) or 2) wherein $R^5$ is a group of the formula: —C(-$L^3$-$R^{10}$)=;

a pharmaceutically acceptable salt or solvate thereof, 8) a compound of 1) or 2) wherein $R^6$ is a group of the formula: -$L^3$-$R^{10}$;

a pharmaceutically acceptable salt or solvate thereof, 9) a compound of any of 1) to 6) or 8) wherein $R^5$ is —N= or —CH=;

a pharmaceutically acceptable salt or solvate thereof, 10) a compound of any of 1) to 9) wherein $R^{10}$ is carboxy and $L^3$ is optionally substituted alkylene;

a pharmaceutically acceptable salt or solvate thereof, 11) a compound of any of 1) to 10) wherein the ring B is a formula of

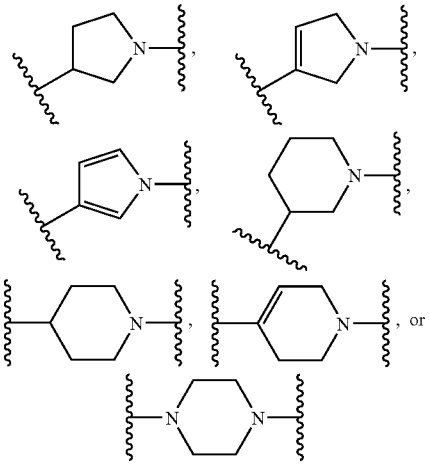

and n is 0; a pharmaceutically acceptable salt or solvate thereof, 12) a compound of any of 1) to 11) wherein the ring A is a benzene ring or a pyridine ring; a pharmaceutically acceptable salt or solvate thereof, 13) a compound of any of 1) to 12) wherein $R^7$ is optionally substituted alkyloxy or optionally substituted alkylthio; a pharmaceutically acceptable salt or solvate thereof, 14) a compound of any of 1) to 13) wherein $R^8$ is a halogen atom, optionally substituted alkyl or optionally substituted alkyloxy, and q is 0 or 1; a pharmaceutically acceptable salt or solvate thereof, 15) a compound of any of 1) to 14) wherein Y is a single bond and n is 0; a pharmaceutically acceptable salt or solvate thereof, 16) a compound of any of 1) to 15) wherein M is sulfonyl, $L^1$ is a single bond and $L^2$ is a single bond; a pharmaceutically acceptable salt or solvate thereof, 17) a compound of the general formula (II):

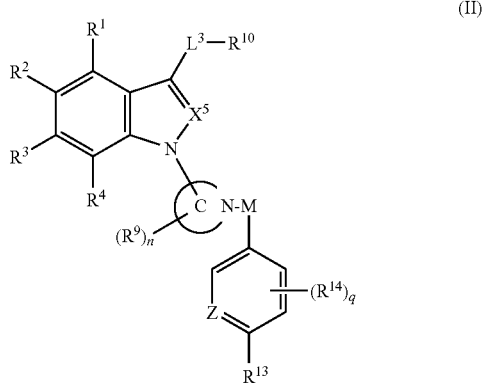

(II)

wherein the ring C is a formula of

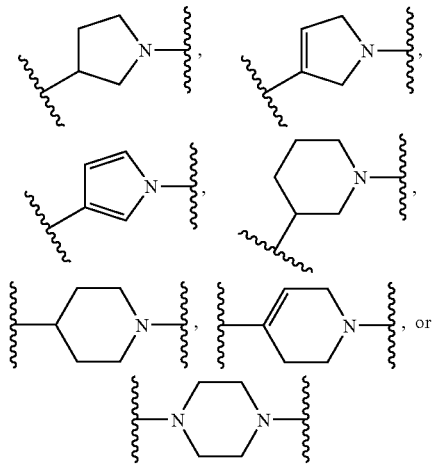

$X^5$ is —N= or —C($R^5$)=;

$R^1$, $R^2$, $R^3$, $R^4$ and $R^5$ are independently hydrogen atoms, a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^9$ is independently a halogen atom, optionally substituted alkyl, optionally substituted alkenyl, optionally substituted alkynyl, optionally substituted cycloalkyl, optionally substituted alkyloxy, oxo, optionally substituted aryl, optionally substituted heteroaryl or an optionally substituted non-aromatic heterocyclic group;

$R^{10}$ is hydroxyalkyl, carboxy, alkyloxycarbonyl, optionally substituted carbamoyl or a carboxy equivalent;

$R^{13}$ is optionally substituted C1-C6 alkyloxy, optionally substituted C2-C6 alkenyloxy, optionally substituted C2-C6 alkynyloxy, optionally substituted C1-C6 alkylthio, optionally substituted C2-C6 alkenylthio, optionally substituted C2-C6 alkynylthio, optionally substituted C3-C6 cycloalkyloxy, optionally substituted C3-C6 cycloalkylthio, optionally substituted aryloxy or optionally substituted arylthio, $R^{14}$ is independently halogen atom, optionally substituted alkyl, optionally substituted cycloalkyl, optionally substituted amino, acyl, optionally substituted alkyloxycarbonyl, optionally substituted carbamoyl, optionally substituted sulfamoyl, cyano, nitro, optionally substituted aryl, optionally substituted arylsulfonyloxy, optionally substituted heteroaryl or an optionally substituted non-aromatic heterocyclic group;

M is carbonyl or sulfonyl;

Z is CH, C($R^{14}$), or N;

$L^3$ is a single bond, optionally substituted alkylene optionally containing one or two heteroatom(s), optionally substituted alkenylene optionally containing one or two heteroatom(s), optionally substituted alkynylene optionally containing one or two heteroatom(s), an oxygen atom, a sulfur atom or a group of —N($R^{11}$)—;

n is 0, 1 or 2; and q is 0, 1, 2 or 3;

a pharmaceutically acceptable salt or solvate thereof, 18) a compound of 17) wherein M is sulfonyl;

a pharmaceutically acceptable salt or solvate thereof, 19) a compound of 17) or 18) wherein $R^{10}$ is carboxy;

a pharmaceutically acceptable salt or solvate thereof, 20) a compound of any of 17) to 19) wherein $X^5$ is —N= or CH=;

a pharmaceutically acceptable salt or solvate thereof, 21) a compound of any of 17) to 20) wherein $L^3$ is optionally substituted alkylene;

a pharmaceutically acceptable salt or solvate thereof, 22) a compound of any of 17) to 21) wherein $R^5$ is a hydrogen atom, a halogen atom or alkyl;

a pharmaceutically acceptable salt or solvate thereof, 23) a compound of any of 17) to 22) wherein one of $R^1$ to $R^4$ is a hydrogen atom, a halogen atom, optionally substituted alkyl, optionally substituted alkyloxy, optionally substituted amino, optionally substituted carbamoyl, optionally substituted aryl, optionally substituted heteroaryl or an optionally substituted non-aromatic heterocyclic group, and others of $R^1$ to $R^4$ are a hydrogen atom, a halogen atom or optionally substituted alkyl;

a pharmaceutically acceptable salt or solvate thereof, 24) a compound of any of 17) to 23) wherein $R^{13}$ is optionally substituted C1-C6 alkyloxy or optionally substituted C1-C6 alkylthio;

a pharmaceutically acceptable salt or solvate thereof, 25) a compound of any of 17) to 24) wherein $R^{14}$ is a halogen atom, optionally substituted alkyl or optionally substituted alkyloxy;

a pharmaceutically acceptable salt or solvate thereof, 26) a compound of any of 17) to 25) wherein $R^9$ is alkyl or oxo, and n is 0 or 1;

a pharmaceutically acceptable salt or solvate thereof, 27) a pharmaceutical composition comprising the compound of any of 1) to 26), pharmaceutically acceptable salt or solvate thereof as an active ingredient, 28) a pharmaceutical composition of 27) which is a DP receptor antagonist, 29) a pharmaceutical composition of 27) which is a therapeutic agent for allergy, 30) a pharmaceutical composition of 28) wherein the therapeutic agent for allergy is a medicine for asthma, 31) a method for treating a disease related to DP receptor characterized by administration of the compound of any of 1) to 26), pharmaceutically acceptable salt or solvate thereof, 32) a method of 31) wherein the disease related to DP receptor is asthma, 33) use of the compound of any of 1) to 26), pharmaceutically acceptable salt or solvate thereof, in the manufacturing of a therapeutic agent for treating diseases related to DP receptor, and 34) use of the compound of 33), pharmaceutically acceptable salt or solvate thereof wherein the disease related to DP receptor is asthma, The present invention also includes the following inventions;

(1) a compound of the general formula (I-a):

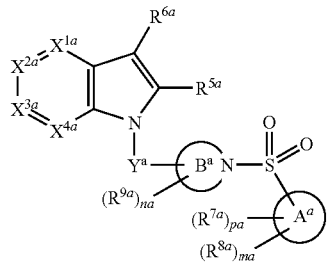

(I-a)

wherein the ring $A^a$ is an aromatic carbocyclic ring or an aromatic heterocyclic ring;

the ring $B^a$ is a 4- to 8-membered nitrogen-containing heterocyclic ring containing one or two nitrogen atom(s);

$X^{1a}$ is —N= or —C($R^{1a}$)=;
$X^{2a}$ is —N= or —C($R^{2a}$)=;
$X^{3a}$ is —N= or —C($R^{3a}$)=;
$X^{4a}$ is —N= or —C($R^{4a}$)=;

$R^{1a}$, $R^{2a}$, $R^{3a}$ and $R^{4a}$ are independently a hydrogen atom, a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, an optionally substituted heteroaryloxy, optionally substituted heteroarylthio, optionally substituted heteroarylsulfinyl, optionally substituted heteroarylsulfonyl, optionally substituted heteroarylsulfonyloxy, an optionally substituted non-aromatic heterocyclic group or a group of the formula: $-Z^a-R^{10a}$, wherein $R^{10a}$ is hydroxyalkyl, carboxy, alkyloxycarbonyl, optionally substituted carbamoyl or optionally substituted tetrazolyl, and Z is a single bond, alkylene, alkenylene, alkynylene, —O-alkylene or —S-alkylene;

$R^{5a}$ and $R^{6a}$ are independently a hydrogen atom, optionally substituted alkyl, optionally substituted aryl, optionally substituted heteroaryl or a group of the formula: $-Z^a-R^{10a}$, wherein $R^{10a}$ is hydroxyalkyl, carboxy, alkyloxycarbonyl, optionally substituted carbamoyl or optionally substituted tetrazolyl, and Za is a single bond, alkylene, alkenylene, alkynylene, —O-alkylene or —S-alkylene, provided that at least one of $R^{1a}$ to $R^{6a}$ is a group of the formula: $-Z^a-R^{10a}$.

$R^{7a}$ is optionally substituted alkyloxy, optionally substituted alkylthio, optionally substituted cycloalkyloxy, optionally substituted cycloalkylthio, optionally substituted aryloxy, optionally substituted arylthio, optionally substituted heteroaryloxy or optionally substituted heteroarylthio;

$R^{8a}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{9a}$ is independently optionally substituted alkyl or optionally substituted aryl;

$Y^a$ is a single bond, alkylene, alkenylene or alkynylene;
ma is 0, 1 or 2;
na is 0, 1 or 2; and
pa is 0 or 1;
a pharmaceutically acceptable salt or solvate thereof, (2) a compound of (1) wherein $R^{6a}$ is a group of the formula: $-Z^a-R^{10a}$, and $R^{1a}$ to $R^{5a}$ are not groups of the formula: $-Z^a-R^{10a}$;

a pharmaceutically acceptable salt or hydrate thereof, (3) a compound of (1) wherein $R^{5a}$ is a group of the formula: $-Z^a-R^{10a}$, and $R^{1a}$ to $R^{4a}$ and $R^{6a}$ are not groups of the formula: $-Z^a-R^{10a}$;
a pharmaceutically acceptable salt or hydrate thereof,
(4) a compound of (1) wherein $R^{1a}$ is a group of the formula: $-Z^a-R^{10a}$, and $R^{2a}$ to $R^{6a}$ are not groups of the formula: $-Z^a-R^{10a}$;
a pharmaceutically acceptable salt or hydrate thereof,
(5) a compound of any of (1) to (4) wherein the ring $B^a$ is a formula of

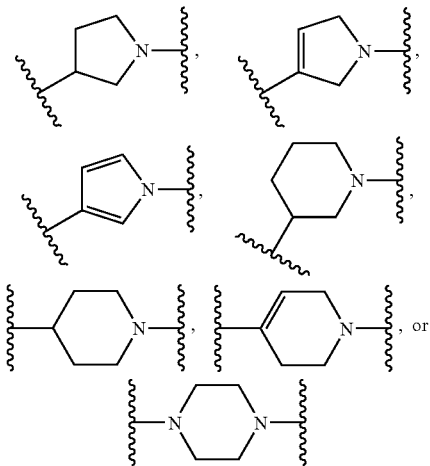

and na is 0; a pharmaceutically acceptable salt or hydrate thereof,
(6) a compound of any of (1) to (5) wherein the ring $A^a$ is a benzene ring or a pyridine ring; a pharmaceutically acceptable salt or hydrate thereof,
(7) a compound of any of (1) to (6) wherein pa is 1; a pharmaceutically acceptable salt or hydrate thereof,
(8) a compound of any of (1) to (7) wherein Ya is a single bond; a pharmaceutically acceptable salt or hydrate thereof,
(9) a compound of any of (1) to (8) wherein $R^{10}$ is carboxy; a pharmaceutically acceptable salt or hydrate thereof,
(10) a compound of any of (1) to (9) wherein $-X^{1a}=X^{2a}-X^{3a}=X^{4a}-$ is $-C(R^{1a})=C(R^{2a})-C(R^{3a})=C(R^{4a})-$, $-N=C(R^{2a})-C(R^{3a})=C(R^{4a})-$, $-C(R^{1a})=N-C(R^{3a})=C(R^{4a})-$, $-C(R^{1a})=C(R^{2a})-N=C(R^{4a})-$ or $-C(R^{1a})=C(R^{2a})-C(R^{3a})=N-$;
a pharmaceutically acceptable salt or hydrate thereof,
(11) a compound of the formula (II-a):

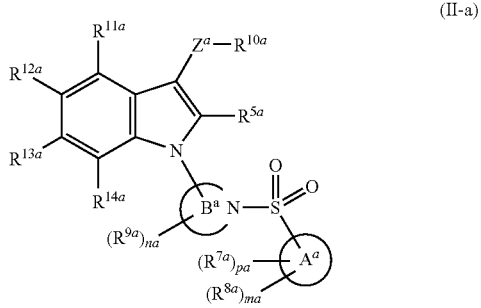

(II-a)

wherein the ring $A^a$ is an aromatic carbocyclic ring or an aromatic heterocyclic ring;

the ring $B^a$ is a 4- to 8-membered nitrogen-containing heterocyclic ring containing one or two nitrogen atom(s);

$R^{11a}$, $R^{12a}$, $R^{13a}$ and $R^{14a}$ are independently a hydrogen atom, a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, an optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{5a}$ is a hydrogen atom, optionally substituted alkyl, optionally substituted aryl or optionally substituted heteroaryl;

$R^{7a}$ is optionally substituted alkyloxy, optionally substituted alkylthio, optionally substituted cycloalkyloxy, optionally substituted cycloalkylthio, optionally substituted aryloxy, optionally substituted arylthio, optionally substituted heteroaryloxy or optionally substituted heteroarylthio;

$R^{8a}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{9a}$ is independently optionally substituted alkyl or optionally substituted aryl;

$R^{10a}$ is hydroxyalkyl, carboxy, alkyloxycarbonyl, optionally substituted carbamoyl or optionally substituted tetrazolyl;

$Z^a$ is a single bond, alkylene, alkenylene, alkynylene, —O-alkylene or —S-alkylene;

ma is 0, 1 or 2;

na is 0, 1 or 2 and pa is 0 or 1;

a pharmaceutically acceptable salt or hydrate thereof,

(12) a compound of (11) wherein the ring $B^a$ is a ring of the formula of

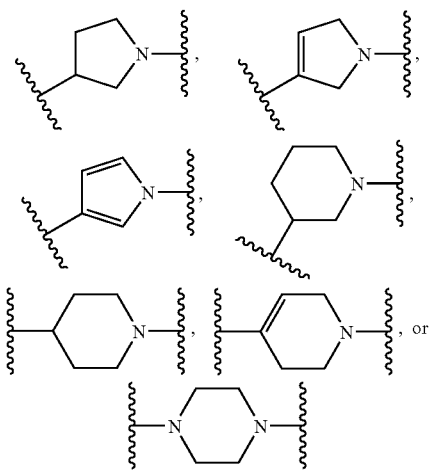

and na is 0;
a pharmaceutically acceptable salt or hydrate thereof,
(13) a compound of (11) or (12) wherein the ring $A^a$ is a benzene ring or a pyridine ring; a pharmaceutically acceptable salt or hydrate thereof,
(14) a compound of any of (11) to (13) wherein pa is 1; a pharmaceutically acceptable salt or hydrate thereof,
(15) a compound of any of (11) to (14) wherein $R^{10a}$ is carboxy; a pharmaceutically acceptable salt or hydrate thereof,
(16) a pharmaceutical composition comprising the compound of any of (1) to (15), pharmaceutically acceptable salt or hydrate thereof as an active ingredient,
(17) a pharmaceutical composition of (16) which has a PGD2 receptor antagonistic activity,
(18) a pharmaceutical composition of (16) which is a therapeutic agent for allergy,
(19) a pharmaceutical composition of (16) which is a therapeutic agent for asthma,
(20) a method for treating a disease related to DP receptor characterized by administration of the compound of any of (1) to (15), pharmaceutically acceptable salt or hydrate thereof,
(21) a method of (20) wherein the disease related to DP receptor is asthma,
(22) use of the compound of any of (1) to (15), pharmaceutically acceptable salt or hydrate thereof, in the manufacturing of a therapeutic agent for treating diseases related to DP receptor, and
(23) use of the compound of (22), pharmaceutically acceptable salt or hydrate thereof wherein the disease related to DP receptor is asthma.

Terms herein used are explained below. In the present specification each term is used under the unified definition and has the same meaning when used alone or in combination with other terms.

In the present specification, a term of "halogen atom" means a fluorine atom, a chlorine atom, a bromine atom and an iodine atom. A fluorine atom, a chlorine atom and a bromine atom are preferable.

In the present specification, a term of "hetero atom" means an oxygen atom, a sulfur atom and a nitrogen atom.

In the present specification, a term of "alkyl" includes a monovalent straight or branched hydrocarbon group having one to eight carbon atom(s). For example, methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl and the like are exemplified. C1-C6 alkyl is preferred. C1-C4 alkyl is further preferred. When a number of carbon is specified, it means "alkyl" having the carbon number within the range.

In the present specification, a term of "alkenyl" includes a monovalent straight or branched hydrocarbon group having two to eight carbon atoms and one or more double bond(s). For example, vinyl, allyl, 1-propenyl, 2-butenyl, 2-pentenyl, 2-hexenyl, 2-heptenyl, 2-octenyl and the like are exemplified. C2-C6 alkenyl is preferred. Moreover, C2-C4 alkenyl is further preferred.

In the present specification, a term of "alkynyl" includes a monovalent straight or branched hydrocarbon group having two to eight carbon atoms and one or more triple bond(s). For example, ethynyl, 1-propynyl, 2-propynyl, 2-butynyl, 2-pentynyl, 2-hexynyl, 2-heptynyl, 2-octynyl and the like are exemplified. C2-C6 alkynyl is preferred. Moreover, C2-C4 alkynyl is further preferred.

In the present specification, a term of "cycloalkyl" includes a cycloalkyl having three to eight carbon atoms and for example, cyclopropyl, cyclobutyl, cyclopentyl, cyclohexyl, cycloheptyl, cyclooctyl and the like are exemplified. C3-C6 cycloalkyl is preferred.

In the present specification, a term of "cycloalkenyl" includes a cycloalkenyl having three to eight carbon atoms and for example, cyclopropenyl, cyclobutenyl, cyclopentenyl, cyclohexenyl, cycloheptenyl, cyclooctenyl and the like are exemplified. C3-C6 cycloalkenyl is preferred.

In the present specification, a term of "alkyloxy" includes a group wherein an oxygen atom is substituted with one "alkyl" above and for example, methyloxy, ethyloxy, n-propyloxy, isopropyloxy, n-butyloxy, isobutyloxy, sec-butyloxy, tert-butyloxy, n-pentyloxy, isopentyloxy, 2-pentyloxy, 3-pentyloxy, n-hexyloxy, isohexyloxy, 2-hexyloxy, 3-hexyloxy, n-heptyloxy, n-octyloxy, and the like are exemplified. C1-C6 alkyloxy is preferred. Moreover, C1-C4 alkyloxy is further preferred. When a number of carbon is specified, it means "alkyloxy" having the carbon number within the range.

In the present specification, a term of "alkenyloxy" includes a group wherein an oxygen atom is substituted with one "alkenyl" above and for example, vinyloxy, allyloxy, 1-propenyloxy, 2-butenyloxy, 2-pentenyloxy, 2-hexenyloxy, 2-heptenyloxy, 2-octenyloxy and the like are exemplified. C2-C6 alkenyloxy is preferred. Moreover, C2-C4 alkenyloxy is further preferred. When a number of carbon is specified, it means "alkenyloxy" having the carbon number within the range.

In the present specification, a term of "alkynyloxy" includes a group wherein an oxygen atom is substituted with one "alkynyl" above and for example, ethynyloxy, 1-propynyloxy, 2-propynyloxy, 2-butynyloxy, 2-pentynyloxy, 2-hexynyloxy, 2-heptynyloxy, 2-octynyloxy and the like are exemplified. C2-C6 alkynyloxy is preferred. Moreover, C2-C4 alkynyloxy is further preferred. When a number of carbon is specified, it means "alkynyloxy" having the carbon number within the range.

In the present specification, a term of "cycloalkyloxy" includes a group wherein an oxygen atom is substituted with one "cycloalkyl" above and for example, cyclopropyloxy, cyclobutyloxy, cyclopentyloxy, cyclohexyloxy, cycloheptyloxy and cyclooctyloxy are exemplified. C3-C6 cycloalkyloxy is preferred. When a number of carbon is specified, it means "cycloalkyloxy" having the carbon number within the range.

In the present specification, a term of "cycloalkenyloxy" includes a group wherein an oxygen atom is substituted with one "cycloalkenyl" above and for example, cyclopropenyloxy, cyclobutenyloxy, cyclopentenyloxy, cyclohexenyloxy, cycloheptenyloxy and cyclooctenyloxy are exemplified. C3-C6 cycloalkenyloxy is preferred. When a number of carbon is specified, it means "cycloalkenyloxy" having the carbon number within the range.

In the present specification, a term of "alkylthio" includes a group wherein a sulfur atom is substituted with one "alkyl" above, and for example, methylthio, ethylthio, n-propylthio, isopropylthio, n-butylthio, isobutylthio, sec-butylthio, tert-butylthio, n-pentylthio, isopentylthio, 2-pentylthio, 3-pentylthio, n-hexylthio, isohexylthio, 2-hexylthio, 3-hexylthio, n-heptylthio, n-octylthio, and the like are exemplified. C1-C6 Alkylthio is preferred. Moreover, C1-C4 alkylthio is further preferred. When a number of carbon is specified, it means "alkylthio" having the carbon number within the range.

In the present specification, a term of "alkenylthio" includes a group wherein a sulfur atom is substituted with one "alkenyl" above, and for example, vinylthio, allylthio, 1-propenylthio, 2-butenylthio, 2-pentenylthio, 2-hexenylthio, 2-heptenylthio, 2-octenylthio and the like are exemplified. C2-C6 Alkenylthio is preferred. Moreover, C2-C4 alkylthio is further preferred. When a number of carbon is specified, it means "alkenylthio" having the carbon number within the range.

In the present specification, a term of "alkynylthio" includes a group wherein a sulfur atom is substituted with one "alkynyl" above and for example, ethynylthio, 1-propynylthio, 2-propynylthio, 2-butynylthio, 2-pentynylthio, 2-hexynylthio, 2-heptynylthio, 2-octynylthio and the like are exemplified. C2-C6 alkynylthio is preferred. Moreover, C2-C4 alkynylthio is further preferred. When a number of carbon is specified, it means "alkynylthio" having the carbon number within the range.

In the present specification, a term of "alkylsulfinyl" includes a group wherein sulfinyl is substituted with one "alkyl" above and for example, methylsulfinyl, ethylsulfinyl, n-propylsulfinyl, isopropylsulfinyl, n-butylsulfinyl, isobutylsulfinyl, sec-butylsulfinyl, tert-butylsulfinyl, n-pentylsulfinyl, isopentylsulfinyl, 2-pentylsulfinyl, 3-pentylsulfinyl, n-hexylsulfinyl, isohexylsulfinyl, 2-hexylsulfinyl, 3-hexylsulfinyl, n-heptylsulfinyl, n-octylsulfinyl and the like are exemplified. C1-C6 alkylsulfinyl is preferred. Moreover, C1-C4 alkylsulfinyl is further preferred.

In the present specification, a term of "alkylsulfonyl" includes a group wherein sulfonyl is substituted with one "alkyl" above and for example, methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, 2-pentylsulfonyl, 3-pentylsulfonyl, n-hexylsulfonyl, isohexylsulfonyl, 2-hexylsulfonyl, 3-hexylsulfonyl, n-heptylsulfonyl, n-octylsulfonyl and the like are exemplified. C1-C6 alkylsulfonyl is preferred. Moreover, C1-C4 alkylsulfonyl is further preferred.

In the present specification, a term of "alkylsulfonyloxy" includes a group wherein an oxygen atom is substituted with one "alkylsulfonyl" above and for example, methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, n-pentylsulfonyloxy, isopentylsulfonyloxy, 2-pentylsulfonyloxy, 3-pentylsulfonyloxy, n-hexylsulfonyloxy, isohexylsulfonyloxy, 2-hexylsulfonyloxy, 3-hexylsulfonyloxy, n-heptylsulfonyloxy, n-octylsulfonyloxy and the like are exemplified. C1-C6 alkylsulfonyl is preferred. Moreover, C1-C4 alkylsulfonyl is further preferred.

In the present specification, a term of "cycloalkylthio" includes a group wherein a sulfur atom is substituted with one "cycloalkyl" above and for example, cyclopropylthio, cyclobutylthio, cyclopentylthio, cyclohexylthio, cycloheptylthio, cyclooctylthio and the like are exemplified. C3-C6 cycloalkylthio is preferred. When a number of carbon is specified, it means "cycloalkylthio" having the carbon number within the range.

In the present specification, a term of "cycloalkylsulfinyl" includes a group in which sulfinyl is substituted with one "cycloalkyl" above. For example, cyclopropylsulfinyl, cyclobutylsulfinyl, cyclopentylsulfinyl, cyclohexylsulfinyl, cycloheptylsulfinyl, and cyclooctylsulfinyl are exemplified. Preferably C3-C6 cycloalkylsulfinyl is exemplified.

In the present specification, a term of "cycloalkylsulfonyl" includes a group in which sulfonyl is substituted with one "cycloalkyl" above. For example, cyclopropylsulfonyl, cyclobutylsulfonyl, cyclopentylsulfonyl, cyclohexylsulfonyl, cycloheptylsulfonyl, and cyclooctylsulfonyl are exemplified. Preferably C3-C6 cycloalkylsulfonyl is exemplified.

In the present specification, a term of "cycloalkylsulfonyloxy" includes a group in which an oxygen atom is substituted with one "cycloalkylsulfonyl" above. For example, cyclopropylsulfonyloxy, cyclobutylsulfonyloxy, cyclopentyl sulfonyloxy, cyclohexyl sulfonyloxy, cycloheptylsulfonyloxy, and cyclooctylsulfonyloxy are exemplified. Preferably C3-C6 cycloalkylsulfonyloxy is exemplified.

In the present specification, a term of "cycloalkenylthio" includes a group in which a sulfur atom is substituted with one "cycloalkenyl" above. For example, cyclopropenylthio, cyclobutenylthio, cyclopentenylthio, cyclohexenylthio, cycloheptenylthio, and cyclooctenylthio are exemplified. Preferably C3-C6 cycloalkenylthio is exemplified. When a number of carbon is specified, it means "cycloalkenylthio" having the carbon number within the range.

In the present specification, a term of "cycloalkenylsulfinyl" includes a group in which sulfinyl is substituted with one "cycloalkenyl" above. For example, cyclopropenylsulfinyl, cyclobutenylsulfinyl, cyclopentenylsulfinyl, cyclohexenylsulfinyl, cycloheptenylsulfinyl, and cyclooctenylsulfinyl are exemplified. Preferably C3-C6 cycloalkenylsulfinyl is exemplified.

In the present specification, a term of "cycloalkenylsulfonyl" includes a group in which sulfonyl is substituted with one "cycloalkenyl" above. For example, cyclopropenylsulfonyl, cyclobutenylsulfonyl, cyclopentenylsulfonyl, cyclohexenylsulfonyl, cycloheptenylsulfonyl, and cyclooctenylsulfonyl are exemplified. Preferably C3-C6 cycloalkenylsulfonyl is exemplified.

In the present specification, a term of "cycloalkenylsulfonyloxy" includes a group in which an oxygen atom is substituted with one "cycloalkenylsulfonyl" described above. For example, cyclopropenylsulfonyloxy, cyclobutenylsulfonyloxy, cyclopentenylsulfonyloxy, cyclohexenylsulfonyloxy, cycloheptenylsulfonyloxy, and cyclooctenylsulfonyloxy are exemplified. Preferably C3-C6 cycloalkenylsulfonyloxy is exemplified.

In the present specification, a term of "alkyloxycarbonyl" includes a group in which carbonyl is substituted with one "alkyloxy" above. For example, methyloxycarbonyl, ethyloxycarbonyl, n-propyloxycarbonyl, isopropyloxycarbonyl, n-butyloxycarbonyl, tert-butyloxycarbonyl and n-pentyloxycarbonyl are exemplified. Preferably C1-C4 alkyloxycarbonyl is exemplified. Moreover, C1-C2 alkyloxycarbonyl is further preferable.

In the present specification, a term of "alkenyloxycarbonyl" includes a group in which carbonyl is substituted with one "alkenyloxy" above. For example, vinyloxycarbonyl, allyloxycarbonyl, 1-propenyloxycarbonyl, 2-butenyloxycarbonyl and 2-pentenyloxyarbonyl are exemplified. Preferably C2-C4 alkyloxycarbonyl is exemplified.

In the present specification, a term of "alkynyloxycarbonyl" includes a group in which carbonyl is substituted with one "alkynyloxy" above. For example, ethynyloxycarbonyl, 1-propynyloxycarbonyl, 2-propynyloxycarbonyl, 2-butynyloxyarbonyl and 2-pentynyloxycarbonyl are exemplified. Preferably C2-C4 alkynyloxycarbonyl is exemplified.

In the present specification, a term of "acyl" includes alkylcarbonyl wherein the part of alkyl is "alkyl" before, alkenylcarbonyl wherein the part of alkenyl is "alkenyl" before, alkynylcarbonyl wherein the part of alkynyl is "alkynyl" before, cycloalkylcarbonyl wherein the part of cycloalkyl is "cycloalkyl" before, arylcarbonyl wherein the part of aryl is "aryl" below, heteroarylcarbonyl wherein the part of heteroaryl is "heteroaryl" below and non-aromatic heterocycliccarbonyl wherein the part of non-aromatic heterocyclic group is "non-aromatic heterocyclic group" below. "Alkyl", "alkenyl", "alkynyl", "cycloalkyl", "aryl", "heteroaryl" and "non-aromatic heterocyclic group" may be substituted respectively with substituent groups exemplified in "optionally substituted alkyl", "optionally substituted alkenyl", "optionally substituted alkynyl", "optionally substituted cycloalkyl", "optionally substituted aryl", "optionally substituted heteroaryl" and "optionally substituted non-aromatic heterocyclic group" below. Examples of the acyl group include acetyl, propionyl, butyroyl, cyclohexylcarbonyl, benzoyl, pyridinecarbonyl and the like.

In the present specification, a term of "optionally substituted amino" includes an amino group which may be substituted with one or two group(s) of "alkyl" before, "alkenyl" before, "alkynyl" before, "cycloalkyl" before, "cycloalkynyl" before, "aryl" below, "heteroaryl" below, "acyl" before, "alkyloxycarbonyl" before, "alkenyloxycarbonyl" before, "alkynyloxycarbonyl" before, "alkyl sulfonyl", "alkenylsulfonyl", "alkynylsulfonyl", "arylsulfonyl" and/or "heteroarylsulfonyl" before. Examples of the optionally substituted amino group include amino, methylamino, dimethylamino, ethylamino, diethylamino, ethylmethylamino, benzylamino, acetylamino, benzoylamino, methyloxycarbonylamino and methanesulfonylamino. Preferably, amino, methylamino, dimethylamino, ethylmethylamino, diethylamino, acetylamino and methanesulfonylamino are exemplified.

In the present specification, a term of "optionally substituted carbamoyl" includes an aminocarbonyl group wherein the part of optionally substituted amino is "optionally substituted amino" before and examples of the optionally substituted carbamoyl group includes carbamoyl, N-methylcarbamoyl, N,N-dimethylcarbamoyl, N-ethyl-N-methylcarbamoyl, N,N-diethylcarbamoyl, N-phenylcarbamoyl, N-benzylcarbamoyl, N-acetylcarbamoyl and N-methylsulfonylcarbamoyl etc. Preferably, carbamoyl, N-methylcarbamoyl, N,N-dimethylcarbamoyl and N-methylsulfonylcarbamoyl etc. are exemplified.

In the present specification, a term of "optionally substituted sulfamoyl" includes an aminosulfonyl group wherein the part of optionally substituted amino is "optionally substituted amino" before and examples of the optionally substituted sulfamoyl group include sulfamoyl, N-methylsulfamoyl, N,N-dimethylsulfamoyl, N-ethyl-N-methyl sulfamoyl, N,N-diethylsulfamoyl, N-phenylsulfamoyl, N-benzylsulfamoyl, N-acetylsulfamoyl and N-methylsulfonylsulfamoyl etc. Preferably, sulfamoyl, N-methylsulfamoyl, N,N-dimethylsulfamoyl and N-methylsulfonylsulfamoyl etc. are exemplified.

In the present specification, a term of "alkylene" means a straight or branched alkylene group having one to eight carbon atom(s) and for example, methylene, ethylene, 1-methylethylene, trimethylene, 1-methyltrimethylene, pentamethylene, hexamethylene, and the like. Preferably C1-C4 alkylene is exemplified. Moreover, C1-C2 alkylene is further preferred.

In the present specification, a term of "aryl" includes an aromatic monocyclic or aromatic fused cyclic hydrocarbons and it may be fused with "cycloalkyl" before, "cycloalkenyl" before or "non-aromatic heterocyclic group" below at any possible position. Both of monocyclic ring and fused ring may be substituted at any position and for example, phenyl, 1-naphthyl, 2-naphthyl, anthryl, tetrahydronaphthyl, 1,3-benzodioxolyl, 1,4-benzodioxanyl etc. are exemplified. Phenyl, 1-naphthyl and 2-naphthyl are preferred. Moreover, phenyl is further preferred.

In the present specification, a term of "non-aromatic heterocyclic group" of $R^1$, $R^2$, $R^3$, $R^4$, $R^5$, $R^6$, $R^{1a}$, $R^{2a}$, $R^{3a}$, $R^{4a}$, $R^{5a}$, $R^{6a}$, $R^{11a}$, $R^{12a}$, $R^{13a}$ and $R^{14a}$ includes a 5- to 7-membered non-aromatic heterocyclic ring containing one or more of heteroatom(s) selected independently from oxygen, sulfur and nitrogen atoms or a multicyclic ring formed by fusing the two or more rings thereof. For example, pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidyl (e.g., piperidino, 2-piperidyl), piperazinyl (e.g., 1-piperazinyl), indolinyl (e.g., 1-indolinyl), isoindolinyl (e.g., isoindolinyl), morpholinyl (e.g., morpholino, 3-morpholinyl) etc. are exemplified.

In the present specification, a term of "non-aromatic heterocyclic group" of $R^8$, $R^9$, $R^{11}$, $R^{12}$, $R^{14}$, $R^{8a}$ and $R^{9a}$ includes a 5- to 7-membered non-aromatic heterocyclic ring containing one or more of heteroatom(s) selected independently from oxygen, sulfur and nitrogen atoms or a multicyclic ring formed by fusing the two or more rings thereof. For example, pyrrolidinyl (e.g., 1-pyrrolidinyl, 2-pyrrolidinyl), piperidyl (e.g., piperidino, 2-piperidyl), piperazinyl (e.g., 1-piperazinyl), morpholinyl (e.g., morpholino, 3-morpholinyl) etc. are exemplified.

In the present specification, a term of "heteroaryl" in $R^1$, $R^2$, $R^3$, $R^4$, $R^5$, $R^6$, $R^{1a}$, $R^{2a}$, $R^{3a}$, $R^{4a}$, $R^{5a}$, $R^{6a}$, $R^{11a}$, $R^{12a}$, $R^{13a}$ and $R^{14a}$ includes a 5- to 6-membered aromatic ring containing one or more of heteroatom(s) selected independently from oxygen, sulfur and nitrogen atoms and it may be fused with "cycloalkyl" before, "aryl" before, "non-aromatic heterocyclic group" before or other heteroaryl at any possible position. The heteroaryl group may be substituted at any position whenever it is a monocyclic ring or a fused ring. For example, pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolidinyl (e.g., 2-indolidinyl, 6-indolidinyl), isoindolynyl (e.g., 2-isoindolynyl), indolyl (e.g., 1-indolyl, 2-indolyl, 3-indolyl), indazolyl (e.g., 3-indazolyl), purinyl (e.g., 8-purinyl), quinolidinyl (e.g., 2-quinolidinyl), isoquinolyl (e.g., 3-isoquinolyl), quinolyl (e.g., 2-quinolyl, 5-quinolyl), phtharazinyl (e.g., 1-phtharazinyl), naphthylidinyl (e.g., 2-naphthylidinyl), quinolanyl (e.g., 2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzoimidazolyl (e.g., 2-benzoimidazolyl), benzoisoxazolyl (e.g., 3-benzoisoxazolyl), benzooxazolyl (e.g., 2-benzooxazolyl), benzooxadiazolyl (e.g., 4-benzooxadiazolyl), benzoisothiazolyl (e.g., 3-benzoisothiazolyl), benzothiazolyl (e.g., 2-benzothiazolyl), benzofuryl (e.g., 3-benzofuryl), benzothienyl (e.g., 2-benzothienyl), dibenzothienyl (e.g., 2-dibenzothienyl) and benzodioxolyl (e.g., 1,3-benzodioxolyl) etc. are exemplified.

In the present specification, a term of "heteroaryl" in $R^8$, $R^9$, $R^{11}$, $R^{12}$, $R^{14}$, $R^{8a}$ and $R^{9a}$ includes a 5- to 6-membered aromatic ring containing one or more of heteroatom(s) selected independently from oxygen, sulfur and nitrogen atoms and it may be fused with "cycloalkyl" before, "aryl" before, "non-aromatic heterocyclic group" before or other heteroaryl at any possible position. The heteroaryl group may be substituted at any position whenever it is a monocyclic ring or a fused ring. For example, furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), oxadiazolyl (e.g., 1,3,4-oxadiazolyl), thiadiazolyl (e.g., 1,3,4-thiadiazolyl), benzoimidazolyl (e.g., 2-benzoimidazolyl), benzoisoxazolyl (e.g., 3-benzoisoxazolyl), benzooxazolyl (e.g., 2-benzooxazolyl), benzofuryl (e.g., 3-benzofuryl), benzothienyl (e.g., 2-benzothienyl) etc. are exemplified.

In the present specification, a term of "aryloxy" includes a group in which an oxygen atom is substituted with one "aryl" before and for example, phenyloxy and naphthyloxy etc. are exemplified.

In the present specification, a term of "arylthio" includes a group in which a sulfur atom is substituted with one "aryl" before and for example, phenylthio and naphthylthio etc. are exemplified.

In the present specification, a term of "arylsulfinyl" includes a group in which sulfinyl is substituted with one "aryl" before and for example, phenylsulfinyl and naphthylsulfinyl etc. are exemplified.

In the present specification, a term of "arylsulfonyl" includes a group in which sulfonyl is substituted with one "aryl" before and for example, phenylsulfonyl and naphthylsulfoinyl etc. are exemplified.

In the present specification, examples of "arylsulfonyloxy" include phenylsulfonyloxy and naphthylsulfonyloxy etc.

In the present specification, a term of "aryloxycarbonyl" includes a group in which carbonyl is substituted with one "aryloxy" before and for example, phenyloxycarbonyl, 1-naphthyloxycarbonyl and 2-naphthyloxycarbonyl etc. are exemplified.

In the present specification, a term of "heteroaryloxy" includes a group in which an oxygen atom is substituted with one "heteroaryl" before. For example, pyrrolyloxy, furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy, pyridazinyloxy, tetrazolyloxy, oxadiazolyloxy, thiadiazolyloxy, indolidinyloxy, isoindolynyloxy, indolyloxy, indazolyloxy, purinyloxy, quinolidinyloxy, isoquinolyloxy, quinolyloxy, phtharazinyloxy, naphthylidinyloxy, quinolanyloxy, quinazolinyloxy, cinnolinyloxy, pteridinyloxy, carbazolyloxy, phenanthridinyloxy, acridinyloxy, dibenzofuranyloxy, benzoimidazolyloxy, benzoisoxazolyloxy, benzooxazolyloxy, benzooxadiazolyloxy, benzoisothiazolyloxy, benzothiazolyloxy, benzofuryloxy, benzothienyloxy, dibenzothienyloxy and benzodioxolyloxy are exemplified. Preferably furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy and pyridazinyloxy are exemplified.

In the present specification, a term of "heteroarylthio" includes a group in which a sulfur atom is substituted with one "heteroaryl" before. For example, pyrrolylthio, furylthio, thienylthio, imidazolylthio, pyrazolylthio, isothiazolylthio, isoxazolylthio, oxazolylthio, thiazolylthio, pyridylthio, pyrazinylthio, pyrimidinylthio, pyridazinylthio, tetrazolylthio, oxadiazolylthio, thiadiazolylthio, indolidinylthio, isoindolynylthio, indolylthio, indazolylthio, purinylthio, quinolidinylthio, isoquinolylthio, quinolylthio, phtharazinylthio, naphthylidinylthio, quinolanylthio, quinazolinylthio, cinnolinylthio, pteridinylthio, carbazolylthio, phenanthridinylthio, acridinylthio, dibenzofuranylthio, benzoimidazolylthio, benzoisoxazolylthio, benzooxazolylthio, benzooxadiazolylthio, benzoisothiazolylthio, benzothiazolylthio, benzofurylthio, benzothienylthio, dibenzothienylthio and benzodioxolylthio etc. are exemplified. Preferably furylthio, thienylthio, imidazolylthio, pyrazolylthio, isothiazolylthio, isoxazolylthio, oxazolylthio, thiazolylthio, pyridylthio, pyrazinylthio, pyrimidinylthio, and pyridazinylthio etc. are exemplified.

In the present specification, a term of "heteroarylsulfinyl" includes a group in which sulfinyl is substituted with one "heteroaryl" before. For example, pyrrolylsulfinyl, furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl, pyridazinylsulfinyl, tetrazolylsulfinyl, oxadiazolylsulfinyl, thiadiazolylsulfinyl, indolidinylsulfinyl, isoindolylsulfinyl, indolylsulfinyl, indazolylsulfinyl, purinylsulfinyl, quinolidinylsulfinyl, isoquinolylsulfinyl, quinolylsulfinyl, phtharazinylsulfinyl, naphthylidinylsulfinyl, quinolanylsulfinyl, quinazolinylsulfinyl, cinnolinylsulfinyl, pteridinylsulfinyl, carbazolylsulfinyl, phenanthridinylsulfinyl, acridinylsulfinyl, dibenzofuranylsulfinyl, benzoimidazolylsulfinyl, benzoisoxazolylsulfinyl, benzooxazolylsulfinyl, benzooxadiazolylsulfinyl, benzoisothiazolylsulfinyl, benzothiazolylsulfinyl, benzofurylsulfinyl, benzothienylsulfinyl, dibenzothienylsulfinyl and benzodioxolylsulfinyl etc. are exemplified. Preferably furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl and pyridazinylsulfinyl etc. are exemplified.

In the present specification, a term of "heteroarylsulfonyl" includes a group in which sulfonyl is substituted with one "heteroaryl" before. For example, pyrrolylsulfonyl, furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl, pyridazinylsulfonyl, tetrazolylsulfonyl, oxadiazolylsulfonyl, thiadiazolylsulfonyl, indolizinylsulfonyl, isoindolylsulfonyl, indolylsulfonyl, indazolylsulfonyl, purinylsulfonyl, quinolidinylsulfonyl, isoquinolylsulfonyl, quinolylsulfonyl, phtharazinylsulfonyl, naphthilidinylsulfonyl, quinolanylsulfonyl, quinazolinylsulfonyl, cinnolinyl sulfonyl, pteridinyl sulfonyl, carbazolylsulfonyl, phenanthridinylsulfonyl, acridinylsulfonyl, dibenzofuranylsulfonyl, benzoimidazolylsulfonyl, benzoisoxazolylsulfonyl, benzooxazolylsulfonyl, benzooxadiazolylsulfonyl, benzoisothiazolylsulfonyl, benzothiazolylsulfonyl, benzofurylsulfonyl, benzothienylsulfonyl, dibenzothienylsulfonyl and benzodioxolylsulfonyl are exemplified. Preferably furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl and pyridazinylsulfonyl are exemplified.

In the present specification, a term of "heteroarylsulfonyloxy" includes a group in which an oxygen atom is substituted with one "heteroarylsulfonyl" before. For example, pyrrolylsulfonyloxy, furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy, pyridazinylsulfonyloxy, tetrazolylsulfonyloxy, oxadiazolylsulfonyloxy, thiadiazolylsulfonyloxy, indolizinylsulfonyloxy, isoindolylsulfonyloxy, indolylsulfonyloxy, indazolylsulfonyloxy, purinylsulfonyloxy, quinolidinylsulfonyloxy, isoquinolylsulfonyloxy, quinolylsulfonyloxy, phtharazinylsulfonyloxy, naphthilidinylsulfonyloxy, quinolanyl sulfonyloxy, quinazolinylsulfonyloxy, cinnolinylsulfonyloxy, pteridinylsulfonyloxy, carbazolylsulfonyloxy, phenanthridinylsulfonyloxy, acridinylsulfonyloxy, dibenzofuranylsulfonyloxy, benzoimidazolylsulfonyloxy, benzoisoxazolylsulfonyloxy, benzooxazolylsulfonyloxy, benzooxadiazolylsulfonyloxy, benzoisothiazolylsulfonyloxy, benzothiazolylsulfonyloxy, benzofuryl sulfonyloxy, benzothienylsulfonyloxy, dibenzothienylsulfonyloxy and benzodioxolylsulfonyloxy etc. are exemplified. Preferably, furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy and pyridazinylsulfonyloxy etc. are exemplified.

In the present specification, a term of "aromatic carbocyclic ring" includes an aromatic monocyclic or aromatic fused carbocyclic ring and for example, a benzene ring, a naphthalene ring and an anthracene ring are exemplified. A benzene ring is preferred.

In the present specification, a term of "aromatic heterocyclic ring" includes an aromatic monocyclic or aromatic fused heterocyclic ring. For example, a pyrrole ring, a furan ring, a thiophen ring, a pyrazole ring, an imidazole ring, an isothiazole ring, an isoxazole ring, an oxazole ring, a thiazole ring, a pyrazine ring, a pyrimidine ring, a pyridazine ring, a tetrazole ring, an oxadiazole ring, a thiadiazole ring, an indolizine ring, an isoindole ring, an indole ring, an indazole ring, a purine ring, a quinolidine ring, an isoquinoline ring, a quinoline ring, a phtharazine ring, a naphthyridine ring, a quinolane ring, a quinazoline ring, a cinnoline ring, a pteridine ring, a carbazole ring, a phenanthridine ring, an acridine ring, a dibenzofuran ring, a benzoimidazole ring, a benzoisoxazole ring, a benzooxazole ring, a benzooxadiazole ring, a benzoisothiazole ring, a benzothiazole ring, a benzofuran ring, a benzothiophen ring, a dibenzothiophen ring and a benzodixolane ring are exemplified. Preferably a pyridine ring, a furan ring and a thiophen ring are exemplified.

In the present specification, a term of "C1-C6 alkylene" includes a straight or branched alkylene group having one to six carbon atom(s), and for example, —CH$_2$—, —CH(CH$_3$)—, —C(CH$_3$)$_2$—, —CH$_2$CH$_2$—, —CH(CH$_3$)CH$_2$—, —C(CH$_3$)$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH$_2$CH$_2$CH$_2$CH$_2$CH$_2$— are exemplified. Preferably, —CH$_2$—, —CH$_2$CH$_2$—, —CH$_2$CH$_2$CH$_2$— and —CH$_2$CH$_2$CH$_2$CH$_2$— are exemplified.

In the present specification, a term of "alkylene optionally containing one or two heteroatom(s)" of "optionally substituted alkylene optionally containing one or two heteroatom(s)" includes a straight or branched alkylene group having one to six carbon atoms, optionally containing one or two heteroatom(s) which may be substituted with "alkyl" above, and for example, —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$O—, —OCH$_2$—, —CH$_2$CH$_2$O—, —OCH$_2$CH$_2$—, —CH$_2$S—, —SCH$_2$—, —CH$_2$CH$_2$S—, —SCH$_2$CH$_2$—, —CH$_2$CH$_2$OCH$_2$CH$_2$—, —OCH$_2$CH$_2$O—, —OCH$_2$O—, —NHCH$_2$—, —N(CH$_3$)CH$_2$—, —N$^+$(CH$_3$)$_2$CH$_2$—, —NHCH$_2$CH$_2$CH$_2$— and —N(CH$_3$)CH$_2$CH$_2$CH$_2$— etc. are exemplified. Preferably, —CH$_2$—, —CH$_2$CH$_2$—, —CH$_2$CH$_2$CH$_2$—, —CH$_2$CH$_2$CH$_2$CH$_2$—, —OCH$_2$CH$_2$O—, —OCH$_2$O— and —N(CH$_3$)CH$_2$CH$_2$CH$_2$— are exemplified.

In the present specification, a term of "alkenylene optionally containing one or two heteroatom(s)" of "optionally substituted alkylene optionally containing one or two heteroatom(s)" includes a straight or branched alkenylene group having two to six carbon atoms, optionally containing one or two heteroatom(s) which may be substituted with "alkyl" above, and for example, —CH═CHCH═CH—, —CH═CHO—, —OCH═CH—, —CH═CHS—, —SCH═CH—, —CH═CHNH—, —NHCH═CH—, —CH═CH—CH═N— and —N═CH—CH═CH— are exemplified. Preferably, —CH═CHCH═CH—, —CH═CHCH═N— and —N═CHCH═CH— are exemplified.

In the present specification, a term of "alkynylene optionally containing one or two heteroatom(s)" includes a straight or branched alkynylene group having two to six carbon atoms, optionally containing one or two heteroatom(s) which may be substituted with "alkyl" above, and for example, —C≡CCH$_2$—, —CH$_2$C≡CCH$_2$—, —CH$_2$C≡CCH$_2$O—, —OCH$_2$C≡CH—, —CH$_2$C≡CCH$_2$S—, —SCH$_2$C≡CH—, —CH$_2$C≡CCH$_2$NH—, —NHCH$_2$C≡CH—, —CH$_2$C≡CCH$_2$N(CH$_3$)— and —N(CH$_3$)CH$_2$C≡CH— are exemplified. Especially, —CH$_2$C≡CCH$_2$— and —OCH$_2$C≡CH— are preferred.

In the present specification, a term of "3- to 8-membered nitrogen-containing non-aromatic heterocyclic ring" includes a ring of the formula of

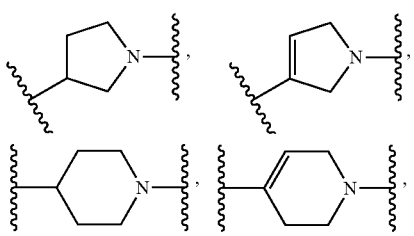

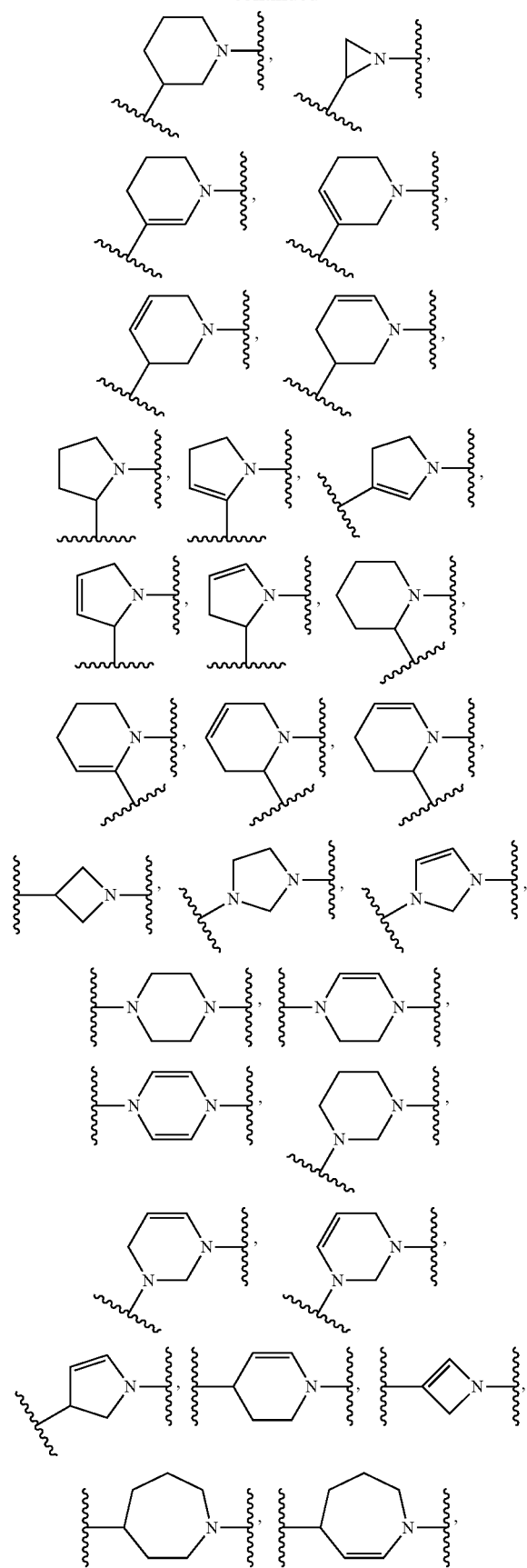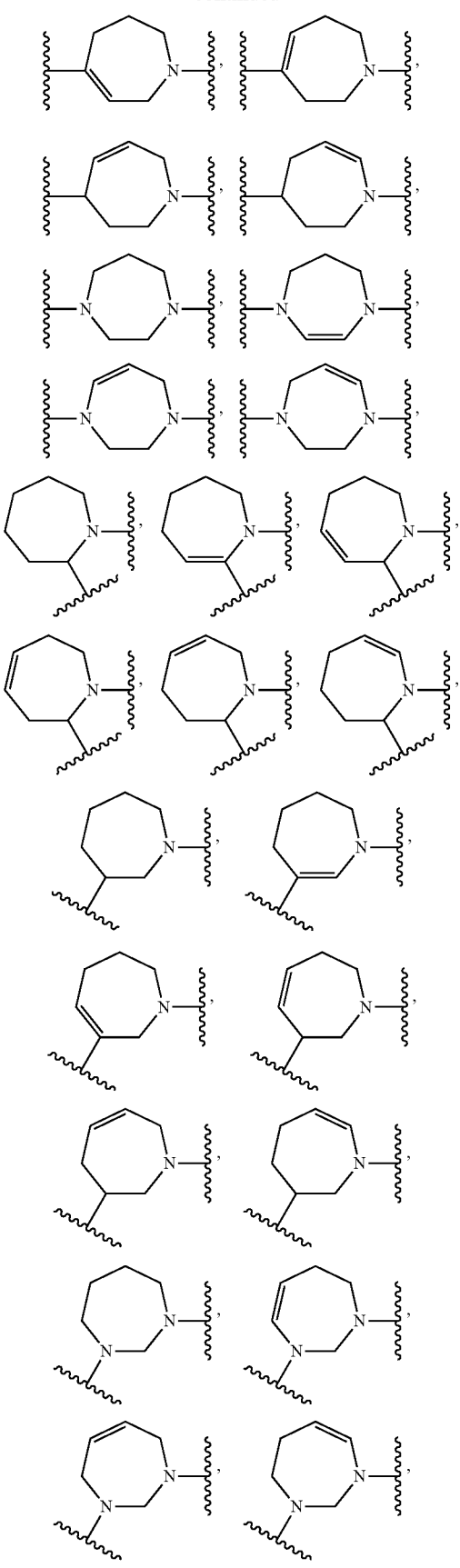

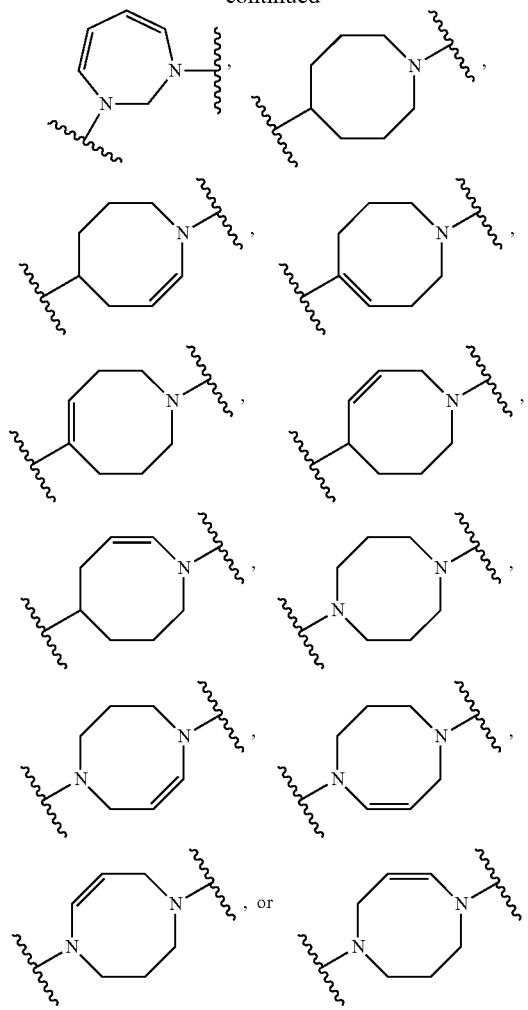

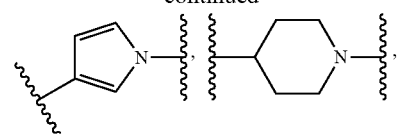
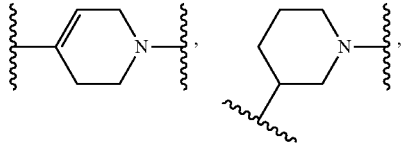
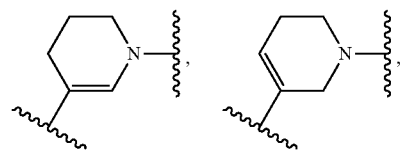
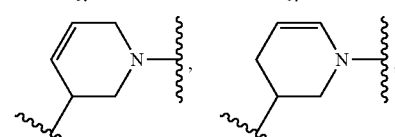
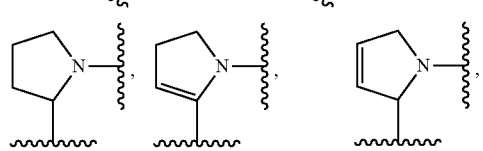
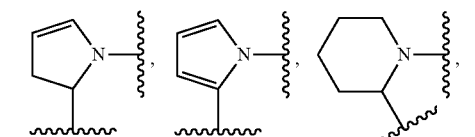
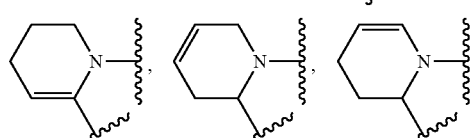
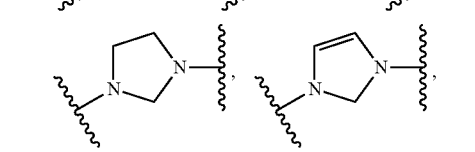
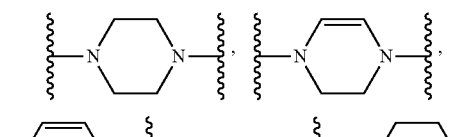
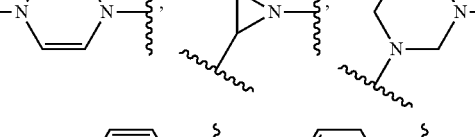
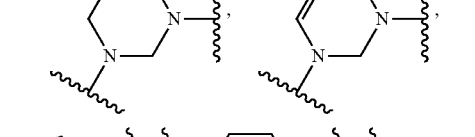
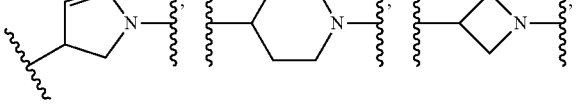

In the present specification, a term of "3- to 8-nitrogen-containing aromatic heterocyclic ring" includes a 3- to 8-membered aromatic heterocyclic ring containing one or more of nitrogen atom(s), and further optionally an oxygen atom and/or sulfur atom in the ring. For example, pyrrolyl (e.g., 1-pyrrolyl, 2-pyrrolyl, 3-pyrrolyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl) and thiadiazolyl (e.g., 1,3,4-thiadiazolyl) are exemplified.

In the present specification, a term of "4- to 8-membered nitrogen-containing heterocyclic ring containing one or two nitrogen atom(s)" means a ring of the formula of

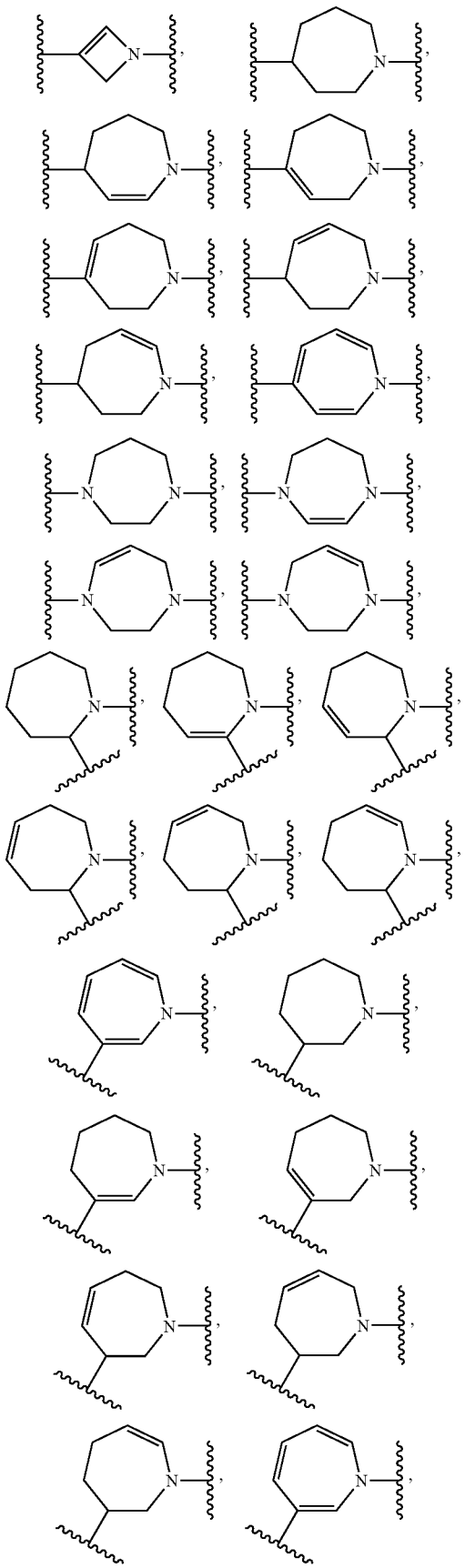
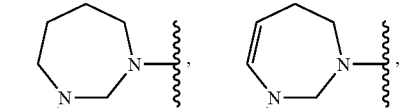
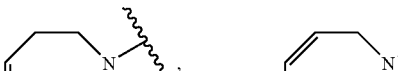
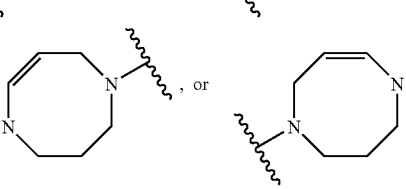

In the present specification, examples of substituents in "optionally substituted alkyl", "optionally substituted alkyloxy", "optionally substituted alkylthio", "optionally substituted alkylsulfinyl", "optionally substituted alkylsulfonyl", "optionally substituted alkylsulfonyloxy" and "the optionally substituted alkyloxycarbonyl" include cycloalkyl, alkylene optionally containing one or two heteroatom(s), hydroxy, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, aryl optionally substituted with a substituent group B at one to three position(s) (e.g., phenyl), heteroaryl optionally substituted with a substituent group C at one to three position(s)

(e.g., pyridyl, furyl, thienyl, imidazolyl, oxazolyl, thiazolyl, pyrazolyl), an optionally substituted non-aromatic heterocyclic ring group which may be substituted with a substituent group C at one to three position(s) (e.g., morpholinyl, pyrrolidinyl, piperazinyl), aryloxy optionally substituted with a substituent group B at one to three position(s) (e.g., phenyloxy), alkylsulfonyl and the like. These can be substituted with one to three substituent(s) at any possible position.

In the present specification, examples of substituents in "optionally substituted alkenyl", "optionally substituted alkynyl", "optionally substituted alkenyloxy", "optionally substituted alkynyloxy", "optionally substituted alkenylthio", "optionally substituted alkynylthio", "optionally substituted alkenyloxycarbonyl", "optionally substituted alkynyloxycarbonyl", "optionally substituted cycloalkyl", "optionally substituted cycloalkenyl", "optionally substituted cycloalkyloxy, "optionally substituted cycloalkenyloxy", "optionally substituted cycloalkylthio", "optionally substituted cycloalkenylthio", "optionally substituted cycloalkylsulfinyl", "optionally substituted cycloalkenylsulfinyl", "optionally substituted cycloalkylsulfonyl", "optionally substituted cycloalkenylsulfonyl", "optionally substituted cycloalkylsulfonyloxy", "optionally substituted cycloalkenylsulfonyloxy", "optionally substituted alkenyloxycarbonyl", "optionally substituted C1-C6 alkylene", "optionally substituted alkylene", "optionally substituted alkenylene" and "the optionally substituted alkynylene" include alkyl optionally substituted with a substituent group D at one to three position(s), cycloalkyl, alkylene optionally containing one or two heteroatom(s), hydroxy, oxo, alkyoxyl optionally substituted with a substituent group A at one to three position(s), mercapto, alkylthio, a halogen atom, nitro, cyano, carboxy, alkyloxycarbonyl, optionally substituted amino, optionally substituted carbamoyl, acyl acyloxy, aryl optionally substituted with a substituent group B at one to three position(s) (e.g., phenyl), heteroaryl optionally substituted with a substituent group C at one to three position(s) (e.g., pyridyl, furyl, thienyl, imidazolyl, oxazolyl, thiazolyl, pyrazolyl), non-aromatic heterocyclic group optionally substituted with a substituent group C at one to three position(s) (e.g., morpholinyl, pyrrolidinyl, piperazinyl), aryloxy optionally substituted with a substituent group C at one to three position(s) (e.g., phenyloxy), alkylsulfonyl and the like. These can be substituted with one or more substituent(s) at any possible position.

In the present specification, examples of substituents in "optionally substituted aryl", "optionally substituted phenoxy", "optionally substituted aryloxy", "optionally substituted phenylthio", "optionally substituted arylthio", ""optionally substituted arylsulfinyl", "optionally substituted arylsulfonyl", "optionally substituted arylsulfonyloxy", "optionally substituted heteroaryl", "optionally substituted heteroaryloxy", "optionally substituted heteroarylthio", "optionally substituted heteroarylsulfinyl", "optionally substituted heteroarylsulfonyl", "optionally substituted heteroarylsulfonyloxy" and "optionally substituted non-aromatic heterocyclic group" include alkyl optionally substituted with a substituent group D at one to three position(s), cycloalkyl, alkenyl, alkynyl, hydroxy, alkyloxy optionally substituted with a substituent group A at one to three position(s), aryloxy optionally substituted with a substituent group B at one to three position(s) (e.g., phenoxy), mercapto, alkylthio, a halogen atom, nitro, cyano, carboxy, alkyloxycarbonyl, acyl, alkylsulfonyl, optionally substituted amino, optionally substituted carbamoyl, aryl optionally substituted with a substituent group B at one to three position(s) (e.g., phenyl), heteroaryl optionally substituted with a substituent group C at one to three position(s) (e.g., pyridyl, furyl, thienyl, imidazolyl, oxazolyl, thiazolyl, pyrazolyl), non-aromatic heterocyclic group optionally substituted with a substituent group C at one to three position(s) (e.g., morpholinyl, pyrrolidinyl, piperazinyl) and the like. These can be substituted with one or more substituent(s) at any possible position.

Substituent group A is comprised of a halogen atom and phenyl optionally substituted with one to three substituent(s) selected from the Substituent group B.

Substituent group B is comprised of a halogen atom, alkyl, alkyloxy, cyano and nitro.

Substituent group C is comprised of a halogen atom and alkyl.

Substituent group D is comprised of a halogen atom and alkyloxy.

In the specification a term of "carboxy equivalent" means a biological equivalent and includes substituents having the same polar effect as a carboxy group. For example, —CONHCN, —CONHOH, —CONHOMe, —CONHOt-Bu, —CONHOCH$_2$Ph, —SO$_3$H, —SO$_2$NH$_2$, —SO$_2$NHMe, —NHCONH$_2$, —NHCONMe$_2$, —P(=O)(OH)$_2$, —P(=O)(OH)(OEt), —P(=O)(OH)NH$_2$, —P(=O)(OH)NHMe, —CONHSO$_2$Ph, —SO$_2$NHCOMe, —SO$_2$NHCOPh, and the formulae of;

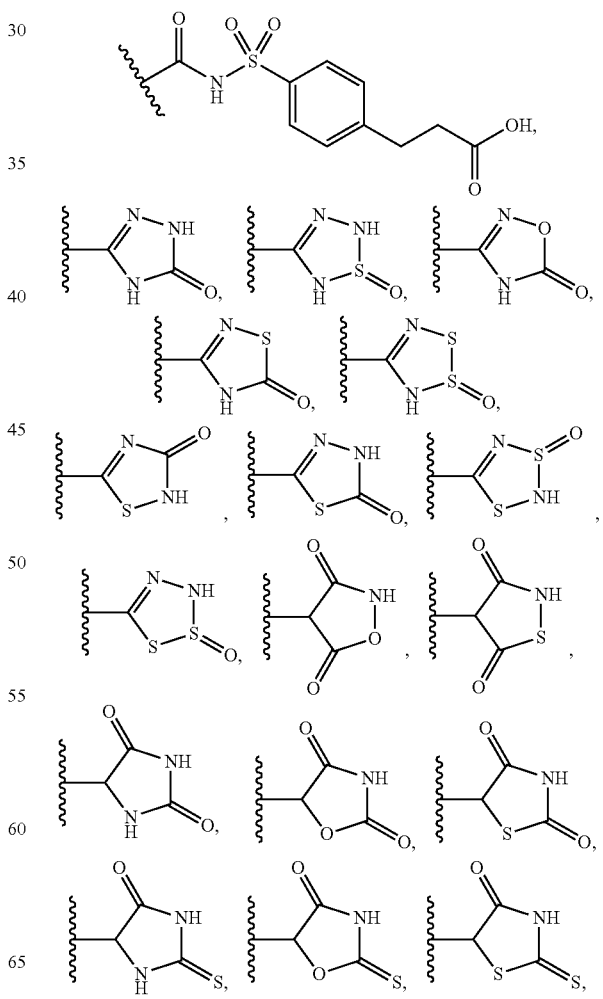

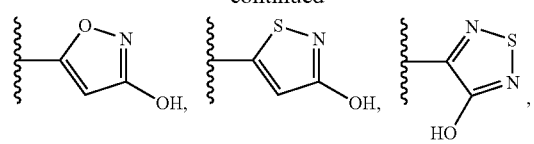
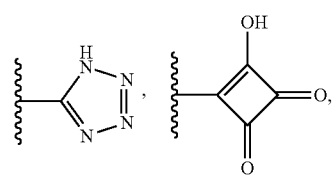
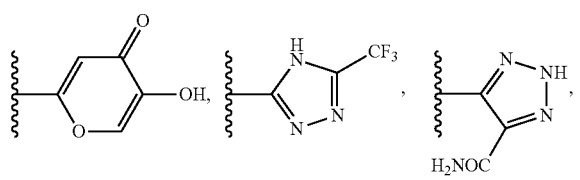
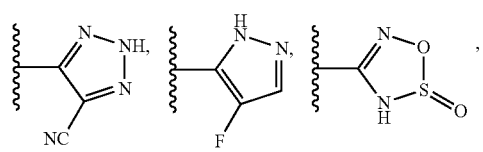
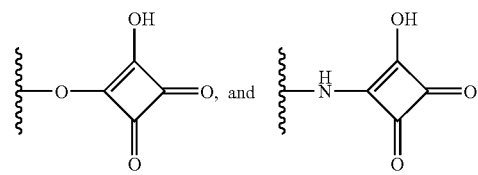
are exemplified. Preferably, —CONHOt-Bu, —CONHOCH₂Ph, —SO₃H, —CONHSO₂Ph, —SO₂NHCOMe, —SO₂NHCOPh, and the formulae of;
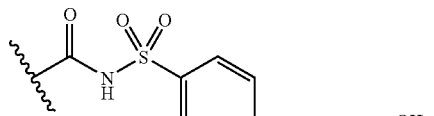
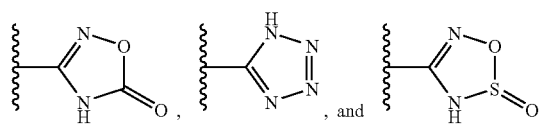
are exemplified.
A compound of the general formula (I) includes a compound of the general formula of
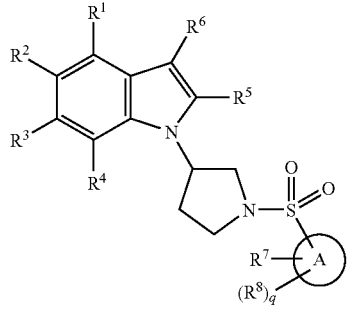
(Ia-1)
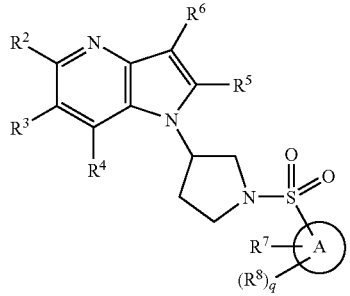
(Ia-2)
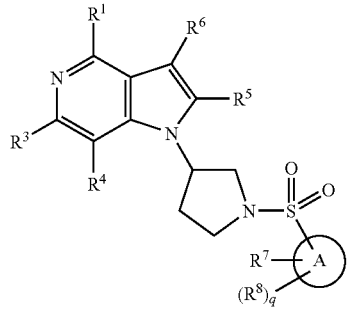
(Ia-3)
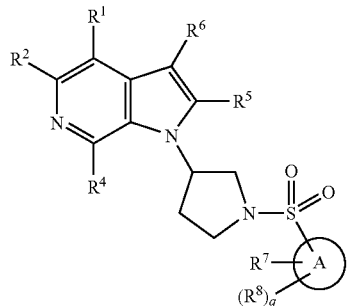
(Ia-4)
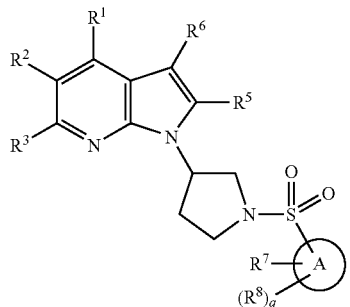
(Ia-5)

-continued
(Ib-1)
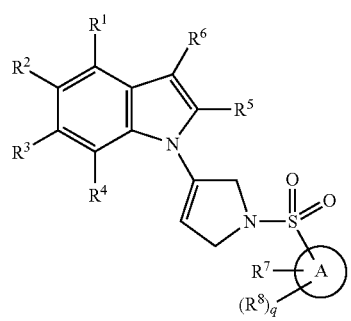
(Ib-2)
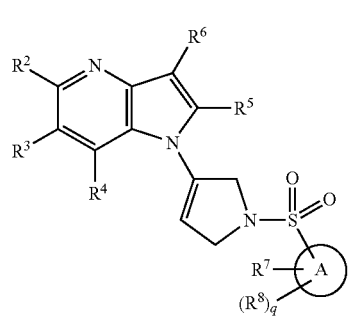
(Ib-3)
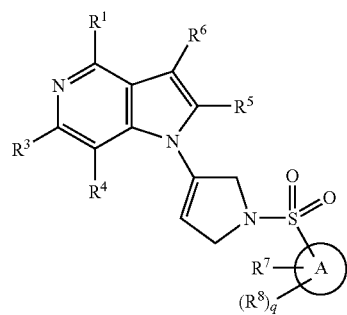
(Ib-4)
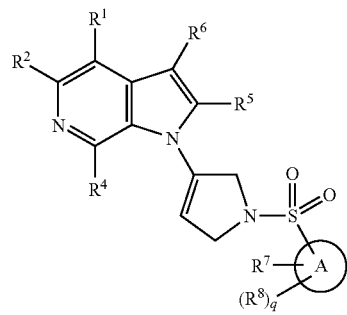
(Ib-5)
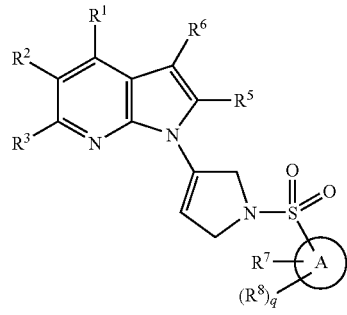
-continued
(Ic-1)
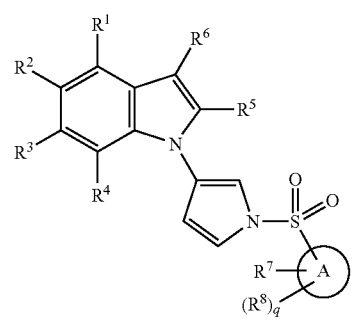
(Ic-2)
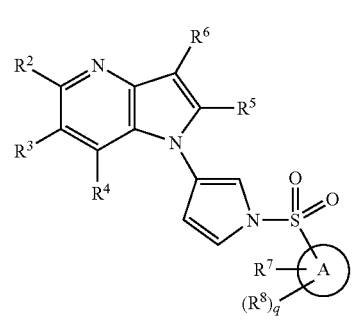
(Ic-3)
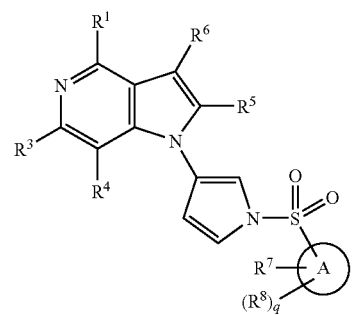
(Ic-4)
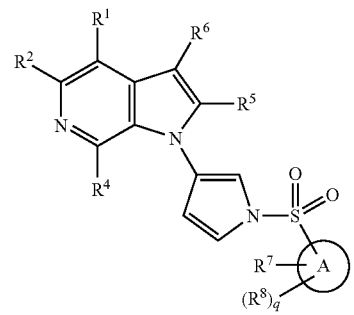
(Ic-5)
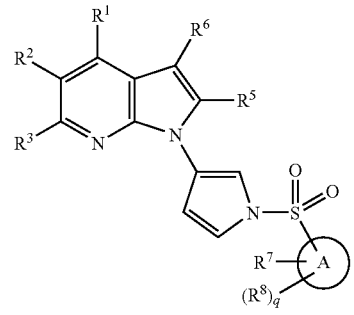

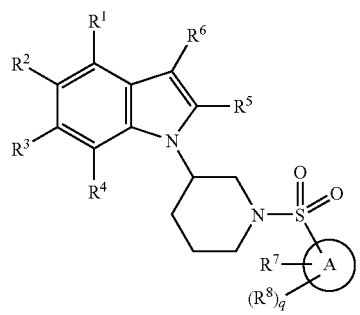 (Id-1)
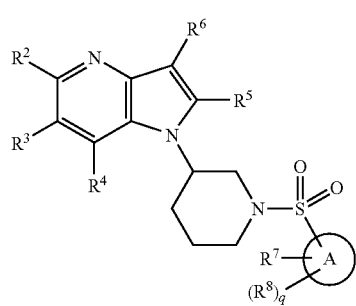 (Id-2)
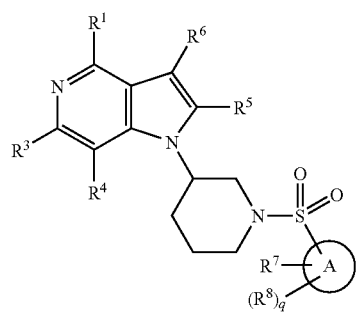 (Id-3)
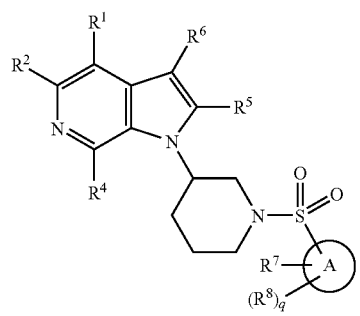 (Id-4)
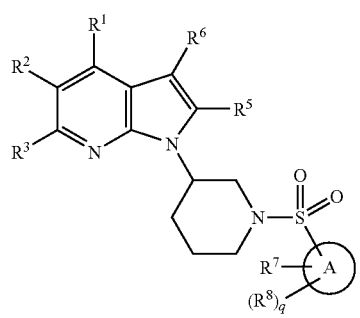 (Id-5)
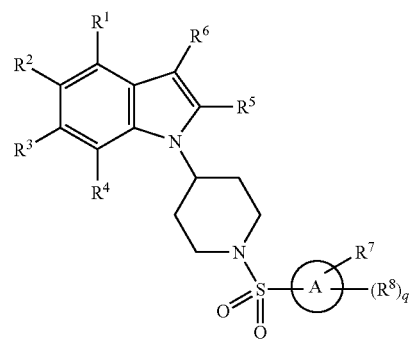 (Ie-1)
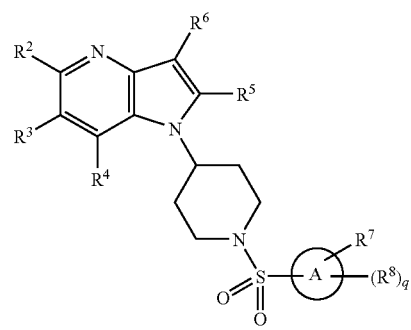 (Ie-2)
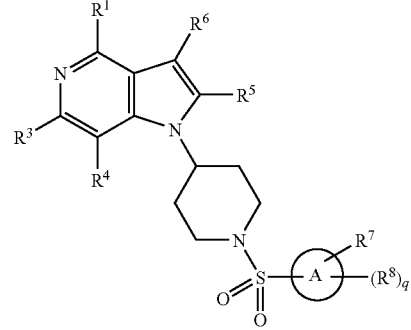 (Ie-3)
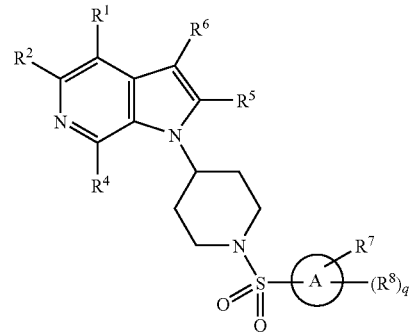 (Ie-4)

(Ie-5)
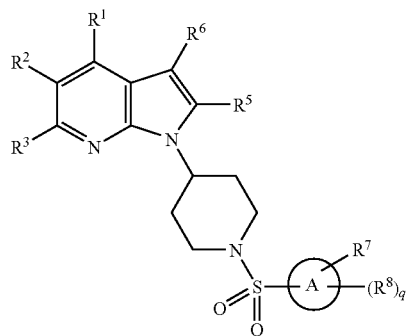
(If-1)
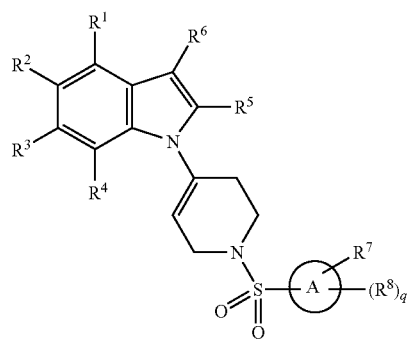
(If-2)
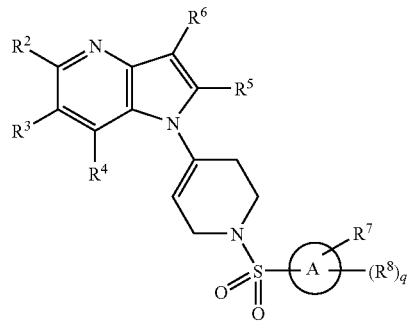
(If-3)
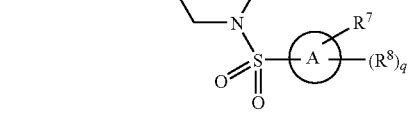
(If-4)
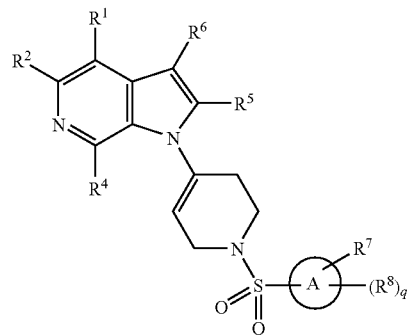
(If-5)
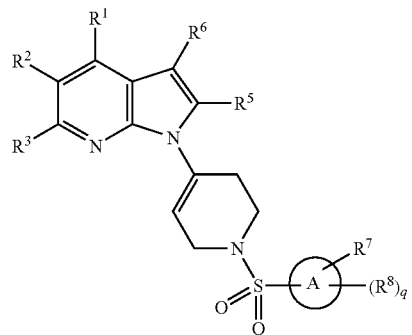
(Ia-6)
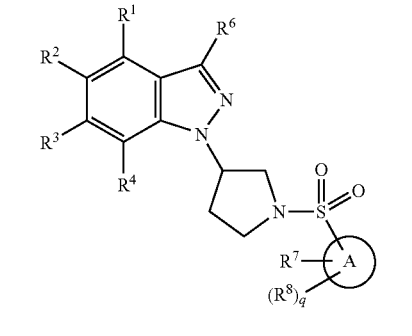
(Ib-6)
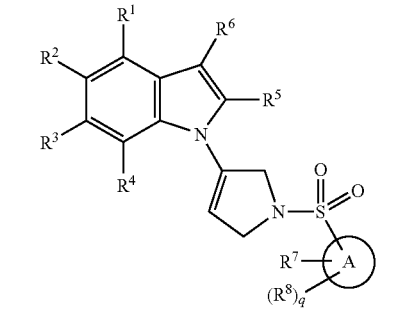
(Ic-6)
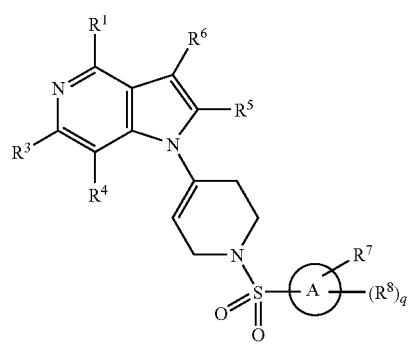

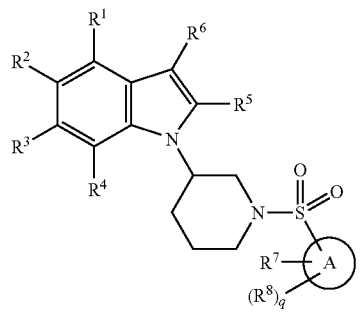 (Id-6)
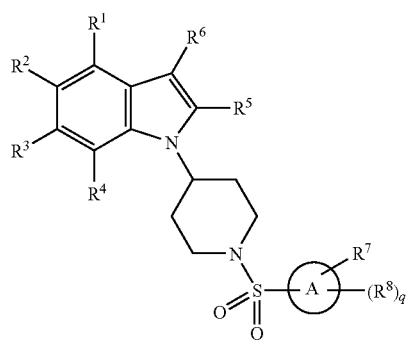 (Ie-6)
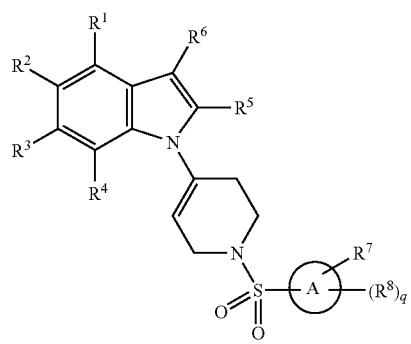 (If-6)
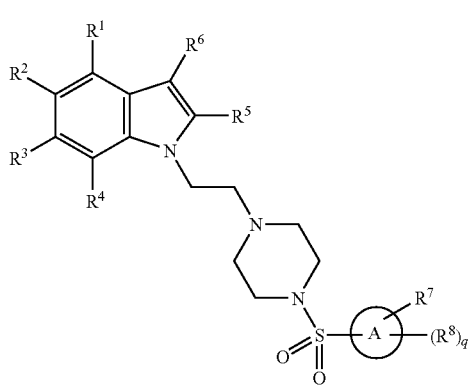 (Ig-1)
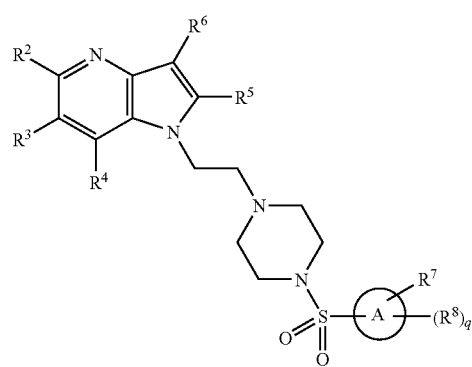 (Ig-2)
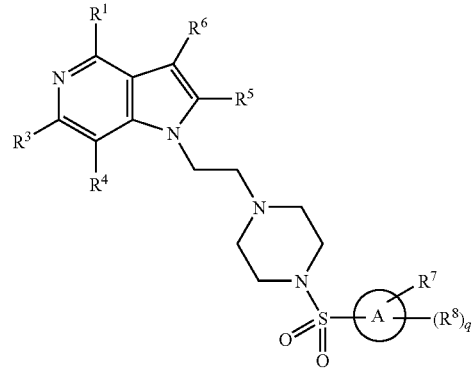 (Ig-3)
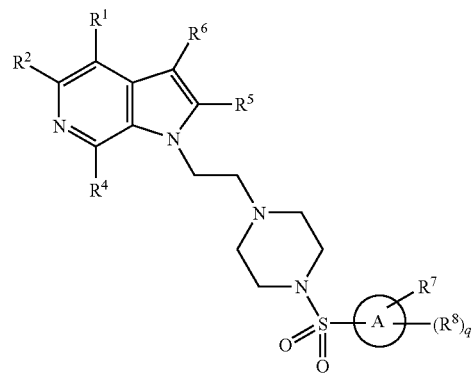 (Ig-4)
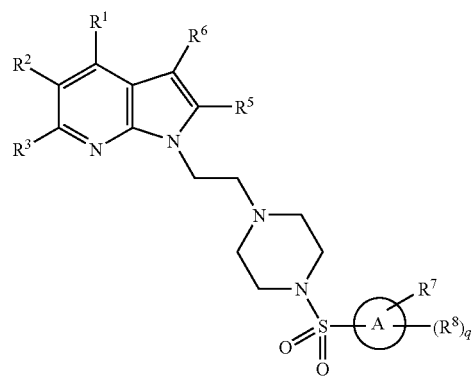 (Ig-5)

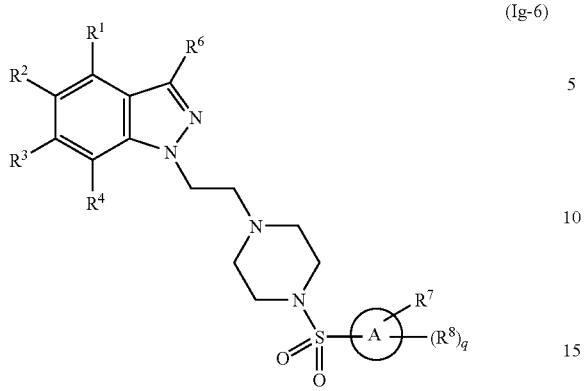
(Ig-6)
Among the compounds of the general formulae above, the compounds of the formulae of
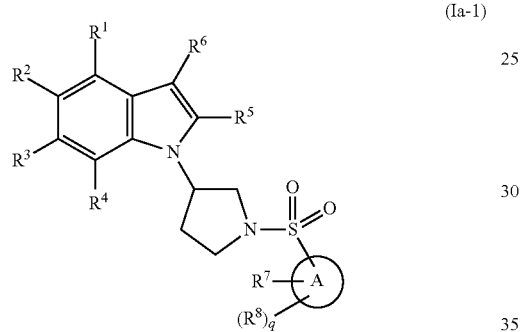
(Ia-1)
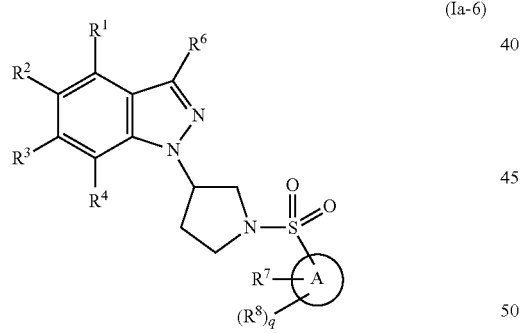
(Ia-6)
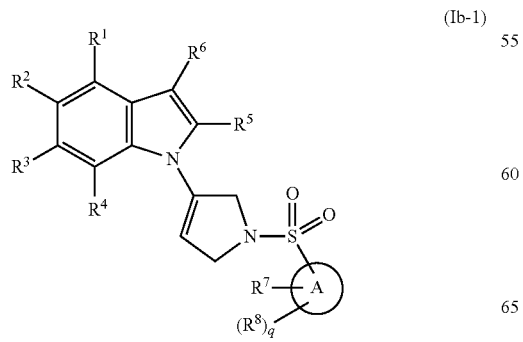
(Ib-1)
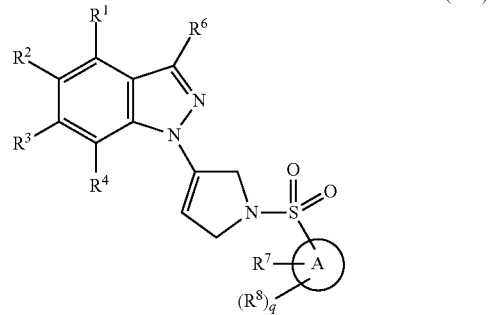
(Ib-6)
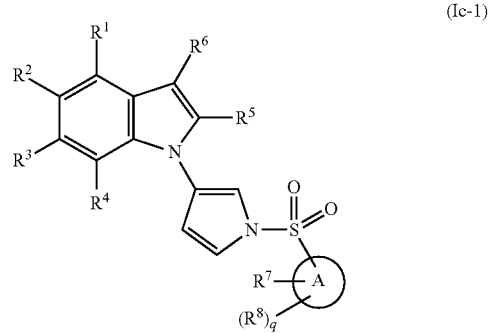
(Ic-1)
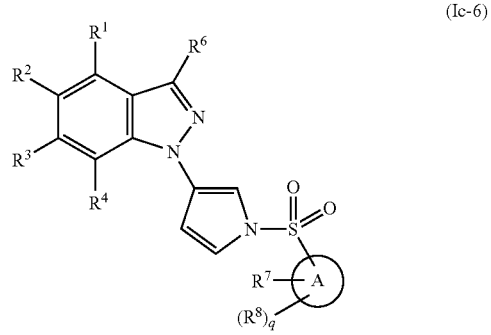
(Ic-6)
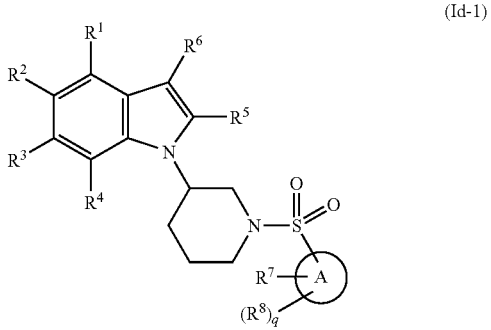
(Id-1)
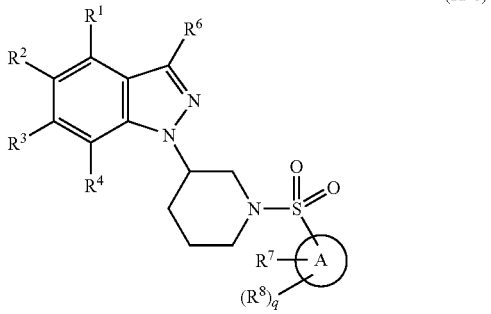
(Id-6)

(Ie-1)
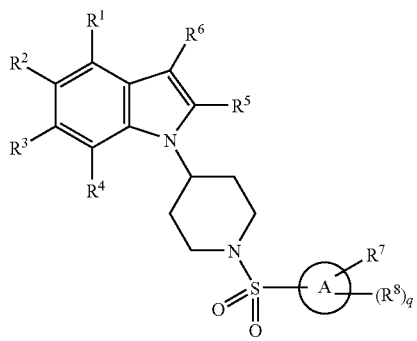
(Ie-6)
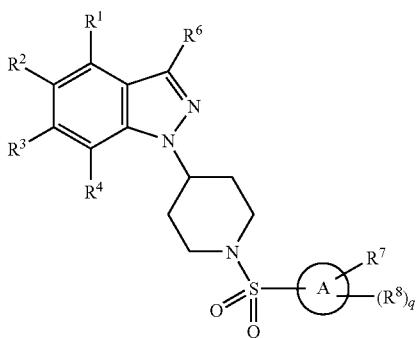
(If-1)
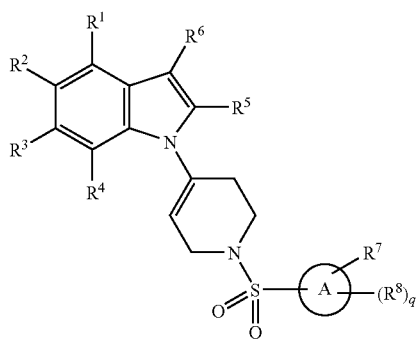
(If-6)
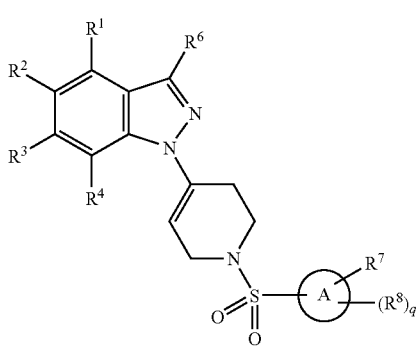
(Ig-1)
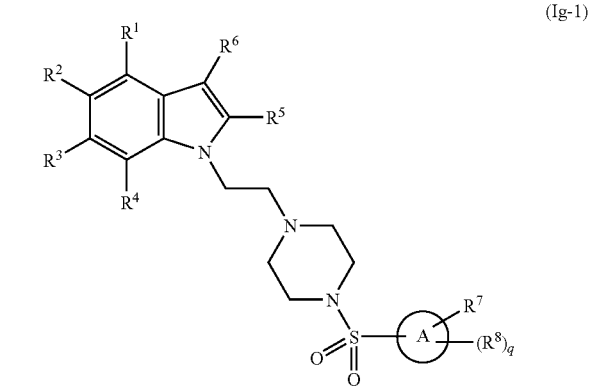
(Ig-6)
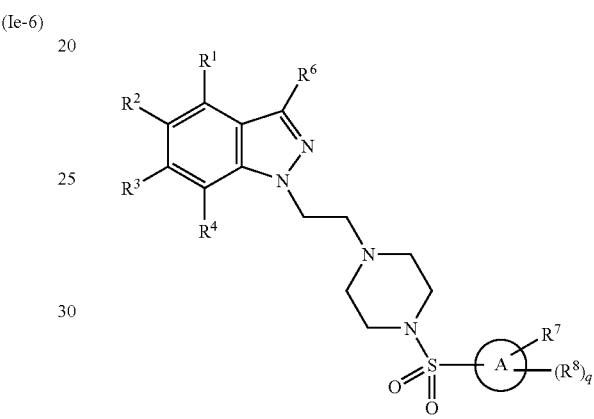
are preferable, and moreover the compounds of the formulae of
(Ia-1)
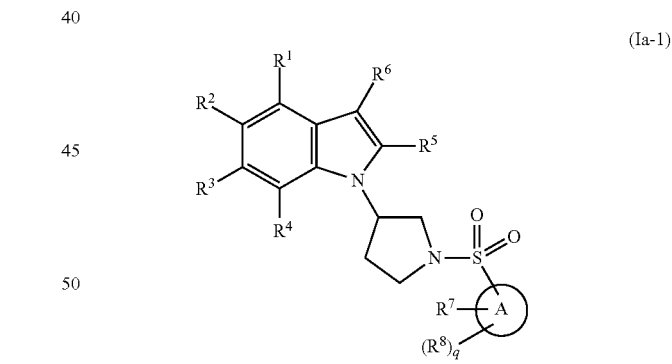
(Ia-6)
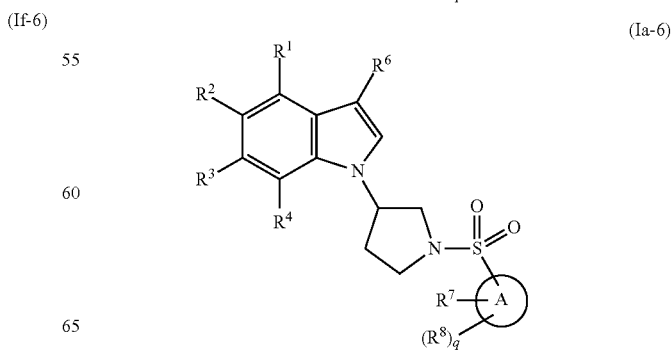

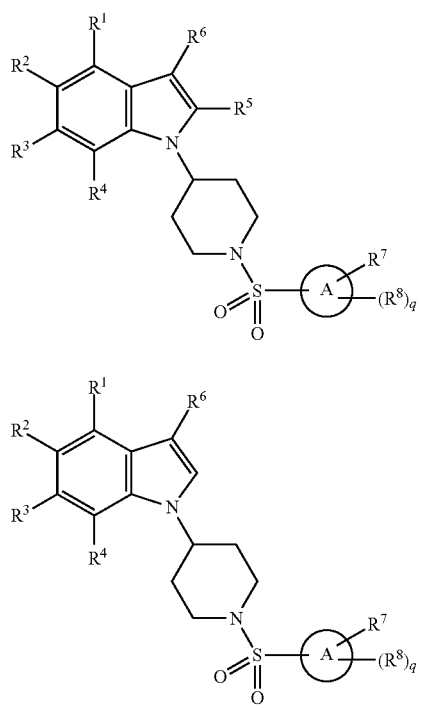
(Ie-1)
(Ie-6)
are further preferable.
Examples of the group of the formula:
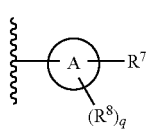
include the group of the formula of
(A-1)
(A-2)
(A-3)
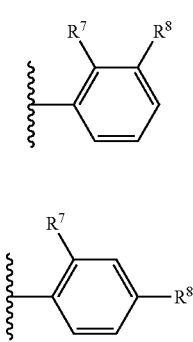
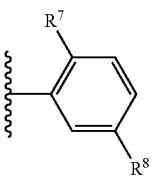
(A-4)
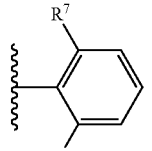
(A-5)
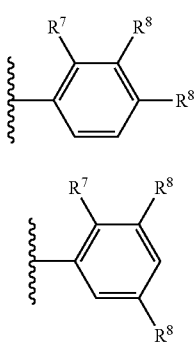
(A-6)
(A-7)
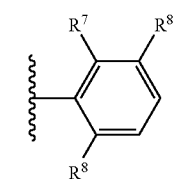
(A-8)
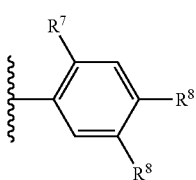
(A-9)
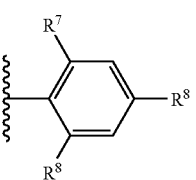
(A-10)
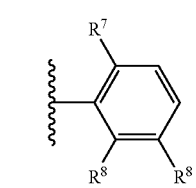
(A-11)
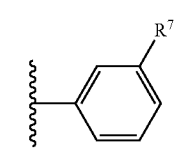
(B-1)

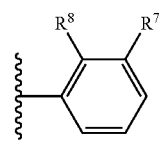 (B-2)
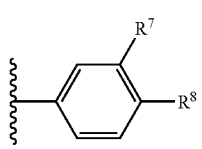 (B-3)
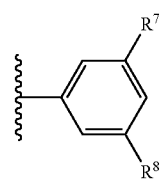 (B-4)
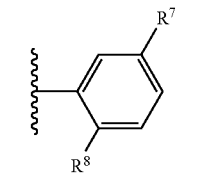 (B-5)
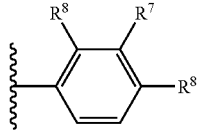 (B-6)
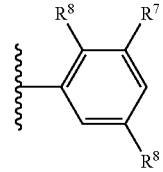 (B-7)
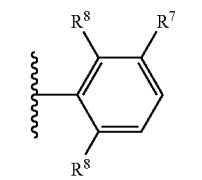 (B-8)
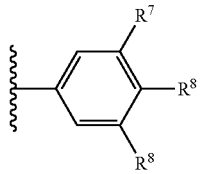 (B-9)
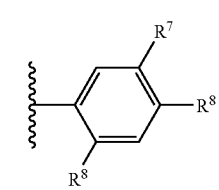 (B-10)
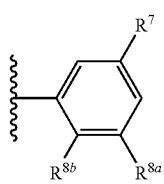 (B-11)
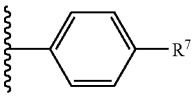 (C-1)
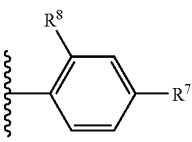 (C-2)
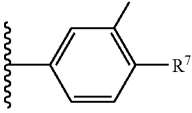 (C-3)
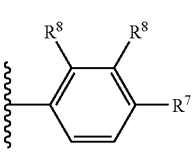 (C-4)
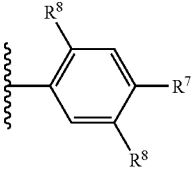 (C-5)
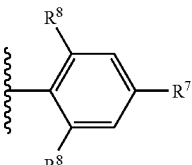 (C-6)
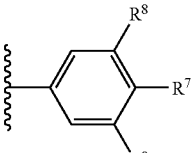 (C-7)
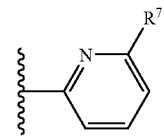 (D-1)
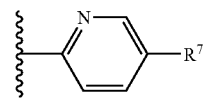 (D-2)

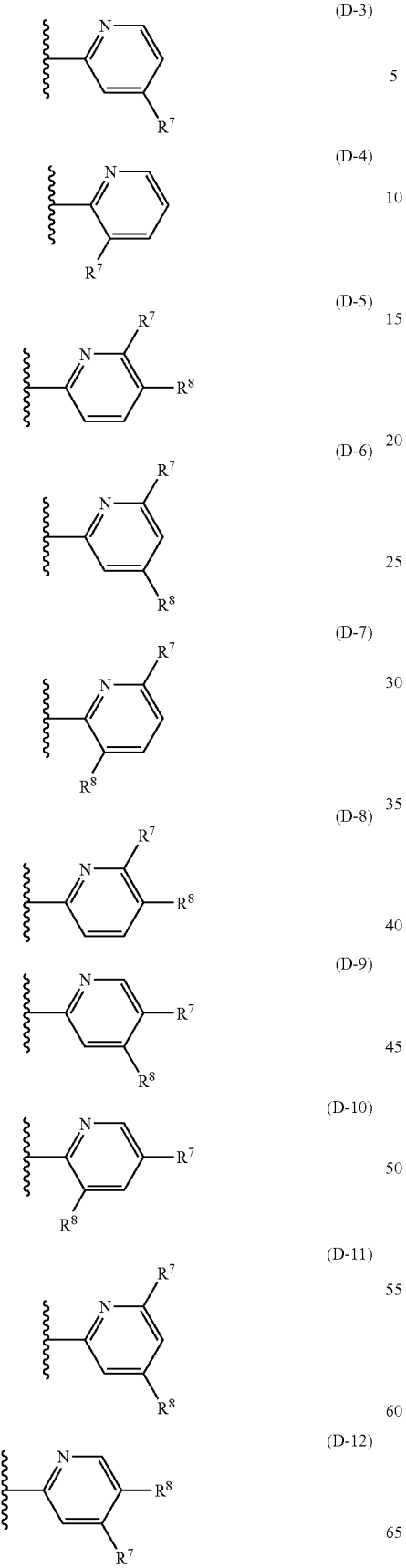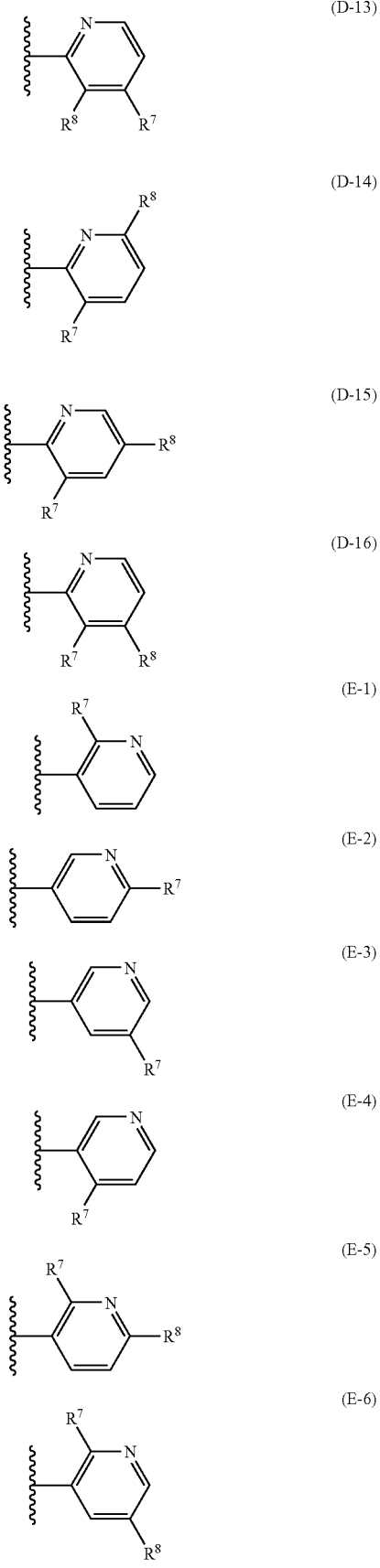

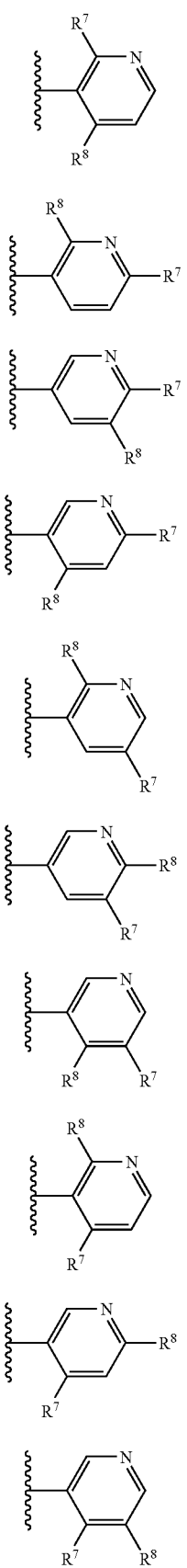
(E-7)
(E-8)
(E-9)
(E-10)
(E-11)
(E-12)
(E-13)
(E-14)
(E-15)
(E-16)
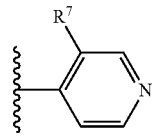 (F-1)
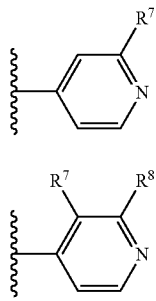 (F-2)
(F-3)
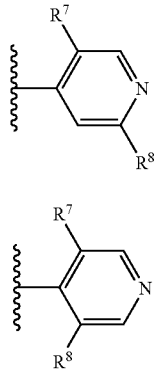 (F-4)
(F-5)
(F-6)
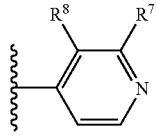 (F-7)
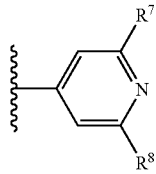 (F-8)
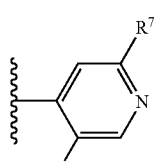
Among the groups above, the groups of the formula of
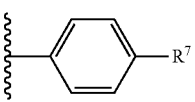 (C-1)

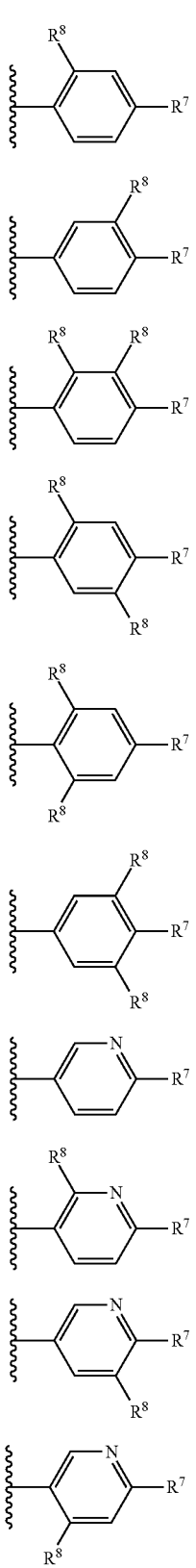

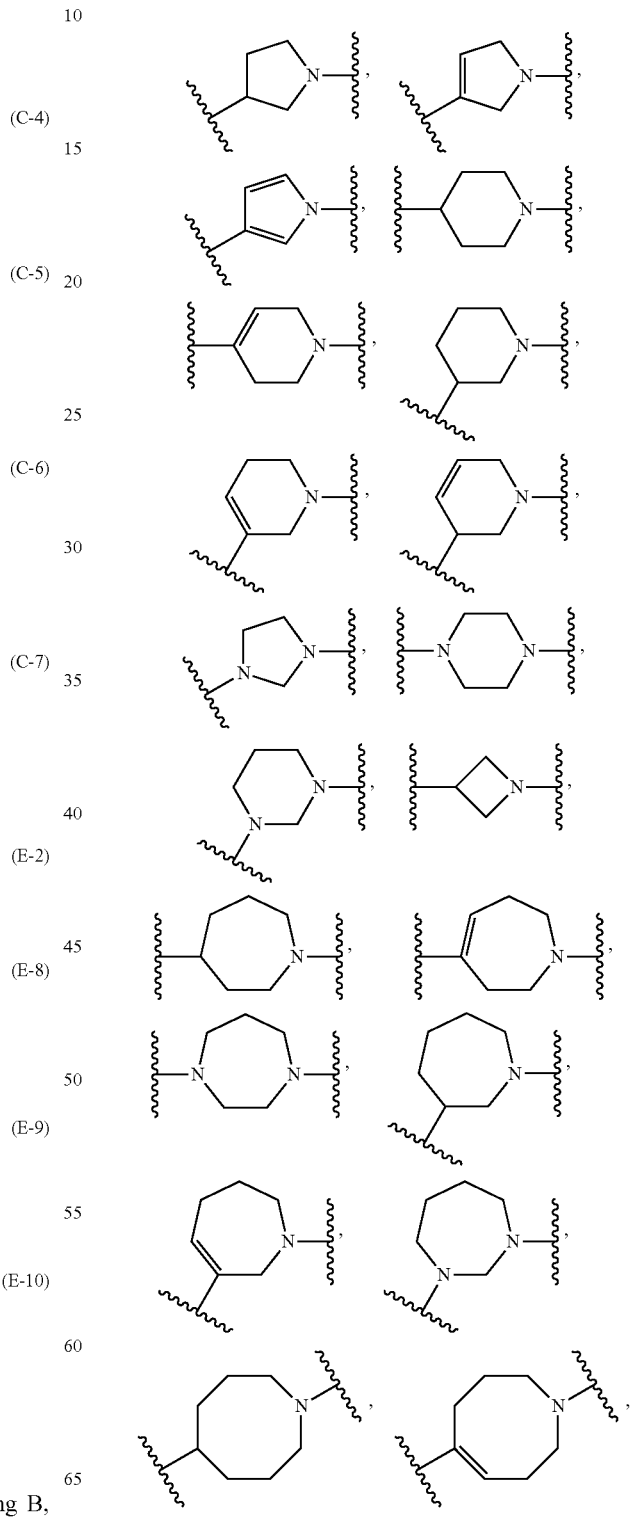

the compound of general formula (I) are shown with (Ia) to (III). Compounds having possible combination of them are preferable.

In the ring A, (Ia) a benzen ring, a furan ring, a thiophen ring or a pyridine ring is preferable, and further (Ib) a benzene ring or a pyridine ring is more preferable.

In the ring B, (Ic) a group of the formula of is preferable.

Groups of preferred substituents in the ring A, ring B, $X^1=X^2-X^3=X^4X^5$, $R^1 \sim R^4$, $R^6$-$R^9$, M, Y, $L^1$, $L^2$, $L^3$, n and q of -continued

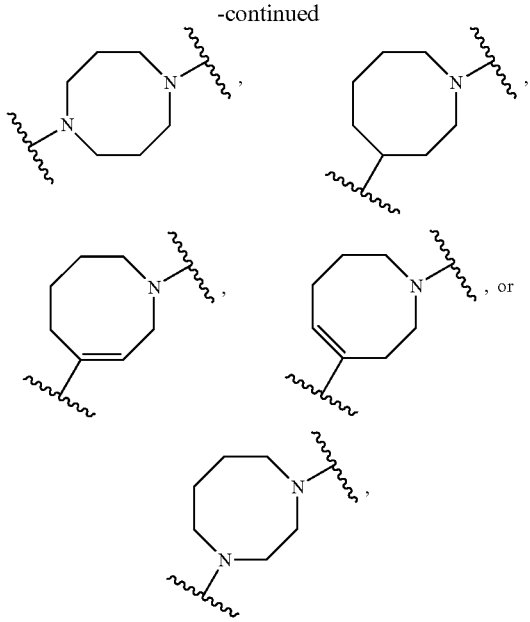

is preferable, (Id) a group of the formula of

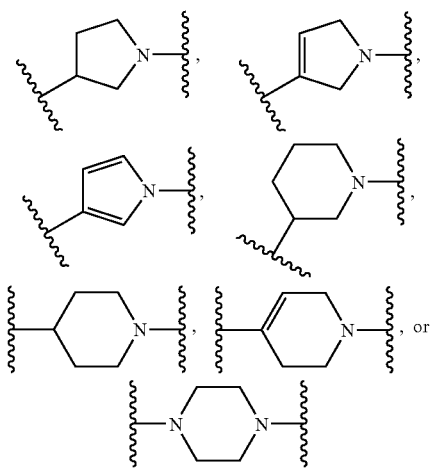

is more preferable, and (Ie) a group of the formula of

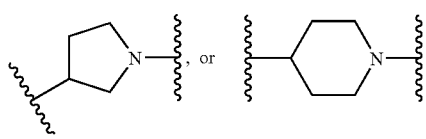

is most preferable.

In $-X^1=X^2-X^3=X^4-$, (If) the formula of $-C(R^1)=C(R^2)-N=C(R^4)-$, $-C(R^1)=C(R^2)-C(R^3)=N-$ or $-C(R^1)=C(R^2)-C(R^3)=C(R^4)-$ is preferable, and further (Ig) the formula of $-C(R^1)=C(R^2)-C(R^3)=C(R^4)-$ is more preferable.

In $X^5$, (Ih) $-N=$, $-CH=$, $-C(\text{a halogen atom})=$ or $-C(\text{alkyl})=$ is preferable, and further (Ii) $-N=$ or $-CH=$ is more preferable.

In $R^6$, (Ij) a hydrogen atom, optionally substituted alkyl or $-Z-R^{10}$ is preferable, and further (Ik) $-Z-R^{10}$ is more preferable.

In $R^1$ to $R^4$ a preferable group is independent, and (II) a hydrogen atom, a halogen atom, optionally substituted alkyl, optionally substituted alkoxy, optionally substituted amino, cyano, nitro, optionally substituted aryl, optionally substituted heteroaryl or $-Z-R^{10}$ is preferable and further (Im) a hydrogen atom, a halogen atom, optionally substituted alkyl, optionally substituted alkoxy, optionally substituted aryl or optionally substituted heteroaryl is more preferable, provided that at least one of $R^1$ to $R^6$ is $-Z-R^{10}$.

In $R^7$, (In) optionally substituted C1-C6 alkyloxy, optionally substituted C1-C6 alkylthio, optionally substituted C5-C6 cycloalkyloxy or optionally substituted aryloxy is preferable, and further (Io) optionally substituted C1-C6 alkyloxy or optionally substituted C1-C6 alkylthio is more preferable.

In $R^8$, (Ip) a halogen atom, optionally substituted alkyl, cyano, nitro, optionally substituted aryl or optionally substituted heteroaryl is preferable, and further (Iq) a halogen atom or optionally substituted alkyl is further preferable.

In $R^9$, (Ir) optionally substituted alkyl or oxo is preferable and further (Is) alkyl is preferable.

In $R^{10}$, (It) carboxy, alkyloxycarbonyl, optionally substituted carbamoyl or a carboxy equivalent is preferable, and further (Iu) carboxy is more preferable.

In M, (Iv) sulfonyl or carbonyl is preferable and further (Iw) sulfonyl is more preferable.

In Y, (Ix) a single bond or optionally substituted alkylene optionally containing ore or two heteroatom(s) is preferable, and further (Iy) a single bond is more preferable.

In $L^1$, (Iz) a single bond, optionally substituted alkylene optionally containing ore or two heteroatom(s) or $-NH-$ is preferable, and further (IIa) a single bond is more preferable.

In $L^2$, (IIb) a single bond, optionally substituted alkylene optionally containing ore or two heteroatom(s) or $-NH-$ is preferable, and further (IIc) a single bond is more preferable.

In $L^3$, (IId) a single bond, methylene or —O-methylene is preferable, and moreover (IIe) a single bond or methylene is more preferable. Further, (If) a single bond or (IIg) methylene is most preferable.

In n, (IIh) 0, 1 or 2 is preferable, and further (IIi) 0 is more preferable.

In q, (IIj) 0 or 1 is preferable, and further (IIk) 1 or (IIl) 0 is more preferable.

Groups of preferred substituents in the ring C, $X^5$, $R^1$ to $R^4$, $R^9$ to $R^{10}$, $R^{13}$ to $R^{14}$, M, $L^3$, n and q of the compound of general formula (II) are shown with (Id) above to (Ii) above, (Il) above to (Iw) above, (IIh) above to (III) above and (IIm) to (IIo). Compounds having possible combination of them are preferable.

In the ring C, (Id) above is preferable and further (Ie) above is more preferable.

In $X^5$, (Ih) above is preferable and further (Il) above is more preferable.

In $R^1$ to $R^4$ a preferable group is independent, (II) above is preferable and further (Im) above is more preferable.

In $R^9$, (Ir) above is preferable and further (Is) above is more preferable.

In $R^{10}$, (It) above is preferable and further (Iu) above is more preferable.

In $R^{13}$, (In) above is preferable and further (Io) above is more preferable.

In $R^{14}$, (Ip) above is preferable and further (Iq) above is more preferable.

In M, (Iv) above is preferable and further (Iw) above is more preferable.

In n, (IIh) above is preferable and further (IIi) above is more preferable.

In q, (IIj) above is preferable and further (IIk) above or (III) above is more preferable.

In Z, (IIm) CH, C($R^{14}$) or N is preferable, and further (IIn) CH or (IIo) N is more preferable.

Groups of preferred substituents in the ring $A^a$, the ring $B^a$, -$X^{1a}$=$X^{2a}$-$X^{3a}$=$X^{4a}$-, $R^{1a}$ to $R^{10a}$, $Y^a$, $Z^a$, ma, na and pa of the compound of general formula (I-a) are shown with (Ia) above to (Id) above, (Il) above to (Im) above, (Ip) above to (Iq) above, (Is) above, (Iu) above, (Iy) above, (IIh) above to (IIk) above and (IIp) to (IIIc). Compounds having possible combination of them are preferable.

In the ring $A^a$, (Ia) above is preferable and further (Ib) above is more preferable.

In the ring $B^a$, (Ic) above is preferable and further (Id) above is more preferable.

In the formula of -$X^{1a}$=$X^{2a}$-$X^{3a}$=$X^{4a}$-, (IIp) a formula of —C($R^{1a}$)=C($R^{2a}$)—N=C($R^{4a}$)-, —C($R^{1a}$)=C($R^{2a}$)—C($R^{3a}$)=N— or —C($R^{1a}$)=C($R^{2a}$)—C($R^{3a}$)=C($R^{4a}$)— is preferable, and further (IIq) a formula of —C($R^{1a}$)=C($R^{2a}$)—C($R^{3a}$)=C($R^{4a}$)— is more preferable.

In $R^{1a}$ and $R^{6a}$ a preferable group is independent, (IIr) a hydrogen atom, optionally substituted alkyl or -$Z^a$-$R^{10a}$ is preferable and further (IIs) a hydrogen atom or -$Z^a$-$R^{10a}$ is more preferable.

In $R^{2a}$ to $R^{5a}$ a preferable group is independent, (Il) above is preferable and further (Im) above is more preferable, provided that at least one of $R^{1a}$ to $R^{6a}$ is -$Z^a$-$R^{10a}$.

In $R^7$, (IIt) optionally substituted alkyloxy, optionally substituted alkylthio, optionally substituted cycloalkyloxy or optionally substituted aryloxy is preferable, and further (IIu) optionally substituted alkyloxy or optionally substituted alkylthio is more preferable.

In $R^8$, (Ip) above is preferable and further (Iq) above is more preferable.

In $R^9$, (IIv) optionally substituted alkyloxy is preferable and further (Is) above is more preferable.

In $R^{10}$, (IIw) carboxy or alkyloxycarbonyl is preferable and further (Iu) above is more preferable.

In Y, (IIx) a single bond, alkylene or alkenylene is preferable, and further (Iy) above is more preferable.

In m, (IIy) 0, 1 or 2 is preferable, and (IIz) 0 or 1 is more preferable.

In n, (IIh) above is preferable and further (IIi) above is more preferable.

In p, (IIj) above is preferable and further (IIk) above is more preferable.

In Z, (IIIa) CH, C($R^{14}$) or N is preferable, and further (IIIb) CH or (IIIc) N is more preferable.

Groups of preferred substituents in the ring $A^a$, the ring $B^a$, $R^{5a}$, $R^{7a}$ to $R^{14a}$, Za, ma, na and pa of the compound of general formula (II-a) are shown with (Ia) above to (Id) above, (Il) above to (Im) above, (Ip) above to (Iq) above, (Is) above, (Iu) above, (IIh) above to (IIk) above, (IIt) above to (IIw) above, (IIy) above to (IIz) above and (IIId) to (IIIe). Compounds having possible combination of them are preferable.

In the ring $A^a$, (Ia) above is preferable and further (Ib) above is more preferable.

In the ring $B^a$, (Ic) above is preferable and further (Id) above is more preferable.

In $R^{11a}$ to $R^{14a}$ a preferable group is independent, (Il) above is preferable and further (Im) above is more preferable.

In $R^7$, (IIt) above is preferable and further (IIu) above is more preferable.

In $R^8$, (Ip) optionally substituted alkyl is preferable and further (Iq) above is more preferable.

In $R^9$, (IIv) above is preferable and further (Is) above is more preferable.

In $R^{10}$, (IIw) above is preferable and further (Iu) above is more preferable.

In m, (IIy) above is preferable and further (IIz) above is more preferable.

In n, (IIh) above is preferable and further (IIi) above is more preferable.

In p, (IIj) above is preferable and further (IIk) above is more preferable.

In $R^5$, (IIId) a hydrogen atom or optionally substituted alkyl is preferable and further (IIIe) a hydrogen atom is more preferable.

Effect of Invention

The compounds of the present invention are useful as a therapeutic agent, especially for treating allergic diseases, since they have an excellent DP receptor antagonistic activity and high safety.

BEST MODE FOR CARRYING OUT THE INVENTION

The compounds of the present invention can be prepared by the method A, B or C set forth below. In addition, a racemate or an optical isomer is included in structural formulae of (I), (III) to (XI) and (I').

Method A is set forth below,

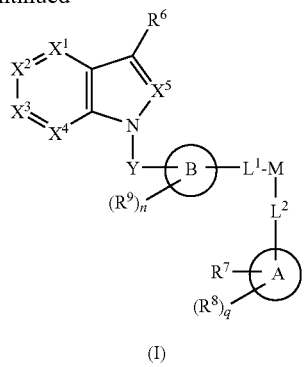

(I)

wherein the ring A, the ring B, $X^1$, $X^2$, $X^3$, $X^4$, $X^5$, $R^6$, $R^7$, $R^8$, $R^9$, M, Y, $L^1$, $L^2$, m, n and p are the same as 1) before; $L^a$ and $L^b$ are independently a halogen atom, a hydroxyl group, methanesulfonyloxy or p-toluenesulfonyloxy; Pa is COOt-Bu.

Step 1 is a process in which a compound of the formula (III) is condensed with a compound of the formula (IV) to give a compound of the formula (V).

The reaction can be carried out by reacting 1 to 5 equivalents of the compound (IV) compared to the compound (III) in an inert solvent at 0° C. to 150° C. for 5 minutes to 48 hours.

The reaction may be conducted under the presence of 1 to 5 equivalents of a base. Examples of the preferable base include sodium hydride, potassium carbonate, sodium carbonate, potassium bicarbonate, sodium bicarbonate, potassium hydroxide, sodium hydroxide and the like.

Examples of the preferable inert solvent include tetrahydrofuran, N,N-dimethylformamide, dimethylsulfoxide, water and the like, which can be used alone or as a mixed solvent.

Step 2 is a process in which a compound of the formula (V) is deprotected under an acidic condition to give a compound of the formula (VI).

The reaction can be carried out by using 1 to 20 equivalents of the acid compared to the compound (V) in an inert solvent at 0° C. to 150° C. for 5 minutes to 48 hours.

Examples of the preferable inert solvent include ethyl acetate, methylene chloride, tetrahydrofuran, N,N-dimethylformamide, methanol, dioxane, water and the like, which can be used alone or as a mixed solvent.

Step 3 is a process in which a compound of the formula (VI) is condensed with a compound of the formula (VII), and the product is hydrolyzed under a basic condition if necessary to give a compound of the formula (I).

The reaction can be carried out by reacting 0.8 to 2 equivalents of the compound of the formula (VII) compared to the compound (VI) in an inert solvent at 0° C. to 150° C. for 5 minutes to 48 hours.

Examples of the preferable inert solvent include ethyl acetate, methylene chloride, tetrahydrofuran, N,N-dimethylformamide, dimethylsulfoxide, water and the like, which can be used alone or as a mixed solvent.

The reaction may be conducted under the presence of 1 to 5 equivalents of a base compared to the compound of the formula (VII). Examples of the preferable base include triethylamine, diisopropylethylamine, pyridine, potassium carbonate, sodium carbonate, cesium carbonate, potassium bicarbonate, sodium bicarbonate and the like.

Hydrolysis can be conducted in an inert solvent by reacting 1 to 5 equivalent(s) of a base compared to the compound of the formula (VII) at 0° C. to 150° C. for 5 minutes to 48 hours.

Examples of the preferable inert solvent include tetrahydrofuran, methanol, N,N-dimethylformamide, water and the like, which can be used alone or as a mixed solvent.

A product of each step, the compound (V), (VI) or (I), can be purified in a conventional method such as a column chromatography or re-crystallization etc.

Method B is set forth below,

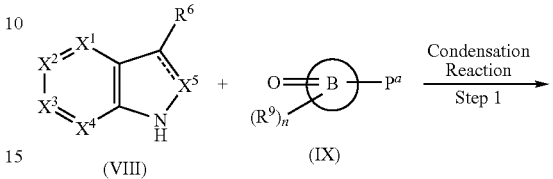

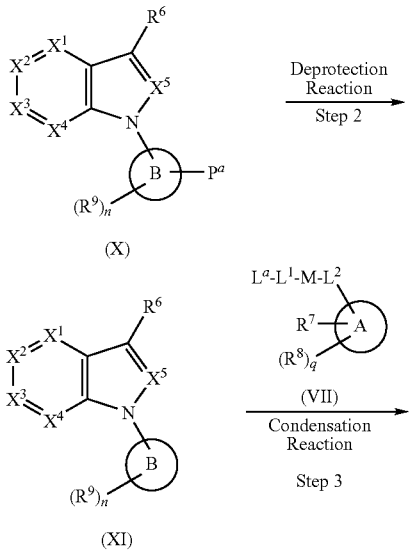

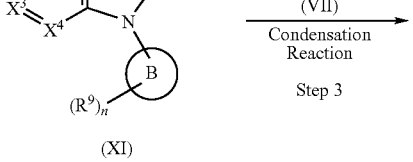

(I)

wherein the ring A, the ring B, $X^1$, $X^2$, $X^3$, $X^4$, $R^5$, $R^6$, $R^7$, $R^8$, $R^9$, M, Y, $L^1$, $L^2$, m, n and p are the same as 1) before; $L^a$ and $L^b$ is a halogen atom, a hydroxy group, methanesulfoxy or p-toluenesulfonyloxy; pa is COOt-Bu; the dotted line means a bond or non-bond Step 1 is a process in which a compound of the formula (VIII) is condensed with a compound of the formula (IX) under a presence of $NaBH(OCOCH_3)_3$ to give a compound of the formula (X).

The reaction can be carried out by reacting 1 to 4 equivalents of the compound (IX) and 1 to 4 equivalents of NaBH$(OCOCH_3)_3$ compared to the compound (VIII) in an inert solvent at 0° C. to 150° C. for 5 minutes to 48 hours.

Examples of the preferable inert solvent include acetic acid, water and the like, which can be used alone or as a mixed solvent.

In addition, dehydrogenation is possible using 2,3-dichloro-5,6-dicyano-1,4-benzoquinone(DDQ), cesium ammonium nitrate(CAN) and the like in a compound of the formula (VIII) wherein the dotted line means non-bonding.

Step 2 is a process in which a compound of the formula (X) is deprotected under an acidic condition to give a compound of the formula (XI).

The reaction can be carried out by using 1 to 20 equivalents of the acid compared to the compound (V) in an inert solvent at 0° C. to 150° C. for 5 minutes to 48 hours.

Examples of the preferable inert solvent include ethyl acetate, methylene chloride, tetrahydrofuran, N,N-dimethylformamide, methanol, dioxane, water and the like, which can be used alone or as a mixed solvent.

Step 3 is a process in which a compound of the formula ($X^1$) is condensed with a compound of the formula (VII), and the product is hydrolyzed under a basic condition if necessary to give a compound of the formula (I').

The reaction can be carried out by reacting 0.8 to 2 equivalents of the compound of the formula (VII) compared to the compound (VI) in an inert solvent at 0° C. to 150° C. for 5 minutes to 48 hours.

Examples of the preferable inert solvent include ethyl acetate, methylene chloride, tetrahydrofuran, N,N-dimethylformamide, dimethylsulfoxide, water and the like, which can be used alone or as a mixed solvent.

The reaction may be conducted under the presence of 1 to 5 equivalents of a base. Examples of the preferable base include triethylamine, diisopropylethylamine, pyridine, potassium carbonate, sodium carbonate, cesium carbonate, potassium bicarbonate, sodium bicarbonate and the like.

Hydrolysis can be conducted in an inert solvent by reacting 1 to 5 equivalent(s) of a base compared to the compound of the formula (VII) at 0° C. to 150° C. for 5 minutes to 48 hours.

Examples of the preferable inert solvent include tetrahydrofuran, methanol, N,N-dimethylformamide, water and the like, which can be used alone or as a mixed solvent.

A product of each step, the compound (IX), (X) or (I') can be purified in a conventional method such as a column chromatography or re-crystallization etc.

Method C is set forth below,

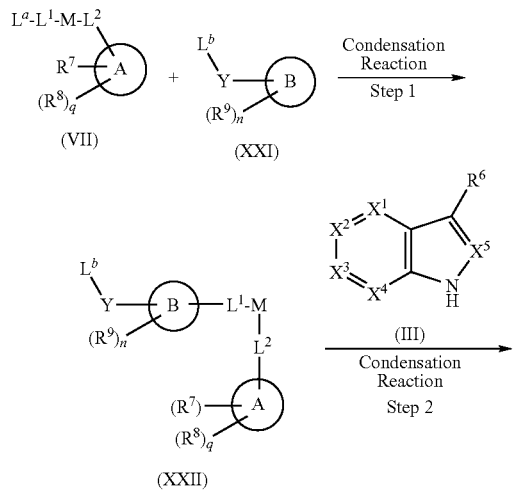

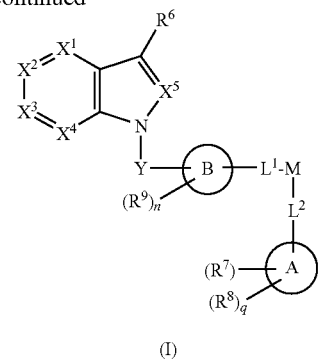

(I)

wherein the ring A, the ring B, $X^1$, $X^2$, $X^3$, $X^4$, $R^5$, $R^6$, $R^7$, $R^8$, $R^9$, M, Y, $L^1$, $L^2$, n and p are the same as 1) before; $L^a$ and $L^b$ is a halogen atom, a hydroxy group, methanesulfoxy or p-toluenesulfonyloxy.

Step 1 is a process in which a compound of the formula (VII) is condensed with a compound of the formula (XXI) to give a compound of the formula (XXII).

The reaction can be carried out by reacting 0.8 to 2 equivalents of the compound (VII) compared to the compound (XXI) in an inert solvent at 0° C. to 150° C. for 5 minutes to 48 hours.

Examples of the preferable inert solvent include ethyl acetate, methylene chloride, tetrahydrofuran, N,N-dimethylformamide, dimethylsulfoxide, water and the like, which can be used alone or as a mixed solvent.

The reaction may be conducted under the presence of 1 to 5 equivalents of a base compared to the compound (VII). Examples of the preferable base include triethylamine, diisopropylethylamine, pyridine, potassium carbonate, sodium carbonate, cesium carbonate, potassium bicarbonate, sodium bicarbonate and the like.

Step 2 is a process in which a compound of the formula (III) is condensed with a compound of the formula (XXII) to give a compound of the formula (I).

The reaction can be carried out by reacting 1 to 5 equivalents of the compound (XXII) compared to the compound (III) in an inert solvent at 0° C. to 150° C. for 5 minutes to 48 hours.

The reaction may be conducted under the presence of 1 to 5 equivalents of a base. Examples of the preferable base include sodium hydride, potassium carbonate, sodium carbonate, potassium bicarbonate, sodium bicarbonate, potassium hydroxide, sodium hydroxide and the like.

Examples of the preferable inert solvent include tetrahydrofuran, N,N-dimethylformamide, dimethylsulfoxide, water and the like, which can be used alone or as a mixed solvent.

Hydrolysis can be conducted in an inert solvent by reacting 1 to 5 equivalent(s) of a base compared to the compound of the formula (III) at 0° C. to 150° C. for 5 minutes to 48 hours.

A product of each step, the compound (XXII) or (I), can be purified in a conventional method such as a column chromatography or re-crystallization etc.

In addition, when a substituent on the ring A is a fluorine atom in the compound of the formula (I) or (I'), it can be substituted with $R^7$ by reacting with $R^7H$ in an inert solvent under a basic condition.

The compound of the formula (III) or (VIII) is available from commercial products or synthesized compounds. Examples of synthetic methods are shown below, but not limited thereto. Additionally, chemical structures of the formulae (XII) to (XX) and (XXIV) include a racemate or an optical isomer.

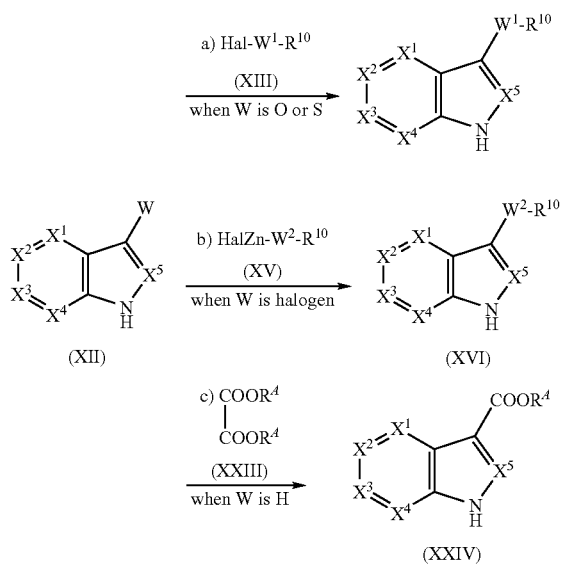

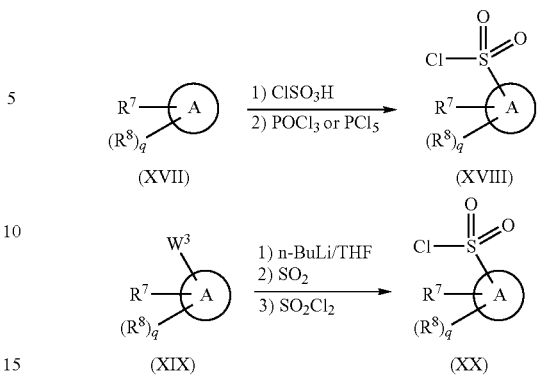

wherein the ring A, $R^7$ and q are the same as 1) before; $W^3$ is a halogen atom.

d) The compound of the formula (XVII) is 1) converted to a $SO_3H$ derivative by treating with $ClSO_3Cl$, and 2) followed by chlorination of the hydroxy group by the reaction with $POCl_3$ or $PCl_5$ to give the compound of the formula (XVIII).

e) The compound of the formula (XIX) is 1) lithiated by n-BuLi, and 2) followed by conversion to a $SO_2Li$ derivative by the reaction with $SO_2$, and finally 3) reacted with $SO_2Cl_2$ to give the compound of the formula (XX). A bromine atom or an iodine atom is preferable as $W^3$.

In this specification, a term of "solvate" includes, for example, a solvate with an organic solvent, a hydrate and the like. In a case of forming the solvate with an organic solvent, any number of molecules of the organic solvent may be coordinated. In a case of forming the hydrate, any number of water molecules may be coordinated. A hydrate is usually preferred.

A term of "compound of the present invention" includes a pharmaceutically acceptable salt and a solvate thereof. Examples of the salt include salts with alkaline metal (lithium, sodium and potassium etc.), alkaline earth metal (magnesium and calcium etc.), ammonium, organic bases and amino acids and salts with inorganic acids (hydrochloric acid, hydrobromic acid, phosphoric acid and sulfuric acid, etc.) and organic acids (acetic acid, citric acid, maleic acid, fumaric acid, benzenesulfonic acid and p-toluenesulfonic acid etc.). These salts can be formed by the usual method.

A compound of the present invention is not limited to the specified isomer but includes all possible isomers and racemates.

A compound of the present invention shows an excellent DP receptor antagonistic activity as described in the following examples. Accordingly, a pharmaceutical composition of the present invention can be used as a therapeutic agent for preventing and/or treating allergic diseases such as asthma, allergic rhinitis, allergic dermatitis, allergic conjunctivitis, food allergy and the like; systemic mastocytosis; systemic disorder of mastcell-activation; lung emphysema; chronic bronchitis; chronic obstructive lung disease; skin disorder characterized by pruritus such as atopic dermatitis and hives; diseases occurring secondarily due to behavior accompanied by pruritus such as cataract and retinal detachment; brain damages such as cerebrovascular disorder, degenerative brain disorder and demyelinating disease; sleep-waking disorder; Churg-Strauss syndrome; papular dermatitis such as filariasis; vasculitis; polyarteritis; cutaneous eosoiophilic granuloma; autoimmune diseases such as multiple sclerosis and transplant rejection; eosoiophilic pneumonopathy; histiocytosis; pneumonia; aspergillosis; pleurisy; sarcoidosis; pulmowherein $X^1$, $X^2$, $X^3$, $X^4$, $R^5$ and $R^{10}$ are the same as 1) before; $R^4$ is a hydrogen atom or alkyl; W is a hydrogen atom, an oxygen atom, a sulfur atom or a halogen atom; $W^1$ is alkylene, alkenylene or alkynylene; $W^2$ is —O-alkylene or —S-alkylene.

a) When W is an oxygen atom or a sulfur atom, the compound of the formula (XII) can be reacted with a compound of the formula (XIII) in an inert solvent at 0° C. to 150° C. for 5 minutes to 48 hours to give a compound of the formula (XIV).

Examples of the inert solvent include tetrahydrofuran, N,N-dimethylformamide and the like, which can be used alone or as a mixed solvent.

Examples of the preferred base include sodium hydride, potassium carbonate, sodium carbonate, potassium bicarbonate, sodium bicarbonate and the like.

b) When W is a halogen atom the compound of the formula (XII) can be reacted with a compound of the formula (XV) in an inert solvent at 0° C. to 150° C. for 5 minutes to 48 hours to give a compound of the formula (XVI).

Examples of the inert solvent include tetrahydrofuran, N,N-dimethylformamide and the like, which can be used alone or as a mixed solvent.

The compound of the formula (VII) is available from commercial products or synthesized compounds. Examples of synthetic methods are shown below, but not limited thereto. Additionally, chemical structures of the formulae (XVII) to (XX) include a racemate or an optical isomer.

c) When W is a hydrogen atom, the compound of the formula (XII) can be condensed with a compound of the formula (XXIII) in an inert solvent (e.g., ether, tetrahydrofuran, N,N-dimethylformamide etc.) at 0° C. to 150° C. for 5 minutes to 48 hours and the resulting compound is reacted with hydrazine hydrate and potassium hydroxide at 0° C. to 150° C. for 5 minutes to 48 hours to give a compound of the formula (XXIV).

nary fibrosis; eosinophilia; skin flush such as face flush by nicotinic acid; filariasis; schistosomiasis; trichinelliasis; coccidioidomycosis; tuberculosis; bronchial cancer; lymphoma; Hodgkin's disease and the like.

When a compound of the present invention is administered to a human in order to treat the diseases above, oral administration through a powder, granule, tablet, capsule, pill, liquid formulation and the like, or parenteral administration through an injection, suppository, transdermal formulation, inhalant and the like is possible.

A pharmaceutical composition can be obtained by mixing a therapeutically effective amount of a compound of the present invention with a pharmaceutical additives such as an excipient, binder, wetting agent, disintegrating agent, lubricant and the like, which is suitable to the selected formulation. An injection can be formulated by sterilization together with a suitable carrier.

In the treatment of the diseases related to PGD2 receptor above, it is possible to use the compound of the present invention combined with or in a coupled formulation with the other therapeutic agent. In the case of treating inflammatory diseases including allergy, the compound can be used combined with or in a coupled formulation with leukotriene receptor antagonist (e.g., montelukast sodium, zafirlukast, pranlukast hydrate, leukotriene B4 receptor antagonist); leukotriene synthesis inhibit such as zileuton, PDE IV inhibitor (e.g., theophylline, cilomilast, roflumilast), corticosteroid (e.g., prednisolone, fluticasone, budesonide, ciclesonide), β2-agonist (e.g., salbutamol, salmeterol, formoterol), anti IgE antibody (e.g., omalizumab), histamine H1 receptor antagonist (e.g., chlorpheniramine, loratadine, cetirizine), immunosuppressant (tacrolimus, cyclosporin), thromboxane A2 receptor antagonist (e.g., ramatroban), chemokine receptor (especially CCR-1, CCR-2, CCR-3) antagonist, other prostanoid receptor antagonist (e.g., CRTH2 antagonist), adhesion molecule antagonist (e.g., VLA-4 antagonist), cytokine antagonist (e.g., anti-IL-4 antibody, anti-IL-3 antibody), Non-steroidal anti-inflammatory agent (e.g., propionic acid derivative such as ibuprofen, ketoprofen and naproxen etc.; acetic acid derivative such as indomethacin, and diclofenac etc.; salicylic acid such as acetyl salicylic acid; cyclooxigenase-2 inhibitor such as celecoxib and etoricoxib).

Further, uses combined with or in a coupled formulation with antitussive agent (e.g., codein, hydrocodein), cholesterol lowering agent (lovastatin, simvastatin, fluvastatin. rosuvastatin), anticholinergic drug (e.g., tiotropium, ipratropium, flutropium, oxitropium) are also possible.

Dose of the compounds of the present invention depends on condition of diseases, route of administration, age and body weight of a patient. In the case of oral administration to an adult, the dose range is usually 0.1 to 100 mg/kg/day, preferably 1 to 20 mg/kg/day.

EXAMPLES

The present invention is illustrated more in detail below by examples and test examples, but not limited to these examples.

In examples, the following abbreviations are used;
Me: methyl
BOC: tert-butoxycarbonyl
DDQ: 2,3-dichloro-5,6-dicyano-1,4-benzoquinone
DMAP: N,N-dimethylaminopyridine
THF: tetrahydrofuran
DMF: N,N-dimethylformamide
MeOH: Methanol Example 1

Preparation of the compound I-9

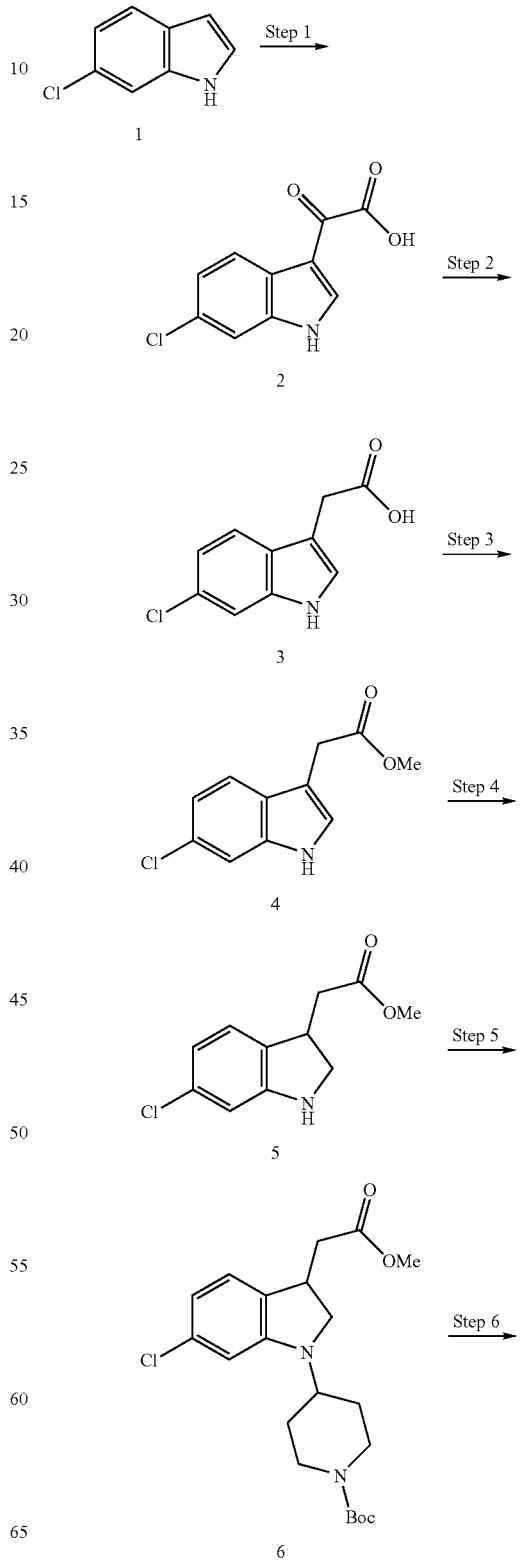

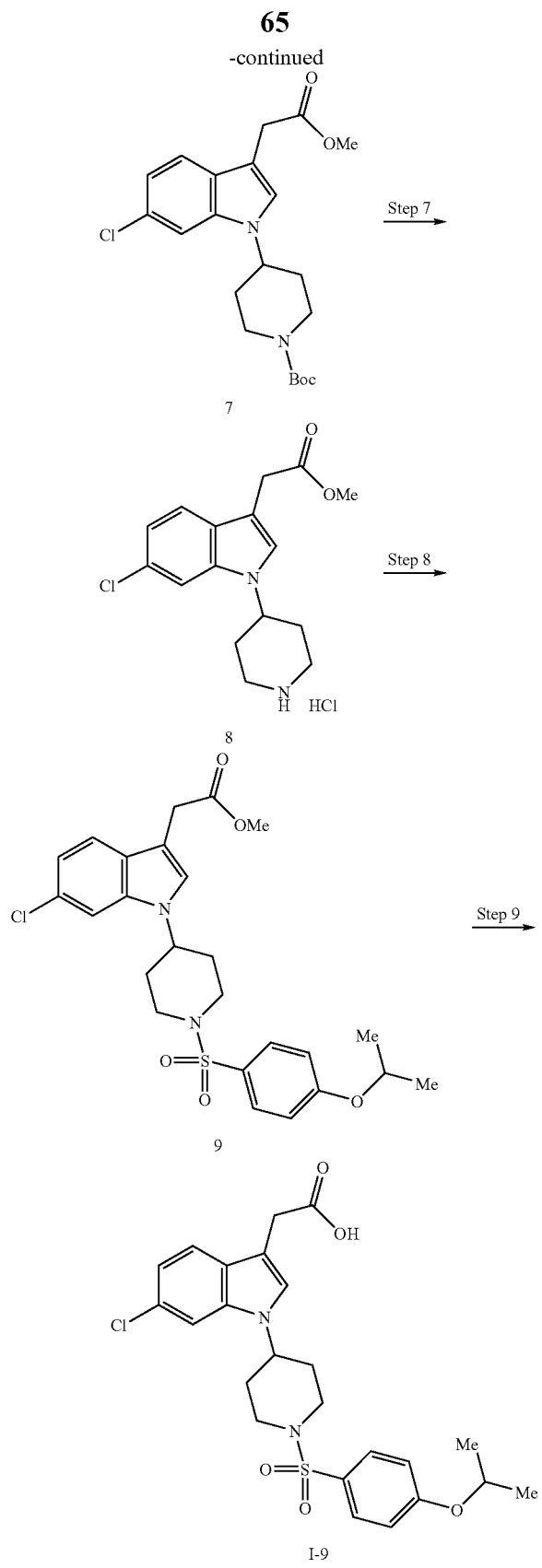

Step 1

Oxalyl chloride (5.03 g, 39.6 mmol) was added to a solution of the compound (1) (5.0 g, 33.0 mmol) in diethyl ether (40 mL) at 0° C. and stirred at the same temperature for 15 minutes. A saturated aqueous solution of sodium bicarbonate (60 mL) and THF (10 mL) were added to the reaction solution and heated to reflux. The reaction solution was cooled and adjusted to pH 2-3 by adding diluted hydrochloric acid. The resulting crystalline was collected by filtration, washed with water and dried to give the compound (2) (3.55 g, 48% yield).

Step 2

Hydrazine monohydrate (2.2 mL) and potassium hydroxide (5.29 g, 94.2 mmol) were added to the compound (2) (3.55 g, 15.7 mmol) and stirred at 180° C. for 3 hours and 40 minutes. The reaction solution was cooled, water (50 mL) and chloroform (20 mL) were added and the mixture was extracted. After the obtained aqueous layer was adjusted to pH 1-2 by adding diluted hydrochloric acid, the mixture was extracted with diethyl ether (100 mL) and the organic layer was washed with water and dried. The organic layer was concentrated and the resulting residue [the compound (2)] was used in the next step without further purification.

Step 3

2,2-Dimethoxypropane (20 mL) and concentrated hydrochloric acid (2 mL) were added to the residue obtained in Step 2 and stirred under heating at 50° C. for 10 minutes. After the reaction solution was cooled, the reaction solution was extracted with ethyl acetate and the organic layer was washed with water, a saturated aqueous solution of sodium bicarbonate and saturated brine successively, dried and concentrated. The resulting residue was purified by a silica gel column chromatography (hexane:ethyl acetate=5:1) and thebeluent was concentrated to give a oily compound (3) (3.22 g, 91.7% yield).

$^1$H-NMR (CDCl$_3$) δ ppm: 3.71 (s, 3H), 3.83 (s, 2H), 7.03-7.10 (m, 2H), 7.25 (d, J=1.8 Hz, 1H), 7.48 (d, J=8.4 Hz, 1H), 8.22 (brs, 1H).

Step 4

After diluted hydrochloric acid (2 mL) was added to a solution of the compound (3) (3.2 g, 14.3 mmol) in MeOH (20 mL), BH$_3$-pyridine (10.1 mL, 100 mmol) was added at 0° C. and the mixture was stirred at the same temperature for 40 minutes, further at room temperature for 30 minutes. The reaction solution was diluted with water (50 mL) and extracted with diethyl ether (50 mL). The obtained aqueous layer was adjusted to pH 7-8 by adding sodium hydroxide and extracted with ethyl acetate (50 mL). The organic layer was washed with water, dried and concentrated to give the oily compound (5) (2.08 g, 64.4% yield).

Step 5

1-(tert-Butoxycarbonyl)-4-piperidone (1.39 g, 6.98 mmol) and sodium triacetoxyhydroborate (1.48 g, 6.98 mmol) were added to a solution of the compound (5) (1.39 g, 4.65 mmol) in acetic acid (6 mL) and stirred at room temperature for 1 hour. The reaction solution was diluted with water, extracted with ethyl acetate, and the organic layer was washed with a saturated aqueous solution of sodium bicarbonate and water successively, dried and concentrated. The resulting residue was purified by a silica gel column chromatography (hexane:ethyl acetate=10:1) and the eluent was concentrated to give the residue [the compound (6)], which was directly used in the next step without further purification.

Step 6

A solution of DDQ (1.11 g) in THF (3 mL) was added to a solution of the residue [the compound (6)] obtained in Step 5 in THF (5 mL) at 0° C. and stirred at room temperature for 18 hours. A saturated aqueous solution of sodium bicarbonate (15 mL) was added to the reaction solution, extracted with ethyl acetate (35 mL) and the organic layer was washed with water, dried and concentrated. The resulting residue was purified by a silica gel column chromatography (hexane:ethyl acetate=6:1), the eluent was concentrated and the residue was crystallized from hexane-ethyl acetate to give the compound (7) (1.6 g, 84% yield).

Step 7

A 4N solution of hydrochloric acid in ethyl acetate (4 mL) was added to a solution of the compound (7) (1.59 g, 3.91 mmol) in ethyl acetate (4 mL) and stirred at room temperature for 2 hours. n-Hexane (6 mL) was added to the reaction solution and the precipitated crystalline was collected by filtration to give the compound (8) (1.22 g, 91% yield).
$^1$H-NMR (DMSO-d$_6$) δ p pm: 2.06-2.27 (m, 4H), 3.04-3.44 (m, 4H), 3.61 (s, 3H), 3.78 (s, 2H), 4.72 (m, 1H), 7.06 (dd, J=1.8, 8.4 Hz, 1H), 7.34 (s, 1H), 7.51 (d, J=8.4 Hz, 1H), 7.75 (d, J=1.8 Hz, 1H), 9.19 (brs, 1H).

Step 8

4-Isopropyloxybenzenesulfonylchloride (258 mg, 1.1 mmol) and triethylamine (0.42 mL) were added to a solution of the compound (8) (343 mg, 1.0 mmol) in THF (3 mL) and stirred at room temperature for 18 hours. Water (10 mL) was added to the reaction solution, extracted with ethyl acetate and the extract was washed with a saturated brine dried and concentrated. The resulting residue was purified by a silica gel column chromatography (hexane:ethyl acetate=4:1). The eluent was concentrated and the residue was crystallized from hexane-ethyl acetate to give the compound (9) (405 mg, 80% yield).

Step 9

The compound (9) (405 mg, 0.8 mmol) was dissolved in MeOH (2.0 mL)-THF (2.0 mL). A 4N aqueous solution of sodium hydroxide (0.5 mL, 2.0 mmol) was added thereto and stirred at room temperature for 18 hours. After the reaction solution was diluted with water and acidified by adding diluted hydrochloric acid, the mixture was extracted with ethyl acetate and the extract was washed with water, dried and concentrated. The residue was crystallized from hexane-ethyl acetate to give the compound I-9 (422 mg, 99% yield).

$^1$H-NMR (DMSO-d$_6$) δ ppm: 1.33 (d, 6H, J=6.0 Hz), 1.91-1.99 (m, 4H), 3.33 (br, 2H), 3.61 (s, 2H), 3.76 (d, 2H, J=12.0 Hz), 4.44 (m, 1H), 4.77 (m, 1H), 7.00 (dd, 1H, J=6.6 Hz, 1.8 Hz), 7.17 (d, 2H, 9.3 Hz), 7.42 (s, 1H), 7.47 (d, 2H, 8.7 Hz), 7.65-7.71 (m, 3H), 12.26 (br. 1H).

Example 2

Preparation of the compound I-18

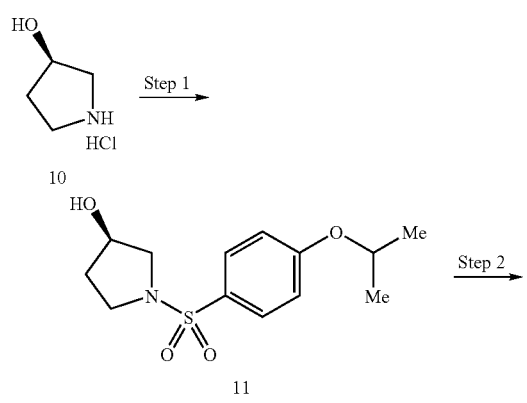

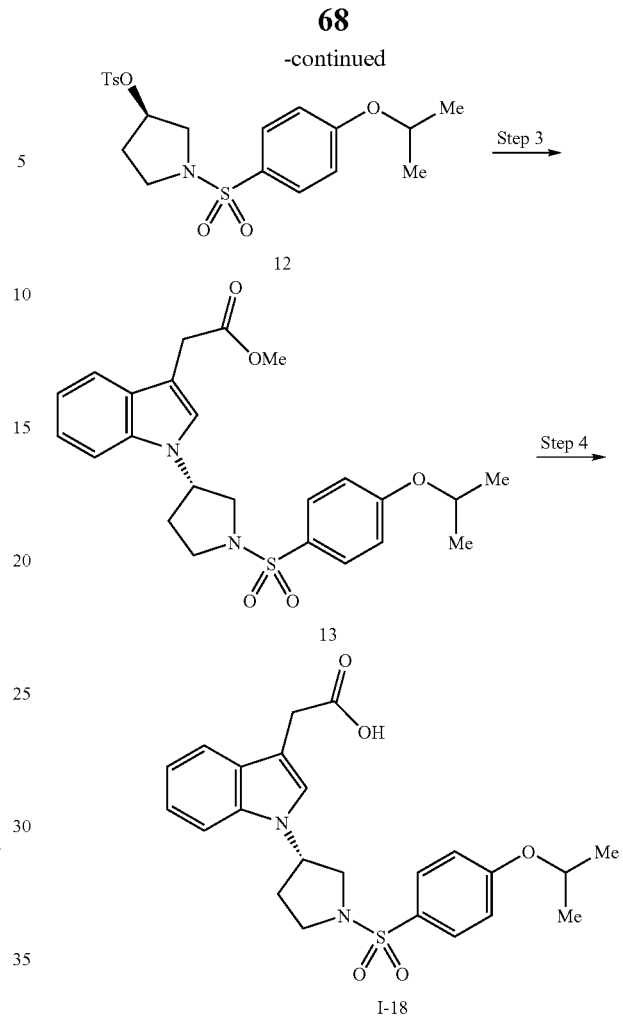

Step 1

4-Isopropyloxybenzenesulfonylchloride (5.9 g, 25.4 mmol) and triethylamine (8.4 mL) were added to a solution of (R)-pyrrolidine hydrochloride (10) (3.0 g, 24.2 mmol) in a mixture of THF (20 mL)-DMF (10 mL) and the mixture was stirred at 0° C. for 5 hours. Water (20 mL) was added to the reaction solution and extracted with ethyl acetate (40 mL). The organic layer was washed with diluted hydrochloric acid and water successively, dried and concentrated. The resulting residue [the compound (2)] was directly used in the next step without further purification.

Step 2 p-Toluenesulfonylchloride (6.9 g, 36.3 mmol) and DMAP (295 mg, 2.4 mmol) were added to a solution of the compound (2) (6.9 g, 24.2 mmol) in pyridine (20 mL) and stirred at room temperature for 18 hours. Water (30 mL) was added to the reaction solution and extracted with ethyl acetate (60 mL). The organic layer was washed with diluted hydrochloric acid and water successively, dried and concentrated. The resulting residue was purified by a silica gel column chromatography (hexane:ethyl acetate=4:1), the eluent was concentrated and the residue was crystallized from hexane-ethyl acetate to give the compound (3) (8.28 g, 78% yield).

$^1$H-NMR (CDCl$_3$) δ ppm: 1.38 (d, J=6.3 Hz, 6H), 1.95-2.04 (m, 2H), 2.46 (s, 3H), 3.17-3.49 (m, 4H), 4.64 (m, 1H), 4.94 (m, 1H), 6.94 (d, J=8.7 Hz, 2H), 7.33 (d, J=8.7 Hz, 1H), 7.64-7.70 (m, 4H).

Step 3

NaH (60%) (47 mg, 1.17 mmol) was added at 0° C. to a solution of indole-3-acetic acid methyl ester (200 mg, 1.05 mmol) in DMF (1.5 mL) and stirred for 30 minutes. To the reaction solution, was added a solution of the compound (3) (697 mg, 1.58 mmol) in DMF (4.5 mL) and stirred at 80° C. for 18 hours. After the reaction solution was cooled, water (10 mL) was added and extracted with ethyl acetate (20 mL). The organic layer was washed with diluted hydrochloric acid and water successively, dried and concentrated. The resulting residue was purified by a silica gel column chromatography (hexane:ethyl acetate=3:1) and the eluent was concentrated to give the compound (4) (117 mg, 24% yield).

Step 4

The compound (4) (170 mg, 0.37 mmol) was dissolved in MeOH (1.5 mL)-THF (1.5 mL). A 4M aqueous solution of sodium hydroxide (0.23 mL, 0.93 mmol) was added and the mixture was stirred at room temperature for 18 hours. After the reaction solution was diluted with water and acidified by adding diluted hydrochloric acid, the mixture was extracted with ethyl acetate and the extract was washed with water, dried and concentrated. The residue was crystallized from hexane-ethyl acetate to give the compound I-18 (132 mg, 80% yield).

$^1$H-NMR (DMSO-$d_6$) δ ppm: 1.32 (d, 6H, J=5.7 Hz), 2.12 (m, 1H), 2.28 (m, 1H), 3.24-3.67 (m, 6H), 4.76 (m, 1H), 5.06 (m, 1H), 7.00-7.14 (m, 5H), 7.35 (d, 1H, J=8.1 Hz), 7.38 (d, 1H, J=7.8 Hz), 7.74 (d, 2H), 12.20 (br, 1H).

The compounds I-1 to I-8, I-10 to I-17 and I-19 to I-37 were prepared in the same manner as described above. The structures and physical properties were shown in Table 1-7.

TABLE 1

| Compound No. | Structure | $^1$H-NMR δ ppm |
|---|---|---|
| I-1 | [Structure: HO₂C-CH₂-indole-N-piperidine-N-SO₂-phenyl-O-CH(Me)₂] | (DMSO-d6) 1.33 (d, 6H, J = 6.0 Hz), 1.93-1.99 (m, 4H), 3.34 (br, 2H), 3.61 (s, 2H), 3.78 (d, 2H, J = 11.4 Hz), 4.41 (m, 1H), 4.77 (d, 1H), 6.98 (m, 1H), 7.06 (m, 1H), 7.16 (m, 2H), 7.35 (s, 1H), 7.46 (dd, 2H, 7.5 Hz), 7.71 (d, 2H), 12.19 (br, 1H) |
| I-2 | [Structure: HO₂C-CH₂-indole-N-piperidine-N-SO₂-phenyl-O-CH₂-Me] | (DMSO-d6) 1.38 (dd, 3H, J = 6.9 Hz), 1.93-1.99 (m, 4H), 3.34 (br, 2H), 3.61 (s, 2H), 3.78 (d, 2H, J = 11.1 Hz), 4.15 (dd, 2H), 4.39 (m, 1H), 6.98 (m, 1H), 7.07 (m, 1H), 7.18 (d, 2H), 7.35 (s, 1H), 7.46 (dd, 2H, 8.7 Hz), 7.72 (d, 2H), 12.18 (br, 1H) |
| I-3 | [Structure: HO₂C-CH₂-indole-N-piperidine-N-SO₂-phenyl-O-Me] | (DMSO-d6) 1.93-2.01 (m, 4H), 3.34 (s, 2H), 3.61 (s, 2H), 3.78 (d, 2H, J = 11.7 Hz), 3.88 (ds, 3H), 4.40 (m, 1H), 6.98 (m, 1H), 7.07 (m, 1H), 7.20 (m, 2H), 7.36 (s, 1H), 7.46 (dd, 2H, 9.0 Hz), 7.73 (d, 2H), 12.18 (br, 1H) |
| I-4 | [Structure: HO₂C-CH₂-indole-N-piperidine-N-SO₂-phenyl-F] | (DMSO-d6) 1.96-2.02 (m, 4H), 3.34 (br, 2H), 3.62 (s, 2H), 3.82 (d, 2H, J = 11.7 Hz), 4.42 (m, 1H), 6.98 (m, 1H), 7.07 (m, 1H), 7.36 (s, 1H), 7.42-7.58 (m, 4H), 7.85-7.91 (m, 2H), 12.19 (br, 1H) |

TABLE 1-continued

| Compound No. | Structure | ¹H-NMR δ ppm |
|---|---|---|
| I-5 | 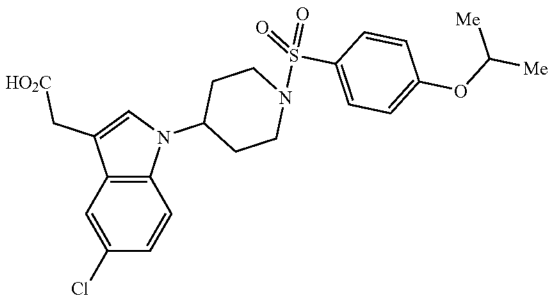 | (DMSO-d6) 1.33 (d, 6H, J = 5.7 Hz), 1.97 (br, 4H), 3.33 (br, 2H), 3.61 (s, 2H), 3.76 (d, 2H, J = 12.3 Hz), 4.42 (m, 1H), 4.77 (m, 1H), 7.07 (d, 1H, J = 8.7 Hz), 7.17 (d, 2H, J = 8.1 Hz), 7.45-7.52 (m, 3H), 7.70 (d, 2H, J = 8.1 Hz), 12.23 (br, 1H) |
| I-6 | 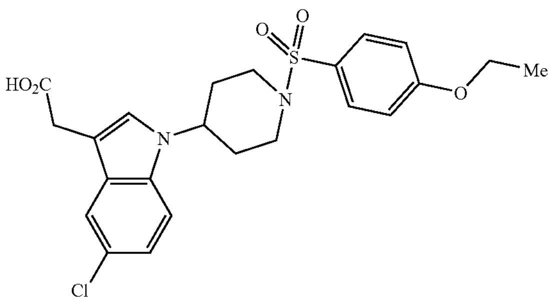 | (DMSO-d6) 1.38 (dd, 3H, J = 6.9 Hz), 1.93-1.99 (m, 4H), 3.33 (br, 2H), 3.62 (s, 2H), 3.78 (d, 2H, J = 11.7 Hz), 4.13 (dd, 2H), 4.41 (m, 1H), 7.07 (dd, 1H, J = 8.7 Hz, 1.8 Hz), 7.18 (d, 2H, 8.7 Hz), 7.45-7.52 (m, 3H), 7.72 (d, 2H, 9.0 Hz), 12.23 (br, 1H) |

TABLE 2

| Compound No. | Structure | ¹H-NMR δ ppm |
|---|---|---|
| I-7 | 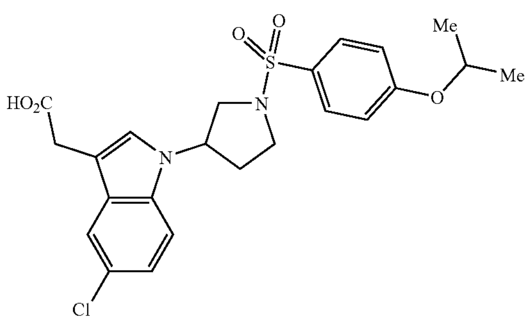 | (DMSO-d6) 1.32 (d, 6H, J = 6.0 Hz), 2.12 (m, 1H), 2.28 (m, 1H), 3.25-3.33 (m, 3H), 3.43-3.58 (m, 3H), 4.75 (m, 1H), 5.08 (m, 1H), 7.10-7.19 (m, 4H), 7.41 (d, 1H, J = 9.0 Hz), 7.53 (dd, 1H), 7.73 (d, 2H, J = 8.4 Hz), 12.26 (br, 1H) |
| I-8 | 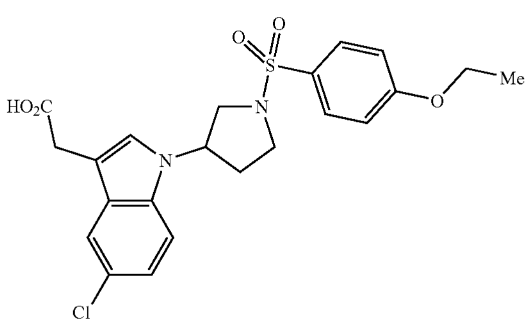 | (DMSO-d6) 1.38 (dd, 3H, J = 6.9 Hz), 2.11 (m, 1H), 2.28 (m, 1H), 3.23-3.33 (m, 3H), 3.42-3.60 (m, 3H), 4.14 (dd, 2H), 5.08 (m, 1H), 7.11-7.15 (m, 4H), 7.42 (d, 1H, J = 8.7 Hz), 7.53 (d, 1H, J = 1.8 Hz), 7.74 (d, 2H, J = 9.0 Hz), 12.26 (br, 1H) |

TABLE 2-continued

| Compound No. | Structure | ¹H-NMR δ ppm |
|---|---|---|
| I-9 | 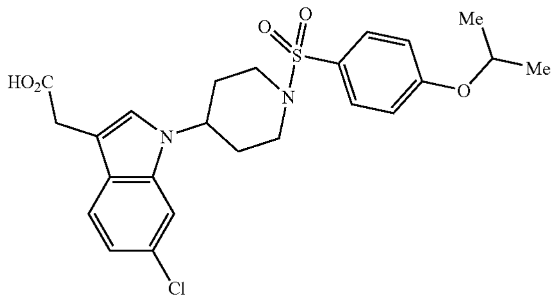 | (DMSO-d6) 1.33 (d, 6H, J = 6.0 Hz), 1.91-1.99 (m, 4H), 3.33 (br, 2H), 3.61 (s, 2H), 3.76 (d, 2H, J = 12.0 Hz), 4.44 (m, 1H), 4.77 (m, 1H), 7.00 (dd, 1H, J = 6.6 Hz, 1.8 Hz), 7.17 (d, 2H, 9.3 Hz), 7.42 (s, 1H), 7.47 (d, 2H, 8.7 Hz), 7.65-7.71 (m, 3H), 12.26 (br, 1H) |
| I-10 | 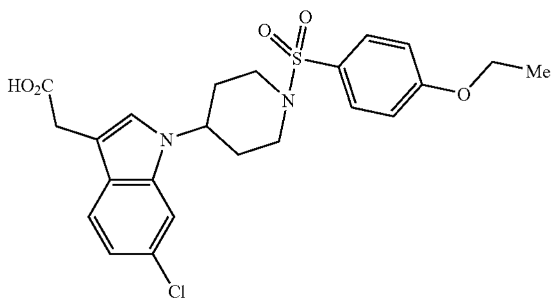 | (DMSO-d6) 1.38 (dd, J = 6.9 Hz), 1.93-1.99 (m, 4H), 3.33 (br, 2H), 3.61 (s, 2H), 3.78 (d, 2H, J = 11.1 Hz), 4.15 (dd, 2H), 4.42 (m, 1H), 7.00 (dd, 1H, J = 8.1 Hz, 2.1 Hz), 7.19 (d, 2H, 9.0 Hz), 7.42 (s, 1H), 7.47 (d, 2H, 8.4 Hz), 7.65-7.71 (m, 3H), 12.24 (br, 1H) |
| I-11 | 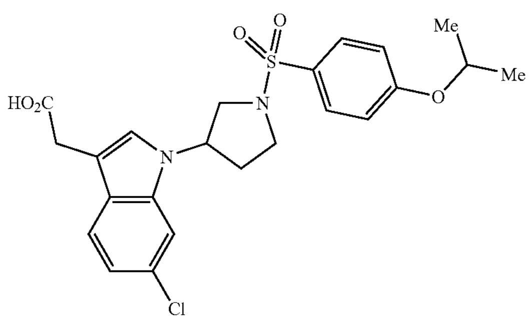 | (DMSO-d6) 1.32 (d, 6H, J = 6.3 Hz), 2.08 (m, 1H), 2.28 (m, 1H), 3.22-3.30 (m, 3H), 3.43-3.58 (m, 3H), 4.76 (m, 1H), 5.09 (m, 1H), 7.05 (dd, 1H, J = 6.6 Hz, 1.8 Hz), 7.10-7.15 (m, 3H), 7.48 (d, 1H, J = 8.4 Hz), 7.55 (d, 1H, J = 1.8 Hz), 7.74 (d, 2H, J = 8.7 Hz), 12.26 (br, 1H) |
| I-12 | 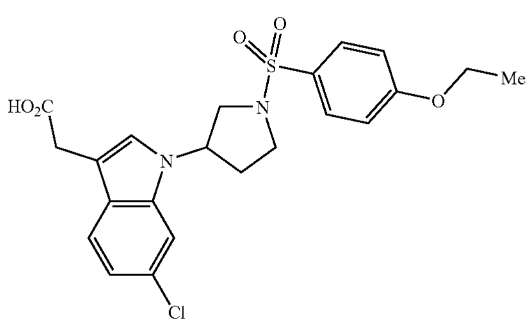 | (DMSO-d6) 1.38 (d, 3H, J = 6.9 Hz), 2.09 (m, 1H), 2.27 (m, 1H), 3.22-3.30 (m, 3H), 3.42-3.59 (m, 3H), 4.14 (dd, 2H), 5.10 (m, 1H), 7.05 (dd, 1H, J = 8.4 Hz, 1.8 Hz), 7.07-7.14 (m, 3H), 7.48 (d, 1H, J = 8.4 Hz), 7.54 (d, 1H, J = 1.8 Hz), 7.75 (d, 2H, J = 8.7 Hz), 12.24 (br, 1H) |

TABLE 3

| Compound No. | Structure | ¹H-NMR δ ppm |
|---|---|---|
| I-13 | 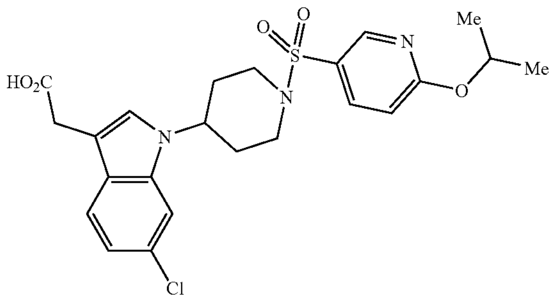 | (DMSO-d6) 1.36 (d, 6H, J = 6.0 Hz), 1.99 (br, 4H), 3.33 (br, 2H), 3.62 (s, 2H), 3.79 (d, 2H, J = 11.1 Hz), 4.46 (m, 1H), 5.37 (d, 1H), 7.01 (d, 1H, J = 8.4 Hz), 7.44 (s, 1H), 7.48 (d, 2H, J = 5.7 Hz), 7.63 (s, 1H), 8.04 (dd, 1H), 8.57 (d, 1H), 12.23 (br, 1H) |
| I-14 | 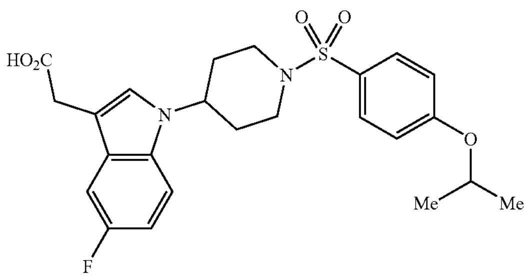 | (DMSO-d6) 1.33 (d, 6H, J = 4.0 Hz), 1.97-2.10 (m, 4H), 2.44-2.51 (m, 4H), 3.60 (s, 2H), 3.78 (d, 2H, J = 7 Hz), 4.42 (m, 1H), 4.75-4.79 (m, 1H), 6.89-6.95 (m, 1H), 7.65-7.19 (d, 2H, J = 6 Hz), 7.21-7.24 (m, 1H), 7.47-7.48 (m, 1H), 7.71 (d, 2H, J = 6 Hz) |
| I-15 | 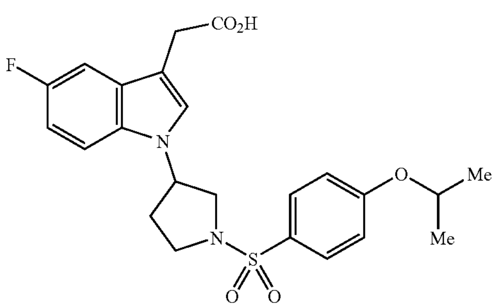 | (CDCl3) 1.39 (d, 6H, J = 4.0 Hz), 2.16-2.30 (m, 1H), 2.32-2.34 (m, 1H), 3.43-3.56 (m, 4H), 3.65-3.76 (m, 2H), 4.63-4.67 (m, 1H), 4.86-4.88 (m, 1H), 6.95 (m, 2H), 6.97 (d, 2 H, J = 6 Hz), 7.11-7.12 (1H, m), 7.12 (d, 1H, J = 8 Hz), 7.75 (d, 2H, J = 6 Hz) |
| I-16 | 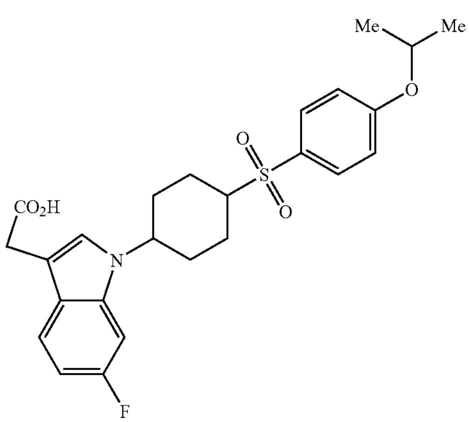 | (CDCl3) 1.40 (d, 6H, J = 4.0 Hz), 2.06-2.12 (m, 6H), 2.43-2.49 (m, 2H), 3.75 (s, 2H), 3.99 (d, 3H), J = 7 Hz), 4.64-4.68 (m, 1H), 6.89 (d, 2H, J = 7 Hz), 7.00 (d, 2H, J = 5 Hz), 7.09 (s, 1H), 7.47-7.51 (m, 1H), 7.72 (d, 2H, J = 5 Hz) |

TABLE 3-continued
| Compound No. | Structure | $^1$H-NMR δ ppm |
|---|---|---|
| I-17 | 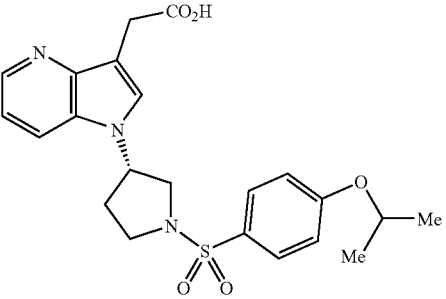 | (DMSO-d6) 1.32 (d, 6H, J = 6.0 Hz), 2.16 (m, 1H), 2.31 (m, 1H), 3.22-3.64 (m, 6H), 4.75 (m, 1H), 5.12 (m, 1H), 7.09-7.15 (m, 3H), 7.41 (s, 1H), 7.48 (d, 1H, J = 8.4 Hz), 7.73 (d, 2H, J = 9.0 Hz), 7.82 (dd, 2H, J = 8.1 Hz, 0.9 Hz), 8.32 (dd, 1H, J = 4.5 Hz) |
| I-18 | 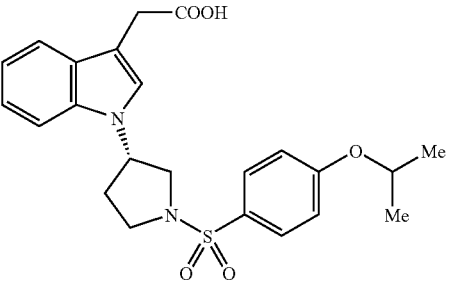 | (DMSO-d6) 1.32 (d, 6H, J = 5.7 Hz), 2.12 (m, 1H), 2.28 (m, 1H), 3.24-3.67 (m, 6H), 4.76 (m, 1H), 5.06 (m, 1H), 7.00-7.14 (m, 5H), 7.35 (d, 1H, J = 8.1 Hz), 7.38 (d, 1H, J = 7.8 Hz), 7.74 (d, 2H), 12.20 (br, 1H) |
TABLE 4
| Compound No. | Structure | $^1$H-NMR δ ppm |
|---|---|---|
| I-19 | 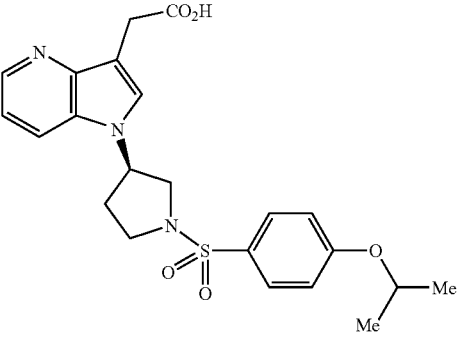 | (DMSO-d6) 1.32 (d, 6H, J = 6.0 Hz), 2.16 (m, 1H), 2.31 (m, 1H), 3.24-3.64 (m, 6H), 4.75 (m 1H), 5.12 (m, 1H), 7.09-7.15 (m, 3H), 7.41 (s, 1H), 7.72 (d, 2H, J = 8.7 Hz), 7.82 (dd, 1H, J = 8.4 Hz, 1.2 Hz), 8.32 (dd, 1H, J = 4.5 Hz). |
| I-20 | 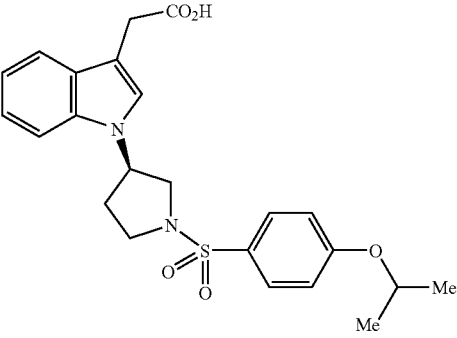 | (DMSO-d6) 1.32 (d, 6H, J = 6.0 Hz), 2.11 (m, 1H), 2.28 (m, 1H), 3.24-3.61 (m, 6H), 4.76 (m, 1H), 5.06 (m, 1H), 7.00-7.14 (m, 6H), 7.36 (d, 2H, J = 8.1 Hz), 7.48 (d, 1H, J = 7.5 Hz), 7.74 (d, 2H, J = 9.0 Hz). |

TABLE 4-continued

| Compound No. | Structure | $^1$H-NMR δ ppm |
|---|---|---|
| I-21 | 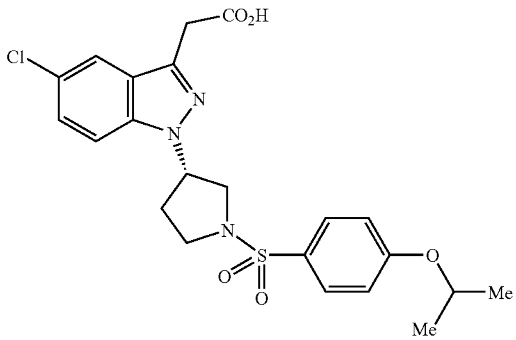 | (DMSO-d6) 1.32 (d, 6H, J = 6.0 Hz), 2.16-2.32 (m, 2H), 3.34-3.51 (m, 3H), 3.69 (dd, 1H, J = 10.5, 6.9 Hz), 3.78 (d, 2H), 4.73 (m, 1H), 5.35 (m, 1H), 7.06 (d, 2H), 7.39 (dd, 1 H, J = 8.7, 1.8 Hz), 7.64-7.68 (m, 3H), 7.75 (d, 1H), 12.53 (br, 1H). |
| I-22 | 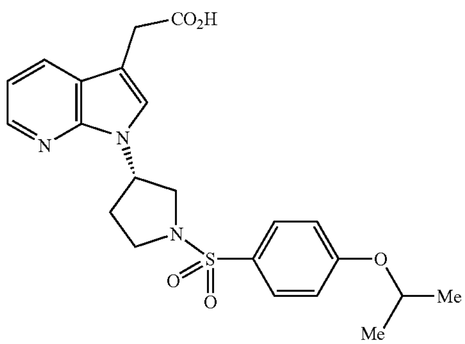 | (DMSO-d6) 1.32 (d, 6H, J = 6.0 Hz), 2.20-2.37 (m, 2H), 3.30-3.49 (m, 6H), 3.61 (s, 2H), 4.75 (m, 1H), 5.24 (m, 1H), 7.06-7.11 (m, 3H), 7.27 (s, 1H), 7.71 (d, 2H, J = 8.7 Hz), 7.91 (d, 1H, J = 8.1 Hz), 8.18 (d, 1H, 4.8 Hz), 12.31 (br, 1H). |
| I-23 | 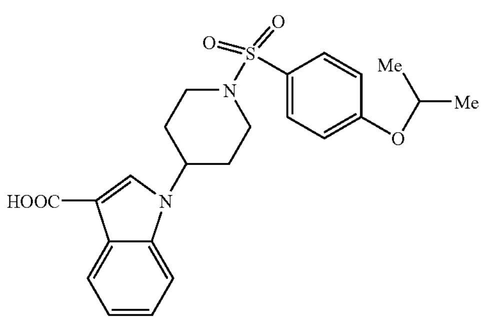 | (DMSO-d6) 1.10 (d, J = 4 Hz, 6H), 1.83-1.86 (m, 4H), 3.55 (m, 4H), 4.28 (m, 1H), 4.52-4.56 (m, 1H), 6.95 (d, J = 5.0 Hz, 4H), 7.36-7.39 (m, 1H), 7.48 (d, J = 5.0 Hz, 2H), 7.76-7.78 (m, 1H), 7.86 (s, 1H) |

TABLE 5

| Compound No. | Structure | $^1$H-NMR δ ppm |
|---|---|---|
| I-24 | 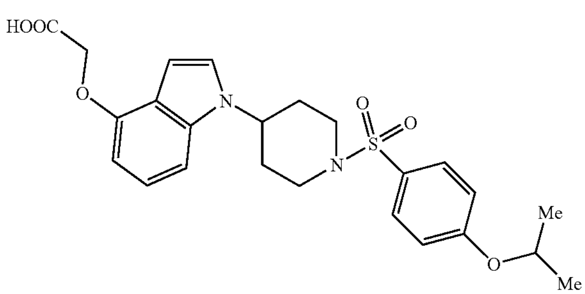 | (DMSO-d6) 1.33 (d, 6H, J = 6.0 Hz), 1.97-2.04 (m, 4H), 2.48-2.57 (m, 2H), 3.78 (d, 2 H, J = 10.8 Hz), 4.40 (m, 1H), 4.72 (s, 2H), 4.77 (m, 1H), 6.37 (d, 1H, J = 7.5 Hz), 6.46 (3, 1H, J = 3.0 Hz), 6.95 (dd, 1H, J = 8.4 Hz), 7.11 (d, 1H), 7.17 (d, 2H, J = 9.0 Hz), 7.38 (d, 1H, J = 3.3 Hz), 7.70 (d, 2H), 12.97 (br, 1 H). |

TABLE 5-continued

| Compound No. | Structure | $^1$H-NMR δ ppm |
|---|---|---|
| I-25 | 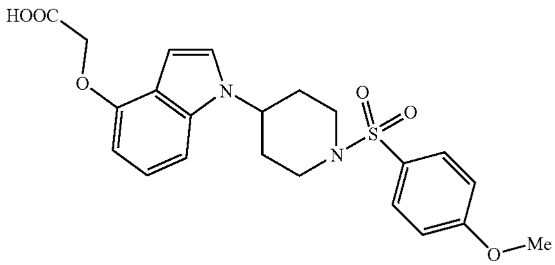 | (DMSO-d6) 1.98-2.05 (m, 4H), 2.44-2.51 (m, 2H), 3.79 (d, 2H, J = 11.7 Hz), 3.88 (s, 3H), 4.39 (m, 1H), 4.73 (s, 2H), 6.37 (d, 1 H, J = 7.5 Hz), 6.46 (3, 1H, J = 3.0 Hz), 6.95 (dd, 1H, J = 8.1 Hz), 7.10 (d, 1H), 7.21 (d, 2H, J = 9.0 Hz), 7.39 (d, 2H), 7.74 (d, 2H), 12.95 (br, 1H). |
| I-26 | 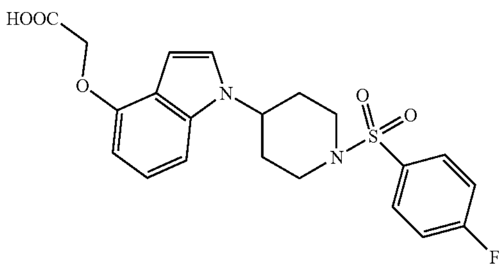 | (DMSO-d6) 1.97-2.04 (m, 4H), 2.49-2.57 (m, 2H), 3.82 (d, 2H, J = 12.0 Hz), 4.41 (m, 1H), 4.73 (s, 2H), 6.37 (d, 1H, J = 7.5 Hz), 6.46 (3, 1H, J = 3.3 Hz), 6.96 (dd, 1H, J = 8.1 Hz), 7.09 (d, 1H), 7.39 (d, 1H), 7.35 (dd, 2H, J = 9.0 Hz), 7.88 (dd, 1H), 12.98 (br, 1 H). |
| I-27 | 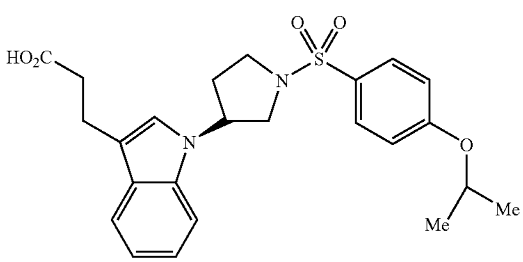 | (CDCl3) 1.39 (d, J = 4 Hz, 6H), 2.11-2.17 (m, 1H), 2.27-2.33 (m, 1H), 2.70 (t, J = 5 Hz, 2H), 3.03 (t, J = 5 Hz, 2H), 3.40-3.49 (m, 1H), 3.49-3.54 (m, 1H), 3.66-3.71 (m, 1H), 4.63-4.67 (m, 1H), 4.89-4.93 (m, 1H), 6.82 (s, 1H), 6.98 (d, J = 6 Hz, 2H), 7.1-7.13 (m, 1H), 7.20 (s, 2H), 7.57 (d, J = 5 Hz, 1H), 7.76 (d, J = 6 Hz, 2H) |
| I-28 | 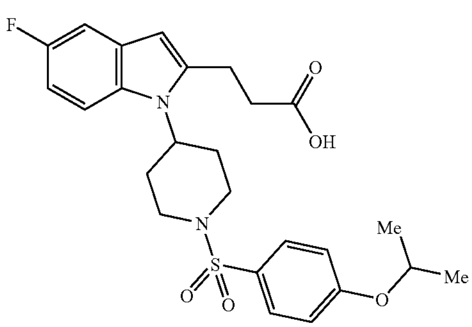 | (DMSO-d6) 1.34 (d, 6H, J = 6.0 Hz), 1.76 (d, 2H, J = 9.9 Hz), 2.34 (ddd, 2H), 2.58 (dd, 2H, J = 7.8 Hz), 2.67 (dd, 1H), 2.94 (dd, 2H), 3.86 (d, 2H, 11.4 Hz), 4.36 (m, 1H), 4.78 (m, 1H), 6.15 (s, 1H), 6.78 (ddd, 1H, J = 12.0, 9.3, 3.0 Hz), 7.18 (m, 4H), 7.75 (d, 2H, J = 9.0 Hz), 12.29 (br, 1H). |

TABLE 6

| Compound No. | Structure | ¹H-NMR δ ppm |
|---|---|---|
| I-29 | 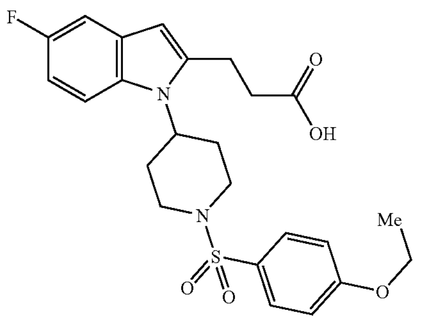 | (DMSO-d6) 1.39 (t, 6H, J = 6.9 Hz), 1.77 (d, 2H, J = 11.7 Hz), 2.34 (ddd, 2H), 2.58 (dd, 2H, J = 7.8 Hz), 2.65 (dd, 1H), 2.94 (dd, 2H), 3.86 (d, 2H, 11.4 Hz), 4.16 (dd, 2H), 4.35 (m, 1H), 6.15 (s, 1H), 6.78 (ddd, 1H, J = 12.0, 9.3, 3.0 Hz), 7.17-7.21 (m, 4H), 7.77 (d, 2H, J = 9.0 Hz), 12.25 (br, 1H). |
| I-30 | 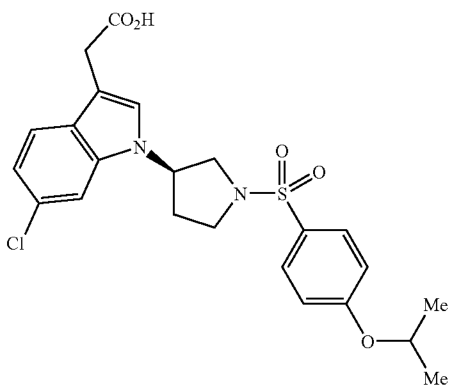 | (DMSO-d6) 1.32 (d, 6H, J = 6.0 Hz), 2.16-2.32 (m, 2H), 3.34-3.51 (m, 3H), 3.69 (dd, 1H, J = 10.5, 6.9 Hz), 3.78 (d, 2H), 4.73 (m, 1H), 5.35 (m, 1H), 7.06 (d, 2H), 7.39 (dd, 1H, J = 8.7, 1.8 Hz), 7.64-7.68 (m, 3H), 7.75 (d, 1H), 12.53 (br, 1). |
| I-31 | 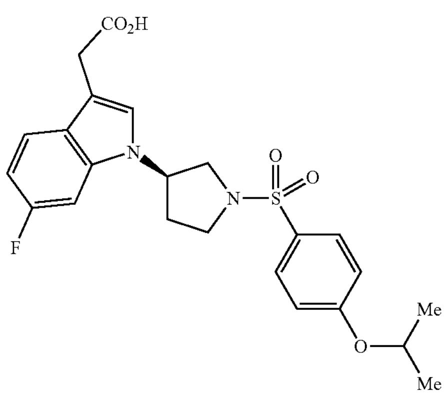 | (DMSO-d6) 1.32 (d, 6H, J = 6.0 hz), 2.03-2.35 (m, 2H), 3.22-3.56 (m, 6H), 4.75 (m, 1H), 5.03 (m, 1H), 6.89 (dd, 1H, J = 7.8 Hz), 7.10-7.13 (m, 3H), 7.28 (d, 1H, J = 8.7 Hz), 7.47 (dd, 1H), 7.74 (d, 2H, J = 8.4 Hz), 12.25 (br, 1H). |
| I-32 | 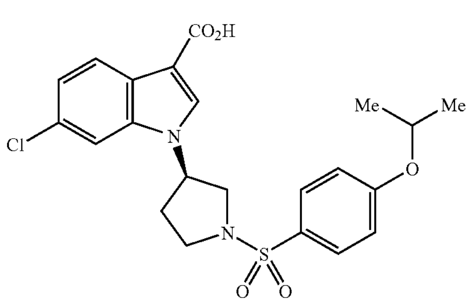 | (CDCl3-d6) 1.38 (d, 6H, J = 6.3 Hz), 2.25-2.49 (m, 2H), 3.45-3.60 (m, 3H), 3.75 (d, 1H, J = 10.8 Hz, 6.6 Hz), 4.65 (m, 1H), 4.89 (m, 1H), 6.96 (d, 2H, J = 9.0 Hz), 7.27-7.31 (m, 2H), 7.74 (d, 2H), 7.84 (s, 1H), 8.12 (d, 1H, J = 8.4 Hz) |

TABLE 6-continued

| Compound No. | Structure | $^1$H-NMR δ ppm |
|---|---|---|
| I-33 | 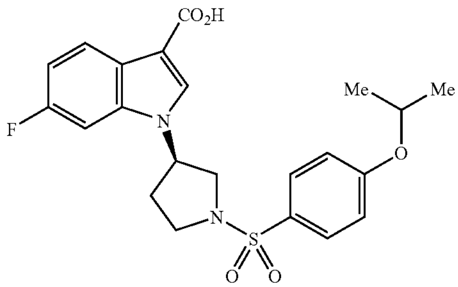 | (CDCl3-d6) 1.38 (d, 6H, J = 6.3 Hz), 2.25-2.50 (m, 2H), 3.45-3.63 (m, 3H), 3.75 (d, 1H, J = 11.1 Hz, 6.9 Hz), 4.65 (m, 1H), 4.86 (m, 1H), 6.94-7.10 (m, 4H), 7.74 (d, 2H, J = 6.9 Hz), 7.83 (s, 1H), 8.14 (dd, 1H, J = 9.0 Hz, 5.4 Hz). |

TABLE 7

| Compound No. | Structure | $^1$H-NMR δ ppm |
|---|---|---|
| I-34 | 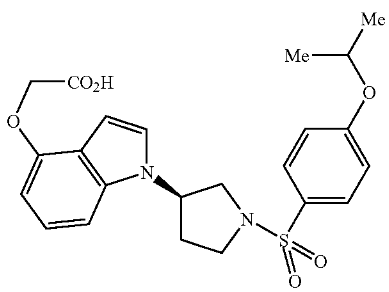 | (DMSO-d6) 1.32 (d, 6H, J = 6.0 Hz), 2.11-2.35 (m, 2H), 3.23-3.61 (m, 4H), 4.74-4.81 (m, 3H), 5.03 (m, 1H), 6.41 (m, 2H), 7.00 (m, 2H), 7.11-7.14 (m, 3H), 7.73 (d, 8.7 Hz). |
| I-35 | 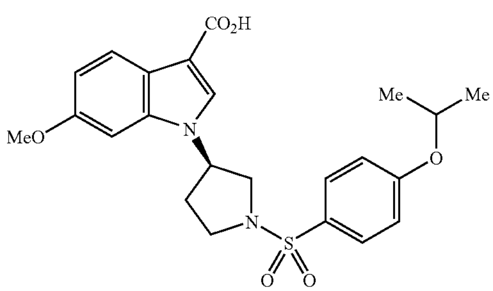 | (DMSO-d6) 1.32 (d, 6H, J = 6.0 Hz), 2.14-2.40 (m, 2H), 3.21-3.56 (m, 4H), 3.79 (s, 3H), 4.74 (m, 1H), 5.11 (m, 1H), 6.85 (dd, 1H, J = 9.0 Hz, 1.8 Hz), 7.08-7.11 (m, 3H), 7.72 (d, 2H, J = 9.0 Hz), 7.85 (d, 2H). |
| I-36 | 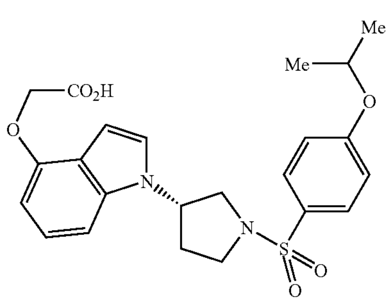 | (DMSO-d6) 1.32 (d, 6H, J = 6.0 Hz), 2.11-2.35 (m, 2H), 3.23-3.61 (m, 4H), 4.74-4.81 (m, 3H), 5.03 (m, 1H), 6.41 (m, 2H), 7.00 (m, 2H), 7.11-7.14 (m, 3H), 7.73 (d, 8.7 Hz). |

TABLE 7-continued
| Compound No. | Structure | $^1$H-NMR δ ppm |
|---|---|---|
| I-37 | 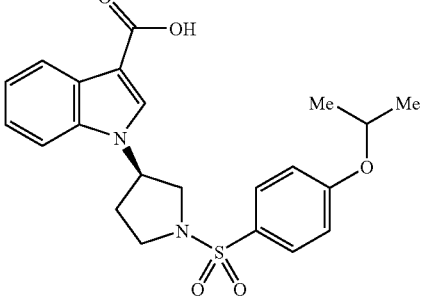 | (DMSO-d6) 1.32 (d, 6H, J = 6.0 Hz), 2.28-2.36 (m, 2H), 3.21-3.58 (m, 4H), 4.74 (m, 1H), 5.14 (m, 1H), 7.09 (d, 2H, J = 9.0 Hz), 7.22 (m, 2H), 7.49-7.52 (m, 1H), 7.71 (d, 2H), 7.97 (s, 1H), 8.01-8.03 (m, 1H). |
Further, compounds of Tables 8-12 are prepared in the same manner as described above.
TABLE 8
| Compound No. | Structure |
|---|---|
| II-1 | 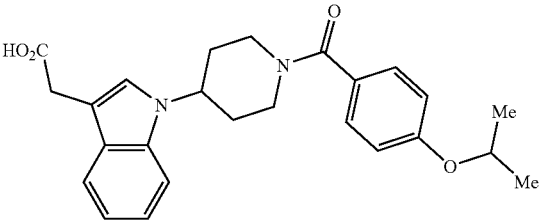 |
| II-2 | 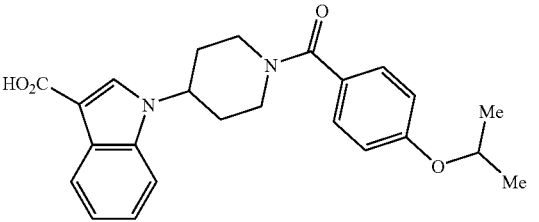 |
| II-3 | 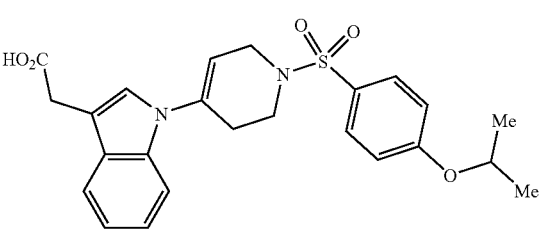 |
| II-4 | 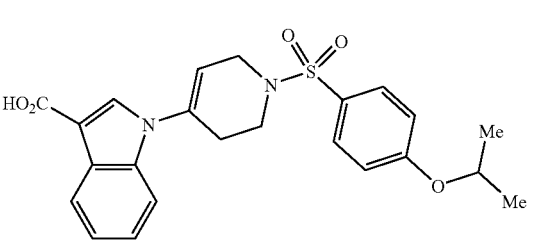 |

TABLE 8-continued
| Compound No. | Structure |
|---|---|
| II-5 | 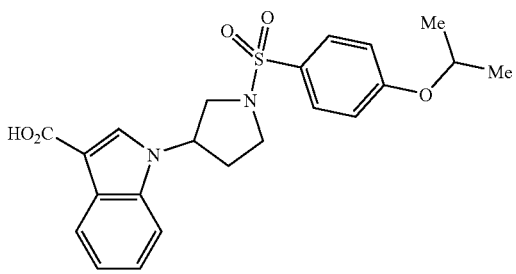 |
| II-6 | 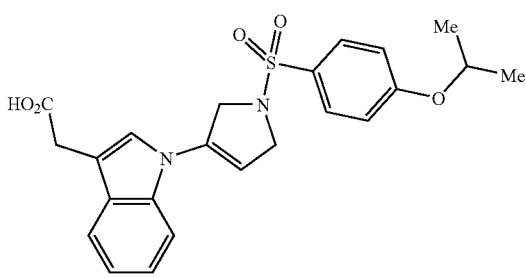 |
TABLE 9
| 化合物番号 | 構造 |
|---|---|
| II-7 | 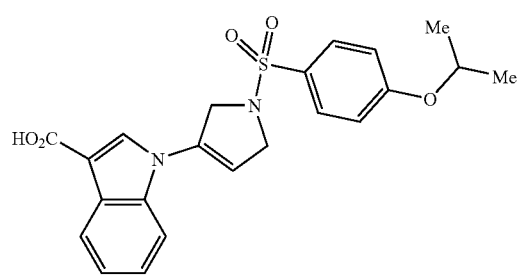 |
| II-8 | 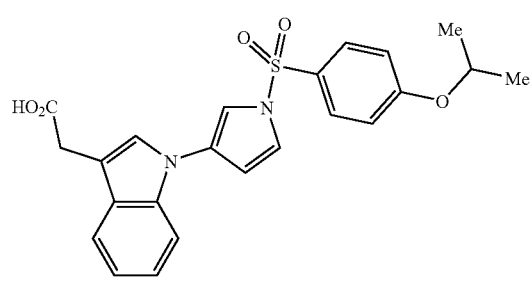 |
| II-9 | 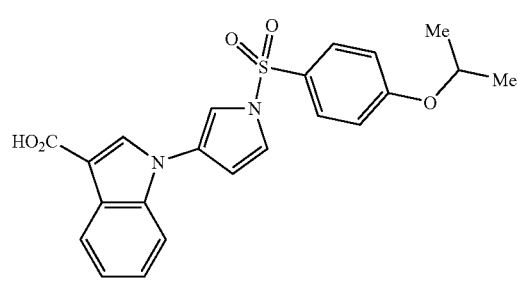 |

TABLE 9-continued
| 化合物番号 | 構造 |
|---|---|
| II-10 | 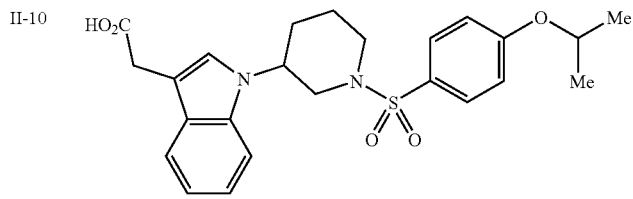 |
| II-11 | 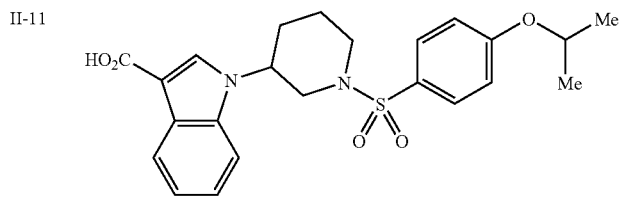 |
| II-12 | 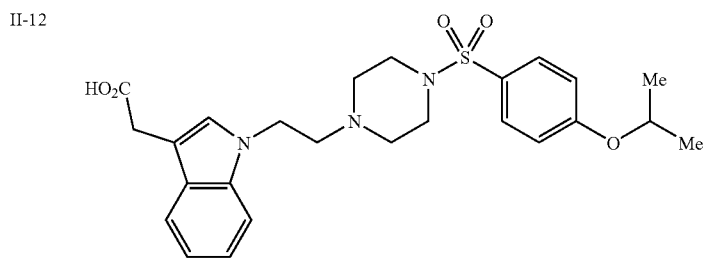 |
TABLE 10
| Compound No. | Structure |
|---|---|
| II-13 | 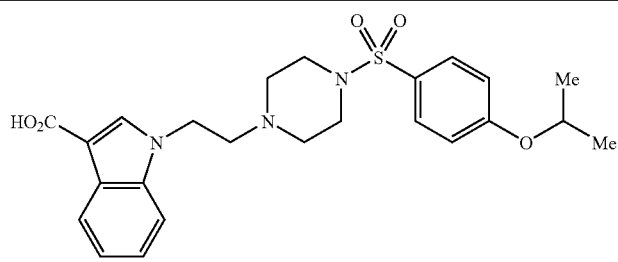 |
| II-14 | 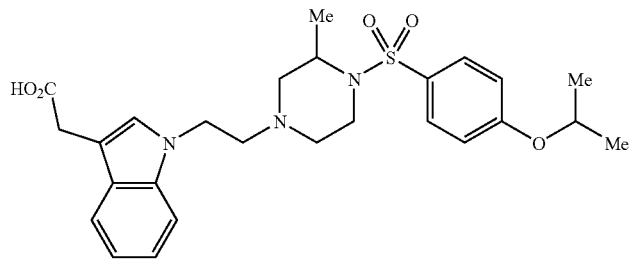 |
| II-15 | 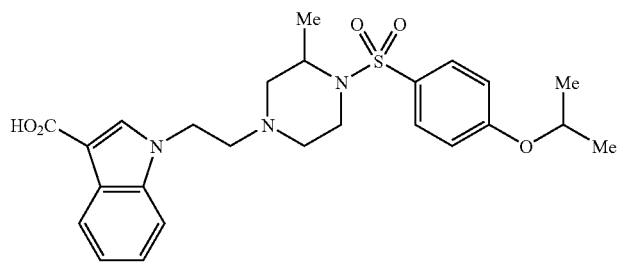 |

TABLE 10-continued
| Compound No. | Structure |
|---|---|
| II-16 | 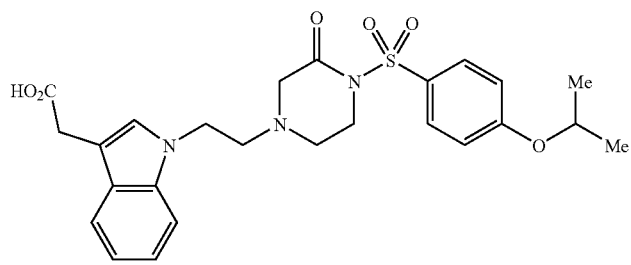 |
| II-17 | 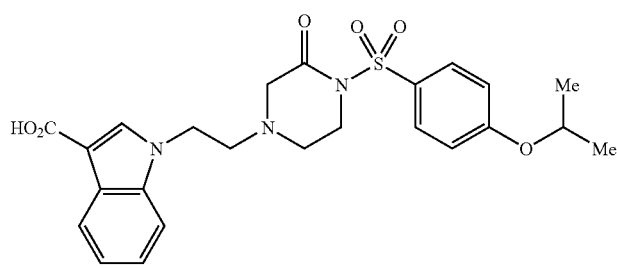 |
| II-18 | 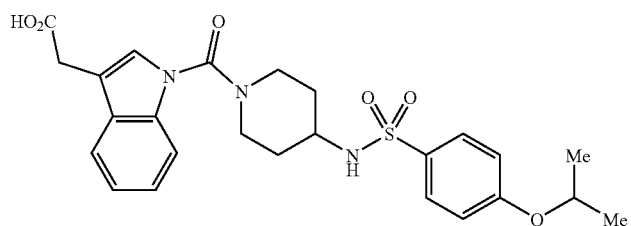 |
TABLE 11
| Compound No. | Structure |
|---|---|
| II-19 | 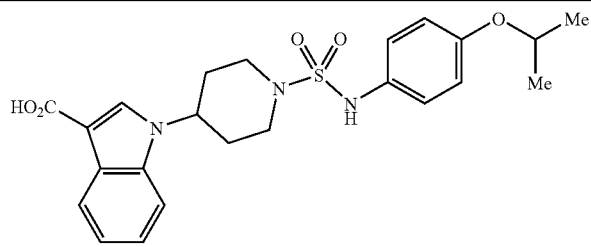 |
| II-20 | 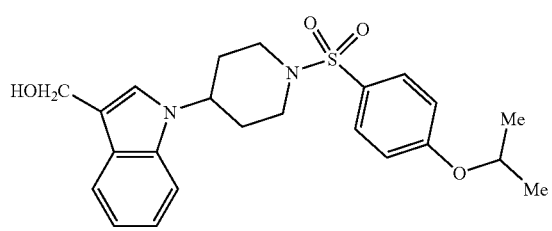 |
| II-21 | 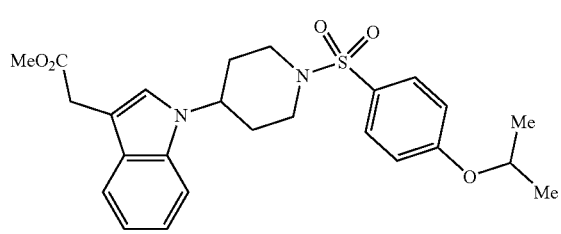 |

TABLE 11-continued
| Compound No. | Structure |
|---|---|
| II-22 | 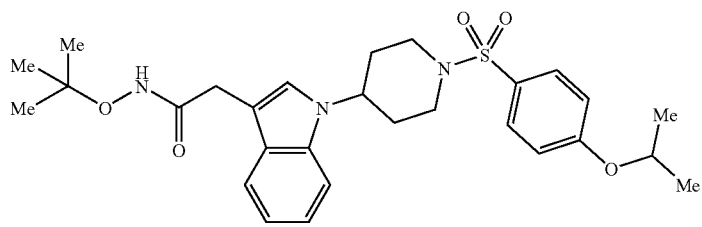 |
| II-23 | 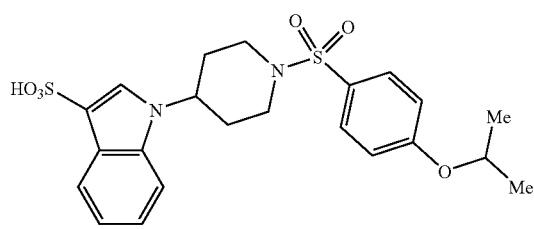 |
| II-24 | 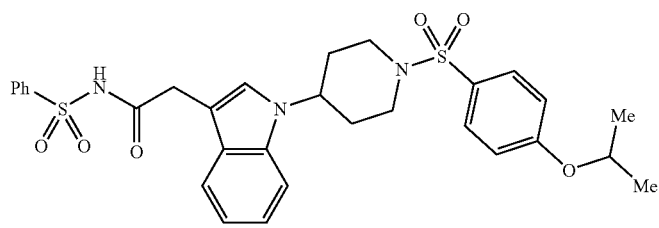 |
TABLE 12
| Compound No. | Structure |
|---|---|
| II-25 | 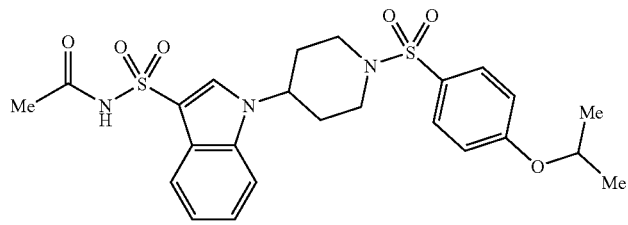 |
| II-26 | 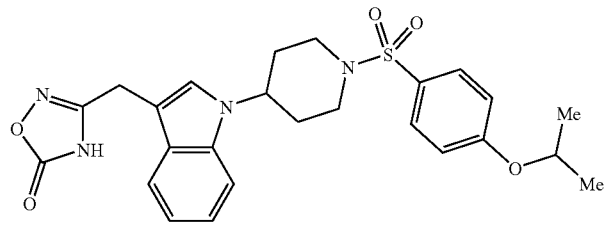 |
| II-27 | 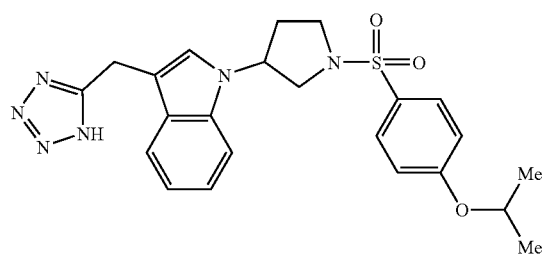 |

TABLE 12-continued

| Compound No. | Structure |
|---|---|
| II-28 | 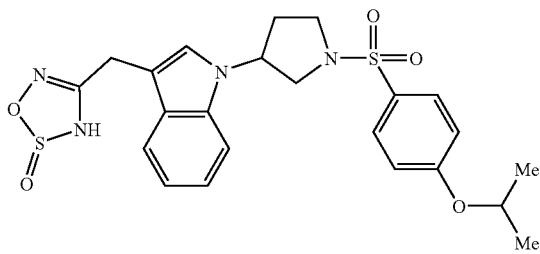 |
| II-29 | 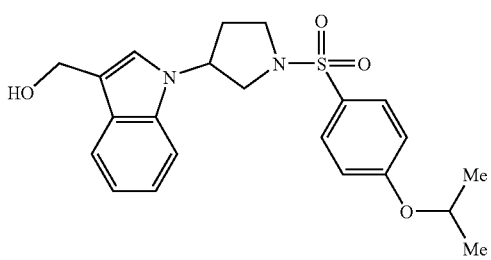 |
| II-30 | 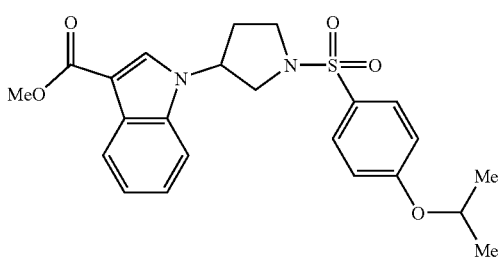 |

Further, a compound of the formula below

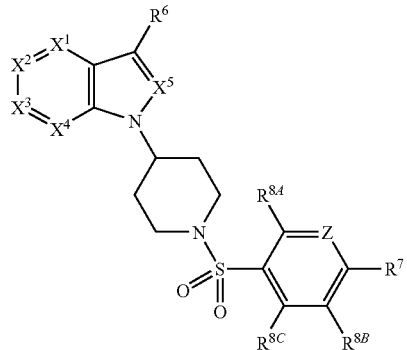

(IA)

wherein -$X^1$=$X^2$-$X^3$=$X^4$- is —C($R^1$)=C($R^2$)—C($R^3$)=C($R^4$)—, —N=C($R^2$)—C($R^3$)=C($R^4$)—, —C($R^1$)=N—C($R^3$)=C($R^4$)—, —C($R^1$)=C($R^2$)—N=C($R^4$)— or —C($R^1$)=C($R^2$)—C($R^3$)=N—;

$X^5$ is —N= or —C($R^5$)=;

$R^1$, $R^2$, $R^3$, $R^4$, $R^5$ and $R^6$ are independently a hydrogen atom, a fluorine atom, a chlorine atom, a bromine atom, methyl, trifluoromethyl, methyloxy, difluoromethyloxy, N-methylamino, methylcarbonylamino, cyano, nitro, phenyl, 2-pyridyl, 2-furyl, 1,3-oxazol-2-yl, morpholino, N-methylcarbamoyl, carboxy, carboxymethyl or carboxymethyloxy;

Z is =N— or =C($R^{8D}$)—;

$R^7$ is independently methyloxy, ethyloxy, propyloxy, isopropyloxy, n-butyloxy, isopropyloxy, s-butyloxy, difluoromethyloxy, benzyloxy, phenoxy, methylthio, ethylthio, isopropylthio, s-butylthio, difluoromethylthio, benzylthio or phenylthio; and $R^{8A}$, $R^{8B}$, $R^{8C}$ and $R^{8D}$ are independently a hydrogen atom, a fluorine atom, a chlorine atom, a bromine atom or methyl, is prepared in the same manner as described above.

A combination of -$X^1$=$X^2$-$X^3$=$X^4$-, $X^5$ and $R^6$ (part A) is shown in Tables 13-31. A combination of $R^{8A}$, Z, $R^{8B}$, and $R^{8C}$ (part B) is shown in Tables 32-40.

TABLE 13

| No. | X1 | X2 | X3 | X4 | X5 | R6 |
|---|---|---|---|---|---|---|
| S-1 | C—COOH | CH | CH | CH | CH | H |
| S-2 | CH | C—COOH | CH | CH | CH | H |
| S-3 | CH | CH | C—COOH | CH | CH | H |
| S-4 | CH | CH | CH | C—COOH | CH | H |
| S-5 | CH | CH | CH | CH | C—COOH | H |

TABLE 13-continued

| No. | X1 | X2 | X3 | X4 | X5 | R6 |
|---|---|---|---|---|---|---|
| S-6 | CH | CH | CH | CH | CH | COOH |
| S-7 | CH | CH | CH | CH | N | COOH |
| S-8 | C—COOH | C—Cl | CH | CH | CH | H |
| S-9 | CH | C—COOH | C—Cl | CH | CH | H |
| S-10 | CH | CH | C—COOH | C—Cl | CH | H |
| S-11 | CH | CH | CH | C—COOH | C—Cl | H |
| S-12 | CH | CH | CH | CH | C—COOH | Cl |
| S-13 | C—Cl | CH | CH | CH | CH | COOH |
| S-14 | CH | C—Cl | CH | CH | CH | COOH |
| S-15 | CH | CH | C—Cl | CH | CH | COOH |
| S-16 | CH | CH | C—Cl | CH | N | COOH |
| S-17 | CH | CH | CH | C—Cl | CH | COOH |
| S-18 | CH | CH | CH | CH | C—Cl | COOH |
| S-19 | C—COOH | C—Me | CH | CH | CH | H |
| S-20 | CH | C—COOH | C—Me | CH | CH | H |
| S-21 | CH | CH | C—COOH | C—Me | CH | H |
| S-22 | CH | CH | CH | C—COOH | C—Me | H |
| S-23 | CH | CH | CH | CH | C—COOH | Me |
| S-24 | C—Me | CH | CH | CH | CH | COOH |
| S-25 | CH | C—Me | CH | CH | CH | COOH |
| S-26 | CH | CH | C—Me | CH | CH | COOH |
| S-27 | CH | CH | C—Me | CH | N | COOH |
| S-28 | CH | CH | CH | C—Me | CH | COOH |
| S-29 | CH | CH | CH | CH | C—Me | COOH |
| S-30 | C—COOH | C—CF3 | CH | CH | CH | H |
| S-31 | CH | C—COOH | C—CF3 | CH | CH | H |

TABLE 14

| No. | X1 | X2 | X3 | X4 | X5 | R6 |
|---|---|---|---|---|---|---|
| S-32 | CH | CH | C—COOH | C—CF3 | CH | H |
| S-33 | CH | CH | CH | C—COOH | C—CF3 | H |
| S-34 | CH | CH | CH | CH | C—COOH | CF3 |
| S-35 | C—CF3 | CH | CH | CH | CH | COOH |
| S-36 | CH | C—CF3 | CH | CH | CH | COOH |
| S-37 | CH | CH | C—CF3 | CH | CH | COOH |
| S-38 | CH | CH | C—CF3 | CH | N | COOH |
| S-39 | CH | CH | CH | C—CF3 | CH | COOH |
| S-40 | CH | CH | CH | CH | C—CF3 | COOH |
| S-41 | C—COOH | C—OMe | CH | CH | CH | H |
| S-42 | CH | C—COOH | C—OMe | CH | CH | H |
| S-43 | CH | CH | C—COOH | C—OMe | CH | H |
| S-44 | CH | CH | CH | C—COOH | C—OMe | H |
| S-45 | CH | CH | CH | CH | C—COOH | OMe |
| S-46 | C—OMe | CH | CH | CH | CH | COOH |
| S-47 | CH | C—OMe | CH | CH | CH | COOH |
| S-48 | CH | CH | C—OMe | CH | CH | COOH |
| S-49 | CH | CH | C—OMe | CH | N | COOH |
| S-50 | CH | CH | CH | C—OMe | CH | COOH |
| S-51 | CH | CH | CH | CH | C—OMe | COOH |
| S-52 | C—COOH | C—OCHF2 | CH | CH | CH | H |
| S-53 | CH | C—COOH | C—OCHF2 | CH | CH | H |
| S-54 | CH | CH | C—COOH | C—OCHF2 | CH | H |
| S-55 | CH | CH | CH | C—COOH | C—OCHF2 | H |
| S-56 | CH | CH | CH | CH | C—COOH | OCHF2 |
| S-57 | C—OCHF2 | CH | CH | CH | CH | COOH |
| S-58 | CH | C—OCHF2 | CH | CH | CH | COOH |
| S-59 | CH | CH | C—OCHF2 | CH | CH | COOH |
| S-60 | CH | CH | C—OCHF2 | CH | N | COOH |
| S-61 | CH | CH | CH | C—OCHF2 | CH | COOH |
| S-62 | CH | CH | CH | CH | C—OCHF2 | COOH |

TABLE 15

| No. | X1 | X2 | X3 | X4 | X5 | R6 |
|---|---|---|---|---|---|---|
| S-63 | C—COOH | C—SMe | CH | CH | CH | H |
| S-64 | CH | C—COOH | C—SMe | CH | CH | H |
| S-65 | CH | CH | C—COOH | C—SMe | CH | H |
| S-66 | CH | CH | CH | C—COOH | C—SMe | H |
| S-67 | CH | CH | CH | CH | C—COOH | SMe |
| S-68 | C—SMe | CH | CH | CH | CH | COOH |
| S-69 | CH | C—SMe | CH | CH | CH | COOH |
| S-70 | CH | CH | C—SMe | CH | CH | COOH |
| S-71 | CH | CH | C—SMe | CH | N | COOH |
| S-72 | CH | CH | CH | C—SMe | CH | COOH |
| S-73 | CH | CH | CH | CH | C—SMe | COOH |
| S-74 | C—COOH | C—SO2Me | CH | CH | CH | H |
| S-75 | CH | C—COOH | C—SO2Me | CH | CH | H |
| S-76 | CH | CH | C—COOH | C—SO2Me | CH | H |
| S-77 | CH | CH | CH | C—COOH | C—SO2Me | H |
| S-78 | CH | CH | CH | CH | C—COOH | SO2Me |
| S-79 | C—SO2Me | CH | CH | CH | CH | COOH |
| S-80 | CH | C—SO2Me | CH | CH | CH | COOH |
| S-81 | CH | CH | C—SO2Me | CH | CH | COOH |
| S-82 | CH | CH | C—SO2Me | CH | N | COOH |
| S-83 | CH | CH | CH | C—SO2Me | CH | COOH |
| S-84 | CH | CH | CH | CH | C—SO2Me | COOH |
| S-85 | C—COOH | C—NHMe | CH | CH | CH | H |
| S-86 | CH | C—COOH | C—NHMe | CH | CH | H |
| S-87 | CH | CH | C—COOH | C—NHMe | CH | H |
| S-88 | CH | CH | CH | C—COOH | C—NHMe | H |
| S-89 | CH | CH | CH | CH | C—COOH | NHMe |
| S-90 | C—NHMe | CH | CH | CH | CH | COOH |
| S-91 | CH | C—NHMe | CH | CH | CH | COOH |
| S-92 | CH | CH | C—NHMe | CH | CH | COOH |
| S-93 | CH | CH | C—NHMe | CH | N | COOH |

TABLE 16

| No. | X1 | X2 | X3 | X4 | X5 | R6 |
|---|---|---|---|---|---|---|
| S-94 | CH | CH | CH | C—NHMe | CH | COOH |
| S-95 | CH | CH | CH | CH | C—NHMe | COOH |
| S-96 | C—COOH | C—NHCOMe | CH | CH | CH | H |
| S-97 | CH | C—COOH | C—NHCOMe | CH | CH | H |
| S-98 | CH | CH | C—COOH | C—NHCOMe | CH | H |
| S-99 | CH | CH | CH | C—COOH | C—NHCOMe | H |
| S-100 | CH | CH | CH | CH | C—COOH | NHCOMe |
| S-101 | C—NHCOMe | CH | CH | CH | CH | COOH |
| S-102 | CH | C—NHCOMe | CH | CH | CH | COOH |
| S-103 | CH | CH | C—NHCOMe | CH | CH | COOH |
| S-104 | CH | CH | C—NHCOMe | CH | N | COOH |
| S-105 | CH | CH | CH | C—NHCOMe | CH | COOH |
| S-106 | CH | CH | CH | CH | C—NHCOMe | COOH |
| S-107 | C—COOH | C—CN | CH | CH | CH | H |
| S-108 | CH | C—COOH | C—CN | CH | CH | H |
| S-109 | CH | CH | C—COOH | C—CN | CH | H |
| S-110 | CH | CH | CH | C—COOH | C—CN | H |
| S-111 | CH | CH | CH | CH | C—COOH | CN |
| S-112 | C—CN | CH | CH | CH | CH | COOH |
| S-113 | CH | C—CN | CH | CH | CH | COOH |
| S-114 | CH | CH | C—CN | CH | CH | COOH |
| S-115 | CH | CH | C—CN | CH | N | COOH |
| S-116 | CH | CH | CH | C—CN | CH | COOH |
| S-117 | CH | CH | CH | CH | C—CN | COOH |
| S-118 | C—COOH | C—NO2 | CH | CH | CH | H |
| S-119 | CH | C—COOH | C—NO2 | CH | CH | H |
| S-120 | CH | CH | C—COOH | C—NO2 | CH | H |
| S-121 | CH | CH | CH | C—COOH | C—NO2 | H |
| S-122 | CH | CH | CH | CH | C—COOH | NO2 |
| S-123 | C—NO2 | CH | CH | CH | CH | COOH |
| S-124 | CH | C—NO2 | CH | CH | CH | COOH |

TABLE 17

| No. | X1 | X2 | X3 | X4 | X5 | R6 |
|---|---|---|---|---|---|---|
| S-125 | CH | CH | C—NO2 | CH | CH | COOH |
| S-126 | CH | CH | C—NO2 | CH | N | COOH |
| S-127 | CH | CH | CH | C—NO2 | CH | COOH |
| S-128 | CH | CH | CH | CH | C—NO2 | COOH |
| S-129 | C—COOH | C—Ph | CH | CH | CH | H |
| S-130 | CH | C—COOH | C—Ph | CH | CH | H |
| S-131 | CH | CH | C—COOH | C—Ph | CH | H |
| S-132 | CH | CH | CH | C—COOH | C—Ph | H |
| S-133 | CH | CH | CH | CH | C—COOH | Ph |
| S-134 | C—Ph | CH | CH | CH | CH | COOH |
| S-135 | CH | C—Ph | CH | CH | CH | COOH |
| S-136 | CH | CH | C—Ph | CH | CH | COOH |
| S-137 | CH | CH | C—Ph | CH | N | COOH |
| S-138 | CH | CH | CH | C—Ph | CH | COOH |
| S-139 | CH | CH | CH | CH | C—Ph | COOH |
| S-140 | C—COOH | C-2-pyridyl | CH | CH | CH | H |
| S-141 | CH | C—COOH | C-2-pyridyl | CH | CH | H |
| S-142 | CH | CH | C—COOH | C-2-pyridyl | CH | H |
| S-143 | CH | CH | CH | C—COOH | C-2-pyridyl | H |
| S-144 | CH | CH | CH | CH | C—COOH | 2-pyridyl |
| S-145 | C-2-pyridyl | CH | CH | CH | CH | COOH |
| S-146 | CH | C-2-pyridyl | CH | CH | CH | COOH |
| S-147 | CH | CH | C-2-pyridyl | CH | CH | COOH |
| S-148 | CH | CH | C-2-pyridyl | CH | N | COOH |
| S-149 | CH | CH | CH | C-2-pyridyl | CH | COOH |
| S-150 | CH | CH | CH | CH | C-2-pyridyl | COOH |
| S-151 | C—COOH | C-2-furyl | CH | CH | CH | H |
| S-152 | CH | C—COOH | C-2-furyl | CH | CH | H |
| S-153 | CH | CH | C—COOH | C-2-furyl | CH | H |
| S-154 | CH | CH | CH | C—COOH | C-2-furyl | H |
| S-155 | CH | CH | CH | CH | C—COOH | 2-furyl |

TABLE 18

| No. | X1 | X2 | X3 | X4 | X5 | R6 |
|---|---|---|---|---|---|---|
| S-156 | C-2-furyl | CH | CH | CH | CH | COOH |
| S-157 | CH | C-2-furyl | CH | CH | CH | COOH |
| S-158 | CH | CH | C-2-furyl | CH | CH | COOH |
| S-159 | CH | CH | C-2-furyl | CH | N | COOH |
| S-160 | CH | CH | CH | C-2-furyl | CH | COOH |
| S-161 | CH | CH | CH | CH | C-2-furyl | COOH |
| S-162 | C—COOH | C-1,3-oxazol-2-yl | CH | CH | CH | H |
| S-163 | CH | C—COOH | C-1,3-oxazol-2-yl | CH | CH | H |
| S-164 | CH | CH | C—COOH | C-1,3-oxazol-2-yl | CH | H |
| S-165 | CH | CH | CH | C—COOH | C-1,3-oxazol-2-yl | H |
| S-166 | CH | CH | CH | CH | C—COOH | C-1,3-oxazol-2-yl |
| S-167 | C-1,3-oxazol-2-yl | CH | CH | CH | CH | COOH |
| S-168 | CH | C-1,3-oxazol-2-yl | CH | CH | CH | COOH |
| S-169 | CH | CH | C-1,3-oxazol-2-yl | CH | CH | COOH |
| S-170 | CH | CH | C-1,3-oxazol-2-yl | CH | N | COOH |
| S-171 | CH | CH | CH | C-1,3-oxazol-2-yl | CH | COOH |
| S-172 | CH | CH | CH | CH | C-1,3-oxazol-2-yl | COOH |
| S-173 | C—COOH | C-morpholino | CH | CH | CH | H |
| S-174 | CH | C—COOH | C-morpholino | CH | CH | H |
| S-175 | CH | CH | C—COOH | C-morpholino | CH | H |
| S-176 | CH | CH | CH | C—COOH | C-morpholino | H |
| S-177 | CH | CH | CH | CH | C—COOH | morpholino |
| S-178 | C-morpholino | CH | CH | CH | CH | COOH |
| S-179 | CH | C-morpholino | CH | CH | CH | COOH |
| S-180 | CH | CH | C-morpholino | CH | CH | COOH |
| S-181 | CH | CH | C-morpholino | CH | N | COOH |
| S-182 | CH | CH | CH | C-morpholino | CH | COOH |
| S-183 | CH | CH | CH | CH | C-morpholino | COOH |
| S-184 | C—COOH | C—CONHMe | CH | CH | CH | H |
| S-185 | CH | C—COOH | C—CONHMe | CH | CH | H |
| S-186 | CH | CH | C—COOH | C—CONHMe | CH | H |

TABLE 19

| No. | X1 | X2 | X3 | X4 | X5 | R6 |
|---|---|---|---|---|---|---|
| S-187 | CH | CH | CH | C—COOH | C—CONHMe | H |
| S-188 | CH | CH | CH | CH | C—COOH | CONHMe |
| S-189 | C—CONHMe | CH | CH | CH | CH | COOH |
| S-190 | CH | C—CONHMe | CH | CH | CH | COOH |
| S-191 | CH | CH | C—CONHMe | CH | CH | COOH |
| S-192 | CH | CH | C—CONHMe | CH | N | COOH |
| S-193 | CH | CH | CH | C—CONHMe | CH | COOH |
| S-194 | CH | CH | CH | CH | C—CONHMe | COOH |
| S-195 | C—CH2COOH | CH | CH | CH | CH | H |
| S-196 | CH | C—CH2COOH | CH | CH | CH | H |
| S-197 | CH | CH | C—CH2COOH | CH | CH | H |
| S-198 | CH | CH | CH | C—CH2COOH | CH | H |
| S-199 | CH | CH | CH | CH | C—CH2COOH | H |
| S-200 | CH | CH | CH | CH | CH | CH2COOH |
| S-201 | CH | CH | CH | CH | N | CH2COOH |
| S-202 | C—CH2COOH | C—Cl | CH | CH | CH | H |
| S-203 | CH | C—CH2COOH | C—Cl | CH | CH | H |
| S-204 | CH | CH | C—CH2COOH | C—Cl | CH | H |
| S-205 | CH | CH | CH | C—CH2COOH | C—Cl | H |
| S-206 | CH | CH | CH | CH | C—CH2COOH | Cl |
| S-207 | C—Cl | CH | CH | CH | CH | CH2COOH |
| S-208 | CH | C—Cl | CH | CH | CH | CH2COOH |
| S-209 | CH | CH | C—Cl | CH | CH | CH2COOH |
| S-210 | CH | CH | C—Cl | CH | N | CH2COOH |
| S-211 | CH | CH | CH | C—Cl | CH | CH2COOH |
| S-212 | CH | CH | CH | CH | C—Cl | CH2COOH |
| S-213 | C—CH2COOH | C—Me | CH | CH | CH | H |
| S-214 | CH | C—CH2COOH | C—Me | CH | CH | H |
| S-215 | CH | CH | C—CH2COOH | C—Me | CH | H |
| S-216 | CH | CH | CH | C—CH2COOH | C—Me | H |
| S-217 | CH | CH | CH | CH | C—CH2COOH | Me |

TABLE 20

| No. | X1 | X2 | X3 | X4 | X5 | R6 |
|---|---|---|---|---|---|---|
| S-218 | C—Me | CH | CH | CH | CH | CH2COOH |
| S-219 | CH | C—Me | CH | CH | CH | CH2COOH |
| S-220 | CH | CH | C—Me | CH | CH | CH2COOH |
| S-221 | CH | CH | C—Me | CH | N | CH2COOH |
| S-222 | CH | CH | CH | C—Me | CH | CH2COOH |
| S-223 | CH | CH | CH | CH | C—Me | CH2COOH |
| S-224 | C—CH2COOH | C—CF3 | CH | CH | CH | H |
| S-225 | CH | C—CH2COOH | C—CF3 | CH | CH | H |
| S-226 | CH | CH | C—CH2COOH | C—CF3 | CH | H |
| S-227 | CH | CH | CH | C—CH2COOH | C—CF3 | H |
| S-228 | CH | CH | CH | CH | C—CH2COOH | CF3 |
| S-229 | C—CF3 | CH | CH | CH | CH | CH2COOH |
| S-230 | CH | C—CF3 | CH | CH | CH | CH2COOH |
| S-231 | CH | CH | C—CF3 | CH | CH | CH2COOH |
| S-232 | CH | CH | C—CF3 | CH | N | CH2COOH |
| S-233 | CH | CH | CH | C—CF3 | CH | CH2COOH |
| S-234 | CH | CH | CH | CH | C—CF3 | CH2COOH |
| S-235 | C—CH2COOH | C—OMe | CH | CH | CH | H |
| S-236 | CH | C—CH2COOH | C—OMe | CH | CH | H |
| S-237 | CH | CH | C—CH2COOH | C—OMe | CH | H |
| S-238 | CH | CH | CH | C—CH2COOH | C—OMe | H |
| S-239 | CH | CH | CH | CH | C—CH2COOH | OMe |
| S-240 | C—OMe | CH | CH | CH | CH | CH2COOH |
| S-241 | CH | C—OMe | CH | CH | CH | CH2COOH |
| S-242 | CH | CH | C—OMe | CH | CH | CH2COOH |
| S-243 | CH | CH | C—OMe | CH | N | CH2COOH |
| S-244 | CH | CH | CH | C—OMe | CH | CH2COOH |
| S-245 | CH | CH | CH | CH | C—OMe | CH2COOH |
| S-246 | C—CH2COOH | C—OCHF2 | CH | CH | CH | H |
| S-247 | CH | C—CH2COOH | C—OCHF2 | CH | CH | H |
| S-248 | CH | CH | C—CH2COOH | C—OCHF2 | CH | H |

TABLE 21

| No. | X1 | X2 | X3 | X4 | X5 | R6 |
|---|---|---|---|---|---|---|
| S-249 | CH | CH | CH | C—CH2COOH | C—OCHF2 | H |
| S-250 | CH | CH | CH | CH | C—CH2COOH | OCHF2 |
| S-251 | C—OCHF2 | CH | CH | CH | CH | CH2COOH |
| S-252 | CH | C—OCHF2 | CH | CH | CH | CH2COOH |
| S-253 | CH | CH | C—OCHF2 | CH | CH | CH2COOH |
| S-254 | CH | CH | C—OCHF2 | CH | N | CH2COOH |
| S-255 | CH | CH | CH | C—OCHF2 | CH | CH2COOH |
| S-256 | CH | CH | CH | CH | C—OCHF2 | CH2COOH |
| S-257 | C—CH2COOH | C—SMe | CH | CH | CH | H |
| S-258 | CH | C—CH2COOH | C—SMe | CH | CH | H |
| S-259 | CH | CH | C—CH2COOH | C—SMe | CH | H |
| S-260 | CH | CH | CH | C—CH2COOH | C—SMe | H |
| S-261 | CH | CH | CH | CH | C—CH2COOH | SMe |
| S-262 | C—SMe | CH | CH | CH | CH | CH2COOH |
| S-263 | CH | C—SMe | CH | CH | CH | CH2COOH |
| S-264 | CH | CH | C—SMe | CH | CH | CH2COOH |
| S-265 | CH | CH | C—SMe | CH | N | CH2COOH |
| S-266 | CH | CH | CH | C—SMe | CH | CH2COOH |
| S-267 | CH | CH | CH | CH | C—SMe | CH2COOH |
| S-268 | C—CH2COOH | C—SO2Me | CH | CH | CH | H |
| S-269 | CH | C—CH2COOH | C—SO2Me | CH | CH | H |
| S-270 | CH | CH | C—CH2COOH | C—SO2Me | CH | H |
| S-271 | CH | CH | CH | C—CH2COOH | C—SO2Me | H |
| S-272 | CH | CH | CH | CH | C—CH2COOH | SO2Me |
| S-273 | C—SO2Me | CH | CH | CH | CH | CH2COOH |
| S-274 | CH | C—SO2Me | CH | CH | CH | CH2COOH |
| S-275 | CH | CH | C—SO2Me | CH | CH | CH2COOH |
| S-276 | CH | CH | C—SO2Me | CH | N | CH2COOH |
| S-277 | CH | CH | CH | C—SO2Me | CH | CH2COOH |
| S-278 | CH | CH | CH | CH | C—SO2Me | CH2COOH |
| S-279 | C—CH2COOH | C—NHMe | CH | CH | CH | H |

TABLE 22

| No. | X1 | X2 | X3 | X4 | X5 | R6 |
|---|---|---|---|---|---|---|
| S-280 | CH | C—CH2COOH | C—NHMe | CH | CH | H |
| S-281 | CH | CH | C—CH2COOH | C—NHMe | CH | H |
| S-282 | CH | CH | CH | C—CH2COOH | C—NHMe | H |
| S-283 | CH | CH | CH | CH | C—CH2COOH | NHMe |
| S-284 | C—NHMe | CH | CH | CH | CH | CH2COOH |
| S-285 | CH | C—NHMe | CH | CH | CH | CH2COOH |
| S-286 | CH | CH | C—NHMe | CH | CH | CH2COOH |
| S-287 | CH | CH | C—NHMe | CH | N | CH2COOH |
| S-288 | CH | CH | CH | C—NHMe | CH | CH2COOH |
| S-289 | CH | CH | CH | CH | C—NHMe | CH2COOH |
| S-290 | C—CH2COOH | C—NHCOMe | CH | CH | CH | H |
| S-291 | CH | C—CH2COOH | C—NHCOMe | CH | CH | H |
| S-292 | CH | CH | C—CH2COOH | C—NHCOMe | CH | H |
| S-293 | CH | CH | CH | C—CH2COOH | C—NHCOMe | H |
| S-294 | CH | CH | CH | CH | C—CH2COOH | NHCOMe |
| S-295 | C—NHCOMe | CH | CH | CH | CH | CH2COOH |
| S-296 | CH | C—NHCOMe | CH | CH | CH | CH2COOH |
| S-297 | CH | CH | C—NHCOMe | CH | CH | CH2COOH |
| S-298 | CH | CH | C—NHCOMe | CH | N | CH2COOH |
| S-299 | CH | CH | CH | C—NHCOMe | CH | CH2COOH |
| S-300 | CH | CH | CH | CH | C—NHCOMe | CH2COOH |
| S-301 | C—CH2COOH | C—CN | CH | CH | CH | H |
| S-302 | CH | C—CH2COOH | C—CN | CH | CH | H |
| S-303 | CH | CH | C—CH2COOH | C—CN | CH | H |
| S-304 | CH | CH | CH | C—CH2COOH | C—CN | H |
| S-305 | CH | CH | CH | CH | C—CH2COOH | CN |
| S-306 | C—CN | CH | CH | CH | CH | CH2COOH |
| S-307 | CH | C—CN | CH | CH | CH | CH2COOH |
| S-308 | CH | CH | C—CN | CH | CH | CH2COOH |
| S-309 | CH | CH | C—CN | CH | N | CH2COOH |
| S-310 | CH | CH | CH | C—CN | CH | CH2COOH |

TABLE 23

| No. | X1 | X2 | X3 | X4 | X5 | R6 |
|---|---|---|---|---|---|---|
| S-311 | CH | CH | CH | CH | C—CN | CH2COOH |
| S-312 | C—CH2COOH | C—NO2 | CH | CH | CH | H |
| S-313 | CH | C—CH2COOH | C—NO2 | CH | CH | H |
| S-314 | CH | CH | C—CH2COOH | C—NO2 | CH | H |
| S-315 | CH | CH | CH | C—CH2COOH | C—NO2 | H |
| S-316 | CH | CH | CH | CH | C—CH2COOH | NO2 |
| S-317 | C—NO2 | CH | CH | CH | CH | CH2COOH |
| S-318 | CH | C—NO2 | CH | CH | CH | CH2COOH |
| S-319 | CH | CH | C—NO2 | CH | CH | CH2COOH |
| S-320 | CH | CH | C—NO2 | CH | N | CH2COOH |
| S-321 | CH | CH | CH | C—NO2 | CH | CH2COOH |
| S-322 | CH | CH | CH | CH | C—NO2 | CH2COOH |
| S-323 | C—CH2COOH | C Ph | CH | CH | CH | H |
| S-324 | CH | C—CH2COOH | C Ph | CH | CH | H |
| S-325 | CH | CH | C—CH2COOH | C Ph | CH | H |
| S-326 | CH | CH | CH | C—CH2COOH | C Ph | H |
| S-327 | CH | CH | CH | CH | C—CH2COOH | Ph |
| S-328 | C Ph | CH | CH | CH | CH | CH2COOH |
| S-329 | CH | C Ph | CH | CH | CH | CH2COOH |
| S-330 | CH | CH | C Ph | CH | CH | CH2COOH |
| S-331 | CH | CH | C Ph | CH | N | CH2COOH |
| S-332 | CH | CH | CH | C Ph | CH | CH2COOH |
| S-333 | CH | CH | CH | CH | C Ph | CH2COOH |
| S-334 | C—CH2COOH | C-2-pyridyl | CH | CH | CH | H |
| S-335 | CH | C—CH2COOH | C-2-pyridyl | CH | CH | H |
| S-336 | CH | CH | C—CH2COOH | C-2-pyridyl | CH | H |
| S-337 | CH | CH | CH | C—CH2COOH | C-2-pyridyl | H |
| S-338 | CH | CH | CH | CH | C—CH2COOH | 2-pyridyl |
| S-339 | C-2-pyridyl | CH | CH | CH | CH | CH2COOH |
| S-340 | CH | C-2-pyridyl | CH | CH | CH | CH2COOH |
| S-341 | CH | CH | C-2-pyridyl | CH | CH | CH2COOH |

TABLE 24

| No. | X1 | X2 | X3 | X4 | X5 | R6 |
|---|---|---|---|---|---|---|
| S-342 | CH | CH | C-2-pyridyl | CH | N | CH2COOH |
| S-343 | CH | CH | CH | C-2-pyridyl | CH | CH2COOH |
| S-344 | CH | CH | CH | CH | C-2-pyridyl | CH2COOH |
| S-345 | C—CH2COOH | C-2-furyl | CH | CH | CH | H |
| S-346 | CH | C—CH2COOH | C-2-furyl | CH | CH | H |
| S-347 | CH | CH | C—CH2COOH | C-2-furyl | CH | H |
| S-348 | CH | CH | CH | C—CH2COOH | C-2-furyl | H |
| S-349 | CH | CH | CH | CH | C—CH2COOH | 2-furyl |
| S-350 | C-2-furyl | CH | CH | CH | CH | CH2COOH |
| S-351 | CH | C-2-furyl | CH | CH | CH | CH2COOH |
| S-352 | CH | CH | C-2-furyl | CH | CH | CH2COOH |
| S-353 | CH | CH | C-2-furyl | CH | N | CH2COOH |
| S-354 | CH | CH | CH | C-2-furyl | CH | CH2COOH |
| S-355 | CH | CH | CH | CH | C-2-furyl | CH2COOH |
| S-356 | C—CH2COOH | C-1,3-oxazol-2-yl | CH | CH | CH | H |
| S-357 | CH | C—CH2COOH | C-1,3-oxazol-2-yl | CH | CH | H |
| S-358 | CH | CH | C—CH2COOH | C-1,3-oxazol-2-yl | CH | H |
| S-359 | CH | CH | CH | C—CH2COOH | C-1,3-oxazol-2-yl | H |
| S-360 | CH | CH | CH | CH | C—CH2COOH | 1,3-oxazol-2-yl |
| S-361 | C-1,3-oxazol-2-yl | CH | CH | CH | CH | CH2COOH |
| S-362 | CH | C-1,3-oxazol-2-yl | CH | CH | CH | CH2COOH |
| S-363 | CH | CH | C-1,3-oxazol-2-yl | CH | CH | CH2COOH |
| S-364 | CH | CH | C-1,3-oxazol-2-yl | CH | N | CH2COOH |
| S-365 | CH | CH | CH | C-1,3-oxazol-2-yl | CH | CH2COOH |
| S-366 | CH | CH | CH | CH | C-1,3-oxazol-2-yl | CH2COOH |
| S-367 | C—CH2COOH | C-morpholino | CH | CH | CH | H |
| S-368 | CH | C—CH2COOH | C-morpholino | CH | CH | H |
| S-369 | CH | CH | C—CH2COOH | C-morpholino | CH | H |
| S-370 | CH | CH | CH | C—CH2COOH | C-morpholino | H |
| S-371 | CH | CH | CH | CH | C—CH2COOH | morpholino |
| S-372 | C-morpholino | CH | CH | CH | CH | CH2COOH |

TABLE 25

| No. | X1 | X2 | X3 | X4 | X5 | R6 |
|---|---|---|---|---|---|---|
| S-373 | CH | C-morpholino | CH | CH | CH | CH2COOH |
| S-374 | CH | CH | C-morpholino | CH | CH | CH2COOH |
| S-375 | CH | CH | C-morpholino | CH | N | CH2COOH |
| S-376 | CH | CH | CH | C-morpholino | CH | CH2COOH |
| S-377 | CH | CH | CH | CH | C-morpholino | CH2COOH |
| S-378 | C—CH2COOH | C—CONHMe | CH | CH | CH | H |
| S-379 | CH | C—CH2COOH | C—CONHMe | CH | CH | H |
| S-380 | CH | CH | C—CH2COOH | C—CONHMe | CH | H |
| S-381 | CH | CH | CH | C—CH2COOH | C—CONHMe | H |
| S-382 | CH | CH | CH | CH | C—CH2COOH | CONHMe |
| S-383 | C—CONHMe | CH | CH | CH | CH | CH2COOH |
| S-384 | CH | C—CONHMe | CH | CH | CH | CH2COOH |
| S-385 | CH | CH | C—CONHMe | CH | CH | CH2COOH |
| S-386 | CH | CH | C—CONHMe | CH | N | CH2COOH |
| S-387 | CH | CH | CH | C—CONHMe | CH | CH2COOH |
| S-388 | CH | CH | CH | CH | C—CONHMe | CH2COOH |
| S-389 | C—OCH2COOH | CH | CH | CH | CH | H |
| S-390 | CH | C—OCH2COOH | CH | CH | CH | H |
| S-391 | CH | CH | C—OCH2COOH | CH | CH | H |
| S-392 | CH | CH | CH | C—OCH2COOH | CH | H |
| S-393 | CH | CH | CH | CH | C—OCH2COOH | H |
| S-394 | CH | CH | CH | CH | CH | OCH2COOH |
| S-395 | CH | CH | CH | CH | N | OCH2COOH |
| S-396 | C—OCH2COOH | C—Cl | CH | CH | CH | H |
| S-397 | CH | C—OCH2COOH | C—Cl | CH | CH | H |
| S-398 | CH | CH | C—OCH2COOH | C—Cl | CH | H |
| S-399 | CH | CH | CH | C—OCH2COOH | C—Cl | H |
| S-400 | CH | CH | CH | CH | C—OCH2COOH | Cl |
| S-401 | C—Cl | CH | CH | CH | CH | OCH2COOH |
| S-402 | CH | C—Cl | CH | CH | CH | OCH2COOH |
| S-403 | CH | CH | C—Cl | CH | CH | OCH2COOH |

TABLE 26

| No. | X1 | X2 | X3 | X4 | X5 | R6 |
|---|---|---|---|---|---|---|
| S-404 | CH | CH | C—Cl | CH | N | OCH2COOH |
| S-405 | CH | CH | CH | C—Cl | CH | OCH2COOH |
| S-406 | CH | CH | CH | CH | C—Cl | OCH2COOH |
| S-407 | C—OCH2COOH | C—Me | CH | CH | CH | H |
| S-408 | CH | C—OCH2COOH | C—Me | CH | CH | H |
| S-409 | CH | CH | C—OCH2COOH | C—Me | CH | H |
| S-410 | CH | CH | CH | C—OCH2COOH | C—Me | H |
| S-411 | CH | CH | CH | CH | C—OCH2COOH | Me |
| S-412 | C—Me | CH | CH | CH | CH | OCH2COOH |
| S-413 | CH | C—Me | CH | CH | CH | OCH2COOH |
| S-414 | CH | CH | C—Me | CH | CH | OCH2COOH |
| S-415 | CH | CH | C—Me | CH | N | OCH2COOH |
| S-416 | CH | CH | CH | C—Me | CH | OCH2COOH |
| S-417 | CH | CH | CH | CH | C—Me | OCH2COOH |
| S-418 | C—OCH2COOH | C—CF3 | CH | CH | CH | H |
| S-419 | CH | C—OCH2COOH | C—CF3 | CH | CH | H |
| S-420 | CH | CH | C—OCH2COOH | C—CF3 | CH | H |
| S-421 | CH | CH | CH | C—OCH2COOH | C—CF3 | H |
| S-422 | CH | CH | CH | CH | C—OCH2COOH | CF3 |
| S-423 | C—CF3 | CH | CH | CH | CH | OCH2COOH |
| S-424 | CH | C—CF3 | CH | CH | CH | OCH2COOH |
| S-425 | CH | CH | C—CF3 | CH | CH | OCH2COOH |
| S-426 | CH | CH | C—CF3 | CH | N | OCH2COOH |
| S-427 | CH | CH | CH | C—CF3 | CH | OCH2COOH |
| S-428 | CH | CH | CH | CH | C—CF3 | OCH2COOH |
| S-429 | C—OCH2COOH | C—OMe | CH | CH | CH | H |
| S-430 | CH | C—OCH2COOH | C—OMe | CH | CH | H |
| S-431 | CH | CH | C—OCH2COOH | C—OMe | CH | H |
| S-432 | CH | CH | CH | C—OCH2COOH | C—OMe | H |
| S-433 | CH | CH | CH | CH | C—OCH2COOH | OMe |
| S-434 | C—OMe | CH | CH | CH | CH | OCH2COOH |

TABLE 27

| No. | X1 | X2 | X3 | X4 | X5 | R6 |
|---|---|---|---|---|---|---|
| S-435 | CH | C—OMe | CH | CH | CH | OCH2COOH |
| S-436 | CH | CH | C—OMe | CH | CH | OCH2COOH |
| S-437 | CH | CH | C—OMe | CH | N | OCH2COOH |
| S-438 | CH | CH | CH | C—OMe | CH | OCH2COOH |
| S-439 | CH | CH | CH | CH | C—OMe | OCH2COOH |
| S-440 | C—OCH2COOH | C—OCHF2 | CH | CH | CH | H |
| S-441 | CH | C—OCH2COOH | C—OCHF2 | CH | CH | H |
| S-442 | CH | CH | C—OCH2COOH | C—OCHF2 | CH | H |
| S-443 | CH | CH | CH | C—OCH2COOH | C—OCHF2 | H |
| S-444 | CH | CH | CH | CH | C—OCH2COOH | OCHF2 |
| S-445 | C—OCHF2 | CH | CH | CH | CH | OCH2COOH |
| S-446 | CH | C—OCHF2 | CH | CH | CH | OCH2COOH |
| S-447 | CH | CH | C—OCHF2 | CH | CH | OCH2COOH |
| S-448 | CH | CH | C—OCHF2 | CH | N | OCH2COOH |
| S-449 | CH | CH | CH | C—OCHF2 | CH | OCH2COOH |
| S-450 | CH | CH | CH | CH | C—OCHF2 | OCH2COOH |
| S-451 | C—OCH2COOH | C—SMe | CH | CH | CH | H |
| S-452 | CH | C—OCH2COOH | C—SMe | CH | CH | H |
| S-453 | CH | CH | C—OCH2COOH | C—SMe | CH | H |
| S-454 | CH | CH | CH | C—OCH2COOH | C—SMe | H |
| S-455 | CH | CH | CH | CH | C—OCH2COOH | SMe |
| S-456 | C—SMe | CH | CH | CH | CH | OCH2COOH |
| S-457 | CH | C—SMe | CH | CH | CH | OCH2COOH |
| S-458 | CH | CH | C—SMe | CH | CH | OCH2COOH |
| S-459 | CH | CH | C—SMe | CH | N | OCH2COOH |
| S-460 | CH | CH | CH | C—SMe | CH | OCH2COOH |
| S-461 | CH | CH | CH | CH | C—SMe | OCH2COOH |
| S-462 | C—OCH2COOH | C—SO2Me | CH | CH | CH | H |
| S-463 | CH | C—OCH2COOH | C—SO2Me | CH | CH | H |
| S-464 | CH | CH | C—OCH2COOH | C—SO2Me | CH | H |
| S-465 | CH | CH | CH | C—OCH2COOH | C—SO2Me | H |

TABLE 28

| No. | X1 | X2 | X3 | X4 | X5 | R6 |
|---|---|---|---|---|---|---|
| S-466 | CH | CH | CH | CH | C—OCH2COOH | SO2Me |
| S-467 | C—SO2Me | CH | CH | CH | CH | OCH2COOH |
| S-468 | CH | C—SO2Me | CH | CH | CH | OCH2COOH |
| S-469 | CH | CH | C—SO2Me | CH | CH | OCH2COOH |
| S-470 | CH | CH | C—SO2Me | CH | N | OCH2COOH |
| S-471 | CH | CH | CH | C—SO2Me | CH | OCH2COOH |
| S-472 | CH | CH | CH | CH | C—SO2Me | OCH2COOH |
| S-473 | C—OCH2COOH | C—NHMe | CH | CH | CH | H |
| S-474 | CH | C—OCH2COOH | C—NHMe | CH | CH | H |
| S-475 | CH | CH | C—OCH2COOH | C—NHMe | CH | H |
| S-476 | CH | CH | CH | C—OCH2COOH | C—NHMe | H |
| S-477 | CH | CH | CH | CH | C—OCH2COOH | NHMe |
| S-478 | C—NHMe | CH | CH | CH | CH | OCH2COOH |
| S-479 | CH | C—NHMe | CH | CH | CH | OCH2COOH |
| S-480 | CH | CH | C—NHMe | CH | CH | OCH2COOH |
| S-481 | CH | CH | CH | C—NHMe | CH | OCH2COOH |
| S-482 | CH | CH | CH | CH | C—NHMe | OCH2COOH |
| S-483 | C—OCH2COOH | C—NHCOMe | CH | CH | CH | H |
| S-484 | CH | C—OCH2COOH | C—NHCOMe | CH | CH | H |
| S-485 | CH | CH | C—OCH2COOH | C—NHCOMe | CH | H |
| S-486 | CH | CH | CH | C—OCH2COOH | C—NHCOMe | H |
| S-487 | CH | CH | CH | CH | C—OCH2COOH | NHCOMe |
| S-488 | C—NHCOMe | CH | CH | CH | CH | OCH2COOH |
| S-489 | CH | C—NHCOMe | CH | CH | CH | OCH2COOH |
| S-490 | CH | CH | C—NHCOMe | CH | CH | OCH2COOH |
| S-491 | CH | CH | C—NHCOMe | CH | N | OCH2COOH |
| S-492 | CH | CH | CH | C—NHCOMe | CH | OCH2COOH |
| S-493 | CH | CH | CH | CH | C—NHCOMe | OCH2COOH |
| S-494 | C—OCH2COOH | C—CN | CH | CH | CH | H |
| S-495 | CH | C—OCH2COOH | C—CN | CH | CH | H |
| S-496 | CH | CH | C—OCH2COOH | C—CN | CH | H |

TABLE 29

| No. | X1 | X2 | X3 | X4 | X5 | R6 |
|---|---|---|---|---|---|---|
| S-497 | CH | CH | CH | C—OCH2COOH | C—CN | H |
| S-498 | CH | CH | CH | CH | C—OCH2COOH | CN |
| S-499 | C—CN | CH | CH | CH | CH | OCH2COOH |
| S-500 | CH | C—CN | CH | CH | CH | OCH2COOH |
| S-501 | CH | CH | C—CN | CH | CH | OCH2COOH |
| S-502 | CH | CH | C—CN | CH | N | OCH2COOH |
| S-503 | CH | CH | CH | C—CN | CH | OCH2COOH |
| S-504 | CH | CH | CH | CH | C—CN | OCH2COOH |
| S-505 | C—OCH2COOH | C—NO2 | CH | CH | CH | H |
| S-506 | CH | C—OCH2COOH | C—NO2 | CH | CH | H |
| S-507 | CH | CH | C—OCH2COOH | C—NO2 | CH | H |
| S-508 | CH | CH | CH | C—OCH2COOH | C—NO2 | H |
| S-509 | CH | CH | CH | CH | C—OCH2COOH | NO2 |
| S-510 | C—NO2 | CH | CH | CH | CH | OCH2COOH |
| S-511 | CH | C—NO2 | CH | CH | CH | OCH2COOH |
| S-512 | CH | CH | C—NO2 | CH | CH | OCH2COOH |
| S-513 | CH | CH | C—NO2 | CH | N | OCH2COOH |
| S-514 | CH | CH | CH | C—NO2 | CH | OCH2COOH |
| S-515 | CH | CH | CH | CH | C—NO2 | OCH2COOH |
| S-516 | C—OCH2COOH | C—Ph | CH | CH | CH | H |
| S-517 | CH | C—OCH2COOH | C—Ph | CH | CH | H |
| S-518 | CH | CH | C—OCH2COOH | C—Ph | CH | H |
| S-519 | CH | CH | CH | C—OCH2COOH | C—Ph | H |
| S-520 | CH | CH | CH | CH | C—OCH2COOH | Ph |
| S-521 | C—Ph | CH | CH | CH | CH | OCH2COOH |
| S-522 | CH | C—Ph | CH | CH | CH | OCH2COOH |
| S-523 | CH | CH | C—Ph | CH | CH | OCH2COOH |
| S-524 | CH | CH | C—Ph | CH | N | OCH2COOH |
| S-525 | CH | CH | CH | C—Ph | CH | OCH2COOH |
| S-526 | CH | CH | CH | CH | C—Ph | OCH2COOH |
| S-527 | C—OCH2COOH | C-2-pyridyl | CH | CH | CH | H |

TABLE 30

| No. | X1 | X2 | X3 | X4 | X5 | R6 |
|---|---|---|---|---|---|---|
| S-528 | CH | C—OCH2COOH | C-2-pyridyl | CH | CH | H |
| S-529 | CH | CH | C—OCH2COOH | C-2-pyridyl | CH | H |
| S-530 | CH | CH | CH | C—OCH2COOH | C-2-pyridyl | H |
| S-531 | CH | CH | CH | CH | C—OCH2COOH | 2-pyridyl |
| S-532 | C-2-pyridyl | CH | CH | CH | CH | OCH2COOH |
| S-533 | CH | C-2-pyridyl | CH | CH | CH | OCH2COOH |
| S-534 | CH | CH | C-2-pyridyl | CH | CH | OCH2COOH |
| S-535 | CH | CH | C-2-pyridyl | CH | N | OCH2COOH |
| S-536 | CH | CH | CH | C-2-pyridyl | CH | OCH2COOH |
| S-537 | CH | CH | CH | CH | C-2-pyridyl | OCH2COOH |
| S-538 | C—OCH2COOH | C-2-furyl | CH | CH | CH | H |
| S-539 | CH | C—OCH2COOH | C-2-furyl | CH | CH | H |
| S-540 | CH | CH | C—OCH2COOH | C-2-furyl | CH | H |
| S-541 | CH | CH | CH | C—OCH2COOH | C-2-furyl | H |
| S-542 | CH | CH | CH | CH | C—OCH2COOH | 2-furyl |
| S-543 | C-2-furyl | CH | CH | CH | CH | OCH2COOH |
| S-544 | CH | C-2-furyl | CH | CH | CH | OCH2COOH |
| S-545 | CH | CH | C-2-furyl | CH | CH | OCH2COOH |
| S-546 | CH | CH | C-2-furyl | CH | N | OCH2COOH |
| S-547 | CH | CH | CH | C-2-furyl | CH | OCH2COOH |
| S-548 | CH | CH | CH | CH | C-2-furyl | OCH2COOH |
| S-549 | C—OCH2COOH | C-1,3-oxazol-2-yl | CH | CH | CH | H |
| S-550 | CH | C—OCH2COOH | C-1,3-oxazol-2-yl | CH | CH | H |
| S-551 | CH | CH | C—OCH2COOH | C-1,3-oxazol-2-yl | CH | H |
| S-552 | CH | CH | CH | C—OCH2COOH | C-1,3-oxazol-2-yl | H |
| S-553 | CH | CH | CH | CH | C—OCH2COOH | 1,3-oxazol-2-yl |
| S-554 | C-1,3-oxazol-2-yl | CH | CH | CH | CH | OCH2COOH |
| S-555 | CH | C-1,3-oxazol-2-yl | CH | CH | CH | OCH2COOH |
| S-556 | CH | CH | C-1,3-oxazol-2-yl | CH | CH | OCH2COOH |
| S-557 | CH | CH | C-1,3-oxazol-2-yl | CH | N | OCH2COOH |
| S-558 | CH | CH | CH | C-1,3-oxazol-2-yl | CH | OCH2COOH |

TABLE 31

| No. | X1 | X2 | X3 | X4 | X5 | R6 |
|---|---|---|---|---|---|---|
| S-559 | CH | CH | CH | CH | C-1,3-oxazol-2-yl | OCH2COOH |
| S-560 | C—OCH2COOH | C-morpholino | CH | CH | CH | H |
| S-561 | CH | C—OCH2COOH | C-morpholino | CH | CH | H |
| S-562 | CH | CH | C—OCH2COOH | C-morpholino | CH | H |
| S-563 | CH | CH | CH | C—OCH2COOH | C-morpholino | H |
| S-564 | CH | CH | CH | CH | C—OCH2COOH | morpholino |
| S-565 | C-morpholino | CH | CH | CH | CH | OCH2COOH |
| S-566 | CH | C-morpholino | CH | CH | CH | OCH2COOH |
| S-567 | CH | CH | C-morpholino | CH | CH | OCH2COOH |
| S-568 | CH | CH | C-morpholino | CH | N | OCH2COOH |
| S-569 | CH | CH | CH | C-morpholino | CH | OCH2COOH |
| S-570 | CH | CH | CH | CH | C-morpholino | OCH2COOH |
| S-571 | C—OCH2COOH | C—CONHMe | CH | CH | CH | H |
| S-572 | CH | C—OCH2COOH | C—CONHMe | CH | CH | H |
| S-573 | CH | CH | C—OCH2COOH | C—CONHMe | CH | H |
| S-574 | CH | CH | CH | C—OCH2COOH | C—CONHMe | H |
| S-575 | CH | CH | CH | CH | C—OCH2COOH | CONHMe |
| S-576 | C—CONHMe | CH | CH | CH | CH | OCH2COOH |
| S-577 | CH | C—CONHMe | CH | CH | CH | OCH2COOH |
| S-578 | CH | CH | C—CONHMe | CH | CH | OCH2COOH |
| S-579 | CH | CH | C—CONHMe | CH | N | OCH2COOH |
| S-580 | CH | CH | CH | C—CONHMe | CH | OCH2COOH |
| S-581 | CH | CH | CH | CH | C—CONHMe | OCH2COOH |

TABLE 32

| No. | $R^7$ | $R^{8a}$ | Z | $R^{8b}$ | $R^{8c}$ |
|---|---|---|---|---|---|
| U-1 | OMe | H | C—H | H | H |
| U-2 | OMe | H | C—H | H | F |
| U-3 | OMe | H | C—H | H | Cl |
| U-4 | OMe | H | C—H | H | Me |
| U-5 | OMe | H | C—H | F | H |
| U-6 | OMe | H | C—H | F | F |
| U-7 | OMe | H | C—H | F | Cl |
| U-8 | OMe | H | C—H | F | Me |
| U-9 | OMe | H | C—H | Cl | H |
| U-10 | OMe | H | C—H | Cl | F |
| U-11 | OMe | H | C—H | Cl | Cl |
| U-12 | OMe | H | C—H | Cl | Me |
| U-13 | OMe | H | C—H | Me | H |
| U-14 | OMe | H | C—H | Me | F |
| U-15 | OMe | H | C—H | Me | Cl |
| U-16 | OMe | H | C—H | Me | Me |
| U-17 | OMe | H | C—F | H | Me |
| U-18 | OMe | H | C—F | Me | H |
| U-19 | OMe | H | C—Me | H | F |
| U-20 | OMe | F | C—H | H | Me |
| U-21 | OMe | H | N | H | H |
| U-22 | OMe | H | N | H | F |
| U-23 | OMe | H | N | H | Cl |
| U-24 | OMe | H | N | H | Me |
| U-25 | OMe | H | N | F | H |
| U-26 | OMe | H | N | Cl | H |
| U-27 | OMe | H | N | Me | H |
| U-28 | OMe | F | N | H | H |
| U-29 | OMe | Cl | N | H | H |
| U-30 | OMe | Me | N | H | H |
| U-31 | OEt | H | C—H | H | H |
| U-32 | OEt | H | C—H | H | F |
| U-33 | OEt | H | C—H | H | Cl |
| U-34 | OEt | H | C—H | H | Me |
| U-35 | OEt | H | C—H | F | H |
| U-36 | OEt | H | C—H | F | Cl |
| U-37 | OEt | H | C—H | Cl | F |
| U-38 | OEt | H | C—H | Cl | Cl |
| U-39 | OEt | H | C—H | Me | H |
| U-40 | OEt | H | C—F | H | Cl |

TABLE 33

| No. | $R^7$ | $R^{8a}$ | Z | $R^{8b}$ | $R^{8c}$ |
|---|---|---|---|---|---|
| U-41 | OEt | H | C—F | Cl | H |
| U-42 | OEt | H | C—Cl | H | F |
| U-43 | OEt | H | C—Cl | H | Cl |
| U-44 | OEt | H | C—Cl | Cl | H |
| U-45 | OEt | F | C—H | H | Cl |
| U-46 | OEt | Cl | C—H | H | Cl |
| U-47 | OEt | H | N | H | H |
| U-48 | OEt | H | N | H | F |
| U-49 | OEt | H | N | H | Cl |
| U-50 | OEt | H | N | H | Me |
| U-51 | OEt | H | N | F | H |
| U-52 | OEt | H | N | Cl | H |
| U-53 | OEt | H | N | Me | H |
| U-54 | OEt | F | N | H | H |
| U-55 | OEt | Cl | N | H | H |
| U-56 | OEt | Me | N | H | H |
| U-57 | $OCHMe_2$ | H | C—H | H | H |
| U-58 | $OCHMe_2$ | H | C—H | H | F |
| U-59 | $OCHMe_2$ | H | C—H | H | Cl |
| U-60 | $OCHMe_2$ | H | C—H | H | Me |
| U-61 | $OCHMe_2$ | H | C—H | F | H |
| U-62 | $OCHMe_2$ | H | C—H | F | F |
| U-63 | $OCHMe_2$ | H | C—H | F | Cl |
| U-64 | $OCHMe_2$ | H | C—H | F | Me |
| U-65 | $OCHMe_2$ | H | C—H | Cl | H |
| U-66 | $OCHMe_2$ | H | C—H | Cl | F |
| U-67 | $OCHMe_2$ | H | C—H | Cl | Cl |
| U-68 | $OCHMe_2$ | H | C—H | Cl | Me |
| U-69 | $OCHMe_2$ | H | C—H | Me | H |
| U-70 | $OCHMe_2$ | H | C—H | Me | F |
| U-71 | $OCHMe_2$ | H | C—H | Me | Cl |
| U-72 | $OCHMe_2$ | H | C—H | Me | Me |
| U-73 | $OCHMe_2$ | H | C—F | H | F |
| U-74 | $OCHMe_2$ | H | C—F | H | Cl |
| U-75 | $OCHMe_2$ | H | C—F | H | Me |
| U-76 | $OCHMe_2$ | H | C—F | F | H |
| U-77 | $OCHMe_2$ | H | C—F | Cl | H |
| U-78 | $OCHMe_2$ | H | C—F | Me | H |
| U-79 | $OCHMe_2$ | H | C—Cl | H | F |
| U-80 | $OCHMe_2$ | H | C—Cl | H | Cl |

TABLE 34

| No. | $R^7$ | $R^{8a}$ | Z | $R^{8b}$ | $R^{8c}$ |
|---|---|---|---|---|---|
| U-81 | OCHMe$_2$ | H | C—Cl | H | Me |
| U-82 | OCHMe$_2$ | H | C—Cl | Cl | H |
| U-83 | OCHMe$_2$ | H | C—Cl | Me | H |
| U-84 | OCHMe$_2$ | H | C—Me | H | F |
| U-85 | OCHMe$_2$ | H | C—Me | H | Cl |
| U-86 | OCHMe$_2$ | H | C—Me | H | Me |
| U-87 | OCHMe$_2$ | H | C—Me | Me | H |
| U-88 | OCHMe$_2$ | F | C—H | H | F |
| U-89 | OCHMe$_2$ | F | C—H | H | Cl |
| U-90 | OCHMe$_2$ | F | C—H | H | Me |
| U-91 | OCHMe$_2$ | Cl | C—H | H | Cl |
| U-92 | OCHMe$_2$ | Cl | C—H | H | Me |
| U-93 | OCHMe$_2$ | Me | C—H | H | Me |
| U-94 | OCHMe$_2$ | H | N | H | H |
| U-95 | OCHMe$_2$ | H | N | H | F |
| U-96 | OCHMe$_2$ | H | N | H | Cl |
| U-97 | OCHMe$_2$ | H | N | H | Me |
| U-98 | OCHMe$_2$ | H | N | F | H |
| U-99 | OCHMe$_2$ | H | N | Cl | H |
| U-100 | OCHMe$_2$ | H | N | Me | H |
| U-101 | OCHMe$_2$ | F | N | H | H |
| U-102 | OCHMe$_2$ | Cl | N | H | H |
| U-103 | OCHMe$_2$ | Me | N | H | H |
| U-104 | OCHMe(Et) | H | C—H | H | H |
| U-105 | OCHMe(Et) | H | C—H | H | F |
| U-106 | OCHMe(Et) | H | C—H | H | Cl |
| U-107 | OCHMe(Et) | H | C—H | H | Me |
| U-108 | OCHMe(Et) | H | C—H | F | H |
| U-109 | OCHMe(Et) | H | C—H | F | F |
| U-110 | OCHMe(Et) | H | C—H | F | Cl |
| U-111 | OCHMe(Et) | H | C—H | F | Me |
| U-112 | OCHMe(Et) | H | C—H | Cl | H |
| U-113 | OCHMe(Et) | H | C—H | Cl | F |
| U-114 | OCHMe(Et) | H | C—H | Cl | Cl |
| U-115 | OCHMe(Et) | H | C—H | Cl | Me |
| U-116 | OCHMe(Et) | H | C—H | Me | H |
| U-117 | OCHMe(Et) | H | C—H | Me | F |
| U-118 | OCHMe(Et) | H | C—H | Me | Cl |
| U-119 | OCHMe(Et) | H | C—H | Me | Me |
| U-120 | OCHMe(Et) | H | C—F | H | F |

TABLE 35

| No. | $R^7$ | $R^{8a}$ | Z | $R^{8b}$ | $R^{8c}$ |
|---|---|---|---|---|---|
| U-121 | OCHMe(Et) | H | C—F | H | Cl |
| U-122 | OCHMe(Et) | H | C—F | H | Me |
| U-123 | OCHMe(Et) | H | C—F | F | H |
| U-124 | OCHMe(Et) | H | C—F | Cl | H |
| U-125 | OCHMe(Et) | H | C—F | Me | H |
| U-126 | OCHMe(Et) | H | C—Cl | H | F |
| U-127 | OCHMe(Et) | H | C—Cl | H | Cl |
| U-128 | OCHMe(Et) | H | C—Cl | H | Me |
| U-129 | OCHMe(Et) | H | C—Cl | Cl | H |
| U-130 | OCHMe(Et) | H | C—Cl | Me | H |
| U-131 | OCHMe(Et) | H | C—Me | H | F |
| U-132 | OCHMe(Et) | H | C—Me | H | Cl |
| U-133 | OCHMe(Et) | H | C—Me | H | Me |
| U-134 | OCHMe(Et) | H | C—Me | Me | H |
| U-135 | OCHMe(Et) | F | C—H | H | F |
| U-136 | OCHMe(Et) | F | C—H | H | Cl |
| U-137 | OCHMe(Et) | F | C—H | H | Me |
| U-138 | OCHMe(Et) | Cl | C—H | H | Cl |
| U-139 | OCHMe(Et) | Cl | C—H | H | Me |
| U-140 | OCHMe(Et) | Me | C—H | H | Me |
| U-141 | OCHMe(Et) | H | N | H | H |
| U-142 | OCHMe(Et) | H | N | H | F |
| U-143 | OCHMe(Et) | H | N | H | Cl |
| U-144 | OCHMe(Et) | H | N | H | Me |
| U-145 | OCHMe(Et) | H | N | F | H |
| U-146 | OCHMe(Et) | H | N | Cl | H |
| U-147 | OCHMe(Et) | H | N | Me | H |
| U-148 | OCHMe(Et) | F | N | H | H |
| U-149 | OCHMe(Et) | Cl | N | H | H |
| U-150 | OCHMe(Et) | Me | N | H | H |

TABLE 35-continued

| No. | $R^7$ | $R^{8a}$ | Z | $R^{8b}$ | $R^{8c}$ |
|---|---|---|---|---|---|
| U-151 | OCHF$_2$ | H | C—H | H | H |
| U-152 | OCHF$_2$ | H | C—H | H | F |
| U-153 | OCHF$_2$ | H | C—H | H | Cl |
| U-154 | OCHF$_2$ | H | C—H | H | Me |
| U-155 | OCHF$_2$ | H | C—H | F | H |
| U-156 | OCHF$_2$ | H | C—H | Cl | H |
| U-157 | OCHF$_2$ | H | C—H | Me | H |
| U-158 | OCHF$_2$ | H | N | H | H |
| U-159 | OCHF$_2$ | H | N | H | F |
| U-160 | OCHF$_2$ | H | N | H | Cl |

TABLE 36

| No. | $R^7$ | $R^{8a}$ | Z | $R^{8b}$ | $R^{8c}$ |
|---|---|---|---|---|---|
| U-161 | OCHF$_2$ | H | N | H | Me |
| U-162 | OCHF$_2$ | H | N | F | H |
| U-163 | OCHF$_2$ | H | N | Cl | H |
| U-164 | OCHF$_2$ | H | N | Me | H |
| U-165 | OCHF$_2$ | F | N | H | H |
| U-166 | OCHF$_2$ | Cl | N | H | H |
| U-167 | OCHF$_2$ | Me | N | H | H |
| U-168 | OCH$_2$Ph | H | C—H | H | H |
| U-169 | OCH$_2$Ph | H | C—H | H | F |
| U-170 | OCH$_2$Ph | H | C—H | H | Cl |
| U-171 | OCH$_2$Ph | H | C—H | H | Me |
| U-172 | OCH$_2$Ph | H | C—H | F | H |
| U-173 | OCH$_2$Ph | H | C—H | Cl | H |
| U-174 | OCH$_2$Ph | H | C—H | Me | H |
| U-175 | OCH$_2$Ph | H | N | H | H |
| U-176 | OCH$_2$Ph | H | N | H | F |
| U-177 | OCH$_2$Ph | H | N | H | Cl |
| U-178 | OCH$_2$Ph | H | N | H | Me |
| U-179 | OCH$_2$Ph | H | N | F | H |
| U-180 | OCH$_2$Ph | H | N | Cl | H |
| U-181 | OCH$_2$Ph | H | N | Me | H |
| U-182 | OCH$_2$Ph | F | N | H | H |
| U-183 | OCH$_2$Ph | Cl | N | H | H |
| U-184 | OCH$_2$Ph | Me | N | H | H |
| U-185 | OCHMe(Ph) | H | C—H | H | H |
| U-186 | OCHMe(Ph) | H | C—H | H | F |
| U-187 | OCHMe(Ph) | H | C—H | H | Cl |
| U-188 | OCHMe(Ph) | H | C—H | H | Me |
| U-189 | OCHMe(Ph) | H | C—H | F | H |
| U-190 | OCHMe(Ph) | H | C—H | Cl | H |
| U-191 | OCHMe(Ph) | H | C—H | Me | H |
| U-192 | OCHMe(Ph) | H | C—H | Me | F |
| U-193 | OCHMe(Ph) | H | C—H | Me | Cl |
| U-194 | OCHMe(Ph) | H | N | H | H |
| U-195 | OCHMe(Ph) | H | N | H | F |
| U-196 | OCHMe(Ph) | H | N | H | Cl |
| U-197 | OCHMe(Ph) | H | N | H | Me |
| U-198 | OCHMe(Ph) | H | N | F | H |
| U-199 | OCHMe(Ph) | H | N | Cl | H |
| U-200 | OCHMe(Ph) | H | N | Me | H |

TABLE 37

| No. | $R^7$ | $R^{8a}$ | Z | $R^{8b}$ | $R^{8c}$ |
|---|---|---|---|---|---|
| U-201 | OCHMe(Ph) | F | N | H | H |
| U-202 | OCHMe(Ph) | Cl | N | H | H |
| U-203 | OCHMe(Ph) | Me | N | H | H |
| U-204 | OPh | H | C—H | H | H |
| U-205 | OPh | H | C—H | H | F |
| U-206 | OPh | H | C—H | H | Cl |
| U-207 | OPh | H | C—H | H | Me |
| U-208 | OPh | H | C—H | F | H |
| U-209 | OPh | H | C—H | Cl | H |
| U-210 | OPh | H | C—H | Me | H |
| U-211 | OPh | H | N | H | H |
| U-212 | OPh | H | N | H | F |
| U-213 | OPh | H | N | H | Cl |

TABLE 37-continued

| No. | R⁷ | R⁸ᵃ | Z | R⁸ᵇ | R⁸ᶜ |
|---|---|---|---|---|---|
| U-214 | OPh | H | N | H | Me |
| U-215 | OPh | H | N | F | H |
| U-216 | OPh | H | N | Cl | H |
| U-217 | OPh | H | N | Me | H |
| U-218 | OPh | F | N | H | H |
| U-219 | OPh | Cl | N | H | H |
| U-220 | OPh | Me | N | H | H |
| U-221 | SMe | H | C—H | H | H |
| U-222 | SMe | H | C—H | H | F |
| U-223 | SMe | H | C—H | H | Cl |
| U-224 | SMe | H | C—H | H | Me |
| U-225 | SMe | H | C—H | F | H |
| U-226 | SMe | H | C—H | Cl | H |
| U-227 | SMe | H | C—H | Me | H |
| U-228 | SMe | H | N | H | H |
| U-229 | SMe | H | N | H | F |
| U-230 | SMe | H | N | H | Cl |
| U-231 | SMe | H | N | H | Me |
| U-232 | SMe | H | N | F | H |
| U-233 | SMe | H | N | Cl | H |
| U-234 | SMe | H | N | Me | H |
| U-235 | SMe | F | N | H | H |
| U-236 | SMe | Cl | N | H | H |
| U-237 | SMe | Me | N | H | H |
| U-238 | SEt | H | C—H | H | H |
| U-239 | SEt | H | C—H | H | F |
| U-240 | SEt | H | C—H | H | Cl |

TABLE 38

| No. | R⁷ | R⁸ᵃ | Z | R⁸ᵇ | R⁸ᶜ |
|---|---|---|---|---|---|
| U-241 | SEt | H | C—H | H | Me |
| U-242 | SEt | H | C—H | F | H |
| U-243 | SEt | H | C—H | Cl | H |
| U-244 | SEt | H | C—H | Me | H |
| U-245 | SEt | H | N | H | H |
| U-246 | SEt | H | N | H | F |
| U-247 | SEt | H | N | H | Cl |
| U-248 | SEt | H | N | H | Me |
| U-249 | SEt | H | N | F | H |
| U-250 | SEt | H | N | Cl | H |
| U-251 | SEt | H | N | Me | H |
| U-252 | SEt | F | N | H | H |
| U-253 | SEt | Cl | N | H | H |
| U-254 | SEt | Me | N | H | H |
| U-255 | SCHMe₂ | H | C—H | H | H |
| U-256 | SCHMe₂ | H | C—H | H | F |
| U-257 | SCHMe₂ | H | C—H | H | Cl |
| U-258 | SCHMe₂ | H | C—H | H | Me |
| U-259 | SCHMe₂ | H | C—H | F | H |
| U-260 | SCHMe₂ | H | C—H | F | F |
| U-261 | SCHMe₂ | H | C—H | F | Cl |
| U-262 | SCHMe₂ | H | C—H | F | Me |
| U-263 | SCHMe₂ | H | C—H | Cl | H |
| U-264 | SCHMe₂ | H | C—H | Cl | F |
| U-265 | SCHMe₂ | H | C—H | Cl | Cl |
| U-266 | SCHMe₂ | H | C—H | Cl | Me |
| U-267 | SCHMe₂ | H | C—H | Me | H |
| U-268 | SCHMe₂ | H | C—H | Me | F |
| U-269 | SCHMe₂ | H | C—H | Me | Cl |
| U-270 | SCHMe₂ | H | C—H | Me | Me |
| U-271 | SCHMe₂ | H | C—F | H | F |
| U-272 | SCHMe₂ | H | C—F | H | Cl |
| U-273 | SCHMe₂ | H | C—F | H | Me |
| U-274 | SCHMe₂ | H | C—F | F | H |
| U-275 | SCHMe₂ | H | C—F | Cl | H |
| U-276 | SCHMe₂ | H | C—F | Me | H |
| U-277 | SCHMe₂ | H | C—Cl | H | F |
| U-278 | SCHMe₂ | H | C—Cl | H | Cl |
| U-279 | SCHMe₂ | H | C—Cl | H | Me |
| U-280 | SCHMe₂ | H | C—Cl | Cl | H |

TABLE 39

| No. | R⁷ | R⁸ᵃ | Z | R⁸ᵇ | R⁸ᶜ |
|---|---|---|---|---|---|
| U-281 | SCHMe₂ | H | C—Cl | Me | H |
| U-282 | SCHMe₂ | H | C-Me | H | F |
| U-283 | SCHMe₂ | H | C-Me | H | Cl |
| U-284 | SCHMe₂ | H | C-Me | H | Me |
| U-285 | SCHMe₂ | H | C-Me | Me | H |
| U-286 | SCHMe₂ | F | C—H | H | F |
| U-287 | SCHMe₂ | F | C—H | H | Cl |
| U-288 | SCHMe₂ | F | C—H | H | Me |
| U-289 | SCHMe₂ | Cl | C—H | H | Cl |
| U-290 | SCHMe₂ | Cl | C—H | H | Me |
| U-291 | SCHMe₂ | Me | C—H | H | Me |
| U-292 | SCHMe₂ | H | N | H | H |
| U-293 | SCHMe₂ | H | N | H | F |
| U-294 | SCHMe₂ | H | N | H | Cl |
| U-295 | SCHMe₂ | H | N | H | Me |
| U-296 | SCHMe₂ | H | N | F | H |
| U-297 | SCHMe₂ | H | N | Cl | H |
| U-298 | SCHMe₂ | H | N | Me | H |
| U-299 | SCHMe₂ | F | N | H | H |
| U-300 | SCHMe₂ | Cl | N | H | H |
| U-301 | SCHMe₂ | Me | N | H | H |
| U-302 | SCHMe(Et) | H | C—H | H | H |
| U-303 | SCHMe(Et) | H | C—H | H | F |
| U-304 | SCHMe(Et) | H | C—H | H | Cl |
| U-305 | SCHMe(Et) | H | C—H | H | Me |
| U-306 | SCHMe(Et) | H | C—H | F | H |
| U-307 | SCHMe(Et) | H | C—H | Cl | H |
| U-308 | SCHMe(Et) | H | C—H | Me | H |
| U-309 | SCHMe(Et) | H | N | H | H |
| U-310 | SCHMe(Et) | H | N | H | F |
| U-311 | SCHMe(Et) | H | N | H | Cl |
| U-312 | SCHMe(Et) | H | N | H | Me |
| U-313 | SCHMe(Et) | H | N | F | H |
| U-314 | SCHMe(Et) | H | N | Cl | H |
| U-315 | SCHMe(Et) | H | N | Me | H |
| U-316 | SCHMe(Et) | F | N | H | H |
| U-317 | SCHMe(Et) | Cl | N | H | H |
| U-318 | SCHMe(Et) | Me | N | H | H |
| U-319 | SCHF₂ | H | C—H | H | H |
| U-320 | SCHF₂ | H | C—H | H | F |

TABLE 40

| No. | R⁷ | R⁸ᵃ | Z | R⁸ᵇ | R⁸ᶜ |
|---|---|---|---|---|---|
| U-321 | SCHF₂ | H | C—H | H | Cl |
| U-322 | SCHF₂ | H | C—H | H | Me |
| U-323 | SCHF₂ | H | N | H | H |
| U-324 | SCH₂Ph | H | C—H | H | H |
| U-325 | SCH₂Ph | H | C—H | H | F |
| U-326 | SCH₂Ph | H | C—H | H | Cl |
| U-327 | SCH₂Ph | H | C—H | H | Me |
| U-328 | SCH₂Ph | H | N | H | H |
| U-329 | SCHMe(Ph) | H | C—H | H | H |
| U-330 | SCHMe(Ph) | H | C—H | H | F |
| U-331 | SCHMe(Ph) | H | C—H | H | Cl |
| U-332 | SCHMe(Ph) | H | C—H | H | Me |
| U-333 | SCHMe(Ph) | H | N | H | H |
| U-334 | SPh | H | C—H | H | H |
| U-335 | SPh | H | C—H | H | F |
| U-336 | SPh | H | C—H | H | Cl |
| U-337 | SPh | H | C—H | H | Me |
| U-338 | SPh | H | N | H | H |

A compound of the formula (IA) is shown below.
(No. of Compound, part A, part B), (IA-1, S-1, U-57), (IA-2, S-2, U-57), (IA-3, S-3, U-57), (IA-4, S-4, U-57), (IA-5, S-5, U-57), (IA-7, S-7, U-57), (IA-8, S-8, U-57), (IA-9, S-9, U-57), (IA-10, S-10, U-57), (IA-11, S-11, U-57), (IA-12, S-12, U-57), (IA-13, S-13, U-57), (IA-14, S-14, U-57), (IA-15, S-15, U-57), (IA-16, S-16, U-57), (IA-17, S-17, U-57), (IA-18, S-18, U-57), (IA-19, S-19, U-57), (IA-20, S-20, U-57), (IA-21, S-21, U-57), (IA-22, S-22, U-57), (IA-23, S-23, U-57), (IA-24, S-24, U-57), (IA-25, S-25, U-57), (IA- 26, S-26, U-57), (IA-27, S-27, U-57), (IA-28, S-28, U-57), (IA-29, S-29, U-57), (IA-30, S-30, U-57), (IA-31, S-31, U-57), (IA-32, S-32, U-57), (IA-33, S-33, U-57), (IA-34, S-34, U-57), (IA-35, S-35, U-57), (IA-36, S-36, U-57), (IA-37, S-37, U-57), (IA-38, S-38, U-57), (IA-39, S-39, U-57), (IA-40, S-40, U-57), (IA-41, S-41, U-57), (IA-42, S-42, U-57), (IA-43, S-43, U-57), (IA-44, S-44, U-57), (IA-45, S-45, U-57), (IA-46, S-46, U-57), (IA-47, S-47, U-57), (IA-48, S-48, U-57), (IA-49, S-49, U-57), (IA-50, S-50, U-57), (IA-51, S-51, U-57), (IA-52, S-52, U-57), (IA-53, S-53, U-57), (IA-54, S-54, U-57), (IA-55, S-55, U-57), (IA-56, S-56, U-57), (IA-57, S-57, U-57), (IA-58, S-58, U-57), (IA-59, S-59, U-57), (IA-60, S-60, U-57), (IA-61, S-61, U-57), (IA-62, S-62, U-57), (IA-63, S-63, U-57), (IA-64, S-64, U-57), (IA-65, S-65, U-57), (IA-66, S-66, U-57), (IA-67, S-67, U-57), (IA-68, S-68, U-57), (IA-69, S-69, U-57), (IA-70, S-70, U-57), (IA-71, S-71, U-57), (IA-72, S-72, U-57), (IA-73, S-73, U-57), (IA-74, S-74, U-57), (IA-75, S-75, U-57), (IA-76, S-76, U-57), (IA-77, S-77, U-57), (IA-78, S-78, U-57), (IA-79, S-79, U-57), (IA-80, S-80, U-57), (IA-81, S-81, U-57), (IA-82, S-82, U-57), (IA-83, S-83, U-57), (IA-84, S-84, U-57), (IA-85, S-85, U-57), (IA-86, S-86, U-57), (IA-87, S-87, U-57), (IA-88, S-88, U-57), (IA-89, S-89, U-57), (IA-90, S-90, U-57), (IA-91, S-91, U-57), (IA-92, S-92, U-57), (IA-93, S-93, U-57), (IA-94, S-94, U-57), (IA-95, S-95, U-57), (IA-96, S-96, U-57), (IA-97, S-97, U-57), (IA-98, S-98, U-57), (IA-99, S-99, U-57), (IA-100, S-100, U-57), (IA-101, S-101, U-57), (IA-102, S-102, U-57), (IA-103, S-103, U-57), (IA-104, S-104, U-57), (IA-105, S-105, U-57), (IA-106, S-106, U-57), (IA-107, S-107, U-57), (IA-108, S-108, U-57), (IA-109, S-109, U-57), (IA-110, S-110, U-57), (IA-111, S-111, U-57), (IA-112, S-112, U-57), (IA-113, S-113, U-57), (IA-114, S-114, U-57), (IA-115, S-115, U-57), (IA-116, S-116, U-57), (IA-117, S-117, U-57), (IA-118, S-118, U-57), (IA-119, S-119, U-57), (IA-120, S-120, U-57), (IA-121, S-121, U-57), (IA-122, S-122, U-57), (IA-123, S-123, U-57), (IA-124, S-124, U-57), (IA-125, S-125, U-57), (IA-126, S-126, U-57), (IA-127, S-127, U-57), (IA-128, S-128, U-57), (IA-129, S-129, U-57), (IA-130, S-130, U-57), (IA-131, S-131, U-57), (IA-132, S-132, U-57), (IA-133, S-133, U-57), (IA-134, S-134, U-57), (IA-135, S-135, U-57), (IA-136, S-136, U-57), (IA-137, S-137, U-57), (IA-138, S-138, U-57), (IA-139, S-139, U-57), (IA-140, S-140, U-57), (IA-141, S-141, U-57), (IA-142, S-142, U-57), (IA-143, S-143, U-57), (IA-144, S-144, U-57), (IA-145, S-145, U-57), (IA-146, S-146, U-57), (IA-147, S-147, U-57), (IA-148, S-148, U-57), (IA-149, S-149, U-57), (IA-150, S-150, U-57), (IA-151, S-151, U-57), (IA-152, S-152, U-57), (IA-153, S-153, U-57), (IA-154, S-154, U-57), (IA-155, S-155, U-57), (IA-156, S-156, U-57), (IA-157, S-157, U-57), (IA-158, S-158, U-57), (IA-159, S-159, U-57), (IA-160, S-160, U-57), (IA-161, S-161, U-57), (IA-162, S-162, U-57), (IA-163, S-163, U-57), (IA-164, S-164, U-57), (IA-165, S-165, U-57), (IA-166, S-166, U-57), (IA-167, S-167, U-57), (IA-168, S-168, U-57), (IA-169, S-169, U-57), (IA-170, S-170, U-57), (IA-171, S-171, U-57), (IA-172, S-172, U-57), (IA-173, S-173, U-57), (IA-174, S-174, U-57), (IA-175, S-175, U-57), (IA-176, S-176, U-57), (IA-177, S-177, U-57), (IA-178, S-178, U-57), (IA-179, S-179, U-57), (IA-180, S-180, U-57), (IA-181, S-181, U-57), (IA-182, S-182, U-57), (IA-183, S-183, U-57), (IA-184, S-184, U-57), (IA-185, S-185, U-57), (IA-186, S-186, U-57), (IA-187, S-187, U-57), (IA-188, S-188, U-57), (IA-189, S-189, U-57), (IA-190, S-190, U-57), (IA-191, S-191, U-57), (IA-192, S-192, U-57), (IA-193, S-193, U-57), (IA-194, S-194, U-57), (IA-195, S-195, U-57), (IA-196, S-196, U-57), (IA-197, S-197, U-57), (IA-198, S-198, U-57), (IA-199, S-199, U-57), (IA-201, S-201, U-57), (IA-202, S-202, U-57), (IA-203, S-203, U-57), (IA-204, S-204, U-57), (IA-205, S-205, U-57), (IA-206, S-206, U-57), (IA-207, S-207, U-57), (IA-210, S-210, U-57), (IA-211, S-211, U-57), (IA-212, S-212, U-57), (IA-213, S-213, U-57), (IA-214, S-214, U-57), (IA-215, S-215, U-57), (IA-216, S-216, U-57), (IA-217, S-217, U-57), (IA-218, S-218, U-57), (IA-219, S-219, U-57), (IA-220, S-220, U-57), (IA-221, S-221, U-57), (IA-222, S-222, U-57), (IA-223, S-223, U-57), (IA-224, S-224, U-57), (IA-225, S-225, U-57), (IA-226, S-226, U-57), (IA-227, S-227, U-57), (IA-228, S-228, U-57), (IA-229, S-229, U-57), (IA-230, S-230, U-57), (IA-231, S-231, U-57), (IA-232, S-232, U-57), (IA-233, S-233, U-57), (IA-234, S-234, U-57), (IA-235, S-235, U-57), (IA-236, S-236, U-57), (IA-237, S-237, U-57), (IA-238, S-238, U-57), (IA-239, S-239, U-57), (IA-240, S-240, U-57), (IA-241, S-241, U-57), (IA-242, S-242, U-57), (IA-243, S-243, U-57), (IA-244, S-244, U-57), (IA-245, S-245, U-57), (IA-246, S-246, U-57), (IA-247, S-247, U-57), (IA-248, S-248, U-57), (IA-249, S-249, U-57), (IA-250, S-250, U-57), (IA-251, S-251, U-57), (IA-252, S-252, U-57), (IA-253, S-253, U-57), (IA-254, S-254, U-57), (IA-255, S-255, U-57), (IA-256, S-256, U-57), (IA-257, S-257, U-57), (IA-258, S-258, U-57), (IA-259, S-259, U-57), (IA-260, S-260, U-57), (IA-261, S-261, U-57), (IA-262, S-262, U-57), (IA-263, S-263, U-57), (IA-264, S-264, U-57), (IA-265, S-265, U-57), (IA-266, S-266, U-57), (IA-267, S-267, U-57), (IA-268, S-268, U-57), (IA-269, S-269, U-57), (IA-270, S-270, U-57), (IA-271, S-271, U-57), (IA-272, S-272, U-57), (IA-273, S-273, U-57), (IA-274, S-274, U-57), (IA-275, S-275, U-57), (IA-276, S-276, U-57), (IA-277, S-277, U-57), (IA-278, S-278, U-57), (IA-279, S-279, U-57), (IA-280, S-280, U-57), (IA-281, S-281, U-57), (IA-282, S-282, U-57), (IA-283, S-283, U-57), (IA-284, S-284, U-57), (IA-285, S-285, U-57), (IA-286, S-286, U-57), (IA-287, S-287, U-57), (IA-288, S-288, U-57), (IA-289, S-289, U-57), (IA-290, S-290, U-57), (IA-291, S-291, U-57), (IA-292, S-292, U-57), (IA-293, S-293, U-57), (IA-294, S-294, U-57), (IA-295, S-295, U-57), (IA-296, S-296, U-57), (IA-297, S-297, U-57), (IA-298, S-298, U-57), (IA-299, S-299, U-57), (IA-300, S-300, U-57), (IA-301, S-301, U-57), (IA-302, S-302, U-57), (IA-303, S-303, U-57), (IA-304, S-304, U-57), (IA-305, S-305, U-57), (IA-306, S-306, U-57), (IA-307, S-307, U-57), (IA-308, S-308, U-57), (IA-309, S-309, U-57), (IA-310, S-310, U-57), (IA-311, S-311, U-57), (IA-312, S-312, U-57), (IA-313, S-313, U-57), (IA-314, S-314, U-57), (IA-315, S-315, U-57), (IA-316, S-316, U-57), (IA-317, S-317, U-57), (IA-318, S-318, U-57), (IA-319, S-319, U-57), (IA-320, S-320, U-57), (IA-321, S-321, U-57), (IA-322, S-322, U-57), (IA-323, S-323, U-57), (IA-324, S-324, U-57), (IA-325, S-325, U-57), (IA-326, S-326, U-57), (IA-327, S-327, U-57), (IA-328, S-328, U-57), (IA-329, S-329, U-57), (IA-330, S-330, U-57), (IA-331, S-331, U-57), (IA-332, S-332, U-57), (IA-333, S-333, U-57), (IA-334, S-334, U-57), (IA-335, S-335, U-57), (IA-336, S-336, U-57), (IA-337, S-337, U-57), (IA-338, S-338, U-57), (IA-339, S-339, U-57), (IA-340, S-340, U-57), (IA-341, S-341, U-57), (IA-342, S-342, U-57), (IA-343, S-343, U-57), (IA-344, S-344, U-57), (IA-345, S-345, U-57), (IA-346, S-346, U-57), (IA-347, S-347, U-57), (IA-348, S-348, U-57), (IA-349, S-349, U-57), (IA-350, S-350, U-57), (IA-351, S-351, U-57), (IA-352, S-352, U-57), (IA-353, S-353, U-57), (IA-354, S-354, U-57), (IA-355, S-355, U-57), (IA-356, S-356, U-57), (IA-357, S-357, U-57), (IA-358, S-358, U-57), (IA-359, S-359, U-57), (IA-360, S-360, U-57), (IA-361, S-361, U-57), (IA-362, S-362, U-57), (IA-363, S-363, U-57), (IA-364, S-364, U-57), (IA-365, S-365, U-57), (IA-366, S-366, U-57), (IA-367, S-367, U-57), (IA-368, S-368, U-57), (IA-369, S-369, U-57), (IA-370, S-370, U-57), (IA-371, S-371, U-57), (IA-372, S-372, U-57), (IA-373, S-373, U-57), (IA-374, S-374, U-57), (IA-375, S-375, U-57), (IA-376, S-376, U-57), (IA-377, S-377, U-57), (IA-378, S-378, U-57), (IA-379, S-379, U-57), (IA-380, S-380, U-57), (IA-381, S-381, U-57), (IA-382, S-382, U-57), (IA-383, S-383, U-57), (IA-384, S-384, U-57), (IA-385, S-385, U-57), (IA-386, S-386, U-57), (IA-387, S-387, U-57), (IA-388, S-388, U-57), (IA-390, S-390, U-57), (IA-391, S-391, U-57), (IA-392, S-392, U-57), (IA-393, S-393, U-57), (IA-394, S-394, U-57), (IA-395, S-395, U-57), (IA-396, S-396, U-57), (IA-397, S-397, U-57), (IA-398, S-398, U-57), (IA-399, S-399, U-57), (IA-400, S-400, U-57), (IA-401, S-401, U-57), (IA-402, S-402, U-57), (IA-403, S-403, U-57), (IA-404, S-404, U-57), (IA-405, S-405, U-57), (IA-406, S-406, U-57), (IA-407, S-407, U-57), (IA-408, S-408, U-57), (IA-409, S-409, U-57), (IA-410, S-410, U-57), (IA-411, S-411, U-57), (IA-412, S-412, U-57), (IA-413, S-413, U-57), (IA-414, S-414, U-57), (IA-415, S-415, U-57), (IA-416, S-416, U-57), (IA-417, S-417, U-57), (IA-418, S-418, U-57), (IA-419, S-419, U-57), (IA-420, S-420, U-57), (IA-421, S-421, U-57), (IA-422, S-422, U-57), (IA-423, S-423, U-57), (IA-424, S-424, U-57), (IA-425, S-425, U-57), (IA-426, S-426, U-57), (IA-427, S-427, U-57), (IA-428, S-428, U-57), (IA-429, S-429, U-57), (IA-430, S-430, U-57), (IA-431, S-431, U-57), (IA-432, S-432, U-57), (IA-433, S-433, U-57), (IA-434, S-434, U-57), (IA-435, S-435, U-57), (IA-436, S-436, U-57), (IA-437, S-437, U-57), (IA-438, S-438, U-57), (IA-439, S-439, U-57), (IA-440, S-440, U-57), (IA-441, S-441, U-57), (IA-442, S-442, U-57), (IA-443, S-443, U-57), (IA-444, S-444, U-57), (IA-445, S-445, U-57), (IA-446, S-446, U-57), (IA-447, S-447, U-57), (IA-448, S-448, U-57), (IA-449, S-449, U-57), (IA-450, S-450, U-57), (IA-451, S-451, U-57), (IA-452, S-452, U-57), (IA-453, S-453, U-57), (IA-454, S-454, U-57), (IA-455, S-455, U-57), (IA-456, S-456, U-57), (IA-457, S-457, U-57), (IA-458, S-458, U-57), (IA-459, S-459, U-57), (IA-460, S-460, U-57), (IA-461, S-461, U-57), (IA-462, S-462, U-57), (IA-463, S-463, U-57), (IA-464, S-464, U-57), (IA-465, S-465, U-57), (IA-466, S-466, U-57), (IA-467, S-467, U-57), (IA-468, S-468, U-57), (IA-469, S-469, U-57), (IA-470, S-470, U-57), (IA-471, S-471, U-57), (IA-472, S-472, U-57), (IA-473, S-473, U-57), (IA-474, S-474, U-57), (IA-475, S-475, U-57), (IA-476, S-476, U-57), (IA-477, S-477, U-57), (IA-478, S-478, U-57), (IA-479, S-479, U-57), (IA-480, S-480, U-57), (IA-481, S-481, U-57), (IA-482, S-482, U-57), (IA-483, S-483, U-57), (IA-484, S-484, U-57), (IA-485, S-485, U-57), (IA-486, S-486, U-57), (IA-487, S-487, U-57), (IA-488, S-488, U-57), (IA-489, S-489, U-57), (IA-490, S-490, U-57), (IA-491, S-491, U-57), (IA-492, S-492, U-57), (IA-493, S-493, U-57), (IA-494, S-494, U-57), (IA-495, S-495, U-57), (IA-496, S-496, U-57), (IA-497, S-497, U-57), (IA-498, S-498, U-57), (IA-499, S-499, U-57), (IA-500, S-500, U-57), (IA-501, S-501, U-57), (IA-502, S-502, U-57), (IA-503, S-503, U-57), (IA-504, S-504, U-57), (IA-505, S-505, U-57), (IA-506, S-506, U-57), (IA-507, S-507, U-57), (IA-508, S-508, U-57), (IA-509, S-509, U-57), (IA-510, S-510, U-57), (IA-511, S-511, U-57), (IA-512, S-512, U-57), (IA-513, S-513, U-57), (IA-514, S-514, U-57), (IA-515, S-515, U-57), (IA-516, S-516, U-57), (IA-517, S-517, U-57), (IA-518, S-518, U-57), (IA-519, S-519, U-57), (IA-520, S-520, U-57), (IA-521, S-521, U-57), (IA-522, S-522, U-57), (IA-523, S-523, U-57), (IA-524, S-524, U-57), (IA-525, S-525, U-57), (IA-526, S-526, U-57), (IA-527, S-527, U-57), (IA-528, S-528, U-57), (IA-529, S-529, U-57), (IA-530, S-530, U-57), (IA-531, S-531, U-57), (IA-532, S-532, U-57), (IA-533, S-533, U-57), (IA-534, S-534, U-57), (IA-535, S-535, U-57), (IA-536, S-536, U-57), (IA-537, S-537, U-57), (IA-538, S-538, U-57), (IA-539, S-539, U-57), (IA-540, S-540, U-57), (IA-541, S-541, U-57), (IA-542, S-542, U-57), (IA-543, S-543, U-57), (IA-544, S-544, U-57), (IA-545, S-545, U-57), (IA-546, S-546, U-57), (IA-547, S-547, U-57), (IA-548, S-548, U-57), (IA-549, S-549, U-57), (IA-550, S-550, U-57), (IA-551, S-551, U-57), (IA-552, S-552, U-57), (IA-553, S-553, U-57), (IA-554, S-554, U-57), (IA-555, S-555, U-57), (IA-556, S-556, U-57), (IA-557, S-557, U-57), (IA-558, S-558, U-57), (IA-559, S-559, U-57), (IA-560, S-560, U-57), (IA-561, S-561, U-57), (IA-562, S-562, U-57), (IA-563, S-563, U-57), (IA-564, S-564, U-57), (IA-565, S-565, U-57), (IA-566, S-566, U-57), (IA-567, S-567, U-57), (IA-568, S-568, U-57), (IA-569, S-569, U-57), (IA-570, S-570, U-57), (IA-571, S-571, U-57), (IA-572, S-572, U-57), (IA-573, S-573, U-57), (IA-574, S-574, U-57), (IA-575, S-575, U-57), (IA-576, S-576, U-57), (IA-577, S-577, U-57), (IA-578, S-578, U-57), (IA-579, S-579, U-57), (IA-580, S-580, U-57), (IA-581, S-581, U-57), (IA-582, S-6, U-58), (IA-583, S-7, U-58), (IA-584, S-15, U-58), (IA-585, S-16, U-58), (IA-586, S-26, U-58), (IA-587, S-27, U-58), (IA-588, S-37, U-58), (IA-589, S-38, U-58), (IA-590, S-48, U-58), (IA-591, S-49, U-58), (IA-592, S-59, U-58), (IA-593, S-60, U-58), (IA-594, S-70, U-58), (IA-595, S-71, U-58), (IA-596, S-81, U-58), (IA-597, S-82, U-58), (IA-598, S-92, U-58), (IA-599, S-93, U-58), (IA-600, S-103, U-58), (IA-601, S-104, U-58), (IA-602, S-114, U-58), (IA-603, S-115, U-58), (IA-604, S-125, U-58), (IA-605, S-126, U-58), (IA-606, S-136, U-58), (IA-607, S-137, U-58), (IA-608, S-147, U-58), (IA-609, S-148, U-58), (IA-610, S-158, U-58), (IA-611, S-159, U-58), (IA-612, S-169, U-58), (IA-613, S-170, U-58), (IA-614, S-180, U-58), (IA-615, S-181, U-58), (IA-616, S-191, U-58), (IA-617, S-192, U-58), (IA-618, S-200, U-58), (IA-619, S-201, U-58), (IA-620, S-209, U-58), (IA-621, S-210, U-58), (IA-622, S-220, U-58), (IA-623, S-221, U-58), (IA-624, S-231, U-58), (IA-625, S-232, U-58), (IA-626, S-242, U-58), (IA-627, S-243, U-58), (IA-628, S-253, U-58), (IA-629, S-254, U-58), (IA-630, S-264, U-58), (IA-631, S-265, U-58), (IA-632, S-275, U-58), (IA-633, S-276, U-58), (IA-634, S-286, U-58), (IA-635, S-287, U-58), (IA-636, S-297, U-58), (IA-637, S-298, U-58), (IA-638, S-308, U-58), (IA-639, S-309, U-58), (IA-640, S-319, U-58), (IA-641, S-320, U-58), (IA-642, S-330, U-58), (IA-643, S-331, U-58), (IA-644, S-341, U-58), (IA-645, S-342, U-58), (IA-646, S-352, U-58), (IA-647, S-353, U-58), (IA-648, S-363, U-58), (IA-649, S-364, U-58), (IA-650, S-374, U-58), (IA-651, S-375, U-58), (IA-652, S-385, U-58), (IA-653, S-386, U-58), (IA-654, S-6, U-59), (IA-655, S-7, U-59), (IA-656, S-15, U-59), (IA-657, S-16, U-59), (IA-658, S-26, U-59), (IA-659, S-27, U-59), (IA-660, S-37, U-59), (IA-661, S-38, U-59), (IA-662, S-48, U-59), (IA-663, S-49, U-59), (IA-664, S-59, U-59), (IA-665, S-60, U-59), (IA-666, S-70, U-59), (IA-667, S-71, U-59), (IA-668, S-81, U-59), (IA-669, S-82, U-59), (IA-670, S-92, U-59), (IA-671, S-93, U-59), (IA-672, S-103, U-59), (IA-673, S-104, U-59), (IA-674, S-114, U-59), (IA-675, S-115, U-59), (IA-676, S-125, U-59), (IA-677, S-126, U-59), (IA-678, S-136, U-59), (IA-679, S-137, U-59), (IA-680, S-147, U-59), (IA-681, S-148, U-59), (IA-682, S-158, U-59), (IA-683, S-159, U-59), (IA-684, S-169, U-59), (IA-685, S-170, U-59), (IA-686, S-180, U-59), (IA-687, S-181, U-59), (IA-688, S-191, U-59), (IA-689, S-192, U-59), (IA-690, S-200, U-59), (IA-691, S-201, U-59), (IA-692, S-209, U-59), (IA-693, S-210, U-59), (IA-694, S-220, U-59), (IA-695, S-221, U-59), (IA-696, S-231, U-59), (IA-697, S-232, U-59), (IA-698, S-242, U-59), (IA-699, S-243, U-59), (IA-700, S-253, U-59), (IA-701, S-254, U-59), (IA-702, S-264, U-59), (IA-703, S-265, U-59), (IA-704, S-275, U-59), (IA-705, S-276, U-59), (IA-706, S-286, U-59), (IA-707, S-287, U-59), (IA-708, S-297, U-59), (IA-709, S-298, U-59), (IA-710, S-308, U-59), (IA-711, S-309, U-59), (IA-712, S-319, U-59), (IA-713, S-320, U-59), (IA-714, S-330, U-59), (IA-715, S-331, U-59), (IA-716, S-341, U-59), (IA-717, S-342, U-59), (IA-718, S-352, U-59), (IA-719, S-353, U-59), (IA-720, S-363, U-59), (IA-721, S-364, U-59), (IA-722, S-374, U-59), (IA-723, S-375, U-59), (IA-724, S-385, U-59), (IA-725, S-386, U-59), (IA-726, S-6, U-60), (IA-727, S-7, U-60), (IA-728, S-15, U-60), (IA-729, S-16, U-60), (IA-730, S-26, U-60), (IA-731, S-27, U-60), (IA-732, S-37, U-60), (IA-733, S-38, U-60), (IA-734, S-48, U-60), (IA-735, S-49, U-60), (IA-736, S-59, U-60), (IA-737, S-60, U-60), (IA-738, S-70, U-60), (IA-739, S-71, U-60), (IA-740, S-81, U-60), (IA-741, S-82, U-60), (IA-742, S-92, U-60), (IA-743, S-93, U-60), (IA-744, S-103, U-60), (IA-745, S-104, U-60), (IA-746, S-114, U-60), (IA-747, S-115, U-60), (IA-748, S-125, U-60), (IA-749, S-126, U-60), (IA-750, S-136, U-60), (IA-751, S-137, U-60), (IA-752, S-147, U-60), (IA-753, S-148, U-60), (IA-754, S-158, U-60), (IA-755, S-159, U-60), (IA-756, S-169, U-60), (IA-757, S-170, U-60), (IA-758, S-180, U-60), (IA-759, S-181, U-60), (IA-760, S-191, U-60), (IA-761, S-192, U-60), (IA-762, S-200, U-60), (IA-763, S-201, U-60), (IA-764, S-209, U-60), (IA-765, S-210, U-60), (IA-766, S-220, U-60), (IA-767, S-221, U-60), (IA-768, S-231, U-60), (IA-769, S-232, U-60), (IA-770, S-242, U-60), (IA-771, S-243, U-60), (IA-772, S-253, U-60), (IA-773, S-254, U-60), (IA-774, S-264, U-60), (IA-775, S-265, U-60), (IA-776, S-275, U-60), (IA-777, S-276, U-60), (IA-778, S-286, U-60), (IA-779, S-287, U-60), (IA-780, S-297, U-60), (IA-781, S-298, U-60), (IA-782, S-308, U-60), (IA-783, S-309, U-60), (IA-784, S-319, U-60), (IA-785, S-320, U-60), (IA-786, S-330, U-60), (IA-787, S-331, U-60), (IA-788, S-341, U-60), (IA-789, S-342, U-60), (IA-790, S-352, U-60), (IA-791, S-353, U-60), (IA-792, S-363, U-60), (IA-793, S-364, U-60), (IA-794, S-374, U-60), (IA-795, S-375, U-60), (IA-796, S-385, U-60), (IA-797, S-386, U-60), (IA-798, S-6, U-61), (IA-799, S-7, U-61), (IA-800, S-15, U-61), (IA-801, S-16, U-61), (IA-802, S-26, U-61), (IA-803, S-27, U-61), (IA-804, S-37, U-61), (IA-805, S-38, U-61), (IA-806, S-48, U-61), (IA-807, S-49, U-61), (IA-808, S-59, U-61), (IA-809, S-60, U-61), (IA-810, S-70, U-61), (IA-811, S-71, U-61), (IA-812, S-81, U-61), (IA-813, S-82, U-61), (IA-814, S-92, U-61), (IA-815, S-93, U-61), (IA-816, S-103, U-61), (IA-817, S-104, U-61), (IA-818, S-114, U-61), (IA-819, S-115, U-61), (IA-820, S-125, U-61), (IA-821, S-126, U-61), (IA-822, S-136, U-61), (IA-823, S-137, U-61), (IA-824, S-147, U-61), (IA-825, S-148, U-61), (IA-826, S-158, U-61), (IA-827, S-159, U-61), (IA-828, S-169, U-61), (IA-829, S-170, U-61), (IA-830, S-180, U-61), (IA-831, S-181, U-61), (IA-832, S-191, U-61), (IA-833, S-192, U-61), (IA-834, S-200, U-61), (IA-835, S-201, U-61), (IA-836, S-209, U-61), (IA-837, S-210, U-61), (IA-838, S-220, U-61), (IA-839, S-221, U-61), (IA-840, S-231, U-61), (IA-841, S-232, U-61), (IA-842, S-242, U-61), (IA-843, S-243, U-61), (IA-844, S-253, U-61), (IA-845, S-254, U-61), (IA-846, S-264, U-61), (IA-847, S-265, U-61), (IA-848, S-275, U-61), (IA-849, S-276, U-61), (IA-850, S-286, U-61), (IA-851, S-287, U-61), (IA-852, S-297, U-61), (IA-853, S-298, U-61), (IA-854, S-308, U-61), (IA-855, S-309, U-61), (IA-856, S-319, U-61), (IA-857, S-320, U-61), (IA-858, S-330, U-61), (IA-859, S-331, U-61), (IA-860, S-341, U-61), (IA-861, S-342, U-61), (IA-862, S-352, U-61), (IA-863, S-353, U-61), (IA-864, S-363, U-61), (IA-865, S-364, U-61), (IA-866, S-374, U-61), (IA-867, S-375, U-61), (IA-868, S-385, U-61), (IA-869, S-386, U-61), (IA-870, S-6, U-65), (IA-871, S-7, U-65), (IA-872, S-15, U-65), (IA-873, S-16, U-65), (IA-874, S-26, U-65), (IA-875, S-27, U-65), (IA-876, S-37, U-65), (IA-877, S-38, U-65), (IA-878, S-48, U-65), (IA-879, S-49, U-65), (IA-880, S-59, U-65), (IA-881, S-60, U-65), (IA-882, S-70, U-65), (IA-883, S-71, U-65), (IA-884, S-81, U-65), (IA-885, S-82, U-65), (IA-886, S-92, U-65), (IA-887, S-93, U-65), (IA-888, S-103, U-65), (IA-889, S-104, U-65), (IA-890, S-114, U-65), (IA-891, S-115, U-65), (IA-892, S-125, U-65), (IA-893, S-126, U-65), (IA-894, S-136, U-65), (IA-895, S-137, U-65), (IA-896, S-147, U-65), (IA-897, S-148, U-65), (IA-898, S-158, U-65), (IA-899, S-159, U-65), (IA-900, S-169, U-65), (IA-901, S-170, U-65), (IA-902, S-180, U-65), (IA-903, S-181, U-65), (IA-904, S-191, U-65), (IA-905, S-192, U-65), (IA-906, S-200, U-65), (IA-907, S-201, U-65), (IA-908, S-209, U-65), (IA-909, S-210, U-65), (IA-910, S-220, U-65), (IA-911, S-221, U-65), (IA-912, S-231, U-65), (IA-913, S-232, U-65), (IA-914, S-242, U-65), (IA-915, S-243, U-65), (IA-916, S-253, U-65), (IA-917, S-254, U-65), (IA-918, S-264, U-65), (IA-919, S-265, U-65), (IA-920, S-275, U-65), (IA-921, S-276, U-65), (IA-922, S-286, U-65), (IA-923, S-287, U-65), (IA-924, S-297, U-65), (IA-925, S-298, U-65), (IA-926, S-308, U-65), (IA-927, S-309, U-65), (IA-928, S-319, U-65), (IA-929, S-320, U-65), (IA-930, S-330, U-65), (IA-931, S-331, U-65), (IA-932, S-341, U-65), (IA-933, S-342, U-65), (IA-934, S-352, U-65), (IA-935, S-353, U-65), (IA-936, S-363, U-65), (IA-937, S-364, U-65), (IA-938, S-374, U-65), (IA-939, S-375, U-65), (IA-940, S-385, U-65), (IA-941, S-386, U-65), (IA-942, S-6, U-65), (IA-943, S-7, U-65), (IA-944, S-15, U-65), (IA-945, S-16, U-65), (IA-946, S-26, U-65), (IA-947, S-27, U-65), (IA-948, S-37, U-65), (IA-949, S-38, U-65), (IA-950, S-48, U-65), (IA-951, S-49, U-65), (IA-952, S-59, U-65), (IA-953, S-60, U-65), (IA-954, S-70, U-65), (IA-955, S-71, U-65), (IA-956, S-81, U-65), (IA-957, S-82, U-65), (IA-958, S-92, U-65), (IA-959, S-93, U-65), (IA-960, S-103, U-65), (IA-961, S-104, U-65), (IA-962, S-114, U-65), (IA-963, S-115, U-65), (IA-964, S-125, U-65), (IA-965, S-126, U-65), (IA-966, S-136, U-65), (IA-967, S-137, U-65), (IA-968, S-147, U-65), (IA-969, S-148, U-65), (IA-970, S-158, U-65), (IA-971, S-159, U-65), (IA-972, S-169, U-65), (IA-973, S-170, U-65), (IA-974, S-180, U-65), (IA-975, S-181, U-65), (IA-976, S-191, U-65), (IA-977, S-192, U-65), (IA-978, S-200, U-65), (IA-979, S-201, U-65), (IA-980, S-209, U-65), (IA-981, S-210, U-65), (IA-982, S-220, U-65), (IA-983, S-221, U-65), (IA-984, S-231, U-65), (IA-985, S-232, U-65), (IA-986, S-242, U-65), (IA-987, S-243, U-65), (IA-988, S-253, U-65), (IA-989, S-254, U-65), (IA-990, S-264, U-65), (IA-991, S-265, U-65), (IA-992, S-275, U-65), (IA-993, S-276, U-65), (IA-994, S-286, U-65), (IA-995, S-287, U-65), (IA-996, S-297, U-65), (IA-997, S-298, U-65), (IA-998, S-308, U-65), (IA-999, S-309, U-65), (IA-1000, S-319, U-65), (IA-1001, S-320, U-65), (IA-1002, S-330, U-65), (IA-1003, S-331, U-65), (IA-1004, S-341, U-65), (IA-1005, S-342, U-65), (IA-1006, S-352, U-65), (IA-1007, S-353, U-65), (IA-1008, S-363, U-65), (IA-1009, S-364, U-65), (IA-1010, S-374, U-65), (IA-1011, S-375, U-65), (IA-1012, S-385, U-65), (IA-1013, S-386, U-65), (IA-1014, S-6, U-69), (IA-1015, S-7, U-69), (IA-1016, S-15, U-69), (IA-1017, S-16, U-69), (IA-1018, S-26, U-69), (IA-1019, S-27, U-69), (IA-1020, S-37, U-69), (IA-1021, S-38, U-69), (IA-1022, S-48, U-69), (IA-1023, S-49, U-69), (IA-1024, S-59, U-69), (IA-1025, S-60, U-69), (IA-1026, S-70, U-69), (IA-1027, S-71, U-69), (IA-1028, S-81, U-69), (IA-1029, S-82, U-69), (IA-1030, S-92, U-69), (IA-1031, S-93, U-69), (IA-1032, S-103, U-69), (IA-1033, S-104, U-69), (IA-1034, S-114, U-69), (IA-1035, S-115, U-69), (IA-1036, S-125, U-69), (IA-1037, S-126, U-69), (IA-1038, S-136, U-69), (IA-1039, S-137, U-69), (IA-1040, S-147, U-69), (IA-1041, S-148, U-69), (IA-1042, S-158, U-69), (IA-1043, S-159, U-69), (IA-1044, S-169, U-69), (IA-1045, S-170, U-69), (IA-1046, S-180, U-69), (IA- 1047, S-181, U-69), (IA-1048, S-191, U-69), (IA-1049, S-192, U-69), (IA-1050, S-200, U-69), (IA-1051, S-201, U-69), (IA-1052, S-209, U-69), (IA-1053, S-210, U-69), (IA-1054, S-220, U-69), (IA-1055, S-221, U-69), (IA-1056, S-231, U-69), (IA-1057, S-232, U-69), (IA-1058, S-242, U-69), (IA-1059, S-243, U-69), (IA-1060, S-253, U-69), (IA-1061, S-254, U-69), (IA-1062, S-264, U-69), (IA-1063, S-265, U-69), (IA-1064, S-275, U-69), (IA-1065, S-276, U-69), (IA-1066, S-286, U-69), (IA-1067, S-287, U-69), (IA-1068, S-297, U-69), (IA-1069, S-298, U-69), (IA-1070, S-308, U-69), (IA-1071, S-309, U-69), (IA-1072, S-319, U-69), (IA-1073, S-320, U-69), (IA-1074, S-330, U-69), (IA-1075, S-331, U-69), (IA-1076, S-341, U-69), (IA-1077, S-342, U-69), (IA-1078, S-352, U-69), (IA-1079, S-353, U-69), (IA-1080, S-363, U-69), (IA-1081, S-364, U-69), (IA-1082, S-374, U-69), (IA-1083, S-375, U-69), (IA-1084, S-385, U-69), (IA-1085, S-386, U-69), (IA-1086, S-6, U-74), (IA-1087, S-7, U-74), (IA-1088, S-15, U-74), (IA-1089, S-16, U-74), (IA-1090, S-26, U-74), (IA-1091, S-27, U-74), (IA-1092, S-37, U-74), (IA-1093, S-38, U-74), (IA-1094, S-48, U-74), (IA-1095, S-49, U-74), (IA-1096, S-59, U-74), (IA-1097, S-60, U-74), (IA-1098, S-70, U-74), (IA-1099, S-71, U-74), (IA-1100, S-81, U-74), (IA-1101, S-82, U-74), (IA-1102, S-92, U-74), (IA-1103, S-93, U-74), (IA-1104, S-103, U-74), (IA-1105, S-104, U-74), (IA-1106, S-114, U-74), (IA-1107, S-115, U-74), (IA-1108, S-125, U-74), (IA-109, S-126, U-74), (IA-1110, S-136, U-74), (IA-1111, S-137, U-74), (IA-1112, S-147, U-74), (IA-1113, S-148, U-74), (IA-1114, S-158, U-74), (IA-1115, S-159, U-74), (IA-1116, S-169, U-74), (IA-1117, S-170, U-74), (IA-1118, S-180, U-74), (IA-1119, S-181, U-74), (IA-1120, S-191, U-74), (IA-1121, S-192, U-74), (IA-1122, S-200, U-74), (IA-1123, S-201, U-74), (IA-1124, S-209, U-74), (IA-1125, S-210, U-74), (IA-1126, S-220, U-74), (IA-1127, S-221, U-74), (IA-1128, S-231, U-74), (IA-1129, S-232, U-74), (IA-1130, S-242, U-74), (IA-1131, S-243, U-74), (IA-1132, S-253, U-74), (IA-1133, S-254, U-74), (IA-1134, S-264, U-74), (IA-1135, S-265, U-74), (IA-1136, S-275, U-74), (IA-1137, S-276, U-74), (IA-1138, S-286, U-74), (IA-1139, S-287, U-74), (IA-1140, S-297, U-74), (IA-1141, S-298, U-74), (IA-1142, S-308, U-74), (IA-1143, S-309, U-74), (IA-1144, S-319, U-74), (IA-1145, S-320, U-74), (IA-1146, S-330, U-74), (IA-1147, S-331, U-74), (IA-1148, S-341, U-74), (IA-1149, S-342, U-74), (IA-1150, S-352, U-74), (IA-1151, S-353, U-74), (IA-1152, S-363, U-74), (IA-1153, S-364, U-74), (IA-1154, S-374, U-74), (IA-1155, S-375, U-74), (IA-1156, S-385, U-74), (IA-1157, S-386, U-74), (IA-1158, S-6, U-1), (IA-1159, S-6, U-2), (IA-1160, S-6, U-3), (IA-1161, S-6, U-4), (IA-1162, S-6, U-5), (IA-1163, S-6, U-6), (IA-1164, S-6, U-7), (IA-1165, S-6, U-8), (IA-1166, S-6, U-9), (IA-1167, S-6, U-10), (IA-1168, S-6, U-11), (IA-1169, S-6, U-12), (IA-1170, S-6, U-13), (IA-1171, S-6, U-14), (IA-1172, S-6, U-15), (IA-1173, S-6, U-16), (IA-1174, S-6, U-17), (IA-1175, S-6, U-18), (IA-1176, S-6, U-19), (IA-1177, S-6, U-20), (IA-1178, S-6, U-21), (IA-1179, S-6, U-22), (IA-1180, S-6, U-23), (IA-1181, S-6, U-24), (IA-1182, S-6, U-25), (IA-1183, S-6, U-26), (IA-1184, S-6, U-27), (IA-1185, S-6, U-28), (IA-1186, S-6, U-29), (IA-1187, S-6, U-30), (IA-1188, S-6, U-31), (IA-1189, S-6, U-32), (IA-1190, S-6, U-33), (IA-1191, S-6, U-34), (IA-1192, S-6, U-35), (IA-1193, S-6, U-36), (IA-1194, S-6, U-37), (IA-1195, S-6, U-38), (IA-1196, S-6, U-39), (IA-1197, S-6, U-40), (IA-1198, S-6, U-41), (IA-1199, S-6, U-42), (IA-1200, S-6, U-43), (IA-1201, S-6, U-44), (IA-1202, S-6, U-45), (IA-1203, S-6, U-46), (IA-1204, S-6, U-47), (IA-1205, S-6, U-48), (IA-1206, S-6, U-49), (IA-1207, S-6, U-50), (IA-1208, S-6, U-51), (IA-1209, S-6, U-52), (IA-1210, S-6, U-53), (IA-1211, S-6, U-54), (IA-1212, S-6, U-55), (IA-1213, S-6, U-56), (IA-1214, S-6, U-62), (IA-1215, S-6, U-63), (IA-1216, S-6, U-64), (IA-1217, S-6, U-66), (IA-1218, S-6, U-67), (IA-1219, S-6, U-68), (IA-1220, S-6, U-70), (IA-1221, S-6, U-71), (IA-1222, S-6, U-72), (IA-1223, S-6, U-73), (IA-1224, S-6, U-75), (IA-1225, S-6, U-76), (IA-1226, S-6, U-77), (IA-1227, S-6, U-78), (IA-1228, S-6, U-79), (IA-1229, S-6, U-80), (IA-1230, S-6, U-81), (IA-1231, S-6, U-82), (IA-1232, S-6, U-83), (IA-1233, S-6, U-84), (IA-1234, S-6, U-85), (IA-1235, S-6, U-86), (IA-1236, S-6, U-87), (IA-1237, S-6, U-88), (IA-1238, S-6, U-89), (IA-1239, S-6, U-90), (IA-1240, S-6, U-91), (IA-1241, S-6, U-92), (IA-1242, S-6, U-93), (IA-1243, S-6, U-94), (IA-1244, S-6, U-95), (IA-1245, S-6, U-96), (IA-1246, S-6, U-97), (IA-1247, S-6, U-98), (IA-1248, S-6, U-99), (IA-1249, S-6, U-100), (IA-1250, S-6, U-101), (IA-1251, S-6, U-102), (IA-1252, S-6, U-103), (IA-1253, S-6, U-104), (IA-1254, S-6, U-105), (IA-1255, S-6, U-106), (IA-1256, S-6, U-107), (IA-1257, S-6, U-108), (IA-1258, S-6, U-109), (IA-1259, S-6, U-110), (IA-1260, S-6, U-111), (IA-1261, S-6, U-112), (IA-1262, S-6, U-113), (IA-1263, S-6, U-114), (IA-1264, S-6, U-115), (IA-1265, S-6, U-116), (IA-1266, S-6, U-117), (IA-1267, S-6, U-118), (IA-1268, S-6, U-119), (IA-1269, S-6, U-120), (IA-1270, S-6, U-121), (IA-1271, S-6, U-122), (IA-1272, S-6, U-123), (IA-1273, S-6, U-124), (IA-1274, S-6, U-125), (IA-1275, S-6, U-126), (IA-1276, S-6, U-127), (IA-1277, S-6, U-128), (IA-1278, S-6, U-129), (IA-1279, S-6, U-130), (IA-1280, S-6, U-131), (IA-1281, S-6, U-132), (IA-1282, S-6, U-133), (IA-1283, S-6, U-134), (IA-1284, S-6, U-135), (IA-1285, S-6, U-136), (IA-1286, S-6, U-137), (IA-1287, S-6, U-138), (IA-1288, S-6, U-139), (IA-1289, S-6, U-140), (IA-1290, S-6, U-141), (IA-1291, S-6, U-142), (IA-1292, S-6, U-143), (IA-1293, S-6, U-144), (IA-1294, S-6, U-145), (IA-1295, S-6, U-146), (IA-1296, S-6, U-147), (IA-1297, S-6, U-148), (IA-1298, S-6, U-149), (IA-1299, S-6, U-150), (IA-1300, S-6, U-151), (IA-1301, S-6, U-152), (IA-1302, S-6, U-153), (IA-1303, S-6, U-154), (IA-1304, S-6, U-155), (IA-1305, S-6, U-156), (IA-1306, S-6, U-157), (IA-1307, S-6, U-158), (IA-1308, S-6, U-159), (IA-1309, S-6, U-160), (IA-1310, S-6, U-161), (IA-1311, S-6, U-162), (IA-1312, S-6, U-163), (IA-1313, S-6, U-164), (IA-1314, S-6, U-165), (IA-1315, S-6, U-166), (IA-1316, S-6, U-167), (IA-1317, S-6, U-168), (IA-1318, S-6, U-169), (IA-1319, S-6, U-170), (IA-1320, S-6, U-171), (IA-1321, S-6, U-172), (IA-1322, S-6, U-173), (IA-1323, S-6, U-174), (IA-1324, S-6, U-175), (IA-1325, S-6, U-176), (IA-1326, S-6, U-177), (IA-1327, S-6, U-178), (IA-1328, S-6, U-179), (IA-1329, S-6, U-180), (IA-1330, S-6, U-181), (IA-1331, S-6, U-182), (IA-1332, S-6, U-183), (IA-1333, S-6, U-184), (IA-1334, S-6, U-185), (IA-1335, S-6, U-186), (IA-1336, S-6, U-187), (IA-1337, S-6, U-188), (IA-1338, S-6, U-189), (IA-1339, S-6, U-190), (IA-1340, S-6, U-191), (IA-1341, S-6, U-192), (IA-1342, S-6, U-193), (IA-1343, S-6, U-194), (IA-1344, S-6, U-195), (IA-1345, S-6, U-196), (IA-1346, S-6, U-197), (IA-1347, S-6, U-198), (IA-1348, S-6, U-199), (IA-1349, S-6, U-200), (IA-1350, S-6, U-201), (IA-1351, S-6, U-202), (IA-1352, S-6, U-203), (IA-1353, S-6, U-204), (IA-1354, S-6, U-205), (IA-1355, S-6, U-206), (IA-1356, S-6, U-207), (IA-1357, S-6, U-208), (IA-1358, S-6, U-209), (IA-1359, S-6, U-210), (IA-1360, S-6, U-211), (IA-1361, S-6, U-212), (IA-1362, S-6, U-213), (IA-1363, S-6, U-214), (IA-1364, S-6, U-215), (IA-1365, S-6, U-216), (IA-1366, S-6, U-217), (IA-1367, S-6, U-218), (IA-1368, S-6, U-219), (IA-1369, S-6, U-220), (IA-1370, S-6, U-221), (IA-1371, S-6, U-222), (IA-1372, S-6, U-223), (IA-1373, S-6, U-224), (IA-1374, S-6, U-225), (IA-1375, S-6, U-226), (IA-1376, S-6, U-227), (IA- 1377, S-6, U-228), (IA-1378, S-6, U-229), (IA-1379, S-6, U-230), (IA-1380, S-6, U-231), (IA-1381, S-6, U-232), (IA-1382, S-6, U-233), (IA-1383, S-6, U-234), (IA-1384, S-6, U-235), (IA-1385, S-6, U-236), (IA-1386, S-6, U-237), (IA-1387, S-6, U-238), (IA-1388, S-6, U-239), (IA-1389, S-6, U-240), (IA-1390, S-6, U-241), (IA-1391, S-6, U-242), (IA-1392, S-6, U-243), (IA-1393, S-6, U-244), (IA-1394, S-6, U-245), (IA-1395, S-6, U-246), (IA-1396, S-6, U-247), (IA-1397, S-6, U-248), (IA-1398, S-6, U-249), (IA-1399, S-6, U-250), (IA-1400, S-6, U-251), (IA-1401, S-6, U-252), (IA-1402, S-6, U-253), (IA-1403, S-6, U-254), (IA-1404, S-6, U-255), (IA-1405, S-6, U-256), (IA-1406, S-6, U-257), (IA-1407, S-6, U-258), (IA-1408, S-6, U-259), (IA-1409, S-6, U-260), (IA-1410, S-6, U-261), (IA-1411, S-6, U-262), (IA-1412, S-6, U-263), (IA-1413, S-6, U-264), (IA-1414, S-6, U-265), (IA-1415, S-6, U-266), (IA-1416, S-6, U-267), (IA-1417, S-6, U-268), (IA-1418, S-6, U-269), (IA-1419, S-6, U-270), (IA-1420, S-6, U-271), (IA-1421, S-6, U-272), (IA-1422, S-6, U-273), (IA-1423, S-6, U-274), (IA-1424, S-6, U-275), (IA-1425, S-6, U-276), (IA-1426, S-6, U-277), (IA-1427, S-6, U-278), (IA-1428, S-6, U-279), (IA-1429, S-6, U-280), (IA-1430, S-6, U-281), (IA-1431, S-6, U-282), (IA-1432, S-6, U-283), (IA-1433, S-6, U-284), (IA-1434, S-6, U-285), (IA-1435, S-6, U-286), (IA-1436, S-6, U-287), (IA-1437, S-6, U-288), (IA-1438, S-6, U-289), (IA-1439, S-6, U-290), (IA-1440, S-6, U-291), (IA-1441, S-6, U-292), (IA-1442, S-6, U-293), (IA-1443, S-6, U-294), (IA-1444, S-6, U-295), (IA-1445, S-6, U-296), (IA-1446, S-6, U-297), (IA-1447, S-6, U-298), (IA-1448, S-6, U-299), (IA-1449, S-6, U-300), (IA-1450, S-6, U-301), (IA-1451, S-6, U-302), (IA-1452, S-6, U-303), (IA-1453, S-6, U-304), (IA-1454, S-6, U-305), (IA-1455, S-6, U-306), (IA-1456, S-6, U-307), (IA-1457, S-6, U-308), (IA-1458, S-6, U-309), (IA-1459, S-6, U-310), (IA-1460, S-6, U-311), (IA-1461, S-6, U-312), (IA-1462, S-6, U-313), (IA-1463, S-6, U-314), (IA-1464, S-6, U-315), (IA-1465, S-6, U-316), (IA-1466, S-6, U-317), (IA-1467, S-6, U-318), (IA-1468, S-6, U-319), (IA-1469, S-6, U-320), (IA-1470, S-6, U-321), (IA-1471, S-6, U-322), (IA-1472, S-6, U-323), (IA-1473, S-6, U-324), (IA-1474, S-6, U-325), (IA-1475, S-6, U-326), (IA-1476, S-6, U-327), (IA-1477, S-6, U-328), (IA-1478, S-6, U-329), (IA-1479, S-6, U-330), (IA-1480, S-6, U-331), (IA-1481, S-6, U-332), (IA-1482, S-6, U-333), (IA-1483, S-6, U-334), (IA-1484, S-6, U-335), (IA-1485, S-6, U-336), (IA-1486, S-6, U-337), (IA-1487, S-6, U-338), (IA-1488, S-7, U-1), (IA-1489, S-7, U-2), (IA-1490, S-7, U-3), (IA-1491, S-7, U-4), (IA-1492, S-7, U-5), (IA-1493, S-7, U-6), (IA-1494, S-7, U-7), (IA-1495, S-7, U-8), (IA-1496, S-7, U-9), (IA-1497, S-7, U-10), (IA-1498, S-7, U-11), (IA-1499, S-7, U-12), (IA-1500, S-7, U-13), (IA-1501, S-7, U-14), (IA-1502, S-7, U-15), (IA-1503, S-7, U-16), (IA-1504, S-7, U-17), (IA-1505, S-7, U-18), (IA-1506, S-7, U-19), (IA-1507, S-7, U-20), (IA-1508, S-7, U-21), (IA-1509, S-7, U-22), (IA-1510, S-7, U-23), (IA-1511, S-7, U-24), (IA-1512, S-7, U-25), (IA-1513, S-7, U-26), (IA-1514, S-7, U-27), (IA-1515, S-7, U-28), (IA-1516, S-7, U-29), (IA-1517, S-7, U-30), (IA-1518, S-7, U-31), (IA-1519, S-7, U-32), (IA-1520, S-7, U-33), (IA-1521, S-7, U-34), (IA-1522, S-7, U-35), (IA-1523, S-7, U-36), (IA-1524, S-7, U-37), (IA-1525, S-7, U-38), (IA-1526, S-7, U-39), (IA-1527, S-7, U-40), (IA-1528, S-7, U-41), (IA-1529, S-7, U-42), (IA-1530, S-7, U-43), (IA-1531, S-7, U-44), (IA-1532, S-7, U-45), (IA-1533, S-7, U-46), (IA-1534, S-7, U-47), (IA-1535, S-7, U-48), (IA-1536, S-7, U-49), (IA-1537, S-7, U-50), (IA-1538, S-7, U-51), (IA-1539, S-7, U-52), (IA-1540, S-7, U-53), (IA-1541, S-7, U-54), (IA-1542, S-7, U-55), (IA-1543, S-7, U-56), (IA-1544, S-7, U-62), (IA-1545, S-7, U-63), (IA-1546, S-7, U-64), (IA-1547, S-7, U-66), (IA-1548, S-7, U-67), (IA-1549, S-7, U-68), (IA-1550, S-7, U-70), (IA-1551, S-7, U-71), (IA-1552, S-7, U-72), (IA-1553, S-7, U-73), (IA-1554, S-7, U-75), (IA-1555, S-7, U-76), (IA-1556, S-7, U-77), (IA-1557, S-7, U-78), (IA-1558, S-7, U-79), (IA-1559, S-7, U-80), (IA-1560, S-7, U-81), (IA-1561, S-7, U-82), (IA-1562, S-7, U-83), (IA-1563, S-7, U-84), (IA-1564, S-7, U-85), (IA-1565, S-7, U-86), (IA-1566, S-7, U-87), (IA-1567, S-7, U-88), (IA-1568, S-7, U-89), (IA-1569, S-7, U-90), (IA-1570, S-7, U-91), (IA-1571, S-7, U-92), (IA-1572, S-7, U-93), (IA-1573, S-7, U-94), (IA-1574, S-7, U-95), (IA-1575, S-7, U-96), (IA-1576, S-7, U-97), (IA-1577, S-7, U-98), (IA-1578, S-7, U-99), (IA-1579, S-7, U-100), (IA-1580, S-7, U-101), (IA-1581, S-7, U-102), (IA-1582, S-7, U-103), (IA-1583, S-7, U-104), (IA-1584, S-7, U-105), (IA-1585, S-7, U-106), (IA-1586, S-7, U-107), (IA-1587, S-7, U-108), (IA-1588, S-7, U-109), (IA-1589, S-7, U-110), (IA-1590, S-7, U-111), (IA-1591, S-7, U-112), (IA-1592, S-7, U-113), (IA-1593, S-7, U-114), (IA-1594, S-7, U-115), (IA-1595, S-7, U-116), (IA-1596, S-7, U-117), (IA-1597, S-7, U-118), (IA-1598, S-7, U-119), (IA-1599, S-7, U-120), (IA-1600, S-7, U-121), (IA-1601, S-7, U-122), (IA-1602, S-7, U-123), (IA-1603, S-7, U-124), (IA-1604, S-7, U-125), (IA-1605, S-7, U-126), (IA-1606, S-7, U-127), (IA-1607, S-7, U-128), (IA-1608, S-7, U-129), (IA-1609, S-7, U-130), (IA-1610, S-7, U-131), (IA-1611, S-7, U-132), (IA-1612, S-7, U-133), (IA-1613, S-7, U-134), (IA-1614, S-7, U-135), (IA-1615, S-7, U-136), (IA-1616, S-7, U-137), (IA-1617, S-7, U-138), (IA-1618, S-7, U-139), (IA-1619, S-7, U-140), (IA-1620, S-7, U-141), (IA-1621, S-7, U-142), (IA-1622, S-7, U-143), (IA-1623, S-7, U-144), (IA-1624, S-7, U-145), (IA-1625, S-7, U-146), (IA-1626, S-7, U-147), (IA-1627, S-7, U-148), (IA-1628, S-7, U-149), (IA-1629, S-7, U-150), (IA-1630, S-7, U-151), (IA-1631, S-7, U-152), (IA-1632, S-7, U-153), (IA-1633, S-7, U-154), (IA-1634, S-7, U-155), (IA-1635, S-7, U-156), (IA-1636, S-7, U-157), (IA-1637, S-7, U-158), (IA-1638, S-7, U-159), (IA-1639, S-7, U-160), (IA-1640, S-7, U-161), (IA-1641, S-7, U-162), (IA-1642, S-7, U-163), (IA-1643, S-7, U-164), (IA-1644, S-7, U-165), (IA-1645, S-7, U-166), (IA-1646, S-7, U-167), (IA-1647, S-7, U-168), (IA-1648, S-7, U-169), (IA-1649, S-7, U-170), (IA-1650, S-7, U-171), (IA-1651, S-7, U-172), (IA-1652, S-7, U-173), (IA-1653, S-7, U-174), (IA-1654, S-7, U-175), (IA-1655, S-7, U-176), (IA-1656, S-7, U-177), (IA-1657, S-7, U-178), (IA-1658, S-7, U-179), (IA-1659, S-7, U-180), (IA-1660, S-7, U-181), (IA-1661, S-7, U-182), (IA-1662, S-7, U-183), (IA-1663, S-7, U-184), (IA-1664, S-7, U-185), (IA-1665, S-7, U-186), (IA-1666, S-7, U-187), (IA-1667, S-7, U-188), (IA-1668, S-7, U-189), (IA-1669, S-7, U-190), (IA-1670, S-7, U-191), (IA-1671, S-7, U-192), (IA-1672, S-7, U-193), (IA-1673, S-7, U-194), (IA-1674, S-7, U-195), (IA-1675, S-7, U-196), (IA-1676, S-7, U-197), (IA-1677, S-7, U-198), (IA-1678, S-7, U-199), (IA-1679, S-7, U-200), (IA-1680, S-7, U-201), (IA-1681, S-7, U-202), (IA-1682, S-7, U-203), (IA-1683, S-7, U-204), (IA-1684, S-7, U-205), (IA-1685, S-7, U-206), (IA-1686, S-7, U-207), (IA-1687, S-7, U-208), (IA-1688, S-7, U-209), (IA-1689, S-7, U-210), (IA-1690, S-7, U-211), (IA-1691, S-7, U-212), (IA-1692, S-7, U-213), (IA-1693, S-7, U-214), (IA-1694, S-7, U-215), (IA-1695, S-7, U-216), (IA-1696, S-7, U-217), (IA-1697, S-7, U-218), (IA-1698, S-7, U-219), (IA-1699, S-7, U-220), (IA-1700, S-7, U-221), (IA-1701, S-7, U-222), (IA-1702, S-7, U-223), (IA-1703, S-7, U-224), (IA-1704, S-7, U-225), (IA-1705, S-7, U-226), (IA-1706, S-7, U-227), (IA-1707, S-7, U-228), (IA-1708, S-7, U-229), (IA-1709, S-7, U-230), (IA-1710, S-7, U-231), (IA-1711, S-7, U-232), (IA-1712, S-7, U-233), (IA- 1713, S-7, U-234), (IA-1714, S-7, U-235), (IA-1715, S-7, U-236), (IA-1716, S-7, U-237), (IA-1717, S-7, U-238), (IA-1718, S-7, U-239), (IA-1719, S-7, U-240), (IA-1720, S-7, U-241), (IA-1721, S-7, U-242), (IA-1722, S-7, U-243), (IA-1723, S-7, U-244), (IA-1724, S-7, U-245), (IA-1725, S-7, U-246), (IA-1726, S-7, U-247), (IA-1727, S-7, U-248), (IA-1728, S-7, U-249), (IA-1729, S-7, U-250), (IA-1730, S-7, U-251), (IA-1731, S-7, U-252), (IA-1732, S-7, U-253), (IA-1733, S-7, U-254), (IA-1734, S-7, U-255), (IA-1735, S-7, U-256), (IA-1736, S-7, U-257), (IA-1737, S-7, U-258), (IA-1738, S-7, U-259), (IA-1739, S-7, U-260), (IA-1740, S-7, U-261), (IA-1741, S-7, U-262), (IA-1742, S-7, U-263), (IA-1743, S-7, U-264), (IA-1744, S-7, U-265), (IA-1745, S-7, U-266), (IA-1746, S-7, U-267), (IA-1747, S-7, U-268), (IA-1748, S-7, U-269), (IA-1749, S-7, U-270), (IA-1750, S-7, U-271), (IA-1751, S-7, U-272), (IA-1752, S-7, U-273), (IA-1753, S-7, U-274), (IA-1754, S-7, U-275), (IA-1755, S-7, U-276), (IA-1756, S-7, U-277), (IA-1757, S-7, U-278), (IA-1758, S-7, U-279), (IA-1759, S-7, U-280), (IA-1760, S-7, U-281), (IA-1761, S-7, U-282), (IA-1762, S-7, U-283), (IA-1763, S-7, U-284), (IA-1764, S-7, U-285), (IA-1765, S-7, U-286), (IA-1766, S-7, U-287), (IA-1767, S-7, U-288), (IA-1768, S-7, U-289), (IA-1769, S-7, U-290), (IA-1770, S-7, U-291), (IA-1771, S-7, U-292), (IA-1772, S-7, U-293), (IA-1773, S-7, U-294), (IA-1774, S-7, U-295), (IA-1775, S-7, U-296), (IA-1776, S-7, U-297), (IA-1777, S-7, U-298), (IA-1778, S-7, U-299), (IA-1779, S-7, U-300), (IA-1780, S-7, U-301), (IA-1781, S-7, U-302), (IA-1782, S-7, U-303), (IA-1783, S-7, U-304), (IA-1784, S-7, U-305), (IA-1785, S-7, U-306), (IA-1786, S-7, U-307), (IA-1787, S-7, U-308), (IA-1788, S-7, U-309), (IA-1789, S-7, U-310), (IA-1790, S-7, U-311), (IA-1791, S-7, U-312), (IA-1792, S-7, U-313), (IA-1793, S-7, U-314), (IA-1794, S-7, U-315), (IA-1795, S-7, U-316), (IA-1796, S-7, U-317), (IA-1797, S-7, U-318), (IA-1798, S-7, U-319), (IA-1799, S-7, U-320), (IA-1800, S-7, U-321), (IA-1801, S-7, U-322), (IA-1802, S-7, U-323), (IA-1803, S-7, U-324), (IA-1804, S-7, U-325), (IA-1805, S-7, U-326), (IA-1806, S-7, U-327), (IA-1807, S-7, U-328), (IA-1808, S-7, U-329), (IA-1809, S-7, U-330), (IA-1810, S-7, U-331), (IA-1811, S-7, U-332), (IA-1812, S-7, U-333), (IA-1813, S-7, U-334), (IA-1814, S-7, U-335), (IA-1815, S-7, U-336), (IA-1816, S-7, U-337), (IA-1817, S-7, U-338), (IA-1819, S-200, U-2), (IA-1820, S-200, U-3), (IA-1821, S-200, U-4), (IA-1822, S-200, U-5), (IA-1823, S-200, U-6), (IA-1824, S-200, U-7), (IA-1825, S-200, U-8), (IA-1826, S-200, U-9), (IA-1827, S-200, U-10), (IA-1828, S-200, U-11), (IA-1829, S-200, U-12), (IA-1830, S-200, U-13), (IA-1831, S-200, U-14), (IA-1832, S-200, U-15), (IA-1833, S-200, U-16), (IA-1834, S-200, U-17), (IA-1835, S-200, U-18), (IA-1836, S-200, U-19), (IA-1837, S-200, U-20), (IA-1838, S-200, U-21), (IA-1839, S-200, U-22), (IA-1840, S-200, U-23), (IA-1841, S-200, U-24), (IA-1842, S-200, U-25), (IA-1843, S-200, U-26), (IA-1844, S-200, U-27), (IA-1845, S-200, U-28), (IA-1846, S-200, U-29), (IA-1847, S-200, U-30), (IA-1849, S-200, U-32), (IA-1850, S-200, U-33), (IA-1851, S-200, U-34), (IA-1852, S-200, U-35), (IA-1853, S-200, U-36), (IA-1854, S-200, U-37), (IA-1855, S-200, U-38), (IA-1856, S-200, U-39), (IA-1857, S-200, U-40), (IA-1858, S-200, U-41), (IA-1859, S-200, U-42), (IA-1860, S-200, U-43), (IA-1861, S-200, U-44), (IA-1862, S-200, U-45), (IA-1863, S-200, U-46), (IA-1864, S-200, U-47), (IA-1865, S-200, U-48), (IA-1866, S-200, U-49), (IA-1867, S-200, U-50), (IA-1868, S-200, U-51), (IA-1869, S-200, U-52), (IA-1870, S-200, U-53), (IA-1871, S-200, U-54), (IA-1872, S-200, U-55), (IA-1873, S-200, U-56), (IA-1874, S-200, U-62), (IA-1875, S-200, U-63), (IA-1876, S-200, U-64), (IA-1877, S-200, U-66), (IA-1878, S-200, U-67), (IA-1879, S-200, U-68), (IA-1880, S-200, U-70), (IA-1881, S-200, U-71), (IA-1882, S-200, U-72), (IA-1883, S-200, U-73), (IA-1884, S-200, U-75), (IA-1885, S-200, U-76), (IA-1886, S-200, U-77), (IA-1887, S-200, U-78), (IA-1888, S-200, U-79), (IA-1889, S-200, U-80), (IA-1890, S-200, U-81), (IA-1891, S-200, U-82), (IA-1892, S-200, U-83), (IA-1893, S-200, U-84), (IA-1894, S-200, U-85), (IA-1895, S-200, U-86), (IA-1896, S-200, U-87), (IA-1897, S-200, U-88), (IA-1898, S-200, U-89), (IA-1899, S-200, U-90), (IA-1900, S-200, U-91), (IA-1901, S-200, U-92), (IA-1902, S-200, U-93), (IA-1903, S-200, U-94), (IA-1904, S-200, U-95), (IA-1905, S-200, U-96), (IA-1906, S-200, U-97), (IA-1907, S-200, U-98), (IA-1908, S-200, U-99), (IA-1909, S-200, U-100), (IA-1910, S-200, U-101), (IA-1911, S-200, U-102), (IA-1912, S-200, U-103), (IA-1913, S-200, U-104), (IA-1914, S-200, U-105), (IA-1915, S-200, U-106), (IA-1916, S-200, U-107), (IA-1917, S-200, U-108), (IA-1918, S-200, U-109), (IA-1919, S-200, U-110), (IA-1920, S-200, U-111), (IA-1921, S-200, U-112), (IA-1922, S-200, U-113), (IA-1923, S-200, U-114), (IA-1924, S-200, U-115), (IA-1925, S-200, U-116), (IA-1926, S-200, U-117), (IA-1927, S-200, U-118), (IA-1928, S-200, U-119), (IA-1929, S-200, U-120), (IA-1930, S-200, U-121), (IA-1931, S-200, U-122), (IA-1932, S-200, U-123), (IA-1933, S-200, U-124), (IA-1934, S-200, U-125), (IA-1935, S-200, U-126), (IA-1936, S-200, U-127), (IA-1937, S-200, U-128), (IA-1938, S-200, U-129), (IA-1939, S-200, U-130), (IA-1940, S-200, U-131), (IA-1941, S-200, U-132), (IA-1942, S-200, U-133), (IA-1943, S-200, U-134), (IA-1944, S-200, U-135), (IA-1945, S-200, U-136), (IA-1946, S-200, U-137), (IA-1947, S-200, U-138), (IA-1948, S-200, U-139), (IA-1949, S-200, U-140), (IA-1950, S-200, U-141), (IA-1951, S-200, U-142), (IA-1952, S-200, U-143), (IA-1953, S-200, U-144), (IA-1954, S-200, U-145), (IA-1955, S-200, U-146), (IA-1956, S-200, U-147), (IA-1957, S-200, U-148), (IA-1958, S-200, U-149), (IA-1959, S-200, U-150), (IA-1960, S-200, U-151), (IA-1961, S-200, U-152), (IA-1962, S-200, U-153), (IA-1963, S-200, U-154), (IA-1964, S-200, U-155), (IA-1965, S-200, U-156), (IA-1966, S-200, U-157), (IA-1967, S-200, U-158), (IA-1968, S-200, U-159), (IA-1969, S-200, U-160), (IA-1970, S-200, U-161), (IA-1971, S-200, U-162), (IA-1972, S-200, U-163), (IA-1973, S-200, U-164), (IA-1974, S-200, U-165), (IA-1975, S-200, U-166), (IA-1976, S-200, U-167), (IA-1977, S-200, U-168), (IA-1978, S-200, U-169), (IA-1979, S-200, U-170), (IA-1980, S-200, U-171), (IA-1981, S-200, U-172), (IA-1982, S-200, U-173), (IA-1983, S-200, U-174), (IA-1984, S-200, U-175), (IA-1985, S-200, U-176), (IA-1986, S-200, U-177), (IA-1987, S-200, U-178), (IA-1988, S-200, U-179), (IA-1989, S-200, U-180), (IA-1990, S-200, U-181), (IA-1991, S-200, U-182), (IA-1992, S-200, U-183), (IA-1993, S-200, U-184), (IA-1994, S-200, U-185), (IA-1995, S-200, U-186), (IA-1996, S-200, U-187), (IA-1997, S-200, U-188), (IA-1998, S-200, U-189), (IA-1999, S-200, U-190), (IA-2000, S-200, U-191), (IA-2001, S-200, U-192), (IA-2002, S-200, U-193), (IA-2003, S-200, U-194), (IA-2004, S-200, U-195), (IA-2005, S-200, U-196), (IA-2006, S-200, U-197), (IA-2007, S-200, U-198), (IA-2008, S-200, U-199), (IA-2009, S-200, U-200), (IA-2010, S-200, U-201), (IA-2011, S-200, U-202), (IA-2012, S-200, U-203), (IA-2013, S-200, U-204), (IA-2014, S-200, U-205), (IA-2015, S-200, U-206), (IA-2016, S-200, U-207), (IA-2017, S-200, U-208), (IA-2018, S-200, U-209), (IA-2019, S-200, U-210), (IA-2020, S-200, U-211), (IA-2021, S-200, U-212), (IA-2022, S-200, U-213), (IA-2023, S-200, U-214), (IA-2024, S-200, U-215), (IA-2025, S-200, U-216), (IA-2026, S-200, U-217), (IA-2027, S-200, U-218), (IA-2028, S-200, U-219), (IA-2029, S-200, U-220), (IA-2030, S-200, U-221), (IA-2031, S-200, U-222), (IA-2032, S-200, U-223), (IA-2033, S-200, U-224), (IA-2034, S-200, U-225), (IA-2035, S-200, U-226), (IA-2036, S-200, U-227), (IA-2037, S-200, U-228), (IA-2038, S-200, U-229), (IA-2039, S-200, U-230), (IA-2040, S-200, U-231), (IA-2041, S-200, U-232), (IA-2042, S-200, U-233), (IA-2043, S-200, U-234), (IA-2044, S-200, U-235), (IA-2045, S-200, U-236), (IA-2046, S-200, U-237), (IA-2047, S-200, U-238), (IA-2048, S-200, U-239), (IA-2049, S-200, U-240), (IA-2050, S-200, U-241), (IA-2051, S-200, U-242), (IA-2052, S-200, U-243), (IA-2053, S-200, U-244), (IA-2054, S-200, U-245), (IA-2055, S-200, U-246), (IA-2056, S-200, U-247), (IA-2057, S-200, U-248), (IA-2058, S-200, U-249), (IA-2059, S-200, U-250), (IA-2060, S-200, U-251), (IA-2061, S-200, U-252), (IA-2062, S-200, U-253), (IA-2063, S-200, U-254), (IA-2064, S-200, U-255), (IA-2065, S-200, U-256), (IA-2066, S-200, U-257), (IA-2067, S-200, U-258), (IA-2068, S-200, U-259), (IA-2069, S-200, U-260), (IA-2070, S-200, U-261), (IA-2071, S-200, U-262), (IA-2072, S-200, U-263), (IA-2073, S-200, U-264), (IA-2074, S-200, U-265), (IA-2075, S-200, U-266), (IA-2076, S-200, U-267), (IA-2077, S-200, U-268), (IA-2078, S-200, U-269), (IA-2079, S-200, U-270), (IA-2080, S-200, U-271), (IA-2081, S-200, U-272), (IA-2082, S-200, U-273), (IA-2083, S-200, U-274), (IA-2084, S-200, U-275), (IA-2085, S-200, U-276), (IA-2086, S-200, U-277), (IA-2087, S-200, U-278), (IA-2088, S-200, U-279), (IA-2089, S-200, U-280), (IA-2090, S-200, U-281), (IA-2091, S-200, U-282), (IA-2092, S-200, U-283), (IA-2093, S-200, U-284), (IA-2094, S-200, U-285), (IA-2095, S-200, U-286), (IA-2096, S-200, U-287), (IA-2097, S-200, U-288), (IA-2098, S-200, U-289), (IA-2099, S-200, U-290), (IA-2100, S-200, U-291), (IA-2101, S-200, U-292), (IA-2102, S-200, U-293), (IA-2103, S-200, U-294), (IA-2104, S-200, U-295), (IA-2105, S-200, U-296), (IA-2106, S-200, U-297), (IA-2107, S-200, U-298), (IA-2108, S-200, U-299), (IA-2109, S-200, U-300), (IA-2110, S-200, U-301), (IA-2111, S-200, U-302), (IA-2112, S-200, U-303), (IA-2113, S-200, U-304), (IA-2114, S-200, U-305), (IA-2115, S-200, U-306), (IA-2116, S-200, U-307), (IA-2117, S-200, U-308), (IA-2118, S-200, U-309), (IA-2119, S-200, U-310), (IA-2120, S-200, U-311), (IA-2121, S-200, U-312), (IA-2122, S-200, U-313), (IA-2123, S-200, U-314), (IA-2124, S-200, U-315), (IA-2125, S-200, U-316), (IA-2126, S-200, U-317), (IA-2127, S-200, U-318), (IA-2128, S-200, U-319), (IA-2129, S-200, U-320), (IA-2130, S-200, U-321), (IA-2131, S-200, U-322), (IA-2132, S-200, U-323), (IA-2133, S-200, U-324), (IA-2134, S-200, U-325), (IA-2135, S-200, U-326), (IA-2136, S-200, U-327), (IA-2137, S-200, U-328), (IA-2138, S-200, U-329), (IA-2139, S-200, U-330), (IA-2140, S-200, U-331), (IA-2141, S-200, U-332), (IA-2142, S-200, U-333), (IA-2143, S-200, U-334), (IA-2144, S-200, U-335), (IA-2145, S-200, U-336), (IA-2146, S-200, U-337), (IA-2147, S-200, U-338), (IA-2148, S-201, U-1), (IA-2149, S-201, U-2), (IA-2150, S-201, U-3), (IA-2151, S-201, U-4), (IA-2152, S-201, U-5), (IA-2153, S-201, U-6), (IA-2154, S-201, U-7), (IA-2155, S-201, U-8), (IA-2156, S-201, U-9), (IA-2157, S-201, U-10), (IA-2158, S-201, U-11), (IA-2159, S-201, U-12), (IA-2160, S-201, U-13), (IA-2161, S-201, U-14), (IA-2162, S-201, U-15), (IA-2163, S-201, U-16), (IA-2164, S-201, U-17), (IA-2165, S-201, U-18), (IA-2166, S-201, U-19), (IA-2167, S-201, U-20), (IA-2168, S-201, U-21), (IA-2169, S-201, U-22), (IA-2170, S-201, U-23), (IA-2171, S-201, U-24), (IA-2172, S-201, U-25), (IA-2173, S-201, U-26), (IA-2174, S-201, U-27), (IA-2175, S-201, U-28), (IA-2176, S-201, U-29), (IA-2177, S-201, U-30), (IA-2178, S-201, U-31), (IA-2179, S-201, U-32), (IA-2180, S-201, U-33), (IA-2181, S-201, U-34), (IA-2182, S-201, U-35), (IA-2183, S-201, U-36), (IA-2184, S-201, U-37), (IA-2185, S-201, U-38), (IA-2186, S-201, U-39), (IA-2187, S-201, U-40), (IA-2188, S-201, U-41), (IA-2189, S-201, U-42), (IA-2190, S-201, U-43), (IA-2191, S-201, U-44), (IA-2192, S-201, U-45), (IA-2193, S-201, U-46), (IA-2194, S-201, U-47), (IA-2195, S-201, U-48), (IA-2196, S-201, U-49), (IA-2197, S-201, U-50), (IA-2198, S-201, U-51), (IA-2199, S-201, U-52), (IA-2200, S-201, U-53), (IA-2201, S-201, U-54), (IA-2202, S-201, U-55), (IA-2203, S-201, U-56), (IA-2204, S-201, U-62), (IA-2205, S-201, U-63), (IA-2206, S-201, U-64), (IA-2207, S-201, U-66), (IA-2208, S-201, U-67), (IA-2209, S-201, U-68), (IA-2210, S-201, U-70), (IA-2211, S-201, U-71), (IA-2212, S-201, U-72), (IA-2213, S-201, U-73), (IA-2214, S-201, U-75), (IA-2215, S-201, U-76), (IA-2216, S-201, U-77), (IA-2217, S-201, U-78), (IA-2218, S-201, U-79), (IA-2219, S-201, U-80), (IA-2220, S-201, U-81), (IA-2221, S-201, U-82), (IA-2222, S-201, U-83), (IA-2223, S-201, U-84), (IA-2224, S-201, U-85), (IA-2225, S-201, U-86), (IA-2226, S-201, U-87), (IA-2227, S-201, U-88), (IA-2228, S-201, U-89), (IA-2229, S-201, U-90), (IA-2230, S-201, U-91), (IA-2231, S-201, U-92), (IA-2232, S-201, U-93), (IA-2233, S-201, U-94), (IA-2234, S-201, U-95), (IA-2235, S-201, U-96), (IA-2236, S-201, U-97), (IA-2237, S-201, U-98), (IA-2238, S-201, U-99), (IA-2239, S-201, U-100), (IA-2240, S-201, U-101), (IA-2241, S-201, U-102), (IA-2242, S-201, U-103), (IA-2243, S-201, U-104), (IA-2244, S-201, U-105), (IA-2245, S-201, U-106), (IA-2246, S-201, U-107), (IA-2247, S-201, U-108), (IA-2248, S-201, U-109), (IA-2249, S-201, U-110), (IA-2250, S-201, U-111), (IA-2251, S-201, U-112), (IA-2252, S-201, U-113), (IA-2253, S-201, U-114), (IA-2254, S-201, U-115), (IA-2255, S-201, U-116), (IA-2256, S-201, U-117), (IA-2257, S-201, U-118), (IA-2258, S-201, U-119), (IA-2259, S-201, U-120), (IA-2260, S-201, U-121), (IA-2261, S-201, U-122), (IA-2262, S-201, U-123), (IA-2263, S-201, U-124), (IA-2264, S-201, U-125), (IA-2265, S-201, U-126), (IA-2266, S-201, U-127), (IA-2267, S-201, U-128), (IA-2268, S-201, U-129), (IA-2269, S-201, U-130), (IA-2270, S-201, U-131), (IA-2271, S-201, U-132), (IA-2272, S-201, U-133), (IA-2273, S-201, U-134), (IA-2274, S-201, U-135), (IA-2275, S-201, U-136), (IA-2276, S-201, U-137), (IA-2277, S-201, U-138), (IA-2278, S-201, U-139), (IA-2279, S-201, U-140), (IA-2280, S-201, U-141), (IA-2281, S-201, U-142), (IA-2282, S-201, U-143), (IA-2283, S-201, U-144), (IA-2284, S-201, U-145), (IA-2285, S-201, U-146), (IA-2286, S-201, U-147), (IA-2287, S-201, U-148), (IA-2288, S-201, U-149), (IA-2289, S-201, U-150), (IA-2290, S-201, U-151), (IA-2291, S-201, U-152), (IA-2292, S-201, U-153), (IA-2293, S-201, U-154), (IA-2294, S-201, U-155), (IA-2295, S-201, U-156), (IA-2296, S-201, U-157), (IA-2297, S-201, U-158), (IA-2298, S-201, U-159), (IA-2299, S-201, U-160), (IA-2300, S-201, U-161), (IA-2301, S-201, U-162), (IA-2302, S-201, U-163), (IA-2303, S-201, U-164), (IA-2304, S-201, U-165), (IA-2305, S-201, U-166), (IA-2306, S-201, U-167), (IA-2307, S-201, U-168), (IA-2308, S-201, U-169), (IA-2309, S-201, U-170), (IA-2310, S-201, U-171), (IA-2311, S-201, U-172), (IA-2312, S-201, U-173), (IA-2313, S-201, U-174), (IA-2314, S-201, U-175), (IA-2315, S-201, U-176), (IA-2316, S-201, U-177), (IA-2317, S-201, U-178), (IA-2318, S-201, U-179), (IA-2319, S-201, U-180), (IA-2320, S-201, U-181), (IA-2321, S-201, U-182), (IA-2322, S-201, U-183), (IA-2323, S-201, U-184), (IA-2324, S-201, U-185), (IA-2325, S-201, U-186), (IA-2326, S-201, U-187), (IA-2327, S-201, U-188), (IA-2328, S-201, U-189), (IA-2329, S-201, U-190), (IA-2330, S-201, U-191), (IA-2331, S-201, U-192), (IA-2332, S-201, U-193), (IA-2333, S-201, U-194), (IA-2334, S-201, U-195), (IA-2335, S-201, U-196), (IA-2336, S-201, U-197), (IA-2337, S-201, U-198), (IA-2338, S-201, U-199), (IA-2339, S-201, U-200), (IA-2340, S-201, U-201), (IA-2341, S-201, U-202), (IA-2342, S-201, U-203), (IA-2343, S-201, U-204), (IA-2344, S-201, U-205), (IA-2345, S-201, U-206), (IA-2346, S-201, U-207), (IA-2347, S-201, U-208), (IA-2348, S-201, U-209), (IA-2349, S-201, U-210), (IA-2350, S-201, U-211), (IA-2351, S-201, U-212), (IA-2352, S-201, U-213), (IA-2353, S-201, U-214), (IA-2354, S-201, U-215), (IA-2355, S-201, U-216), (IA-2356, S-201, U-217), (IA-2357, S-201, U-218), (IA-2358, S-201, U-219), (IA-2359, S-201, U-220), (IA-2360, S-201, U-221), (IA-2361, S-201, U-222), (IA-2362, S-201, U-223), (IA-2363, S-201, U-224), (IA-2364, S-201, U-225), (IA-2365, S-201, U-226), (IA-2366, S-201, U-227), (IA-2367, S-201, U-228), (IA-2368, S-201, U-229), (IA-2369, S-201, U-230), (IA-2370, S-201, U-231), (IA-2371, S-201, U-232), (IA-2372, S-201, U-233), (IA-2373, S-201, U-234), (IA-2374, S-201, U-235), (IA-2375, S-201, U-236), (IA-2376, S-201, U-237), (IA-2377, S-201, U-238), (IA-2378, S-201, U-239), (IA-2379, S-201, U-240), (IA-2380, S-201, U-241), (IA-2381, S-201, U-242), (IA-2382, S-201, U-243), (IA-2383, S-201, U-244), (IA-2384, S-201, U-245), (IA-2385, S-201, U-246), (IA-2386, S-201, U-247), (IA-2387, S-201, U-248), (IA-2388, S-201, U-249), (IA-2389, S-201, U-250), (IA-2390, S-201, U-251), (IA-2391, S-201, U-252), (IA-2392, S-201, U-253), (IA-2393, S-201, U-254), (IA-2394, S-201, U-255), (IA-2395, S-201, U-256), (IA-2396, S-201, U-257), (IA-2397, S-201, U-258), (IA-2398, S-201, U-259), (IA-2399, S-201, U-260), (IA-2400, S-201, U-261), (IA-2401, S-201, U-262), (IA-2402, S-201, U-263), (IA-2403, S-201, U-264), (IA-2404, S-201, U-265), (IA-2405, S-201, U-266), (IA-2406, S-201, U-267), (IA-2407, S-201, U-268), (IA-2408, S-201, U-269), (IA-2409, S-201, U-270), (IA-2410, S-201, U-271), (IA-2411, S-201, U-272), (IA-2412, S-201, U-273), (IA-2413, S-201, U-274), (IA-2414, S-201, U-275), (IA-2415, S-201, U-276), (IA-2416, S-201, U-277), (IA-2417, S-201, U-278), (IA-2418, S-201, U-279), (IA-2419, S-201, U-280), (IA-2420, S-201, U-281), (IA-2421, S-201, U-282), (IA-2422, S-201, U-283), (IA-2423, S-201, U-284), (IA-2424, S-201, U-285), (IA-2425, S-201, U-286), (IA-2426, S-201, U-287), (IA-2427, S-201, U-288), (IA-2428, S-201, U-289), (IA-2429, S-201, U-290), (IA-2430, S-201, U-291), (IA-2431, S-201, U-292), (IA-2432, S-201, U-293), (IA-2433, S-201, U-294), (IA-2434, S-201, U-295), (IA-2435, S-201, U-296), (IA-2436, S-201, U-297), (IA-2437, S-201, U-298), (IA-2438, S-201, U-299), (IA-2439, S-201, U-300), (IA-2440, S-201, U-301), (IA-2441, S-201, U-302), (IA-2442, S-201, U-303), (IA-2443, S-201, U-304), (IA-2444, S-201, U-305), (IA-2445, S-201, U-306), (IA-2446, S-201, U-307), (IA-2447, S-201, U-308), (IA-2448, S-201, U-309), (IA-2449, S-201, U-310), (IA-2450, S-201, U-311), (IA-2451, S-201, U-312), (IA-2452, S-201, U-313), (IA-2453, S-201, U-314), (IA-2454, S-201, U-315), (IA-2455, S-201, U-316), (IA-2456, S-201, U-317), (IA-2457, S-201, U-318), (IA-2458, S-201, U-319), (IA-2459, S-201, U-320), (IA-2460, S-201, U-321), (IA-2461, S-201, U-322), (IA-2462, S-201, U-323), (IA-2463, S-201, U-324), (IA-2464, S-201, U-325), (IA-2465, S-201, U-326), (IA-2466, S-201, U-327), (IA-2467, S-201, U-328), (IA-2468, S-201, U-329), (IA-2469, S-201, U-330), (IA-2470, S-201, U-331), (IA-2471, S-201, U-332), (IA-2472, S-201, U-333), (IA-2473, S-201, U-334), (IA-2474, S-201, U-335), (IA-2475, S-201, U-336), (IA-2476, S-201, U-337), (IA-2477, S-201, U-338)

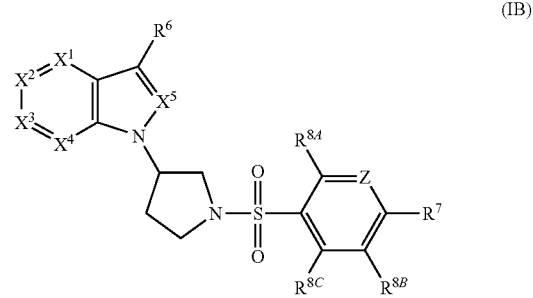

(IB)

wherein -$X^1$=$X^2$-$X^3$=$X^4$ is —C($R^1$)=C($R^2$)—C($R^3$)=C($R^4$)—, —N=C($R^2$)—C($R^3$)=C($R^4$)-, C($R^1$)=N—C($R^3$)=C($R^4$)—, —C($R^1$)=C($R^2$)—N=C($R^4$)— and —C($R^1$)=C($R^2$)—C($R^3$)=N—;

$X^5$ is —N= or —C($R^5$)=;

$R^1$, $R^2$, $R^3$, $R^4$, $R^5$ and $R^6$ are independently a hydrogen atom, a fluorine atom, a chlorine atom, a bromine atom, methyl, trifluoromethyl, methyloxy, difluoromethyloxy, N-methylamino, methylcarbonylamino, cyano, nitro, phenyl, 2-pyridyl, 2-furyl, 1,3-oxazol-2-yl, morpholino, N-methylcarbamoyl, carboxy, carboxymethyl, or carboxymethyloxy;

Z is =N or =C($R^{8D}$)—;

$R^7$ is independently methyloxy, ethyloxy, propyloxy, isopropyloxy, n-butyloxy, isopropyloxy, s-butyloxy, difluoromethyloxy, benzyloxy, phenoxy, methylthio, ethylthio, isopropylthio, s-butylthio, difluoromethylthio, benzylthio or phenylthio; and $R^{8A}$, $R^{8B}$, $R^{8c}$ and $R^{8D}$ are independently, a hydrogen atom, a fluorine atom, a chlorine atom, a bromine atom or methyl;

A compound of the formula (IB) is shown below.
(No. of Compound, part A, part B), (IB-1, S-1, U-57), (IB-2, S-2, U-57), (IB-3, S-3, U-57), (IB-4, S-4, U-57), (IB-5, S-5, U-57), (IB-6, S-6, U-57), (IB-7, S-7, U-57), (IB-8, S-8, U-57), (IB-9, S-9, U-57), (IB-10, S-10, U-57), (IB-11, S-11, U-57), (IB-12, S-12, U-57), (IB-13, S-13, U-57), (IB-14, S-14, U-57), (IB-15, S-15, U-57), (IB-16, S-16, U-57), (IB-17, S-17, U-57), (IB-18, S-18, U-57), (IB-19, S-19, U-57), (IB-20, S-20, U-57), (IB-21, S-21, U-57), (IB-22, S-22, U-57), (IB-23, S-23, U-57), (IB-24, S-24, U-57), (IB-25, S-25, U-57), (IB-26, S-26, U-57), (IB-27, S-27, U-57), (IB-28, S-28, U-57), (IB-29, S-29, U-57), (IB-30, S-30, U-57), (IB-31, S-31, U-57), (IB-32, S-32, U-57), (IB-33, S-33, U-57), (IB-34, S-34, U-57), (IB-35, S-35, U-57), (IB-36, S-36, U-57), (IB-37, S-37, U-57), (IB-38, S-38, U-57), (IB-39, S-39, U-57), (IB-40, S-40, U-57), (IB-41, S-41, U-57), (IB-42, S-42, U-57), (IB-43, S-43, U-57), (IB-44, S-44, U-57), (IB-45, S-45, U-57), (IB-46, S-46, U-57), (IB-47, S-47, U-57), (IB-48, S-48, U-57), (IB-49, S-49, U-57), (IB-50, S-50, U-57), (IB-51, S-51, U-57), (IB-52, S-52, U-57), (IB-53, S-53, U-57), (IB-54, S-54, U-57), (IB-55, S-55, U-57), (IB-56, S-56, U-57), (IB-57, S-57, U-57), (IB-58, S-58, U-57), (IB-59, S-59, U-57), (IB-60, S-60, U-57), (IB-61, S-61, U-57), (IB-62, S-62, U-57), (IB-63, S-63, U-57), (IB-64, S-64, U-57), (IB-65, S-65, U-57), (IB-66, S-66, U-57), (IB-67, S-67, U-57), (IB-68, S-68, U-57), (IB-69, S-69, U-57), (IB-70, S-70, U-57), (IB-71, S-71, U-57), (IB-72, S-72, U-57), (IB-73, S-73, U-57), (IB-74, S-74, U-57), (IB-75, S-75, U-57), (IB-76, S-76, U-57), (IB-77, S-77, U-57), (IB-78, S-78, U-57), (IB-79, S-79, U-57), (IB-80, S-80, U-57), (IB-81, S-81, U-57), (IB-82, S-82, U-57), (IB-83, S-83, U-57), (IB-84, S-84, U-57), (IB-85, S-85, U-57), (IB-86, S-86, U-57), (IB-87, S-87, U-57), (IB-88, S-88, U-57), (IB-89, S-89, U-57), (IB-90, S-90, U-57), (IB-91, S-91, U-57), (IB-92, S-92, U-57), (IB-93, S-93, U-57), (IB-94, S-94, U-57), (IB-95, S-95, U-57), (IB-96, S-96, U-57), (IB-97, S-97, U-57), (IB-98, S-98, U-57), (IB-99, S-99, U-57), (IB-100, S-100, U-57), (IB-101, S-101, U-57), (IB-102, S-102, U-57), (IB-103, S-103, U-57), (IB-104, S-104, U-57), (IB-105, S-105, U-57), (IB-106, S-106, U-57), (IB-107, S-107, U-57), (IB-108, S-108, U-57), (IB-109, S-109, U-57), (IB-110, S-110, U-57), (IB-111, S-111, U-57), (IB-112, S-112, U-57), (IB-113, S-113, U-57), (IB-114, S-114, U-57), (IB-115, S-115, U-57), (IB-116, S-116, U-57), (IB-117, S-117, U-57), (IB-118, S-118, U-57), (IB-119, S-119, U-57), (IB-120, S-120, U-57), (IB-121, S-121, U-57), (IB-122, S-122, U-57), (IB-123, S-123, U-57), (IB-124, S-124, U-57), (IB-125, S-125, U-57), (IB-126, S-126, U-57), (IB-127, S-127, U-57), (IB-128, S-128, U-57), (IB-129, S-129, U-57), (IB-130, S-130, U-57), (IB-131, S-131, U-57), (IB-132, S-132, U-57), (IB-133, S-133, U-57), (IB-134, S-134, U-57), (IB-135, S-135, U-57), (IB-136, S-136, U-57), (IB-137, S-137, U-57), (IB-138, S-138, U-57), (IB-139, S-139, U-57), (IB-140, S-140, U-57), (IB-141, S-141, U-57), (IB-142, S-142, U-57), (IB-143, S-143, U-57), (IB-144, S-144, U-57), (IB-145, S-145, U-57), (IB-146, S-146, U-57), (IB-147, S-147, U-57), (IB-148, S-148, U-57), (IB-149, S-149, U-57), (IB-150, S-150, U-57), (IB-151, S-151, U-57), (IB-152, S-152, U-57), (IB-153, S-153, U-57), (IB-154, S-154, U-57), (IB-155, S-155, U-57), (IB-156, S-156, U-57), (IB-157, S-157, U-57), (IB-158, S-158, U-57), (IB-159, S-159, U-57), (IB-160, S-160, U-57), (IB-161, S-161, U-57), (IB-162, S-162, U-57), (IB-163, S-163, U-57), (IB-164, S-164, U-57), (IB-165, S-165, U-57), (IB-166, S-166, U-57), (IB-167, S-167, U-57), (IB-168, S-168, U-57), (IB-169, S-169, U-57), (IB-170, S-170, U-57), (IB-171, S-171, U-57), (IB-172, S-172, U-57), (IB-173, S-173, U-57), (IB-174, S-174, U-57), (IB-175, S-175, U-57), (IB-176, S-176, U-57), (IB-177, S-177, U-57), (IB-178, S-178, U-57), (IB-179, S-179, U-57), (IB-180, S-180, U-57), (IB-181, S-181, U-57), (IB-182, S-182, U-57), (IB-183, S-183, U-57), (IB-184, S-184, U-57), (IB-185, S-185, U-57), (IB-186, S-186, U-57), (IB-187, S-187, U-57), (IB-188, S-188, U-57), (IB-189, S-189, U-57), (IB-190, S-190, U-57), (IB-191, S-191, U-57), (IB-192, S-192, U-57), (IB-193, S-193, U-57), (IB-194, S-194, U-57), (IB-195, S-195, U-57), (IB-196, S-196, U-57), (IB-197, S-197, U-57), (IB-198, S-198, U-57), (IB-199, S-199, U-57), (IB-200, S-200, U-57), (IB-201, S-201, U-57), (IB-202, S-202, U-57), (IB-203, S-203, U-57), (IB-204, S-204, U-57), (IB-205, S-205, U-57), (IB-206, S-206, U-57), (IB-207, S-207, U-57), (IB-210, S-210, U-57), (IB-211, S-211, U-57), (IB-212, S-212, U-57), (IB-213, S-213, U-57), (IB-214, S-214, U-57), (IB-215, S-215, U-57), (IB-216, S-216, U-57), (IB-217, S-217, U-57), (IB-218, S-218, U-57), (IB-219, S-219, U-57), (IB-220, S-220, U-57), (IB-221, S-221, U-57), (IB-222, S-222, U-57), (IB-223, S-223, U-57), (IB-224, S-224, U-57), (IB-225, S-225, U-57), (IB-226, S-226, U-57), (IB-227, S-227, U-57), (IB-228, S-228, U-57), (IB-229, S-229, U-57), (IB-230, S-230, U-57), (IB-231, S-231, U-57), (IB-232, S-232, U-57), (IB-233, S-233, U-57), (IB-234, S-234, U-57), (IB-235, S-235, U-57), (IB-236, S-236, U-57), (IB-237, S-237, U-57), (IB-238, S-238, U-57), (IB-239, S-239, U-57), (IB-240, S-240, U-57), (IB-241, S-241, U-57), (IB-242, S-242, U-57), (IB-243, S-243, U-57), (IB-244, S-244, U-57), (IB-245, S-245, U-57), (IB-246, S-246, U-57), (IB-247, S-247, U-57), (IB-248, S-248, U-57), (IB-249, S-249, U-57), (IB-250, S-250, U-57), (IB-251, S-251, U-57), (IB-252, S-252, U-57), (IB-253, S-253, U-57), (IB-254, S-254, U-57), (IB-255, S-255, U-57), (IB-256, S-256, U-57), (IB-257, S-257, U-57), (IB-258, S-258, U-57), (IB-259, S-259, U-57), (IB-260, S-260, U-57), (IB-261, S-261, U-57), (IB-262, S-262, U-57), (IB-263, S-263, U-57), (IB-264, S-264, U-57), (IB-265, S-265, U-57), (IB-266, S-266, U-57), (IB-267, S-267, U-57), (IB-268, S-268, U-57), (IB-269, S-269, U-57), (IB-270, S-270, U-57), (IB-271, S-271, U-57), (IB-272, S-272, U-57), (IB-273, S-273, U-57), (IB-274, S-274, U-57), (IB-275, S-275, U-57), (IB-276, S-276, U-57), (IB-277, S-277, U-57), (IB-278, S-278, U-57), (IB-279, S-279, U-57), (IB-280, S-280, U-57), (IB-281, S-281, U-57), (IB-282, S-282, U-57), (IB-283, S-283, U-57), (IB-284, S-284, U-57), (IB-285, S-285, U-57), (IB-286, S-286, U-57), (IB-287, S-287, U-57), (IB-288, S-288, U-57), (IB-289, S-289, U-57), (IB-290, S-290, U-57), (IB-291, S-291, U-57), (IB-292, S-292, U-57), (IB-293, S-293, U-57), (IB-294, S-294, U-57), (IB-295, S-295, U-57), (IB-296, S-296, U-57), (IB-297, S-297, U-57), (IB-298, S-298, U-57), (IB-299, S-299, U-57), (IB-300, S-300, U-57), (IB-301, S-301, U-57), (IB-302, S-302, U-57), (IB-303, S-303, U-57), (IB-304, S-304, U-57), (IB-305, S-305, U-57), (IB-306, S-306, U-57), (IB-307, S-307, U-57), (IB-308, S-308, U-57), (IB-309, S-309, U-57), (IB-310, S-310, U-57), (IB-311, S-311, U-57), (IB-312, S-312, U-57), (IB-313, S-313, U-57), (IB-314, S-314, U-57), (IB-315, S-315, U-57), (IB-316, S-316, U-57), (IB-317, S-317, U-57), (IB-318, S-318, U-57), (IB-319, S-319, U-57), (IB-320, S-320, U-57), (IB-321, S-321, U-57), (IB-322, S-322, U-57), (IB-323, S-323, U-57), (IB-324, S-324, U-57), (IB-325, S-325, U-57), (IB-326, S-326, U-57), (IB-327, S-327, U-57), (IB-328, S-328, U-57), (IB-329, S-329, U-57), (IB-330, S-330, U-57), (IB-331, S-331, U-57), (IB-332, S-332, U-57), (IB-333, S-333, U-57), (IB-334, S-334, U-57), (IB-335, S-335, U-57), (IB-336, S-336, U-57), (IB-337, S-337, U-57), (IB-338, S-338, U-57), (IB-339, S-339, U-57), (IB-340, S-340, U-57), (IB-341, S-341, U-57), (IB-342, S-342, U-57), (IB-343, S-343, U-57), (IB-344, S-344, U-57), (IB-345, S-345, U-57), (IB-346, S-346, U-57), (IB-347, S-347, U-57), (IB-348, S-348, U-57), (IB-349, S-349, U-57), (IB-350, S-350, U-57), (IB-351, S-351, U-57), (IB-352, S-352, U-57), (IB-353, S-353, U-57), (IB-354, S-354, U-57), (IB-355, S-355, U-57), (IB-356, S-356, U-57), (IB-357, S-357, U-57), (IB-358, S-358, U-57), (IB-359, S-359, U-57), (IB-360, S-360, U-57), (IB-361, S-361, U-57), (IB-362, S-362, U-57), (IB-363, S-363, U-57), (IB-364, S-364, U-57), (IB-365, S-365, U-57), (IB-366, S-366, U-57), (IB-367, S-367, U-57), (IB-368, S-368, U-57), (IB-369, S-369, U-57), (IB-370, S-370, U-57), (IB-371, S-371, U-57), (IB-372, S-372, U-57), (IB-373, S-373, U-57), (IB-374, S-374, U-57), (IB-375, S-375, U-57), (IB-376, S-376, U-57), (IB-377, S-377, U-57), (IB-378, S-378, U-57), (IB-379, S-379, U-57), (IB-380, S-380, U-57), (IB-381, S-381, U-57), (IB-382, S-382, U-57), (IB-383, S-383, U-57), (IB-384, S-384, U-57), (IB-385, S-385, U-57), (IB-386, S-386, U-57), (IB-387, S-387, U-57), (IB-388, S-388, U-57), (IB-389, S-389, U-57), (IB-390, S-390, U-57), (IB-391, S-391, U-57), (IB-392, S-392, U-57), (IB-393, S-393, U-57), (IB-394, S-394, U-57), (IB-395, S-395, U-57), (IB-396, S-396, U-57), (IB-397, S-397, U-57), (IB-398, S-398, U-57), (IB-399, S-399, U-57), (IB-400, S-400, U-57), (IB-401, S-401, U-57), (IB-402, S-402, U-57), (IB-403, S-403, U-57), (IB-404, S-404, U-57), (IB-405, S-405, U-57), (IB-406, S-406, U-57), (IB-407, S-407, U-57), (IB-408, S-408, U-57), (IB-409, S-409, U-57), (IB-410, S-410, U-57), (IB-411, S-411, U-57), (IB-412, S-412, U-57), (IB-413, S-413, U-57), (IB-414, S-414, U-57), (IB-415, S-415, U-57), (IB-416, S-416, U-57), (IB-417, S-417, U-57), (IB-418, S-418, U-57), (IB-419, S-419, U-57), (IB-420, S-420, U-57), (IB-421, S-421, U-57), (IB-422, S-422, U-57), (IB-423, S-423, U-57), (IB-424, S-424, U-57), (IB-425, S-425, U-57), (IB-426, S-426, U-57), (IB-427, S-427, U-57), (IB-428, S-428, U-57), (IB- 429, S-429, U-57), (IB-430, S-430, U-57), (IB-431, S-431, U-57), (IB-432, S-432, U-57), (IB-433, S-433, U-57), (IB-434, S-434, U-57), (IB-435, S-435, U-57), (IB-436, S-436, U-57), (IB-437, S-437, U-57), (IB-438, S-438, U-57), (IB-439, S-439, U-57), (IB-440, S-440, U-57), (IB-441, S-441, U-57), (IB-442, S-442, U-57), (IB-443, S-443, U-57), (IB-444, S-444, U-57), (IB-445, S-445, U-57), (IB-446, S-446, U-57), (IB-447, S-447, U-57), (IB-448, S-448, U-57), (IB-449, S-449, U-57), (IB-450, S-450, U-57), (IB-451, S-451, U-57), (IB-452, S-452, U-57), (IB-453, S-453, U-57), (IB-454, S-454, U-57), (IB-455, S-455, U-57), (IB-456, S-456, U-57), (IB-457, S-457, U-57), (IB-458, S-458, U-57), (IB-459, S-459, U-57), (IB-460, S-460, U-57), (IB-461, S-461, U-57), (IB-462, S-462, U-57), (IB-463, S-463, U-57), (IB-464, S-464, U-57), (IB-465, S-465, U-57), (IB-466, S-466, U-57), (IB-467, S-467, U-57), (IB-468, S-468, U-57), (IB-469, S-469, U-57), (IB-470, S-470, U-57), (IB-471, S-471, U-57), (IB-472, S-472, U-57), (IB-473, S-473, U-57), (IB-474, S-474, U-57), (IB-475, S-475, U-57), (IB-476, S-476, U-57), (IB-477, S-477, U-57), (IB-478, S-478, U-57), (IB-479, S-479, U-57), (IB-480, S-480, U-57), (IB-481, S-481, U-57), (IB-482, S-482, U-57), (IB-483, S-483, U-57), (IB-484, S-484, U-57), (IB-485, S-485, U-57), (IB-486, S-486, U-57), (IB-487, S-487, U-57), (IB-488, S-488, U-57), (IB-489, S-489, U-57), (IB-490, S-490, U-57), (IB-491, S-491, U-57), (IB-492, S-492, U-57), (IB-493, S-493, U-57), (IB-494, S-494, U-57), (IB-495, S-495, U-57), (IB-496, S-496, U-57), (IB-497, S-497, U-57), (IB-498, S-498, U-57), (IB-499, S-499, U-57), (IB-500, S-500, U-57), (IB-501, S-501, U-57), (IB-502, S-502, U-57), (IB-503, S-503, U-57), (IB-504, S-504, U-57), (IB-505, S-505, U-57), (IB-506, S-506, U-57), (IB-507, S-507, U-57), (IB-508, S-508, U-57), (IB-509, S-509, U-57), (IB-510, S-510, U-57), (IB-511, S-511, U-57), (IB-512, S-512, U-57), (IB-513, S-513, U-57), (IB-514, S-514, U-57), (IB-515, S-515, U-57), (IB-516, S-516, U-57), (IB-517, S-517, U-57), (IB-518, S-518, U-57), (IB-519, S-519, U-57), (IB-520, S-520, U-57), (IB-521, S-521, U-57), (IB-522, S-522, U-57), (IB-523, S-523, U-57), (IB-524, S-524, U-57), (IB-525, S-525, U-57), (IB-526, S-526, U-57), (IB-527, S-527, U-57), (IB-528, S-528, U-57), (IB-529, S-529, U-57), (IB-530, S-530, U-57), (IB-531, S-531, U-57), (IB-532, S-532, U-57), (IB-533, S-533, U-57), (IB-534, S-534, U-57), (IB-535, S-535, U-57), (IB-536, S-536, U-57), (IB-537, S-537, U-57), (IB-538, S-538, U-57), (IB-539, S-539, U-57), (IB-540, S-540, U-57), (IB-541, S-541, U-57), (IB-542, S-542, U-57), (IB-543, S-543, U-57), (IB-544, S-544, U-57), (IB-545, S-545, U-57), (IB-546, S-546, U-57), (IB-547, S-547, U-57), (IB-548, S-548, U-57), (IB-549, S-549, U-57), (IB-550, S-550, U-57), (IB-551, S-551, U-57), (IB-552, S-552, U-57), (IB-553, S-553, U-57), (IB-554, S-554, U-57), (IB-555, S-555, U-57), (IB-556, S-556, U-57), (IB-557, S-557, U-57), (IB-558, S-558, U-57), (IB-559, S-559, U-57), (IB-560, S-560, U-57), (IB-561, S-561, U-57), (IB-562, S-562, U-57), (IB-563, S-563, U-57), (IB-564, S-564, U-57), (IB-565, S-565, U-57), (IB-566, S-566, U-57), (IB-567, S-567, U-57), (IB-568, S-568, U-57), (IB-569, S-569, U-57), (IB-570, S-570, U-57), (IB-571, S-571, U-57), (IB-572, S-572, U-57), (IB-573, S-573, U-57), (IB-574, S-574, U-57), (IB-575, S-575, U-57), (IB-576, S-576, U-57), (IB-577, S-577, U-57), (IB-578, S-578, U-57), (IB-579, S-579, U-57), (IB-580, S-580, U-57), (IB-581, S-581, U-57), (IB-582, S-6, U-58), (IB-583, S-7, U-58), (IB-584, S-15, U-58), (IB-585, S-16, U-58), (IB-586, S-26, U-58), (IB-587, S-27, U-58), (IB-588, S-37, U-58), (IB-589, S-38, U-58), (IB-590, S-48, U-58), (IB-591, S-49, U-58), (IB-592, S-59, U-58), (IB-593, S-60, U-58), (IB-594, S-70, U-58), (IB-595, S-71, U-58), (IB-596, S-81, U-58), (IB-597, S-82, U-58), (IB-598, S-92, U-58), (IB-599, S-93, U-58), (IB-600, S-103, U-58), (IB-601, S-104, U-58), (IB-602, S-114, U-58), (IB-603, S-115, U-58), (IB-604, S-125, U-58), (IB-605, S-126, U-58), (IB-606, S-136, U-58), (IB-607, S-137, U-58), (IB-608, S-147, U-58), (IB-609, S-148, U-58), (IB-610, S-158, U-58), (IB-611, S-159, U-58), (IB-612, S-169, U-58), (IB-613, S-170, U-58), (IB-614, S-180, U-58), (IB-615, S-181, U-58), (IB-616, S-191, U-58), (IB-617, S-192, U-58), (IB-618, S-200, U-58), (IB-619, S-201, U-58), (IB-620, S-209, U-58), (IB-621, S-210, U-58), (IB-622, S-220, U-58), (IB-623, S-221, U-58), (IB-624, S-231, U-58), (IB-625, S-232, U-58), (IB-626, S-242, U-58), (IB-627, S-243, U-58), (IB-628, S-253, U-58), (IB-629, S-254, U-58), (IB-630, S-264, U-58), (IB-631, S-265, U-58), (IB-632, S-275, U-58), (IB-633, S-276, U-58), (IB-634, S-286, U-58), (IB-635, S-287, U-58), (IB-636, S-297, U-58), (IB-637, S-298, U-58), (IB-638, S-308, U-58), (IB-639, S-309, U-58), (IB-640, S-319, U-58), (IB-641, S-320, U-58), (IB-642, S-330, U-58), (IB-643, S-331, U-58), (IB-644, S-341, U-58), (IB-645, S-342, U-58), (IB-646, S-352, U-58), (IB-647, S-353, U-58), (IB-648, S-363, U-58), (IB-649, S-364, U-58), (IB-650, S-374, U-58), (IB-651, S-375, U-58), (IB-652, S-385, U-58), (IB-653, S-386, U-58), (IB-654, S-6, U-59), (IB-655, S-7, U-59), (IB-656, S-15, U-59), (IB-657, S-16, U-59), (IB-658, S-26, U-59), (IB-659, S-27, U-59), (IB-660, S-37, U-59), (IB-661, S-38, U-59), (IB-662, S-48, U-59), (IB-663, S-49, U-59), (IB-664, S-59, U-59), (IB-665, S-60, U-59), (IB-666, S-70, U-59), (IB-667, S-71, U-59), (IB-668, S-81, U-59), (IB-669, S-82, U-59), (IB-670, S-92, U-59), (IB-671, S-93, U-59), (IB-672, S-103, U-59), (IB-673, S-104, U-59), (IB-674, S-114, U-59), (IB-675, S-115, U-59), (IB-676, S-125, U-59), (IB-677, S-126, U-59), (IB-678, S-136, U-59), (IB-679, S-137, U-59), (IB-680, S-147, U-59), (IB-681, S-148, U-59), (IB-682, S-158, U-59), (IB-683, S-159, U-59), (IB-684, S-169, U-59), (IB-685, S-170, U-59), (IB-686, S-180, U-59), (IB-687, S-181, U-59), (IB-688, S-191, U-59), (IB-689, S-192, U-59), (IB-690, S-200, U-59), (IB-691, S-201, U-59), (IB-692, S-209, U-59), (IB-693, S-210, U-59), (IB-694, S-220, U-59), (IB-695, S-221, U-59), (IB-696, S-231, U-59), (IB-697, S-232, U-59), (IB-698, S-242, U-59), (IB-699, S-243, U-59), (IB-700, S-253, U-59), (IB-701, S-254, U-59), (IB-702, S-264, U-59), (IB-703, S-265, U-59), (IB-704, S-275, U-59), (IB-705, S-276, U-59), (IB-706, S-286, U-59), (IB-707, S-287, U-59), (IB-708, S-297, U-59), (IB-709, S-298, U-59), (IB-710, S-308, U-59), (IB-711, S-309, U-59), (IB-712, S-319, U-59), (IB-713, S-320, U-59), (IB-714, S-330, U-59), (IB-715, S-331, U-59), (IB-716, S-341, U-59), (IB-717, S-342, U-59), (IB-718, S-352, U-59), (IB-719, S-353, U-59), (IB-720, S-363, U-59), (IB-721, S-364, U-59), (IB-722, S-374, U-59), (IB-723, S-375, U-59), (IB-724, S-385, U-59), (IB-725, S-386, U-59), (IB-726, S-6, U-60), (IB-727, S-7, U-60), (IB-728, S-15, U-60), (IB-729, S-16, U-60), (IB-730, S-26, U-60), (IB-731, S-27, U-60), (IB-732, S-37, U-60), (IB-733, S-38, U-60), (IB-734, S-48, U-60), (IB-735, S-49, U-60), (IB-736, S-59, U-60), (IB-737, S-60, U-60), (IB-738, S-70, U-60), (IB-739, S-71, U-60), (IB-740, S-81, U-60), (IB-741, S-82, U-60), (IB-742, S-92, U-60), (IB-743, S-93, U-60), (IB-744, S-103, U-60), (IB-745, S-104, U-60), (IB-746, S-114, U-60), (IB-747, S-115, U-60), (IB-748, S-125, U-60), (IB-749, S-126, U-60), (IB-750, S-136, U-60), (IB-751, S-137, U-60), (IB-752, S-147, U-60), (IB-753, S-148, U-60), (IB-754, S-158, U-60), (IB-755, S-159, U-60), (IB-756, S-169, U-60), (IB-757, S-170, U-60), (IB-758, S-180, U-60), (IB-759, S-181, U-60), (IB-760, S-191, U-60), (IB-761, S-192, U-60), (IB-762, S-200, U-60), (IB-763, S-201, U-60), (IB-764, S-209, U-60), (IB-765, S-210, U-60), (IB-766, S-220, U-60), (IB-767, S-221, U-60), (IB-768, S-231, U-60), (IB-769, S-232, U-60), (IB-770, S-242, U-60), (IB-771, S-243, U-60), (IB-772, S-253, U-60), (IB-773, S-254, U-60), (IB-774, S-264, U-60), (IB-775, S-265, U-60), (IB-776, S-275, U-60), (IB-777, S-276, U-60), (IB-778, S-286, U-60), (IB-779, S-287, U-60), (IB-780, S-297, U-60), (IB-781, S-298, U-60), (IB-782, S-308, U-60), (IB-783, S-309, U-60), (IB-784, S-319, U-60), (IB-785, S-320, U-60), (IB-786, S-330, U-60), (IB-787, S-331, U-60), (IB-788, S-341, U-60), (IB-789, S-342, U-60), (IB-790, S-352, U-60), (IB-791, S-353, U-60), (IB-792, S-363, U-60), (IB-793, S-364, U-60), (IB-794, S-374, U-60), (IB-795, S-375, U-60), (IB-796, S-385, U-60), (IB-797, S-386, U-60), (IB-798, S-6, U-61), (IB-799, S-7, U-61), (IB-800, S-15, U-61), (IB-801, S-16, U-61), (IB-802, S-26, U-61), (IB-803, S-27, U-61), (IB-804, S-37, U-61), (IB-805, S-38, U-61), (IB-806, S-48, U-61), (IB-807, S-49, U-61), (IB-808, S-59, U-61), (IB-809, S-60, U-61), (IB-810, S-70, U-61), (IB-811, S-71, U-61), (IB-812, S-81, U-61), (IB-813, S-82, U-61), (IB-814, S-92, U-61), (IB-815, S-93, U-61), (IB-816, S-103, U-61), (IB-817, S-104, U-61), (IB-818, S-114, U-61), (IB-819, S-115, U-61), (IB-820, S-125, U-61), (IB-821, S-126, U-61), (IB-822, S-136, U-61), (IB-823, S-137, U-61), (IB-824, S-147, U-61), (IB-825, S-148, U-61), (IB-826, S-158, U-61), (IB-827, S-159, U-61), (IB-828, S-169, U-61), (IB-829, S-170, U-61), (IB-830, S-180, U-61), (IB-831, S-181, U-61), (IB-832, S-191, U-61), (IB-833, S-192, U-61), (IB-834, S-200, U-61), (IB-835, S-201, U-61), (IB-836, S-209, U-61), (IB-837, S-210, U-61), (IB-838, S-220, U-61), (IB-839, S-221, U-61), (IB-840, S-231, U-61), (IB-841, S-232, U-61), (IB-842, S-242, U-61), (IB-843, S-243, U-61), (IB-844, S-253, U-61), (IB-845, S-254, U-61), (IB-846, S-264, U-61), (IB-847, S-265, U-61), (IB-848, S-275, U-61), (IB-849, S-276, U-61), (IB-850, S-286, U-61), (IB-851, S-287, U-61), (IB-852, S-297, U-61), (IB-853, S-298, U-61), (IB-854, S-308, U-61), (IB-855, S-309, U-61), (IB-856, S-319, U-61), (IB-857, S-320, U-61), (IB-858, S-330, U-61), (IB-859, S-331, U-61), (IB-860, S-341, U-61), (IB-861, S-342, U-61), (IB-862, S-352, U-61), (IB-863, S-353, U-61), (IB-864, S-363, U-61), (IB-865, S-364, U-61), (IB-866, S-374, U-61), (IB-867, S-375, U-61), (IB-868, S-385, U-61), (IB-869, S-386, U-61), (IB-870, S-6, U-65), (IB-871, S-7, U-65), (IB-872, S-15, U-65), (IB-873, S-16, U-65), (IB-874, S-26, U-65), (IB-875, S-27, U-65), (IB-876, S-37, U-65), (IB-877, S-38, U-65), (IB-878, S-48, U-65), (IB-879, S-49, U-65), (IB-880, S-59, U-65), (IB-881, S-60, U-65), (IB-882, S-70, U-65), (IB-883, S-71, U-65), (IB-884, S-81, U-65), (IB-885, S-82, U-65), (IB-886, S-92, U-65), (IB-887, S-93, U-65), (IB-888, S-103, U-65), (IB-889, S-104, U-65), (IB-890, S-114, U-65), (IB-891, S-115, U-65), (IB-892, S-125, U-65), (IB-893, S-126, U-65), (IB-894, S-136, U-65), (IB-895, S-137, U-65), (IB-896, S-147, U-65), (IB-897, S-148, U-65), (IB-898, S-158, U-65), (IB-899, S-159, U-65), (IB-900, S-169, U-65), (IB-901, S-170, U-65), (IB-902, S-180, U-65), (IB-903, S-181, U-65), (IB-904, S-191, U-65), (IB-905, S-192, U-65), (IB-906, S-200, U-65), (IB-907, S-201, U-65), (IB-908, S-209, U-65), (IB-909, S-210, U-65), (IB-910, S-220, U-65), (IB-911, S-221, U-65), (IB-912, S-231, U-65), (IB-913, S-232, U-65), (IB-914, S-242, U-65), (IB-915, S-243, U-65), (IB-916, S-253, U-65), (IB-917, S-254, U-65), (IB-918, S-264, U-65), (IB-919, S-265, U-65), (IB-920, S-275, U-65), (IB-921, S-276, U-65), (IB-922, S-286, U-65), (IB-923, S-287, U-65), (IB-924, S-297, U-65), (IB-925, S-298, U-65), (IB-926, S-308, U-65), (IB-927, S-309, U-65), (IB-928, S-319, U-65), (IB-929, S-320, U-65), (IB-930, S-330, U-65), (IB-931, S-331, U-65), (IB-932, S-341, U-65), (IB-933, S-342, U-65), (IB-934, S-352, U-65), (IB-935, S-353, U-65), (IB-936, S-363, U-65), (IB-937, S-364, U-65), (IB-938, S-374, U-65), (IB-939, S-375, U-65), (IB-940, S-385, U-65), (IB-941, S-386, U-65), (IB-942, S-6, U-65), (IB-943, S-7, U-65), (IB-944, S-15, U-65), (IB-945, S-16, U-65), (IB-946, S-26, U-65), (IB-947, S-27, U-65), (IB-948, S-37, U-65), (IB-949, S-38, U-65), (IB-950, S-48, U-65), (IB-951, S-49, U-65), (IB-952, S-59, U-65), (IB-953, S-60, U-65), (IB-954, S-70, U-65), (IB-955, S-71, U-65), (IB-956, S-81, U-65), (IB-957, S-82, U-65), (IB-958, S-92, U-65), (IB-959, S-93, U-65), (IB-960, S-103, U-65), (IB-961, S-104, U-65), (IB-962, S-114, U-65), (IB-963, S-115, U-65), (IB-964, S-125, U-65), (IB-965, S-126, U-65), (IB-966, S-136, U-65), (IB-967, S-137, U-65), (IB-968, S-147, U-65), (IB-969, S-148, U-65), (IB-970, S-158, U-65), (IB-971, S-159, U-65), (IB-972, S-169, U-65), (IB-973, S-170, U-65), (IB-974, S-180, U-65), (IB-975, S-181, U-65), (IB-976, S-191, U-65), (IB-977, S-192, U-65), (IB-978, S-200, U-65), (IB-979, S-201, U-65), (IB-980, S-209, U-65), (IB-981, S-210, U-65), (IB-982, S-220, U-65), (IB-983, S-221, U-65), (IB-984, S-231, U-65), (IB-985, S-232, U-65), (IB-986, S-242, U-65), (IB-987, S-243, U-65), (IB-988, S-253, U-65), (IB-989, S-254, U-65), (IB-990, S-264, U-65), (IB-991, S-265, U-65), (IB-992, S-275, U-65), (IB-993, S-276, U-65), (IB-994, S-286, U-65), (IB-995, S-287, U-65), (IB-996, S-297, U-65), (IB-997, S-298, U-65), (IB-998, S-308, U-65), (IB-999, S-309, U-65), (IB-1000, S-319, U-65), (IB-1001, S-320, U-65), (IB-1002, S-330, U-65), (IB-1003, S-331, U-65), (IB-1004, S-341, U-65), (IB-1005, S-342, U-65), (IB-1006, S-352, U-65), (IB-1007, S-353, U-65), (IB-1008, S-363, U-65), (IB-1009, S-364, U-65), (IB-1010, S-374, U-65), (IB-1011, S-375, U-65), (IB-1012, S-385, U-65), (IB-1013, S-386, U-65), (IB-1014, S-6, U-69), (IB-1015, S-7, U-69), (IB-1016, S-15, U-69), (IB-1017, S-16, U-69), (IB-1018, S-26, U-69), (IB-1019, S-27, U-69), (IB-1020, S-37, U-69), (IB-1021, S-38, U-69), (IB-1022, S-48, U-69), (IB-1023, S-49, U-69), (IB-1024, S-59, U-69), (IB-1025, S-60, U-69), (IB-1026, S-70, U-69), (IB-1027, S-71, U-69), (IB-1028, S-81, U-69), (IB-1029, S-82, U-69), (IB-1030, S-92, U-69), (IB-1031, S-93, U-69), (IB-1032, S-103, U-69), (IB-1033, S-104, U-69), (IB-1034, S-114, U-69), (IB-1035, S-115, U-69), (IB-1036, S-125, U-69), (IB-1037, S-126, U-69), (IB-1038, S-136, U-69), (IB-1039, S-137, U-69), (IB-1040, S-147, U-69), (IB-1041, S-148, U-69), (IB-1042, S-158, U-69), (IB-1043, S-159, U-69), (IB-1044, S-169, U-69), (IB-1045, S-170, U-69), (IB-1046, S-180, U-69), (IB-1047, S-181, U-69), (IB-1048, S-191, U-69), (IB-1049, S-192, U-69), (IB-1050, S-200, U-69), (IB-1051, S-201, U-69), (IB-1052, S-209, U-69), (IB-1053, S-210, U-69), (IB-1054, S-220, U-69), (IB-1055, S-221, U-69), (IB-1056, S-231, U-69), (IB-1057, S-232, U-69), (IB-1058, S-242, U-69), (IB-1059, S-243, U-69), (IB-1060, S-253, U-69), (IB-1061, S-254, U-69), (IB-1062, S-264, U-69), (IB-1063, S-265, U-69), (IB-1064, S-275, U-69), (IB-1065, S-276, U-69), (IB-1066, S-286, U-69), (IB-1067, S-287, U-69), (IB-1068, S-297, U-69), (IB-1069, S-298, U-69), (IB-1070, S-308, U-69), (IB-1071, S-309, U-69), (IB-1072, S-319, U-69), (IB-1073, S-320, U-69), (IB-1074, S-330, U-69), (IB-1075, S-331, U-69), (IB-1076, S-341, U-69), (IB-1077, S-342, U-69), (IB-1078, S-352, U-69), (IB-1079, S-353, U-69), (IB-1080, S-363, U-69), (IB-1081, S-364, U-69), (IB-1082, S-374, U-69), (IB-1083, S-375, U-69), (IB-1084, S-385, U-69), (IB-1085, S-386, U-69), (IB-1086, S-6, U-74), (IB-1087, S-7, U-74), (IB-1088, S-15, U-74), (IB-1089, S-16, U-74), (IB-1090, S-26, U-74), (IB-1091, S-27, U-74), (IB-1092, S-37, U-74), (IB-1093, S-38, U-74), (IB-1094, S-48, U-74), (IB-1095, S-49, U-74), (IB-1096, S-59, U-74), (IB-1097, S-60, U-74), (IB-1098, S-70, U-74), (IB-1099, S-71, U-74), (IB-1100, S-81, U-74), (IB-1101, S-82, U-74), (IB- 1102, S-92, U-74), (IB-1103, S-93, U-74), (IB-1104, S-103, U-74), (IB-1105, S-104, U-74), (IB-1106, S-114, U-74), (IB-1107, S-115, U-74), (IB-1108, S-125, U-74), (IB-1109, S-126, U-74), (IB-1110, S-136, U-74), (IB-1111, S-137, U-74), (IB-1112, S-147, U-74), (IB-1113, S-148, U-74), (IB-1114, S-158, U-74), (IB-1115, S-159, U-74), (IB-1116, S-169, U-74), (IB-1117, S-170, U-74), (IB-1118, S-180, U-74), (IB-1119, S-181, U-74), (IB-1120, S-191, U-74), (IB-1121, S-192, U-74), (IB-1122, S-200, U-74), (IB-1123, S-201, U-74), (IB-1124, S-209, U-74), (IB-1125, S-210, U-74), (IB-1126, S-220, U-74), (IB-1127, S-221, U-74), (IB-1128, S-231, U-74), (IB-1129, S-232, U-74), (IB-1130, S-242, U-74), (IB-1131, S-243, U-74), (IB-1132, S-253, U-74), (IB-1133, S-254, U-74), (IB-1134, S-264, U-74), (IB-1135, S-265, U-74), (IB-1136, S-275, U-74), (IB-1137, S-276, U-74), (IB-1138, S-286, U-74), (IB-1139, S-287, U-74), (IB-1140, S-297, U-74), (IB-1141, S-298, U-74), (IB-1142, S-308, U-74), (IB-1143, S-309, U-74), (IB-1144, S-319, U-74), (IB-1145, S-320, U-74), (IB-1146, S-330, U-74), (IB-1147, S-331, U-74), (IB-1148, S-341, U-74), (IB-1149, S-342, U-74), (IB-1150, S-352, U-74), (IB-1151, S-353, U-74), (IB-1152, S-363, U-74), (IB-1153, S-364, U-74), (IB-1154, S-374, U-74), (IB-1155, S-375, U-74), (IB-1156, S-385, U-74), (IB-1157, S-386, U-74), (IB-1158, S-6, U-1), (IB-1159, S-6, U-2), (IB-1160, S-6, U-3), (IB-1161, S-6, U-4), (IB-1162, S-6, U-5), (IB-1163, S-6, U-6), (IB-1164, S-6, U-7), (IB-1165, S-6, U-8), (IB-1166, S-6, U-9), (IB-1167, S-6, U-10), (IB-1168, S-6, U-11), (IB-1169, S-6, U-12), (IB-1170, S-6, U-13), (IB-1171, S-6, U-14), (IB-1172, S-6, U-15), (IB-1173, S-6, U-16), (IB-1174, S-6, U-17), (IB-1175, S-6, U-18), (IB-1176, S-6, U-19), (IB-1177, S-6, U-20), (IB-1178, S-6, U-21), (IB-1179, S-6, U-22), (IB-1180, S-6, U-23), (IB-1181, S-6, U-24), (IB-1182, S-6, U-25), (IB-1183, S-6, U-26), (IB-1184, S-6, U-27), (IB-1185, S-6, U-28), (IB-1186, S-6, U-29), (IB-1187, S-6, U-30), (IB-1188, S-6, U-31), (IB-1189, S-6, U-32), (IB-1190, S-6, U-33), (IB-1191, S-6, U-34), (IB-1192, S-6, U-35), (IB-1193, S-6, U-36), (IB-1194, S-6, U-37), (IB-1195, S-6, U-38), (IB-1196, S-6, U-39), (IB-1197, S-6, U-40), (IB-1198, S-6, U-41), (IB-1199, S-6, U-42), (IB-1200, S-6, U-43), (IB-1201, S-6, U-44), (IB-1202, S-6, U-45), (IB-1203, S-6, U-46), (IB-1204, S-6, U-47), (IB-1205, S-6, U-48), (IB-1206, S-6, U-49), (IB-1207, S-6, U-50), (IB-1208, S-6, U-51), (IB-1209, S-6, U-52), (IB-1210, S-6, U-53), (IB-1211, S-6, U-54), (IB-1212, S-6, U-55), (IB-1213, S-6, U-56), (IB-1214, S-6, U-62), (IB-1215, S-6, U-63), (IB-1216, S-6, U-64), (IB-1217, S-6, U-66), (IB-1218, S-6, U-67), (IB-1219, S-6, U-68), (IB-1220, S-6, U-70), (IB-1221, S-6, U-71), (IB-1222, S-6, U-72), (IB-1223, S-6, U-73), (IB-1224, S-6, U-75), (IB-1225, S-6, U-76), (IB-1226, S-6, U-77), (IB-1227, S-6, U-78), (IB-1228, S-6, U-79), (IB-1229, S-6, U-80), (IB-1230, S-6, U-81), (IB-1231, S-6, U-82), (IB-1232, S-6, U-83), (IB-1233, S-6, U-84), (IB-1234, S-6, U-85), (IB-1235, S-6, U-86), (IB-1236, S-6, U-87), (IB-1237, S-6, U-88), (IB-1238, S-6, U-89), (IB-1239, S-6, U-90), (IB-1240, S-6, U-91), (IB-1241, S-6, U-92), (IB-1242, S-6, U-93), (I B-1243, S-6, U-94), (IB-1244, S-6, U-95), (IB-1245, S-6, U-96), (IB-1246, S-6, U-97), (IB-1247, S-6, U-98), (IB-1248, S-6, U-99), (IB-1249, S-6, U-100), (IB-1250, S-6, U-101), (IB-1251, S-6, U-102), (IB-1252, S-6, U-103), (IB-1253, S-6, U-104), (IB-1254, S-6, U-105), (IB-1255, S-6, U-106), (IB-1256, S-6, U-107), (IB-1257, S-6, U-108), (IB-1258, S-6, U-109), (IB-1259, S-6, U-110), (IB-1260, S-6, U-11), (IB-1261, S-6, U-112), (IB-1262, S-6, U-113), (IB-1263, S-6, U-114), (IB-1264, S-6, U-115), (IB-1265, S-6, U-116), (IB-1266, S-6, U-117), (IB-1267, S-6, U-118), (IB-1268, S-6, U-119), (IB-1269, S-6, U-120), (IB-1270, S-6, U-121), (IB-1271, S-6, U-122), (IB-1272, S-6, U-123), (IB-1273, S-6, U-124), (IB-1274, S-6, U-125), (IB-1275, S-6, U-126), (IB-1276, S-6, U-127), (IB-1277, S-6, U-128), (IB-1278, S-6, U-129), (IB-1279, S-6, U-130), (IB-1280, S-6, U-131), (IB-1281, S-6, U-132), (IB-1282, S-6, U-133), (IB-1283, S-6, U-134), (IB-1284, S-6, U-135), (IB-1285, S-6, U-136), (IB-1286, S-6, U-137), (IB-1287, S-6, U-138), (IB-1288, S-6, U-139), (IB-1289, S-6, U-140), (IB-1290, S-6, U-141), (IB-1291, S-6, U-142), (IB-1292, S-6, U-143), (IB-1293, S-6, U-144), (IB-1294, S-6, U-145), (IB-1295, S-6, U-146), (IB-1296, S-6, U-147), (IB-1297, S-6, U-148), (IB-1298, S-6, U-149), (IB-1299, S-6, U-150), (IB-1300, S-6, U-151), (IB-1301, S-6, U-152), (IB-1302, S-6, U-153), (IB-1303, S-6, U-154), (IB-1304, S-6, U-155), (IB-1305, S-6, U-156), (IB-1306, S-6, U-157), (IB-1307, S-6, U-158), (IB-1308, S-6, U-159), (IB-1309, S-6, U-160), (IB-1310, S-6, U-161), (IB-1311, S-6, U-162), (IB-1312, S-6, U-163), (IB-1313, S-6, U-164), (IB-1314, S-6, U-165), (IB-1315, S-6, U-166), (IB-1316, S-6, U-167), (IB-1317, S-6, U-168), (IB-1318, S-6, U-169), (IB-1319, S-6, U-170), (IB-1320, S-6, U-171), (IB-1321, S-6, U-172), (IB-1322, S-6, U-173), (IB-1323, S-6, U-174), (IB-1324, S-6, U-175), (IB-1325, S-6, U-176), (IB-1326, S-6, U-177), (IB-1327, S-6, U-178), (IB-1328, S-6, U-179), (IB-1329, S-6, U-180), (IB-1330, S-6, U-181), (IB-1331, S-6, U-182), (IB-1332, S-6, U-183), (IB-1333, S-6, U-184), (IB-1334, S-6, U-185), (IB-1335, S-6, U-186), (IB-1336, S-6, U-187), (IB-1337, S-6, U-188), (IB-1338, S-6, U-189), (IB-1339, S-6, U-190), (IB-1340, S-6, U-191), (IB-1341, S-6, U-192), (IB-1342, S-6, U-193), (IB-1343, S-6, U-194), (IB-1344, S-6, U-195), (IB-1345, S-6, U-196), (IB-1346, S-6, U-197), (IB-1347, S-6, U-198), (IB-1348, S-6, U-199), (IB-1349, S-6, U-200), (IB-1350, S-6, U-201), (IB-1351, S-6, U-202), (IB-1352, S-6, U-203), (IB-1353, S-6, U-204), (IB-1354, S-6, U-205), (IB-1355, S-6, U-206), (IB-1356, S-6, U-207), (IB-1357, S-6, U-208), (IB-1358, S-6, U-209), (IB-1359, S-6, U-210), (IB-1360, S-6, U-211), (IB-1361, S-6, U-212), (IB-1362, S-6, U-213), (IB-1363, S-6, U-214), (IB-1364, S-6, U-215), (IB-1365, S-6, U-216), (IB-1366, S-6, U-217), (IB-1367, S-6, U-218), (IB-1368, S-6, U-219), (IB-1369, S-6, U-220), (IB-1370, S-6, U-221), (IB-1371, S-6, U-222), (IB-1372, S-6, U-223), (IB-1373, S-6, U-224), (IB-1374, S-6, U-225), (IB-1375, S-6, U-226), (IB-1376, S-6, U-227), (IB-1377, S-6, U-228), (IB-1378, S-6, U-229), (IB-1379, S-6, U-230), (IB-1380, S-6, U-231), (IB-1381, S-6, U-232), (IB-1382, S-6, U-233), (IB-1383, S-6, U-234), (IB-1384, S-6, U-235), (IB-1385, S-6, U-236), (IB-1386, S-6, U-237), (IB-1387, S-6, U-238), (IB-1388, S-6, U-239), (IB-1389, S-6, U-240), (IB-1390, S-6, U-241), (IB-1391, S-6, U-242), (IB-1392, S-6, U-243), (IB-1393, S-6, U-244), (IB-1394, S-6, U-245), (IB-1395, S-6, U-246), (IB-1396, S-6, U-247), (IB-1397, S-6, U-248), (IB-1398, S-6, U-249), (IB-1399, S-6, U-250), (IB-1400, S-6, U-251), (IB-1401, S-6, U-252), (IB-1402, S-6, U-253), (IB-1403, S-6, U-254), (IB-1404, S-6, U-255), (IB-1405, S-6, U-256), (IB-1406, S-6, U-257), (IB-1407, S-6, U-258), (IB-1408, S-6, U-259), (IB-1409, S-6, U-260), (IB-1410, S-6, U-261), (IB-1411, S-6, U-262), (IB-1412, S-6, U-263), (IB-1413, S-6, U-264), (IB-1414, S-6, U-265), (IB-1415, S-6, U-266), (IB-1416, S-6, U-267), (IB-1417, S-6, U-268), (IB-1418, S-6, U-269), (IB-1419, S-6, U-270), (IB-1420, S-6, U-271), (IB-1421, S-6, U-272), (IB-1422, S-6, U-273), (IB-1423, S-6, U-274), (IB-1424, S-6, U-275), (IB-1425, S-6, U-276), (IB-1426, S-6, U-277), (IB-1427, S-6, U-278), (IB-1428, S-6, U-279), (IB-1429, S-6, U-280), (IB-1430, S-6, U-281), (IB-1431, S-6, U-282), (IB-1432, S-6, U-283), (IB-1433, S-6, U-284), (IB-1434, S-6, U-285), (IB-1435, S-6, U-286), (IB-1436, S-6, U-287), (IB-1437, S-6, U-288), (IB-1438, S-6, U-289), (IB-1439, S-6, U-290), (IB-1440, S-6, U-291), (IB-1441, S-6, U-292), (IB-1442, S-6, U-293), (IB-1443, S-6, U-294), (IB-1444, S-6, U-295), (IB-1445, S-6, U-296), (IB-1446, S-6, U-297), (IB-1447, S-6, U-298), (IB-1448, S-6, U-299), (IB-1449, S-6, U-300), (IB-1450, S-6, U-301), (IB-1451, S-6, U-302), (IB-1452, S-6, U-303), (IB-1453, S-6, U-304), (IB-1454, S-6, U-305), (IB-1455, S-6, U-306), (IB-1456, S-6, U-307), (IB-1457, S-6, U-308), (IB-1458, S-6, U-309), (IB-1459, S-6, U-310), (IB-1460, S-6, U-311), (IB-1461, S-6, U-312), (IB-1462, S-6, U-313), (IB-1463, S-6, U-314), (IB-1464, S-6, U-315), (IB-1465, S-6, U-316), (IB-1466, S-6, U-317), (IB-1467, S-6, U-318), (IB-1468, S-6, U-319), (IB-1469, S-6, U-320), (IB-1470, S-6, U-321), (IB-1471, S-6, U-322), (IB-1472, S-6, U-323), (IB-1473, S-6, U-324), (IB-1474, S-6, U-325), (IB-1475, S-6, U-326), (IB-1476, S-6, U-327), (IB-1477, S-6, U-328), (IB-1478, S-6, U-329), (IB-1479, S-6, U-330), (IB-1480, S-6, U-331), (IB-1481, S-6, U-332), (IB-1482, S-6, U-333), (IB-1483, S-6, U-334), (IB-1484, S-6, U-335), (IB-1485, S-6, U-336), (IB-1486, S-6, U-337), (IB-1487, S-6, U-338), (IB-1488, S-7, U-1), (IB-1489, S-7, U-2), (IB-1490, S-7, U-3), (IB-1491, S-7, U-4), (IB-1492, S-7, U-5), (IB-1493, S-7, U-6), (IB-1494, S-7, U-7), (IB-1495, S-7, U-8), (IB-1496, S-7, U-9), (IB-1497, S-7, U-10), (IB-1498, S-7, U-11), (IB-1499, S-7, U-12), (IB-1500, S-7, U-13), (IB-1501, S-7, U-14), (IB-1502, S-7, U-15), (IB-1503, S-7, U-16), (IB-1504, S-7, U-17), (IB-1505, S-7, U-18), (IB-1506, S-7, U-19), (IB-1507, S-7, U-20), (IB-1508, S-7, U-21), (IB-1509, S-7, U-22), (IB-1510, S-7, U-23), (IB-1511, S-7, U-24), (IB-1512, S-7, U-25), (IB-1513, S-7, U-26), (IB-1514, S-7, U-27), (IB-1515, S-7, U-28), (IB-1516, S-7, U-29), (IB-1517, S-7, U-30), (IB-1518, S-7, U-31), (IB-1519, S-7, U-32), (IB-1520, S-7, U-33), (IB-1521, S-7, U-34), (IB-1522, S-7, U-35), (IB-1523, S-7, U-36), (IB-1524, S-7, U-37), (IB-1525, S-7, U-38), (IB-1526, S-7, U-39), (IB-1527, S-7, U-40), (IB-1528, S-7, U-41), (IB-1529, S-7, U-42), (IB-1530, S-7, U-43), (IB-1531, S-7, U-44), (IB-1532, S-7, U-45), (IB-1533, S-7, U-46), (IB-1534, S-7, U-47), (IB-1535, S-7, U-48), (IB-1536, S-7, U-49), (IB-1537, S-7, U-50), (IB-1538, S-7, U-51), (IB-1539, S-7, U-52), (IB-1540, S-7, U-53), (IB-1541, S-7, U-54), (IB-1542, S-7, U-55), (IB-1543, S-7, U-56), (IB-1544, S-7, U-62), (IB-1545, S-7, U-63), (IB-1546, S-7, U-64), (IB-1547, S-7, U-66), (IB-1548, S-7, U-67), (IB-1549, S-7, U-68), (IB-1550, S-7, U-70), (IB-1551, S-7, U-71), (IB-1552, S-7, U-72), (IB-1553, S-7, U-73), (IB-1554, S-7, U-75), (IB-1555, S-7, U-76), (IB-1556, S-7, U-77), (IB-1557, S-7, U-78), (IB-1558, S-7, U-79), (IB-1559, S-7, U-80), (IB-1560, S-7, U-81), (IB-1561, S-7, U-82), (IB-1562, S-7, U-83), (IB-1563, S-7, U-84), (IB-1564, S-7, U-85), (IB-1565, S-7, U-86), (IB-1566, S-7, U-87), (IB-1567, S-7, U-88), (IB-1568, S-7, U-89), (IB-1569, S-7, U-90), (IB-1570, S-7, U-91), (IB-1571, S-7, U-92), (IB-1572, S-7, U-93), (IB-1573, S-7, U-94), (IB-1574, S-7, U-95), (IB-1575, S-7, U-96), (IB-1576, S-7, U-97), (IB-1577, S-7, U-98), (IB-1578, S-7, U-99), (IB-1579, S-7, U-100), (IB-1580, S-7, U-101), (IB-1581, S-7, U-102), (IB-1582, S-7, U-103), (IB-1583, S-7, U-104), (IB-1584, S-7, U-105), (IB-1585, S-7, U-106), (IB-1586, S-7, U-107), (IB-1587, S-7, U-108), (IB-1588, S-7, U-109), (IB-1589, S-7, U-110), (IB-1590, S-7, U-111), (IB-1591, S-7, U-112), (IB-1592, S-7, U-113), (IB-1593, S-7, U-114), (IB-1594, S-7, U-115), (IB-1595, S-7, U-116), (IB-1596, S-7, U-117), (IB-1597, S-7, U-118), (IB-1598, S-7, U-119), (IB-1599, S-7, U-120), (IB-1600, S-7, U-121), (IB-1601, S-7, U-122), (IB-1602, S-7, U-123), (IB-1603, S-7, U-124), (IB-1604, S-7, U-125), (IB-1605, S-7, U-126), (IB-1606, S-7, U-127), (IB-1607, S-7, U-128), (IB-1608, S-7, U-129), (IB-1609, S-7, U-130), (IB-1610, S-7, U-131), (IB-1611, S-7, U-132), (IB-1612, S-7, U-133), (IB-1613, S-7, U-134), (IB-1614, S-7, U-135), (IB-1615, S-7, U-136), (IB-1616, S-7, U-137), (IB-1617, S-7, U-138), (IB-1618, S-7, U-139), (IB-1619, S-7, U-140), (IB-1620, S-7, U-141), (IB-1621, S-7, U-142), (IB-1622, S-7, U-143), (IB-1623, S-7, U-144), (IB-1624, S-7, U-145), (IB-1625, S-7, U-146), (IB-1626, S-7, U-147), (IB-1627, S-7, U-148), (IB-1628, S-7, U-149), (IB-1629, S-7, U-150), (IB-1630, S-7, U-151), (IB-1631, S-7, U-152), (IB-1632, S-7, U-153), (IB-1633, S-7, U-154), (IB-1634, S-7, U-155), (IB-1635, S-7, U-156), (IB-1636, S-7, U-157), (IB-1637, S-7, U-158), (IB-1638, S-7, U-159), (IB-1639, S-7, U-160), (IB-1640, S-7, U-161), (IB-1641, S-7, U-162), (IB-1642, S-7, U-163), (IB-1643, S-7, U-164), (IB-1644, S-7, U-165), (IB-1645, S-7, U-166), (IB-1646, S-7, U-167), (IB-1647, S-7, U-168), (IB-1648, S-7, U-169), (IB-1649, S-7, U-170), (IB-1650, S-7, U-171), (IB-1651, S-7, U-172), (IB-1652, S-7, U-173), (IB-1653, S-7, U-174), (IB-1654, S-7, U-175), (IB-1655, S-7, U-176), (IB-1656, S-7, U-177), (IB-1657, S-7, U-178), (IB-1658, S-7, U-179), (IB-1659, S-7, U-180), (IB-1660, S-7, U-181), (IB-1661, S-7, U-182), (IB-1662, S-7, U-183), (IB-1663, S-7, U-184), (IB-1664, S-7, U-185), (IB-1665, S-7, U-186), (IB-1666, S-7, U-187), (IB-1667, S-7, U-188), (IB-1668, S-7, U-189), (IB-1669, S-7, U-190), (IB-1670, S-7, U-191), (IB-1671, S-7, U-192), (IB-1672, S-7, U-193), (IB-1673, S-7, U-194), (IB-1674, S-7, U-195), (IB-1675, S-7, U-196), (IB-1676, S-7, U-197), (IB-1677, S-7, U-198), (IB-1678, S-7, U-199), (IB-1679, S-7, U-200), (IB-1680, S-7, U-201), (IB-1681, S-7, U-202), (IB-1682, S-7, U-203), (IB-1683, S-7, U-204), (IB-1684, S-7, U-205), (IB-1685, S-7, U-206), (IB-1686, S-7, U-207), (IB-1687, S-7, U-208), (IB-1688, S-7, U-209), (IB-1689, S-7, U-210), (IB-1690, S-7, U-211), (IB-1691, S-7, U-212), (IB-1692, S-7, U-213), (IB-1693, S-7, U-214), (IB-1694, S-7, U-215), (IB-1695, S-7, U-216), (IB-1696, S-7, U-217), (IB-1697, S-7, U-218), (IB-1698, S-7, U-219), (IB-1699, S-7, U-220), (IB-1700, S-7, U-221), (IB-1701, S-7, U-222), (IB-1702, S-7, U-223), (IB-1703, S-7, U-224), (IB-1704, S-7, U-225), (IB-1705, S-7, U-226), (IB-1706, S-7, U-227), (IB-1707, S-7, U-228), (IB-1708, S-7, U-229), (IB-1709, S-7, U-230), (IB-1710, S-7, U-231), (IB-1711, S-7, U-232), (IB-1712, S-7, U-233), (IB-1713, S-7, U-234), (IB-1714, S-7, U-235), (IB-1715, S-7, U-236), (IB-1716, S-7, U-237), (IB-1717, S-7, U-238), (IB-1718, S-7, U-239), (IB-1719, S-7, U-240), (IB-1720, S-7, U-241), (IB-1721, S-7, U-242), (IB-1722, S-7, U-243), (IB-1723, S-7, U-244), (IB-1724, S-7, U-245), (IB-1725, S-7, U-246), (IB-1726, S-7, U-247), (IB-1727, S-7, U-248), (IB-1728, S-7, U-249), (IB-1729, S-7, U-250), (IB-1730, S-7, U-251), (IB-1731, S-7, U-252), (IB-1732, S-7, U-253), (IB-1733, S-7, U-254), (IB-1734, S-7, U-255), (IB-1735, S-7, U-256), (IB-1736, S-7, U-257), (IB-1737, S-7, U-258), (IB-1738, S-7, U-259), (IB-1739, S-7, U-260), (IB-1740, S-7, U-261), (IB-1741, S-7, U-262), (IB-1742, S-7, U-263), (IB-1743, S-7, U-264), (IB-1744, S-7, U-265), (IB-1745, S-7, U-266), (IB-1746, S-7, U-267), (IB-1747, S-7, U-268), (IB-1748, S-7, U-269), (IB-1749, S-7, U-270), (IB-1750, S-7, U-271), (IB-1751, S-7, U-272), (IB-1752, S-7, U-273), (IB-1753, S-7, U-274), (IB-1754, S-7, U-275), (IB-1755, S-7, U-276), (IB-1756, S-7, U-277), (IB-1757, S-7, U-278), (IB-1758, S-7, U-279), (IB-1759, S-7, U-280), (IB-1760, S-7, U-281), (IB-1761, S-7, U-282), (IB-1762, S-7, U-283), (IB-1763, S-7, U-284), (IB-1764, S-7, U-285), (IB-1765, S-7, U-286), (IB-1766, S-7, U-287), (IB-1767, S-7, U-288), (IB-1768, S-7, U-289), (IB-1769, S-7, U-290), (IB-1770, S-7, U-291), (IB-1771, S-7, U-292), (IB-1772, S-7, U-293), (IB-1773, S-7, U-294), (IB-1774, S-7, U-295), (IB-1775, S-7, U-296), (IB-1776, S-7, U-297), (IB-1777, S-7, U-298), (IB-1778, S-7, U-299), (IB-1779, S-7, U-300), (IB-1780, S-7, U-301), (IB-1781, S-7, U-302), (IB-1782, S-7, U-303), (IB-1783, S-7, U-304), (IB-1784, S-7, U-305), (IB-1785, S-7, U-306), (IB-1786, S-7, U-307), (IB-1787, S-7, U-308), (IB-1788, S-7, U-309), (IB-1789, S-7, U-310), (IB-1790, S-7, U-311), (IB-1791, S-7, U-312), (IB-1792, S-7, U-313), (IB-1793, S-7, U-314), (IB-1794, S-7, U-315), (IB-1795, S-7, U-316), (IB-1796, S-7, U-317), (IB-1797, S-7, U-318), (IB-1798, S-7, U-319), (IB-1799, S-7, U-320), (IB-1800, S-7, U-321), (IB-1801, S-7, U-322), (IB-1802, S-7, U-323), (IB-1803, S-7, U-324), (IB-1804, S-7, U-325), (IB-1805, S-7, U-326), (IB-1806, S-7, U-327), (IB-1807, S-7, U-328), (IB-1808, S-7, U-329), (IB-1809, S-7, U-330), (IB-1810, S-7, U-331), (IB-1811, S-7, U-332), (IB-1812, S-7, U-333), (IB-1813, S-7, U-334), (IB-1814, S-7, U-335), (IB-1815, S-7, U-336), (IB-1816, S-7, U-337), (IB-1817, S-7, U-338), (IB-1818, S-200, U-1), (IB-1819, S-200, U-2), (IB-1820, S-200, U-3), (IB-1821, S-200, U-4), (IB-1822, S-200, U-5), (IB-1823, S-200, U-6), (IB-1824, S-200, U-7), (IB-1825, S-200, U-8), (IB-1826, S-200, U-9), (IB-1827, S-200, U-10), (IB-1828, S-200, U-11), (IB-1829, S-200, U-12), (IB-1830, S-200, U-13), (IB-1831, S-200, U-14), (IB-1832, S-200, U-15), (IB-1833, S-200, U-16), (IB-1834, S-200, U-17), (IB-1835, S-200, U-18), (IB-1836, S-200, U-19), (IB-1837, S-200, U-20), (IB-1838, S-200, U-21), (IB-1839, S-200, U-22), (IB-1840, S-200, U-23), (IB-1841, S-200, U-24), (IB-1842, S-200, U-25), (IB-1843, S-200, U-26), (IB-1844, S-200, U-27), (IB-1845, S-200, U-28), (IB-1846, S-200, U-29), (IB-1847, S-200, U-30), (IB-1848, S-200, U-31), (IB-1849, S-200, U-32), (IB-1850, S-200, U-33), (IB-1851, S-200, U-34), (IB-1852, S-200, U-35), (IB-1853, S-200, U-36), (IB-1854, S-200, U-37), (IB-1855, S-200, U-38), (IB-1856, S-200, U-39), (IB-1857, S-200, U-40), (IB-1858, S-200, U-41), (IB-1859, S-200, U-42), (IB-1860, S-200, U-43), (IB-1861, S-200, U-44), (IB-1862, S-200, U-45), (IB-1863, S-200, U-46), (IB-1864, S-200, U-47), (IB-1865, S-200, U-48), (IB-1866, S-200, U-49), (IB-1867, S-200, U-50), (IB-1868, S-200, U-51), (IB-1869, S-200, U-52), (IB-1870, S-200, U-53), (IB-1871, S-200, U-54), (IB-1872, S-200, U-55), (IB-1873, S-200, U-56), (IB-1874, S-200, U-62), (IB-1875, S-200, U-63), (IB-1876, S-200, U-64), (IB-1877, S-200, U-66), (IB-1878, S-200, U-67), (IB-1879, S-200, U-68), (IB-1880, S-200, U-70), (IB-1881, S-200, U-71), (IB-1882, S-200, U-72), (IB-1883, S-200, U-73), (IB-1884, S-200, U-75), (IB-1885, S-200, U-76), (IB-1886, S-200, U-77), (IB-1887, S-200, U-78), (IB-1888, S-200, U-79), (IB-1889, S-200, U-80), (IB-1890, S-200, U-81), (IB-1891, S-200, U-82), (IB-1892, S-200, U-83), (IB-1893, S-200, U-84), (IB-1894, S-200, U-85), (IB-1895, S-200, U-86), (IB-1896, S-200, U-87), (IB-1897, S-200, U-88), (IB-1898, S-200, U-89), (IB-1899, S-200, U-90), (IB-1900, S-200, U-91), (IB-1901, S-200, U-92), (IB-1902, S-200, U-93), (IB-1903, S-200, U-94), (IB-1904, S-200, U-95), (IB-1905, S-200, U-96), (IB-1906, S-200, U-97), (IB-1907, S-200, U-98), (IB-1908, S-200, U-99), (IB-1909, S-200, U-100), (IB-1910, S-200, U-101), (IB-1911, S-200, U-102), (IB-1912, S-200, U-103), (IB-1913, S-200, U-104), (IB-1914, S-200, U-105), (IB-1915, S-200, U-106), (IB-1916, S-200, U-107), (IB-1917, S-200, U-108), (IB-1918, S-200, U-109), (IB-1919, S-200, U-110), (IB-1920, S-200, U-111), (IB-1921, S-200, U-112), (IB-1922, S-200, U-113), (IB-1923, S-200, U-114), (IB-1924, S-200, U-115), (IB-1925, S-200, U-116), (IB-1926, S-200, U-117), (IB-1927, S-200, U-118), (IB-1928, S-200, U-119), (IB-1929, S-200, U-120), (IB-1930, S-200, U-121), (IB-1931, S-200, U-122), (IB-1932, S-200, U-123), (IB-1933, S-200, U-124), (IB-1934, S-200, U-125), (IB-1935, S-200, U-126), (IB-1936, S-200, U-127), (IB-1937, S-200, U-128), (IB-1938, S-200, U-129), (IB-1939, S-200, U-130), (IB-1940, S-200, U-131), (IB-1941, S-200, U-132), (IB-1942, S-200, U-133), (IB-1943, S-200, U-134), (IB-1944, S-200, U-135), (IB-1945, S-200, U-136), (IB-1946, S-200, U-137), (IB-1947, S-200, U-138), (IB-1948, S-200, U-139), (IB-1949, S-200, U-140), (IB-1950, S-200, U-141), (IB-1951, S-200, U-142), (IB-1952, S-200, U-143), (IB-1953, S-200, U-144), (IB-1954, S-200, U-145), (IB-1955, S-200, U-146), (IB-1956, S-200, U-147), (IB-1957, S-200, U-148), (IB-1958, S-200, U-149), (IB-1959, S-200, U-150), (IB-1960, S-200, U-151), (IB-1961, S-200, U-152), (IB-1962, S-200, U-153), (IB-1963, S-200, U-154), (IB-1964, S-200, U-155), (IB-1965, S-200, U-156), (IB-1966, S-200, U-157), (IB-1967, S-200, U-158), (IB-1968, S-200, U-159), (IB-1969, S-200, U-160), (IB-1970, S-200, U-161), (IB-1971, S-200, U-162), (IB-1972, S-200, U-163), (IB-1973, S-200, U-164), (IB-1974, S-200, U-165), (IB-1975, S-200, U-166), (IB-1976, S-200, U-167), (IB-1977, S-200, U-168), (IB-1978, S-200, U-169), (IB-1979, S-200, U-170), (IB-1980, S-200, U-171), (IB-1981, S-200, U-172), (IB-1982, S-200, U-173), (IB-1983, S-200, U-174), (IB-1984, S-200, U-175), (IB-1985, S-200, U-176), (IB-1986, S-200, U-177), (IB-1987, S-200, U-178), (IB-1988, S-200, U-179), (IB-1989, S-200, U-180), (IB-1990, S-200, U-181), (IB-1991, S-200, U-182), (IB-1992, S-200, U-183), (IB-1993, S-200, U-184), (IB-1994, S-200, U-185), (IB-1995, S-200, U-186), (IB-1996, S-200, U-187), (IB-1997, S-200, U-188), (IB-1998, S-200, U-189), (IB-1999, S-200, U-190), (IB-2000, S-200, U-191), (IB-2001, S-200, U-192), (IB-2002, S-200, U-193), (IB-2003, S-200, U-194), (IB-2004, S-200, U-195), (IB-2005, S-200, U-196), (IB-2006, S-200, U-197), (IB-2007, S-200, U-198), (IB-2008, S-200, U-199), (IB-2009, S-200, U-200), (IB-2010, S-200, U-201), (IB-2011, S-200, U-202), (IB-2012, S-200, U-203), (IB-2013, S-200, U-204), (IB-2014, S-200, U-205), (IB-2015, S-200, U-206), (IB-2016, S-200, U-207), (IB-2017, S-200, U-208), (IB-2018, S-200, U-209), (IB-2019, S-200, U-210), (IB-2020, S-200, U-211), (IB-2021, S-200, U-212), (IB-2022, S-200, U-213), (IB-2023, S-200, U-214), (IB-2024, S-200, U-215), (IB-2025, S-200, U-216), (IB-2026, S-200, U-217), (IB-2027, S-200, U-218), (IB-2028, S-200, U-219), (IB-2029, S-200, U-220), (IB-2030, S-200, U-221), (IB-2031, S-200, U-222), (IB-2032, S-200, U-223), (IB-2033, S-200, U-224), (IB-2034, S-200, U-225), (IB-2035, S-200, U-226), (IB-2036, S-200, U-227), (IB-2037, S-200, U-228), (IB-2038, S-200, U-229), (IB-2039, S-200, U-230), (IB-2040, S-200, U-231), (IB-2041, S-200, U-232), (IB-2042, S-200, U-233), (IB-2043, S-200, U-234), (IB-2044, S-200, U-235), (IB-2045, S-200, U-236), (IB-2046, S-200, U-237), (IB-2047, S-200, U-238), (IB-2048, S-200, U-239), (IB-2049, S-200, U-240), (IB-2050, S-200, U-241), (IB-2051, S-200, U-242), (IB-2052, S-200, U-243), (IB-2053, S-200, U-244), (IB-2054, S-200, U-245), (IB-2055, S-200, U-246), (IB-2056, S-200, U-247), (IB-2057, S-200, U-248), (IB-2058, S-200, U-249), (IB-2059, S-200, U-250), (IB-2060, S-200, U-251), (IB-2061, S-200, U-252), (IB-2062, S-200, U-253), (IB-2063, S-200, U-254), (IB-2064, S-200, U-255), (IB-2065, S-200, U-256), (IB-2066, S-200, U-257), (IB-2067, S-200, U-258), (IB-2068, S-200, U-259), (IB-2069, S-200, U-260), (IB-2070, S-200, U-261), (IB-2071, S-200, U-262), (IB-2072, S-200, U-263), (IB-2073, S-200, U-264), (IB-2074, S-200, U-265), (IB-2075, S-200, U-266), (IB-2076, S-200, U-267), (IB-2077, S-200, U-268), (IB-2078, S-200, U-269), (IB-2079, S-200, U-270), (IB-2080, S-200, U-271), (IB-2081, S-200, U-272), (IB-2082, S-200, U-273), (IB-2083, S-200, U-274), (IB-2084, S-200, U-275), (IB-2085, S-200, U-276), (IB-2086, S-200, U-277), (IB-2087, S-200, U-278), (IB-2088, S-200, U-279), (IB-2089, S-200, U-280), (IB-2090, S-200, U-281), (IB-2091, S-200, U-282), (IB-2092, S-200, U-283), (IB-2093, S-200, U-284), (IB-2094, S-200, U-285), (IB-2095, S-200, U-286), (IB-2096, S-200, U-287), (IB-2097, S-200, U-288), (IB-2098, S-200, U-289), (IB-2099, S-200, U-290), (IB-2100, S-200, U-291), (IB-2101, S-200, U-292), (IB-2102, S-200, U-293), (IB-2103, S-200, U-294), (IB-2104, S-200, U-295), (IB-2105, S-200, U-296), (IB-2106, S-200, U-297), (IB-2107, S-200, U-298), (IB-2108, S-200, U-299), (IB-2109, S-200, U-300), (IB-2110, S-200, U-301), (IB-2111, S-200, U-302), (IB-2112, S-200, U-303), (IB-2113, S-200, U-304), (IB-2114, S-200, U-305), (IB-2115, S-200, U-306), (IB-2116, S-200, U-307), (IB-2117, S-200, U-308), (IB-2118, S-200, U-309), (IB-2119, S-200, U-310), (IB-2120, S-200, U-311), (IB-2121, S-200, U-312), (IB-2122, S-200, U-313), (IB-2123, S-200, U-314), (IB-2124, S-200, U-315), (IB-2125, S-200, U-316), (IB-2126, S-200, U-317), (IB-2127, S-200, U-318), (IB-2128, S-200, U-319), (IB-2129, S-200, U-320), (IB-2130, S-200, U-321), (IB-2131, S-200, U-322), (IB-2132, S-200, U-323), (IB-2133, S-200, U-324), (IB-2134, S-200, U-325), (IB-2135, S-200, U-326), (IB-2136, S-200, U-327), (IB-2137, S-200, U-328), (IB-2138, S-200, U-329), (IB-2139, S-200, U-330), (IB-2140, S-200, U-331), (IB-2141, S-200, U-332), (IB-2142, S-200, U-333), (IB-2143, S-200, U-334), (IB-2144, S-200, U-335), (IB-2145, S-200, U-336), (IB-2146, S-200, U-337), (IB-2147, S-200, U-338), (IB-2148, S-201, U-1), (IB-2149, S-201, U-2), (IB-2150, S-201, U-3), (IB-2151, S-201, U-4), (IB-2152, S-201, U-5), (IB-2153, S-201, U-6), (IB-2154, S-201, U-7), (IB-2155, S-201, U-8), (IB-2156, S-201, U-9), (IB-2157, S-201, U-10), (IB-2158, S-201, U-11), (IB-2159, S-201, U-12), (IB-2160, S-201, U-13), (IB-2161, S-201, U-14), (IB-2162, S-201, U-15), (IB-2163, S-201, U-16), (IB-2164, S-201, U-17), (IB-2165, S-201, U-18), (IB-2166, S-201, U-19), (IB-2167, S-201, U-20), (IB-2168, S-201, U-21), (IB-2169, S-201, U-22), (IB-2170, S-201, U-23), (IB-2171, S-201, U-24), (IB-2172, S-201, U-25), (IB-2173, S-201, U-26), (IB-2174, S-201, U-27), (IB-2175, S-201, U-28), (IB-2176, S-201, U-29), (IB-2177, S-201, U-30), (IB-2178, S-201, U-31), (IB-2179, S-201, U-32), (IB-2180, S-201, U-33), (IB-2181, S-201, U-34), (IB-2182, S-201, U-35), (IB-2183, S-201, U-36), (IB-2184, S-201, U-37), (IB-2185, S-201, U-38), (IB-2186, S-201, U-39), (IB-2187, S-201, U-40), (IB-2188, S-201, U-41), (IB-2189, S-201, U-42), (IB-2190, S-201, U-43), (IB-2191, S-201, U-44), (IB-2192, S-201, U-45), (IB-2193, S-201, U-46), (IB-2194, S-201, U-47), (IB-2195, S-201, U-48), (IB-2196, S-201, U-49), (IB-2197, S-201, U-50), (IB-2198, S-201, U-51), (IB-2199, S-201, U-52), (IB-2200, S-201, U-53), (IB-2201, S-201, U-54), (IB-2202, S-201, U-55), (IB-2203, S-201, U-56), (IB-2204, S-201, U-62), (IB-2205, S-201, U-63), (IB-2206, S-201, U-64), (IB-2207, S-201, U-66), (IB-2208, S-201, U-67), (IB-2209, S-201, U-68), (IB-2210, S-201, U-70), (IB-2211, S-201, U-71), (IB-2212, S-201, U-72), (IB-2213, S-201, U-73), (IB-2214, S-201, U-75), (IB-2215, S-201, U-76), (IB-2216, S-201, U-77), (IB-2217, S-201, U-78), (IB-2218, S-201, U-79), (IB-2219, S-201, U-80), (IB-2220, S-201, U-81), (IB-2221, S-201, U-82), (IB-2222, S-201, U-83), (IB-2223, S-201, U-84), (IB-2224, S-201, U-85), (IB-2225, S-201, U-86), (IB-2226, S-201, U-87), (IB-2227, S-201, U-88), (IB-2228, S-201, U-89), (IB-2229, S-201, U-90), (IB-2230, S-201, U-91), (IB-2231, S-201, U-92), (IB-2232, S-201, U-93), (IB-2233, S-201, U-94), (IB-2234, S-201, U-95), (IB-2235, S-201, U-96), (IB-2236, S-201, U-97), (IB-2237, S-201, U-98), (IB-2238, S-201, U-99), (IB-2239, S-201, U-100), (IB-2240, S-201, U-101), (IB-2241, S-201, U-102), (IB-2242, S-201, U-103), (IB-2243, S-201, U-104), (IB-2244, S-201, U-105), (IB-2245, S-201, U-106), (IB-2246, S-201, U-107), (IB-2247, S-201, U-108), (IB-2248, S-201, U-109), (IB-2249, S-201, U-110), (IB-2250, S-201, U-111), (IB-2251, S-201, U-112), (IB-2252, S-201, U-113), (IB-2253, S-201, U-114), (IB-2254, S-201, U-115), (IB-2255, S-201, U-116), (IB-2256, S-201, U-117), (IB-2257, S-201, U-118), (IB-2258, S-201, U-119), (IB-2259, S-201, U-120), (IB-2260, S-201, U-121), (IB-2261, S-201, U-122), (IB-2262, S-201, U-123), (IB-2263, S-201, U-124), (IB-2264, S-201, U-125), (IB-2265, S-201, U-126), (IB-2266, S-201, U-127), (IB-2267, S-201, U-128), (IB-2268, S-201, U-129), (IB-2269, S-201, U-130), (IB-2270, S-201, U-131), (IB-2271, S-201, U-132), (IB-2272, S-201, U-133), (IB-2273, S-201, U-134), (IB-2274, S-201, U-135), (IB-2275, S-201, U-136), (IB-2276, S-201, U-137), (IB-2277, S-201, U-138), (IB-2278, S-201, U-139), (IB-2279, S-201, U-140), (IB-2280, S-201, U-141), (IB-2281, S-201, U-142), (IB-2282, S-201, U-143), (IB-2283, S-201, U-144), (IB-2284, S-201, U-145), (IB-2285, S-201, U-146), (IB-2286, S-201, U-147), (IB-2287, S-201, U-148), (IB-2288, S-201, U-149), (IB-2289, S-201, U-150), (IB-2290, S-201, U-151), (IB-2291, S-201, U-152), (IB-2292, S-201, U-153), (IB-2293, S-201, U-154), (IB-2294, S-201, U-155), (IB-2295, S-201, U-156), (IB-2296, S-201, U-157), (IB-2297, S-201, U-158), (IB-2298, S-201, U-159), (IB-2299, S-201, U-160), (IB-2300, S-201, U-161), (IB-2301, S-201, U-162), (IB-2302, S-201, U-163), (IB-2303, S-201, U-164), (IB-2304, S-201, U-165), (IB-2305, S-201, U-166), (IB-2306, S-201, U-167), (IB-2307, S-201, U-168), (IB-2308, S-201, U-169), (IB-2309, S-201, U-170), (IB-2310, S-201, U-171), (IB-2311, S-201, U-172), (IB-2312, S-201, U-173), (IB-2313, S-201, U-174), (IB-2314, S-201, U-175), (IB-2315, S-201, U-176), (IB-2316, S-201, U-177), (IB-2317, S-201, U-178), (IB-2318, S-201, U-179), (IB-2319, S-201, U-180), (IB-2320, S-201, U-181), (IB-2321, S-201, U-182), (IB-2322, S-201, U-183), (IB-2323, S-201, U-184), (IB-2324, S-201, U-185), (IB-2325, S-201, U-186), (IB-2326, S-201, U-187), (IB-2327, S-201, U-188), (IB-2328, S-201, U-189), (IB-2329, S-201, U-190), (IB-2330, S-201, U-191), (IB-2331, S-201, U-192), (IB-2332, S-201, U-193), (IB-2333, S-201, U-194), (IB-2334, S-201, U-195), (IB-2335, S-201, U-196), (IB-2336, S-201, U-197), (IB-2337, S-201, U-198), (IB-2338, S-201, U-199), (IB-2339, S-201, U-200), (IB-2340, S-201, U-201), (IB-2341, S-201, U-202), (IB-2342, S-201, U-203), (IB-2343, S-201, U-204), (IB-2344, S-201, U-205), (IB-2345, S-201, U-206), (IB-2346, S-201, U-207), (IB-2347, S-201, U-208), (IB-2348, S-201, U-209), (IB-2349, S-201, U-210), (IB-2350, S-201, U-211), (IB-2351, S-201, U-212), (IB-2352, S-201, U-213), (IB-2353, S-201, U-214), (IB-2354, S-201, U-215), (IB-2355, S-201, U-216), (IB-2356, S-201, U-217), (IB-2357, S-201, U-218), (IB-2358, S-201, U-219), (IB-2359, S-201, U-220), (IB-2360, S-201, U-221), (IB-2361, S-201, U-222), (IB-2362, S-201, U-223), (IB-2363, S-201, U-224), (IB-2364, S-201, U-225), (IB-2365, S-201, U-226), (IB-2366, S-201, U-227), (IB-2367, S-201, U-228), (IB-2368, S-201, U-229), (IB-2369, S-201, U-230), (IB-2370, S-201, U-231), (IB-2371, S-201, U-232), (IB-2372, S-201, U-233), (IB-2373, S-201, U-234), (IB-2374, S-201, U-235), (IB-2375, S-201, U-236), (IB-2376, S-201, U-237), (IB-2377, S-201, U-238), (IB-2378, S-201, U-239), (IB-2379, S-201, U-240), (IB-2380, S-201, U-241), (IB-2381, S-201, U-242), (IB-2382, S-201, U-243), (IB-2383, S-201, U-244), (IB-2384, S-201, U-245), (IB-2385, S-201, U-246), (IB-2386, S-201, U-247), (IB-2387, S-201, U-248), (IB-2388, S-201, U-249), (IB-2389, S-201, U-250), (IB-2390, S-201, U-251), (IB-2391, S-201, U-252), (IB-2392, S-201, U-253), (IB-2393, S-201, U-254), (IB-2394, S-201, U-255), (IB-2395, S-201, U-256), (IB-2396, S-201, U-257), (IB-2397, S-201, U-258), (IB-2398, S-201, U-259), (IB-2399, S-201, U-260), (IB-2400, S-201, U-261), (IB-2401, S-201, U-262), (IB-2402, S-201, U-263), (IB-2403, S-201, U-264), (IB-2404, S-201, U-265), (IB-2405, S-201, U-266), (IB-2406, S-201, U-267), (IB-2407, S-201, U-268), (IB-2408, S-201, U-269), (IB-2409, S-201, U-270), (IB-2410, S-201, U-271), (IB-2411, S-201, U-272), (IB-2412, S-201, U-273), (IB-2413, S-201, U-274), (IB-2414, S-201, U-275), (IB-2415, S-201, U-276), (IB-2416, S-201, U-277), (IB-2417, S-201, U-278), (IB-2418, S-201, U-279), (IB-2419, S-201, U-280), (IB-2420, S-201, U-281), (IB-2421, S-201, U-282), (IB-2422, S-201, U-283), (IB-2423, S-201, U-284), (IB-2424, S-201, U-285), (IB-2425, S-201, U-286), (IB-2426, S-201, U-287), (IB-2427, S-201, U-288), (IB-2428, S-201, U-289), (IB-2429, S-201, U-290), (IB-2430, S-201, U-291), (IB-2431, S-201, U-292), (IB-2432, S-201, U-293), (IB-2433, S-201, U-294), (IB-2434, S-201, U-295), (IB-2435, S-201, U-296), (IB-2436, S-201, U-297), (IB-2437, S-201, U-298), (IB-2438, S-201, U-299), (IB-2439, S-201, U-300), (IB-2440, S-201, U-301), (IB-2441, S-201, U-302), (IB-2442, S-201, U-303), (IB-2443, S-201, U-304), (IB-2444, S-201, U-305), (IB-2445, S-201, U-306), (IB-2446, S-201, U-307), (IB-2447, S-201, U-308), (IB-2448, S-201, U-309), (IB-2449, S-201, U-310), (IB-2450, S-201, U-311), (IB-2451, S-201, U-312), (IB-2452, S-201, U-313), (IB-2453, S-201, U-314), (IB-2454, S-201, U-315), (IB-2455, S-201, U-316), (IB-2456, S-201, U-317), (IB-2457, S-201, U-318), (IB-2458, S-201, U-319), (IB-2459, S-201, U-320), (IB-2460, S-201, U-321), (IB-2461, S-201, U-322), (IB-2462, S-201, U-323), (IB-2463, S-201, U-324), (IB-2464, S-201, U-325), (IB-2465, S-201, U-326), (IB-2466, S-201, U-327), (IB-2467, S-201, U-328), (IB-2468, S-201, U-329), (IB-2469, S-201, U-330), (IB-2470, S-201, U-331), (IB-2471, S-201, U-332), (IB-2472, S-201, U-333), (IB-2473, S-201, U-334), (IB-2474, S-201, U-335), (IB-2475, S-201, U-336), (IB-2476, S-201, U-337), (IB-2477, S-201, U-338)

Test Example 1

DP Inhibitory Activity In Vitro

1) Preparation of Platelet and a Method of cAMP Assay 30 mL of peripheral blood was collected from a healthy volunteer using a syringe containing one ninth amount of 3.8% sodium citrate. After being centrifuged at 180 g for 10 minutes at room temperature, a supernatant was collected and used as Platelet Rich Plasma (PRP). The resulting PRP was washed with wash buffer and centrifuged three times (Washed Platelet: WP) and platelets were counted by a micro-cell counter. WP was added to a plate in amount of $1.5 \times 10^8/$ assay and the plate was treated with 3-isobutyl-1-methylxanthin (IBMX; 0.5 mM) for 5 minutes. A reaction was initiated by adding 100 nM of PGD2 5 min after an addition of a test compound. The reaction was terminated with an addition of 1N hydrochloric acid after 2 minutes and the cells were destructed using 12% triton X-100. An amount of cAMP in the supernatant was assayed by Homogeneous Trangient Fluorescence (HTRF)

2) Receptor Binding Assay

A prepared WP was homogenated and a membrane fraction was collected with high-speed centrifugation. A compound of the present invention was added to the plate and [3H]-PGD2 was also added. A platelet membrane, a protein concentration is 2 mg/mL, was added and mixed in the plate, and placed on ice for 2 hours. The reaction solution was transferred to a low protein-adsorptive filter and washed with a wash solution eight times using a cell harvester. After the final washing, water was removed sufficiently, and scintillator was added. DP inhibitory activity was investigated by measuring [$^3$H] by using Micro Beta.

50% DP-inhibitory concentrations (IC50) in the cAMP assay and Ki values in the receptor binding assay were shown in Table 41.

3) Prostanoid Agonist and Antagonist Assay

Agonistic and antagonistic activities of the compounds of the present invention against prostanoid receptor were evaluated based on intracellular calcium flux or cAMP-production as an indicator using HEK 293 cells expressing human EP1, EP2, EP3, EP4, FP, TP and IP respectively. Any compounds did not show an agonistic activity against each prostanoid. In the other hand, more than twenty times potent antagonistic activity (IC50) was found in every compound compared with IC50 of cAMP assay with WP.

TABLE 41

| Compd. No. | IC50(nM) | Ki (nM) |
|---|---|---|
| I-1 | 4.7 | 7.7 |
| I-5 | 4.1 | 22 |
| I-6 | 4.8 | |
| I-7 | 1.8 | |
| I-8 | 4.9 | |
| I-9 | 2.0 | |
| I-10 | 6.9 | |
| I-11 | 4.9 | |
| I-12 | 6.9 | |
| I-14 | 2.2 | 5.6 |
| I-16 | 1.3 | |
| I-20 | 3.8 | |
| I-21 | 3.0 | |
| I-23 | 1.6 | 1.4 |
| I-30 | 1.2 | 5.4 |
| I-31 | 2.9 | 4.3 |
| I-32 | 7.0 | |

Test Example 2

Test Using Ova Asthma Model of Rat

Brown Norway (BN) Rats were sensitized by i.p. administration of 0.1 mg/mL of ovalbumin (OVA) and 1 mg of aluminum hydroxide gel. A solution of 1% OVA was aerosolized by ultrasonic nebulizer (NE-U17) and the rats were subjected to inhalation exposure of the aerosol for 30 minutes in an exposing chamber 12, 19, 26 and 33 days after the sensitization. One hour before the 4th exposure of the antigen, compounds of the present invention were administered in a dose of 10 mg/kg p.o. once a day for three days consecutively. In a control group, 0.5% of methyl cellulose was administered in place of the compound of the present invention.

Under pentobarbital anesthesia (80 mg/kg, i.p.), acetylcholine (3.9, 7.8, 15.6, 31.3, 62.5, 125, 250 and 500 µg/kg) was injected to jugular vein of the rats successively from a lower dose at intervals of 5 minutes three days after the fourth exposure to the antigen, and immediate contractile reaction of airways (an increase of insufflation pressure) was measured by a modified method of Konnzett & Rössler. Inhibition rate of increased hyperresponsive airway against the control group was calculated based on area under the curve (AUC) obtained from concentration-response curve of acetylcholine.

After the measurement of increased hyperresponsive airway was completed, bronchoalveoli of the rats were washed with 5 mL of saline three times. Total cell number in the washings was counted by a hemacytometer under light microscope, and inhibition rates of infiltration of inflammatory cells against the control group were calculated. Further, mucin in the airway lavage fluid was measured by ELISA method using jacalin, a mucin-binding lectin, and the inhibition rates of mucus-secretion against the control group were calculated.

Results were shown in Table 42.

TABLE 42

| | | inhibition rate (%) | | |
|---|---|---|---|---|
| Compd. No. | dose (mg/kg) | airway hyperresponsiveness | infiltration of inflammatory cells | mucus-secretion |
| I-1 | 10 | 43 | 58 | 52 |
| I-11 | 10 | 77 | 56 | 30 |
| I-23 | 10 | 46 | 79 | 72 |

Test Example 3

Test Using Nasal Congestion Model of Guinea Pig

Methods of measuring nasal airway resistance and evaluating anti-nasal congestion activity using a guinea pig were illustrated below.

A 1% solution of ovalbumin (OVA) was aerosolized by ultrasonic nebulizer, a male Hartley guinea pigs were sensitized by inhalation of the aerosol for 10 minutes twice at an interval of a week and a reaction was initiated by exposure to the antigen 7 days later. Trachea of the guinea pig was incised under pentobarbital anesthesia (30 mg/kg, i.p.), and cannulae were fitted at the sides of nasal cavity and lung respectively. To the lung side, a ventilator supplying 4 mL of air every time at a rate of 60 times/min was connected. Spontaneous breathing of the guinea pig was stopped by the administration of gallamine (2 mg/kg, i.v.) and 4 mL of air every time was supplied at a rate of 70 times/minute to rostrum of nose through the cannula of the nasal side using a ventilator. Air pressure necessary for supplying the air was measured by a transducer fitted at the side branch and used as an indicator for resistance of nasal cavity. Exposure to the antigen was performed by generating the aerosol of 3% OVA solution between the ventilator and the nasal cavity cannula for three minutes. Compounds of the present invention were administered intravenously 10 minutes before the exposure to the antigen. Resistance of nasal cavity was continuously measured during a period from 0 to 30 minutes, and the inhibition rate against the vehicle was obtained based on AUC of the 30 minutes, which was recorded with resistance of nasal cavity (cm $H_2O$) as a longitudinal axis, and time (from 0 to 30 min.) as an abscissa axis.

Formulation Example

The following formulating examples 1-8 are just for illustrative purposes and not intended to limit the range of the present invention. A term of "active ingredient" means the compounds of the present invention, pharmaceutically acceptable salt or hydrate thereof.

Formulation Example 1

A hard-gelatin capsule is prepared with the following ingredients;

| | Amount (mg/capsule) |
|---|---|
| active ingredient | 250 |
| starch (dried) | 200 |
| magnesium stearate | 10 |
| Total | 460 mg |

Formulation Example 2

A tablet is prepared with the following ingredients;

| | Amount (mg/tablet) |
|---|---|
| active ingredient | 250 |
| cellulose(micro crystalline) | 400 |
| silicon dioxide (fume) | 10 |
| stearic acid | 5 |
| Total | 665 mg |

The ingredients above are mixed and compressed to give a tablet weighing 665 mg/tablet.

Formulation Example 3

An aerosol solution is prepared with the following ingredients;

| | weight |
|---|---|
| active ingredient | 0.25 |
| ethanol | 25.75 |
| propellant 22 (chlorodifluoroethane) | 74.00 |
| Total | 100.00 |

The active ingredient and ethanol are mixed and the mixture is added to a part of propellant 22, and the resulting solution is transferred to a filling apparatus after being cooled to −30° C. Next, the necessary amount is provided to a stainless-steel vessel and the content is diluted with the remaining propellant. A valve unit is fitted to the vessel.

Formulation Example 4

A tablet containing 60 mg of an active ingredient is prepared as follows;

| | |
|---|---|
| active ingredient | 60 mg |
| starch | 45 mg |
| microcrystalline cellulose | 35 mg |
| polyvinylpyrrolidone (10% aq. solution) | 4 mg |
| sodium carboxymethylstarch | 4.5 mg |
| magnesium stearate | 0.5 mg |
| talc | 1 mg |
| Total | 150 mg |

The active ingredient, starch and cellulose are put through a sieve of No. 45 mesh US and mixed sufficiently. The resulting powder is mixed with a solution containing polyvinylpyrrolidone and the mixture is put through a sieve of No. 14 mesh US. The granulated powder is dried at 50° C. and put through a sieve of No. 18 mesh US. Sodium carboxymethylstarch, magnesium stearate and talc are put through a sieve of No. 60 mesh US in advance and added to the granulated powder, mixed and compressed by a tableting machine to give a tablet weighing 150 mg/tablet.

Formulation Example 5

A capsule containing 80 mg of an active ingredient is prepared as follows;

| active ingredient | 80 mg |
| --- | --- |
| starch | 59 mg |
| microcrystalline cellulose | 59 mg |
| magnesium stearate | 2 mg |
| Total | 200 mg |

The active ingredient, starch, cellulose and magnesium stearate are mixed, put through a sieve of No. 45 mesh US and filled in hard-gelatin capsules to give a capsule formulation containing 200 mg/capsule.

Formulation Example 6

A suppository containing 225 mg of an active ingredient is prepared as follows;

| active ingredient | 225 mg |
| --- | --- |
| saturated fatty acid gliceride | 2000 mg |
| Total | 2225 mg |

The active ingredient is put through a sieve of No. 60 mesh US and suspended in the saturated fatty acid gliceride melted by the least amount of heating. Then, the mixture was cooled in a mold of 2 g in appearance.

Formulation Example 7

A suspension containing 50 mg of an active ingredient is prepared as follows;

| active ingredient | 50 mg |
| --- | --- |
| sodium carboxymethylcellulose | 50 mg |
| syrup | 1.25 ml |
| solution of benzoic acid | 0.10 ml |
| flavor | q.v. |
| pigment | q.v. |
| Total (adding purified water) | 5 ml |

The active ingredient is put through a sieve of No. 45 mesh US and mixed with sodium carboxymethylcellulose and syrup to give a smooth paste. The solution of benzoic acid and flavor are diluted with a part of water and added to the paste and stirred. A necessary amount of water is added to give the objective suspension.

Formulation Example 8

A formulation for i.v. injection is prepared as follows;

| active ingredient | 100 mg |
| --- | --- |
| saturated fatty acid gliceride | 1000 ml |

The solution containing the active ingredient above is usually injected intravenously to a patient at a rate of 1 ml/min.

INDUSTRIAL APPLICABILITY

It was found that a novel indole derivative had a DP receptor antagonistic activity and was effective on treating allergic diseases.

The invention claimed is:
1. A compound of the general formula (I):

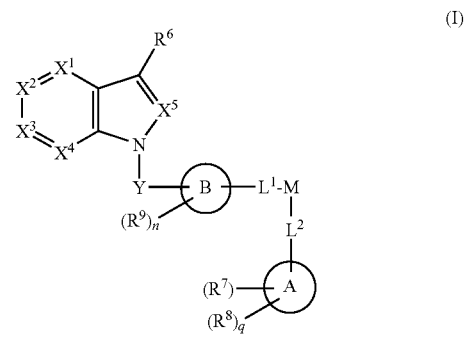

wherein the ring A is an aromatic carbocyclic ring or an aromatic heterocyclic ring;
the ring B is piperidine;
$X^1$ is $-C(R^1)=$;
$X^2$ is $-C(R^2)=$;
$X^3$ is $-C(R^3)=$;
$X^4$ is $-C(R^4)=$;
$X^5$ is $-C(R^5)=$;
$R^1$, $R^2$, $R^3$, $R^4$, $R^5$ and $R^6$ are independently a hydrogen atom, a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, an optionally substituted non-aromatic heterocyclic group or a group of the formula: -$L^3$-$R^{10}$, wherein $R^{10}$ is hydroxyalkyl, carboxy, alkyloxycarbonyl, optionally substituted carbamoyl or a carboxy equivalent, and $L^3$ is a single bond, optionally substituted alkylene optionally containing one or two heteroatom(s), optionally substituted alkenylene optionally containing one or two heteroatom(s), optionally substituted alkynylene optionally containing one or two heteroatom(s), an oxygen atom, a sulfur atom or —N($R^{11}$)—, provided that at least one of $R^1$ to $R^6$ is a group of -$L^3$-$R^{10}$;

$R^7$ is a hydrogen atom, optionally substituted alkyloxy, optionally substituted alkenyloxy, optionally substituted alkynyloxy, optionally substituted cycloalkyloxy, optionally substituted cycloalkenyloxy, optionally substituted aryloxy, optionally substituted heteroaryloxy, optionally substituted alkylthio, optionally substituted alkenylthio, optionally substituted alkynylthio, optionally substituted cycloalkylthio, optionally substituted cycloalkenylthio, optionally substituted arylthio or optionally substituted heteroarylthio;

$R^8$ is independently a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^9$ is independently a halogen atom, optionally substituted alkyl, optionally substituted alkenyl, optionally substituted alkynyl, optionally substituted cycloalkyl, optionally substituted alkyloxy, oxo, optionally substituted aryl, optionally substituted heteroaryl or an optionally substituted non-aromatic heterocyclic group;

M is sulfonyl;

Y is a single bond, optionally substituted alkylene optionally containing one or two heteroatom(s), optionally substituted alkenylene optionally containing one or two heteroatom(s), optionally substituted alkynylene optionally containing one or two heteroatom(s), an oxygen atom, a sulfur atom or —N($R^{11}$)—;

$L^1$ and $L^2$ are independently a single bond, optionally substituted alkylene optionally containing one or two heteroatom(s), optionally substituted alkenylene optionally containing one or two heteroatom(s), optionally substituted alkynylene optionally containing one or two heteroatom(s), or —N($R^{12}$)—;

$R^{11}$ and $R^{12}$ are independently a hydrogen atoms, optionally substituted alkyl, optionally substituted alkenyl, optionally substituted alkynyl, optionally substituted cycloalkyl, acyl, optionally substituted alkyloxy, optionally substituted aryl, optionally substituted heteroaryl or an optionally substituted non-aromatic heterocyclic group;

n is 0, 1 or 2; and q is 0, 1, 2 or 3, provided that $R^7$ is not a hydrogen atom when the ring B is an imidazoline ring and all of Y, $L^1$ and $L^2$ are single bonds;

or a pharmaceutically acceptable salt thereof.

2. A compound of the general formula (II):

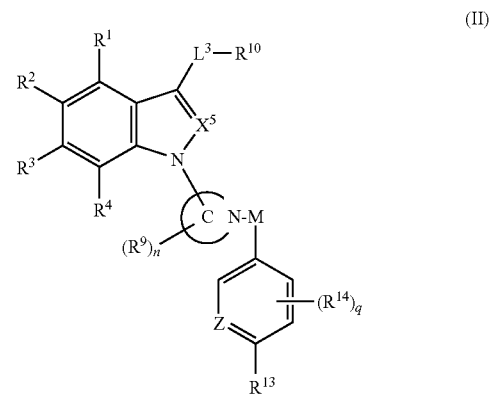

(II)

wherein the ring C is a ring of the formula of

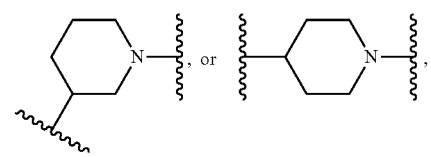

$X^5$ is —C($R^5$)=, $R^1$, $R^2$, $R^3$, $R^4$ and $R^5$ are independently hydrogen atoms, a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^9$ is independently a halogen atom, optionally substituted alkyl, optionally substituted alkenyl, optionally substituted alkynyl, optionally substituted cycloalkyl, optionally substituted alkyloxy, oxo, optionally substituted aryl, optionally substituted heteroaryl or an optionally substituted non-aromatic heterocyclic group;

$R^{10}$ is hydroxyalkyl, carboxy, alkyloxycarbonyl, optionally substituted carbamoyl or a carboxy equivalent;

$R^{13}$ is Optionally substituted C1-C6 alkyloxy, optionally substituted C2-C6 alkenyloxy, optionally substituted C2-C6 alkynyloxy, optionally substituted C1-C6 alkylthio, optionally substituted C2-C6 alkenylthio, optionally substituted C2-C6 alkynylthio, optionally substituted C3-C6 cycloalkyloxy, optionally substituted C3-C6 cycloalkylthio, optionally substituted aryloxy or optionally substituted arylthio;

$R^{11}$ is a hydrogen atom, optionally substituted alkyl, optionally substituted alkenyl, optionally substituted alkynyl, optionally substituted cycloalkyl, acyl, optionally substituted alkyloxy, optionally substituted aryl, optionally substituted heteroaryl or optionally substituted non-aromatic heterocyclic group;

$R^{14}$ is independently halogen atom, optionally substituted alkyl, optionally substituted cycloalkyl, optionally substituted amino, acyl, optionally substituted alkyloxycarbonyl, optionally substituted carbamoyl, optionally substituted sulfamoyl, cyano, nitro, optionally substituted aryl, optionally substituted arylsulfonyloxy, optionally substituted heteroaryl or an optionally substituted non-aromatic heterocyclic group;

M is carbonyl or sulfonyl;

Z is CH, C($R^{14}$), or N;

$L^3$ is a single bond, optionally substituted alkylene optionally containing one or two heteroatom(s), optionally substituted alkenylene optionally containing one or two heteroatom(s), optionally substituted alkynylene optionally containing one or two heteroatom(s), an oxygen atom, a sulfur atom or a group of —N($R^{11}$)—;

n is 0, 1 or 2; and q is 0, 1, 2 or 3;

or a pharmaceutically acceptable salt thereof.

3. A compound of claim 2 wherein M is sulfonyl; or a pharmaceutically acceptable salt thereof.

4. A compound of claim 2 wherein $R^{10}$ is carboxy; or a pharmaceutically acceptable salt thereof.

5. A compound of claim 3 wherein $X^5$ is —CH═; or a pharmaceutically acceptable salt thereof.

6. A compound of claim 2 wherein $L^3$ is optionally substituted alkylene; or a pharmaceutically acceptable salt thereof.

7. A compound of claim 2 wherein $R^5$ is a hydrogen atom, a halogen atom or alkyl; or a pharmaceutically acceptable salt thereof.

8. A compound of claim 2, wherein one of $R^1$ to $R^4$ is a hydrogen atom, a halogen atom, optionally substituted alkyl, optionally substituted alkyloxy, optionally substituted amino, optionally substituted carbamoyl, optionally substituted aryl, optionally substituted heteroaryl or an optionally substituted non-aromatic heterocyclic group, and others of $R^1$ to $R^4$ are a hydrogen atom, a halogen atom or optionally substituted alkyl;

or a pharmaceutically acceptable salt thereof.

9. A compound of claim 2 wherein $R^{13}$ is optionally substituted C1-C6 alkyloxy or optionally substituted C1-C6 alkylthio;

or a pharmaceutically acceptable salt thereof.

10. A compound of claim 2 wherein $R^{14}$ is a halogen atom, optionally substituted alkyl or optionally substituted alkyloxy;

or a pharmaceutically acceptable salt thereof.

11. A compound of claim 2 wherein $R^9$ is alkyl or oxo, and n is 0 or 1;

or a pharmaceutically acceptable salt thereof.

12. A pharmaceutical composition comprising the compound of claim 1, or a pharmaceutically acceptable salt thereof as an active ingredient, and a pharmaceutical additive.

13. A pharmaceutical composition of claim 12 which is a DP receptor antagonist.

14. A pharmaceutical composition of claim 12 which is a therapeutic agent for allergy.

15. A pharmaceutical composition of claim 14 wherein the therapeutic agent for allergy is a medicine for asthma.

16. A method for treating asthma or allergic rhinitis which comprises administering an effective amount of a compound of claim 1, or a pharmaceutically acceptable salt thereof, to a patient in need thereof.

17. A method of claim 16 for treating asthma.

18. A pharmaceutical composition comprising the compound of claim 2, or a pharmaceutically acceptable salt thereof as an active ingredient, and a pharmaceutical additive.

19. A method for treating asthma or allergic rhinitis which comprises administering an effective amount of a compound of claim 2, or a pharmaceutically acceptable salt thereof, to a patient in need thereof.

20. A method of claim 19 for treating asthma.

* * * * *